US010385381B2

(12) United States Patent
Masci et al.

(10) Patent No.: US 10,385,381 B2
(45) Date of Patent: Aug. 20, 2019

(54) SERUM PREPARATION

(76) Inventors: Paul Masci, St. Lucia (AU); John De Jersey, St. Lucia (AU); Martin Lavin, St. Lucia (AU); Julie Phillips, St. Lucia (AU); Goce Dimeski, Hamilton (AU)

( * ) Notice: Subject to any disclaimer, the term of this patent is extended or adjusted under 35 U.S.C. 154(b) by 0 days.

(21) Appl. No.: 13/825,047

(22) PCT Filed: Sep. 20, 2011

(86) PCT No.: PCT/AU2011/001221
§ 371 (c)(1),
(2), (4) Date: Jun. 21, 2013

(87) PCT Pub. No.: WO2012/037609
PCT Pub. Date: Mar. 29, 2012

(65) Prior Publication Data

US 2013/0273584 A1 Oct. 17, 2013

(30) Foreign Application Priority Data

Sep. 20, 2010 (AU) ................................ 2010904233

(51) Int. Cl.
*C12Q 1/56* (2006.01)
*G01N 33/86* (2006.01)
*A61B 5/15* (2006.01)

(52) U.S. Cl.
CPC ............... *C12Q 1/56* (2013.01); *G01N 33/86* (2013.01)

(58) Field of Classification Search
None
See application file for complete search history.

(56) References Cited

U.S. PATENT DOCUMENTS

| | | | | |
|---|---|---|---|---|
| 5,089,415 | A | 2/1992 | La Duca | |
| 5,736,033 | A | 4/1998 | Coleman et al. | |
| 5,922,587 | A * | 7/1999 | Triplett | C07K 14/46 435/212 |
| 6,416,717 | B1 * | 7/2002 | Suzuki | B01L 3/5082 422/549 |
| 6,562,837 | B1 | 5/2003 | Yun-Choi et al. | |
| 6,686,204 | B2 * | 2/2004 | Dubrowny | B01L 3/5082 422/547 |
| 7,745,192 | B2 | 6/2010 | Masci et al. | |

FOREIGN PATENT DOCUMENTS

| | | |
|---|---|---|
| JP | 57-142561 | 9/1982 |
| JP | H05-157747 | 6/1993 |
| JP | H10-206420 | 8/1998 |
| JP | 2000-033081 | 2/2000 |
| JP | 2000-070241 | 3/2000 |
| JP | 2000-083934 | 3/2000 |
| JP | 2001-289842 | 10/2001 |
| SU | 1146002 | 3/1985 |
| UA | 14516 | 5/2006 |
| WO | WO 2000/023078 | 4/2000 |
| WO | 03/082914 | 10/2003 |
| WO | WO 2007/072197 | 6/2007 |
| WO | 2009/079690 | 7/2009 |

OTHER PUBLICATIONS

Speijer, H., et al. 1986 The Journal of Biological Chemistry 261(28): 13258-13267.*
Rooney, A.M., et al. 1994 J Clin Pathol 47: 497-501.*
Kini, R.M., et al. 2001 Haemostasis 31: 218-224.*
Coagulation—Wikipedia, obtained from the internet Feb. 27, 2018 (1 page). (Year: 2018).*
Kini, R.M. (2005 Pathophysiol Haemost Thromb 34: 200-204) (Year: 2005).*
Davidson et al., "Can lithium heparin plasma be used for protein electrophoresis and paraprotein identification?" Ann Clin Biochem 2006; 43: 31-34
Delagrave et al., "Recursive ensemble mutagenesis" Apr. 1993 Protein Eng. 6(3): 327-31.
Dimeski et al., "Correcting and reporting of potassium results in haemolysed samples" Ann. Clin. Biochem. 2005; 42: 119-123.
Dimeski et al., "Evaluation of the Becton-Dickinson rapid serum tube: does it provide a suitable alternative to lithium heparin plasma tubes?" Clin Chem Lab Med 2010; 48(5): 2111-2120.
Dimeski et al., "Extent of bilirubin interference in Beckman-Coulter creatinine methods." Ann Clin Biochem 2008; 45:91-92.
Gonnet et al., "Exhaustive matching of the entire protein sequence database" Jun. 5, 1992 Science 256(5062): 1443-5.
Hofmann, et al., "Blood Coagulation Induced by the Venom of Bothrops atrox. 1. Identification, Purification, and Properties of a Prothrombin Activator," Biochemistry, 1987, vol. 26, pp. 772-780.
International Search Report and Written Opinion of the International Searching Authority, International Patent Application No. PCT/AU2011/001221, dated Oct. 21, 2011, 9 pages.
Kini, R. M., "The intriguing world of prothrombin activators from snake venom" Toxicon (2005) 45: 1133-1145.
Kini et al., "Classification and Nomenclature of Prothrombin Activators Isolated from Snake Venoms" Thromb. Haemost. 2001 85:710-711.
Kunkel et al., "Rapid and Efficient site-specific mutagenesis without phenotypic selection" 1985 Proc. Natl. Acad. Sci. USA, 82: 488-492.
Kuzmic P., "Program DYNAFIT for the Analysis of Enzyme Kinetic Data: Application to HIV Proteinase" 1996 Anal. Biochem. 237: 260-273.
Masci P.P., "The Effects of Australian Snake Venoms on Coagulation and Fibrinolysis" Thesis for Masters of Science in the subject of Biochemistry, Jul. 1986, University of Queensland, St Lucia, Brisbane, Australia.

(Continued)

*Primary Examiner* — Marsha Tsay
(74) *Attorney, Agent, or Firm* — Casimer Jones, S.C.; Mary Ann D. Brown

(57) ABSTRACT

This invention relates to the use of clotting compositions containing prothrombin activators to produce high quality blood serum samples for pathology and other biological assays, and to containers containing such clotting compositions, and related methods of use.

11 Claims, 62 Drawing Sheets

Specification includes a Sequence Listing.

(56) References Cited

OTHER PUBLICATIONS

Masci et al., "Purification and characterization of a prothrombin activator from the venom of the Australian brown snake, *Pseudonaja textilis textilis*" Biochem. Int. 1988; 17(5):825-835.
Morita and Iwanaga, "Prothrombin activator from Echis carinatus venom" Meth Enzymol 1981; 80-pt. C: 303-311.
Nicholson et al., "Digestive properties of the venom of the Australian Coastal Taipan, *Oxyuranus scultellatus* (Peters, 1867)" Toxicon 2006: 48: 422-428.
Nishida et al., "cDNA Cloning and Deduced Amino Acid Sequence of Prothrombin Activator (Ecarin) from Kenyan Echis carinatus venom." Biochemistry 1995; 34: 1771-1778.
O'Keane and Cunningham, "Evaluation of three different specimen types (serum, plasma lithium heparin and serum gel separator) for analysis of certain analytes: clinical significance of differences in results and efficiency in use." Clin Chem Lab Med. 2006; 44: 662-8.
Roberge et al., S. J., "A strategy for a convergent synthesis of N-linked glycopeptides on a solid support" Science 1995 269(5221); 202-204.
Rosing and Tans, "Structural and Functional Properties of Snake Venom Prothrombin Activators" Toxicon 30(12): 1515-1527, 1992.
Schieck et al., "The prothrombin-activating principle from Echis carinatus venom. I. Preparation and biochemical properties" Naunyn-Schmiedeberg's Arch Pharmacol. 1972; 272: 402-416.
Schoni, R., "The Use of Snake Venom-Derived Compounds for New Functional Diagnostic Test Kits in the Field of Haemostasis", Pathophysiology of Haemostasis and Thrombosis, 2005, vol. 34, pp. 234-240.
Smith and Craft, "Heparin reacts stoichiometrically with thrombin during thrombin inhibition in human plasma." Biochem. Biophys. Res. Commun. 1976; 71: 738-45.
Starr et al., "Prothrombin times: an evaluation of four thromboplastins and four machines." Pathology 1980; 12: 567-574.
Thorelli et al., "Cleavage requirements of factor V in tissue-factor induced thrombin generation." Thromb. Haemost. Jul. 1998; 80(1) 92-98.
Wannaslip et al., "Heparin is unsuitable anticoagulant for the detection of plasma ammonia." Clin Chimica Acta 2006; 371: 196-7.
Yamada and Morita, "Purification and Characterization of a Ca2+-Dependent Prothrombin Activator, Multactivase, from the Venom of Echis multisquamatus" J. Biochem. 1997; 122: 991-997.
Yamanouye et al., "Long-term primary culture of secretory cells of Bothrops jararaca gland for venom production in vitro" Nature Protocols 2007; 1: 2763-2766.
Yonemura et al., "Preparation of Recombinant α-Thrombin: High-Level Expression of Recombinant Human Prethrombin-2 and Its Activation by Recombinant Ecarin" J. Biochem. 2004; 135: 577-582.
Loria et al., Characterization of 'basparin A,' a prothrombin-activating metalloproteinase, from the venom of the snake *Bothrops asper* that inhibits platelet aggregation and induces defibrination and thrombosis, Arch Biochem Biophys. Oct. 1, 2003;418(1):13-24.
Joseph et al., Effect of snake venom procoagulants on snake plasma: implications for the coagulation cascade of snakes, Toxicon. Feb. 2002;40(2):175-83.

* cited by examiner

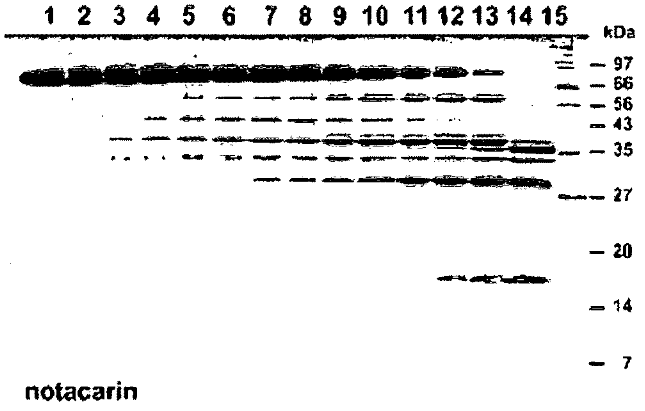
FIGURE 13A
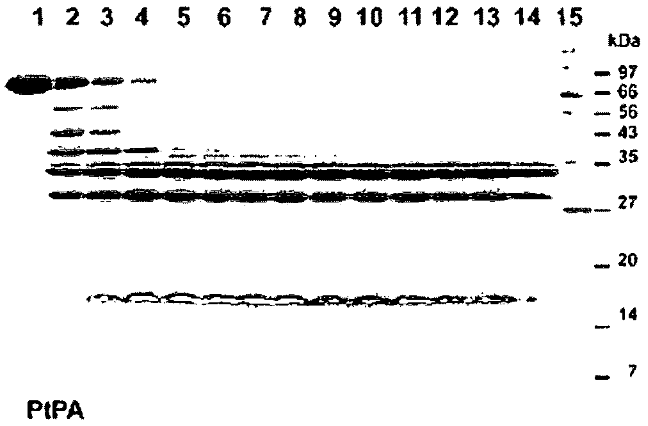
FIGURE 13B
| Lane | Time (min) |
|---|---|
| 1 | 0 |
| 2 | 0.5 |
| 3 | 1 |
| 4 | 2 |
| 5 | 4 |
| 6 | 6 |
| 7 | 8 |
| 8 | 10 |
| 9 | 15 |
| 10 | 20 |
| 11 | 25 |
| 12 | 30 |
| 13 | 45 |
| 14 | 150 |
FIGURE 13C Prothrombin Cleavage N terminal Sequence data

SERUM PREPARATION

This application is a § 371 National Entry of International Patent Application PCT/AU2011/001221, filed Sep. 20, 2011, which is incorporated by reference, and which claims priority to Australian Patent Application 2010904233, filed Sep. 20, 2010.

FIELD OF THE INVENTION

This invention relates generally to using procoagulants to produce high quality blood serum samples for pathology and other biological assays.

BACKGROUND OF THE INVENTION

Blood collection devices, including tubes, are, used to collect blood to produce serum or plasma which is in turn used for biochemical or other pathology assays.

Serum is produced by allowing the blood sample to clot and then centrifuging the sample to separate the blood clot including cells from the serum. Plastic tubes (in place of glass) are now typically used and require procoagulants (often micronised silica particles) to enhance the clotting process. Serum is usually preferred over plasma for biological testing unless urgent results are required, in which case the clotting time for a serum tube is considered too long. Even with existing procoagulants, in most commercial tubes the minimum required clotting time recommended by manufacturers is 30 minutes for blood samples from normal patients, and much longer (typically 60 minutes or longer) for samples from patients taking anti-clotting therapeutic agents such as warfarin or heparin. For patient samples from emergency situations (emergency departments, intensive care, operating theatres etc.) the time is too long and therefore plasma, which can be produced much faster, is often preferred over serum. An alternative purported to address this issue is a blood collection tube for serum production recently developed by Becton-Dickinson (designated BD Rapid Serum Tube, BDT or BD RST) which contains thrombin designed to increase the rate and extent of blood clotting in blood samples.

Plasma is formed by collecting blood in tubes containing anticoagulants followed by centrifugation which can be performed immediately after collection to separate the cells and thus obtain plasma for analysis. Lithium heparin is the most commonly used anticoagulant in these tubes. Citrate, sodium fluoride/potassium oxalate and EDTA are other anticoagulants that are used in some tubes to produce plasma for estimation of a small number of other analytes.

Incomplete Clotting

The coagulation process in preparing a serum sample consumes fibrinogen and entraps platelets and other cells within a network of fibrin. Upon centrifugation the serum is separated from the clot, either by serum separator in the collection device or by aliquoting the serum into a secondary container, to prevent contact with cells. This separation permits the sample to remain stable for extended periods of time. This stability is particularly important if samples are not analysed immediately, or if re-analysis or additional analyses are required.

For some serum samples, coagulation is incomplete after the recommended waiting times. This problem of incomplete clotting is especially prevalent in patients on anti-clotting therapy or specimens collected from anticoagulated taps or cannulae. Contamination of the specimen with anti-coagulant agents during collection may also occur. Such blood can take much longer than the manufacturer's recommended waiting time to clot, or in fact may never fully clot in a standard serum tube (e.g. blood from cardiac surgery patients who are fully heparinised). If a serum sample is centrifuged before clotting is complete, clotting can continue in the serum, leading to clots, microclots or formation of fibrin strings capable of causing analyser or analyte specific problems. The formation of microclots and fibrinogen strings during sample preparation may also occur in plasma tubes, especially post-storage at low temperatures. Lack of timely inversion of lithium heparin tubes after blood collection can lead to small clot formation around the rubber stopper. Droplets of blood not heparinised in a timely manner will clot, and clots do not disintegrate upon heparinisation.

Even the smallest clots are capable of producing clinically significant errors. Thus for accuracy, samples must be manually checked by eye or using automated detection systems if available to ensure they are free of fibrin strands or clots. If strands or clots of insoluble material are present, the sample requires sub-sampling into a new container and re-centrifugation prior to test analysis. Samples that exhibit repeated latent clotting may need to be transferred to a lithium heparin tube to stop ongoing clotting. These actions take additional time. Further, fibrin strands or clots are not always detected (e.g. they may even occur post analyser sampling), and consequential sampling errors may lead to patient care decisions being made on inaccurate results.

Cell Contamination in Plasma Tubes

Specimens obtained in plasma tubes, lithium heparin plasma specifically, may be contaminated with cells. Lithium heparin gel tubes when centrifuged will always present a small "buffy coat like layer" on top of the gel at the bottom of the plasma. This layer contains fibrin, cells and cell stroma. The rapid gel movement during centrifugation leaves some cells in the plasma. If the plasma specimen is mixed (e.g. during sub-sampling or handling), it will become turbid due to suspension of cell-containing material and fibrin, which decreases the specimen integrity. In addition, platelet aggregates can form which may also contain fibrin and/or white blood cells. These aggregates can be large enough to be visible to the unaided eye and have been termed "white particulate matter" due to their typical white colour, and present similar problems to incomplete clotting discussed above.

The presence of cells in the sample can affect analyte concentrations. Certain analytes (e.g. glucose) may be decreased by cell activity and others may be increased by leakage or cell lysis (e.g. lactate dehydrogenase, potassium, phosphate).

Analyte Interference

Although generally there is no difference in concentration of analytes measured in serum or plasma tubes, there are some exceptions.

Plasma tubes that use heparin are not suitable for heparin analysis or cell-based assays. Lithium heparin plasma tubes are not suitable for lithium analysis. Plasma may be unreliable for additional testing of re-testing, due to presence of cells and insoluble fibrin formation upon prolonged storage at 2-8° C.

Further, there have been reports of some serum or plasma tubes producing inaccurate results of analyte levels, due to interaction with the procoagulant or anticoagulant agents within the tubes, or otherwise (Ciuti et al., 1989; Cowley et al., 1985; Davidson et al., 2006; Dimeski et al., 2004;

Dimeski et al., 2005; Dimeski et al., 2010; Hartland et al., 1999; Miles et al., 2004; O'Keane et al., 2006; Wannaslip et al., 2006).

Sample Size

It is desirable to reduce the sample size needed for testing, especially in critically ill patients, patients receiving blood transfusions, and infants, in order to reduce the volume of blood taken from a patient. It is therefore optimal to be able to run all necessary tests using a sample taken in a single blood collection tube. To achieve this, testing methods have been developed using very small sample volumes (e.g. 2 μL) so that typically one serum or plasma tube is used for at least 21 tests, but can be used for between 50-60 or even 70-80 tests, depending on the volume of sample needed for each test. However, where there is doubt over the accuracy of measuring a particular analyte in a serum or plasma tube, it may be necessary to take both a serum tube and a plasma tube from the patient and doing so defeats the goal of reducing the volume of blood taken from the patient.

Problems arising from the use of current methodologies for serum and plasma preparation from blood show that improvements are required to achieve timely, reliable analytical results from a wider variety of blood samples generally.

Snake Venom Prothrombin Activators

Many snake venoms contain prothrombin activators for the purpose of rapid clotting of the blood of their prey. These prothrombin activators are proteolytic enzymes which convert prothrombin present in blood to thrombin which in turn causes clotting.

While snake venom prothrombin activators are known procoagulants, they are also known to possess proteolytic trypsin-like activity (Schieck et al., 1972; Parker, H. W. and Grandison A. G. C., 1977; Masci, P. P., 1986; Nicholson et al., 2006; Lavin and Masci, 2009). It has been postulated that there may be an evolutionary reason that prothrombin activators possess both procoagulant and proteolytic properties in that they act to both kill and digest the prey (Masci, P. P., 1986, page 143). For example, ecarin (prothrombin activator purified from *Echis carinatus* venom) has been shown to have procoagulant activity and as well several other proteolytic activities such as fibrinogenolysis, gelatinolysis, caesionlysis and haemorrhage (Schieck et al., 1972), and a prothrombin activator purified from the venom of *Pseudonaja textilis* (PtPA) is active against a range of chromogenic peptide substrates designed for different proteolytic enzymes (Masci, P.P., 1986).

Many analyte tests that may be performed on blood, serum, or plasma samples involve proteins, including tests measuring proteins as analytes (e.g. total protein, albumin); tests measuring enzyme activity of blood proteins (e.g. gamma-glutamyl transpeptidase used in test for gamma-glutamyl transferase, aspartate aminotransferase, lactate dehydrogenase, creatine kinase, lipase); tests using proteins as reagents (e.g. immunoassays); tests using enzymes in the analytical method (e.g. glucose oxidase). Other commonly used tests involving protein include assays for glucose, urea, urate, alanine aminotransferase, creatine kinase, high-density lipoprotein cholesterol, cholesterol, triglycerides, transferrin, C reactive protein, troponin, cortisol, free thyroxine, free triiodothyronine, thyroid stimulating hormone, and ferritin.

Therefore, despite their procoagulant properties, these snake venom prothrombin activators have never been considered suitable for use in serum tubes for analyte tests, on the basis that their proteolytic activity would degrade analytes being measured (e.g. where the analyte is a protein), or would degrade proteins being used in the reaction to measure analyte levels (e.g. where the analyte test involves use of a protein such as glucose oxidase).

Thrombin Tubes

While thrombin-containing tubes have recently become available as 'faster' clotting tubes, and thrombin possesses both procoagulant and proteolytic activity, thrombin is known to have high specificity for cutting bonds in fibrinogen, activated protein C (APC) and Factor Va. Therefore, unlike the reported trypsin-like activity of the snake venom prothrombin activators, thrombin would not be expected to interfere with analyte tests.

In work leading up to the present invention, it was found that thrombin-containing tubes cannot be used with all blood samples. Thrombin is known to be rapidly and completely inhibited by the heparin-antithrombin III complex present in heparinised blood samples. In investigating the BD RST tubes, it was found that these tubes are ineffective in clotting patient samples containing high doses of heparin (Dimeski et al., 2010).

Development of the Invention

Surprisingly, the present inventors discovered that when used in blood collection devices, including tubes, prothrombin activators are generally capable of producing high quality serum in an acceptable time from a wide variety of blood samples (including those taken from patients on high concentration of anti-clotting therapy, including heparin), decreasing both the serum sample preparation time and the risk of analysis problems due to incomplete clotting and contamination by cells and cell components.

Moreover, the inventors also surprisingly discovered that serum samples obtained from blood samples by addition of prothrombin activators give the same results in a wide range of standard biochemistry analytical tests as serum samples produced in existing blood collection tubes.

These discoveries suggested that prothrombin activators would be suitable for producing serum for the purpose of measuring a wide range of analytes, and have been reduced to practice in blood collection containers for preparing serum samples useful in detecting analytes, related uses and methods, as described hereafter.

SUMMARY OF THE INVENTION

Accordingly, in one aspect the present invention provides the use of a clotting composition comprising, consisting essentially of, or consisting of a prothrombin activator in the preparation of a serum sample that is suitable for detecting an analyte.

The prothrombin activator (sometimes known as prothrombinase) suitably exhibits trypsin-like activity and activates prothrombin (i.e. converts prothrombin to thrombin).

The present invention also provides a container for preparing a serum sample that is suitable for detecting an analyte of interest that is present in the sample, wherein the container contains a clotting composition comprising, consisting essentially of, or consisting of a prothrombin activator as defined herein.

In another aspect, the present invention provides the use of a clotting composition comprising, consisting essentially of, or consisting of a prothrombin activator as defined herein in the preparation or manufacture of a container for preparing a serum sample suitable for detecting an analyte. In another aspect, the present invention provides a container comprising a clotting composition comprising, consisting essentially of, or consisting of a prothrombin activator as defined herein and a blood sample, for preparing a serum sample suitable for detecting an analyte.

In another aspect the present invention provides a method of preparing a serum sample for detecting an analyte of interest, the method comprising contacting a blood sample with a clotting composition comprising, consisting essentially of, or consisting of a prothrombin activator as defined herein for a time and under conditions sufficient to prepare a serum sample. Suitably, the method is carried out in a container as broadly defined above. Suitably, the blood is contacted with the clotting composition for a time and under conditions sufficient to prepare a serum sample and clotted cells. Suitably, the method further comprises separating the serum sample from the clotted cells. In some embodiments the method comprises mixing the clotting composition and blood sample by providing a container containing the blood sample and adding the clotting composition to the container, or providing a container containing the clotting composition and adding or collecting the blood sample into the container.

The present invention also provides a serum sample produced by contacting a blood sample with a clotting composition as broadly described above for a time and under conditions sufficient to produce the serum sample.

The present invention further provides methods of detecting an analyte of interest. These methods generally comprise analysing a serum sample prepared by the method of the present invention for the presence or amount of the analyte of interest.

The present invention also provides methods of diagnosing the presence, absence or severity of a disease or condition in a subject, wherein the presence, absence or severity of the disease or condition is associated with the presence, absence or an aberrant amount of an analyte of interest in the subject. These methods generally comprise providing a serum sample prepared according to the methods broadly described above; and detecting the presence, absence or aberrant amount of the analyte in the serum sample to thereby determine the presence, absence or severity of the disease or condition in the subject.

BRIEF DESCRIPTION OF THE SEQUENCES

A brief description of the sequences in the sequence listing is provided below.

| | |
|---|---|
| SEQ ID NO: 1 | Polypeptide sequence for ecarin from *Echis carinatus* |
| SEQ ID NO: 2 | Partial polypeptide sequence for basparin from *Bothrops asper* venom |
| SEQ ID NO: 3 | Partial polypeptide sequence for carinactivase-1 from *Echis carinatus* venom (prepared as described in Yamada, D., et al., (1996)) - 62 kDa subunit |
| SEQ ID NO: 4 | Partial polypeptide sequence for multactivase from *Echis multisquamatus* venom (prepared as described in Yamada, D., et al., (1997)) |
| SEQ ID NO: 5 | Nucleotide sequence encoding Factor V-like component of PtPA (or pseutarin C) from *Pseudonaja textilis* |
| SEQ ID NO: 6 | Nucleotide sequence encoding Factor V-like component of PtPA (or pseutarin C) from *Pseudonaja textilis* |
| SEQ ID NO: 7 | Polypeptide sequence for Factor V-like component of PtPA (or pseutarin C) from *Pseudonaja textilis* |
| SEQ ID NO: 8 | Polypeptide sequence for Factor V-like component of PtPA (or pseutarin C) from *Pseudonaja textilis* |
| SEQ ID NO: 9 | Nucleotide sequence encoding Factor V-like component of OsPA (or oscutarin C) from *Oxyuranus scutellatus* |
| SEQ ID NO: 10 | Nucleotide sequence encoding Factor V-like component of OsPA (or oscutarin C) from *Oxyuranus scutellatus scutellatus* |
| SEQ ID NO: 11 | Polypeptide sequence for Factor V-like component of OsPA (or oscutarin C) from *Oxyuranus scutellatus scutellatus* |
| SEQ ID NO: 12 | Polypeptide sequence for Factor V-like component of OsPA (or oscutarin C) from *Oxyuranus scutellatus* |
| SEQ ID NO: 13 | Polypeptide sequence for Factor V-like component of OsPA (or oscutarin C) from *Oxyuranus scutellatus* |
| SEQ ID NO: 14 | Nucleotide sequence encoding Factor V-like component of omicarin C from *Oxyuranus microlepidotus* |
| SEQ ID NO: 15 | Nucleotide sequence encoding factor V from *Homo sapiens* |
| SEQ ID NO: 16 | Polypeptide sequence for factor V from *Homo sapiens* |
| SEQ ID NO: 17 | Nucleotide sequence encoding factor V from *Bos taurus* |
| SEQ ID NO: 18 | Polypeptide sequence for factor V from *Bos taurus* |
| SEQ ID NO: 19 | Nucleotide sequence encoding Factor X-like component of PtPA (or pseutarin C) from *Pseudonaja textilis* |
| SEQ ID NO: 20 | Nucleotide sequence encoding Factor X-like component of PtPA (or pseutarin C) from *Pseudonaja textilis* |
| SEQ ID NO: 21 | Nucleotide sequence encoding Factor X-like component of PtPA (or pseutarin C) from *Pseudonaja textilis* |
| SEQ ID NO: 22 | Nucleotide sequence encoding Factor X-like component of PtPA (or pseutarin C) from *Pseudonaja textilis textilis* |
| SEQ ID NO: 23 | Nucleotide sequence encoding Factor X-like component of PtPA (or pseutarin C) from *Pseudonaja textilis textilis* |
| SEQ ID NO: 24 | Nucleotide sequence encoding Factor X-like component of PtPA (or pseutarin C) from *Pseudonaja textilis* |
| SEQ ID NO: 25 | Nucleotide sequence encoding Factor X-like component of PtPA (or pseutarin C) from *Pseudonaja textilis* |
| SEQ ID NO: 26 | Polypeptide sequence for Factor X-like component of PtPA (or pseutarin C) from *Pseudonaja textilis* |
| SEQ ID NO: 27 | Polypeptide sequence for Factor X-like component of PtPA (or pseutarin C) from *Pseudonaja textilis* |
| SEQ ID NO: 28 | Polypeptide sequence for Factor X-like component of PtPA (or pseutarin C) from *Pseudonaja textilis textilis* |
| SEQ ID NO: 29 | Polypeptide sequence for Factor X-like component of PtPA (or pseutarin C) from *Pseudonaja textilis textilis* |

-continued

| | |
|---|---|
| SEQ ID NO: 30 | Polypeptide sequence for Factor X-like component of PtPA (or pseutarin C) from *Pseudonaja textilis* |
| SEQ ID NO: 31 | Nucleotide sequence encoding Factor X-like component of OsPA (or oscutarin C) from *Oxyuranus scutellatus* |
| SEQ ID NO: 32 | Polypeptide sequence for Factor X-like component of OsPA (or oscutarin C) from *Oxyuranus scutellatus* |
| SEQ ID NO: 33 | Nucleotide sequence encoding Factor X-like component of omicarin C from Oxyuranus microlepidotus |
| SEQ ID NO: 34 | Polypeptide sequence for Factor X-like component of omicarin C from *Oxyuranus microlepidotus* |
| SEQ ID NO: 35 | Nucleotide sequence encoding Factor X-like component of porpharin D from *Pseudechis porphyriacus* |
| SEQ ID NO: 36 | Polypeptide sequence for Factor X-like component of porpharin D from *Pseudechis porphyriacus* |
| SEQ ID NO: 37 | Nucleotide sequence encoding Factor X-like component of hopsarin D from *Hoplocephalus stephensii* |
| SEQ ID NO: 38 | Polypeptide sequence for Factor X-like component of hopsarin D from *Hoplocephalus stephensii* |
| SEQ ID NO: 39 | Nucleotide sequence encoding Factor X-like component of notecarin D from *Notechis scutatus* |
| SEQ ID NO: 40 | Polypeptide sequence for Factor X-like component of notecarin D from *Notechis scutatus* |
| SEQ ID NO: 41 | Nucleotide sequence encoding Factor X-like component of trocarin D from *Tropidechis carinatus* |
| SEQ ED NO: 42 | Polypeptide sequence for Factor X-like component of trocarin D from *Tropidechis carinatus* |
| SEQ ID NO: 43 | Nucleotide sequence encoding Factor X-like component of prothrombin activator from *Demansia vestigiata* |
| SEQ ID NO: 44 | Polypeptide sequence for Factor X-like component of prothrombin activator from *Demansia vestigiata* |
| SEQ ID NO: 45 | Nucleotide sequence encoding Factor X-like component of prothrombin activator from *Demansia vestigiata* |
| SEQ ID NO: 46 | Polypeptide sequence for Factor X-like component of prothrombin activator from *Demansia vestigiata* |
| SEQ ID NO: 47 | Nucleotide sequence encoding factor X from *Homo sapiens* |
| SEQ ID NO: 48 | Polypeptide sequence for factor X from *Homo sapiens* |
| SEQ ID NO: 49 | Nucleotide sequence encoding factor X from *Bos taurus* |
| SEQ ID NO: 50 | Polypeptide sequence for factor X from *Bos taurus* |
| SEQ ID NO: 51 | Partial polypeptide sequence for carinactivase-1 from *Echis carinatus* venom (prepared as described in Yamada, D., et al., (1996)) - 17 kDa subunit |
| SEQ ID NO: 52 | Partial polypeptide sequence for carinactivase-1 from *Echis carinatus* venom (prepared as described in Yamada, D., et al., (1996)) - 14 kDa subunit |

BRIEF DESCRIPTION OF THE DRAWINGS

FIG. 12 shows the SDS-PAGE without β-mercaptoethanol (A) and with β-mercaptoethanol (B) of samples incubated for 5 minutes at room temperature in the presence of 5 mM $Ca^{2+}$, and with the following prothrombin activators: carinactivase-1 (lane 2); carinactivase-2 (lane 3); ecarin (lane 4); PtPA (lane 5); OsPA (lane 6); notecarin (lane 7). Lane 1 contained the sample of human prothrombin alone in buffer (no prothrombin activator), and lane 8 contained the sample of highly purified α-thrombin (no prothrombin activator), and "m" represents the molecular weight marker. This experiment is described in more detail in Example 2a.

FIG. 13 shows the SDS-PAGE of the time course of the prothrombin (14 μM) to thrombin activation by PtPA (6 nM) and by notecarin (6 nM), as described in Example 2b.

FIG. 15 is a graph of the absorbance of the pNA generated from S-2238 by different thrombin concentrations over 155 seconds as described in Example 2d. The calculations on the right hand side of the graph align with each line of the graph, for example the top calculation is the highest line, and so on.

FIG. 39 shows TEG plots of the results in Example 5a.

FIG. 57 shows total protein determination carried out under standard Pathology Queensland procedures on normal serum and plasma samples, (n=26), all serum and plasma samples (n=61) and cardiac patient samples (n=11) as described in Example 12a.

FIG. 58 shows the time taken for two different PtPA concentrations to clot plasma at selected time points over a period of two weeks (336 hours) when stored at different temperatures, as described in Example 15a.

DETAILED DESCRIPTION OF THE INVENTION

1. Definitions

Figure 1:
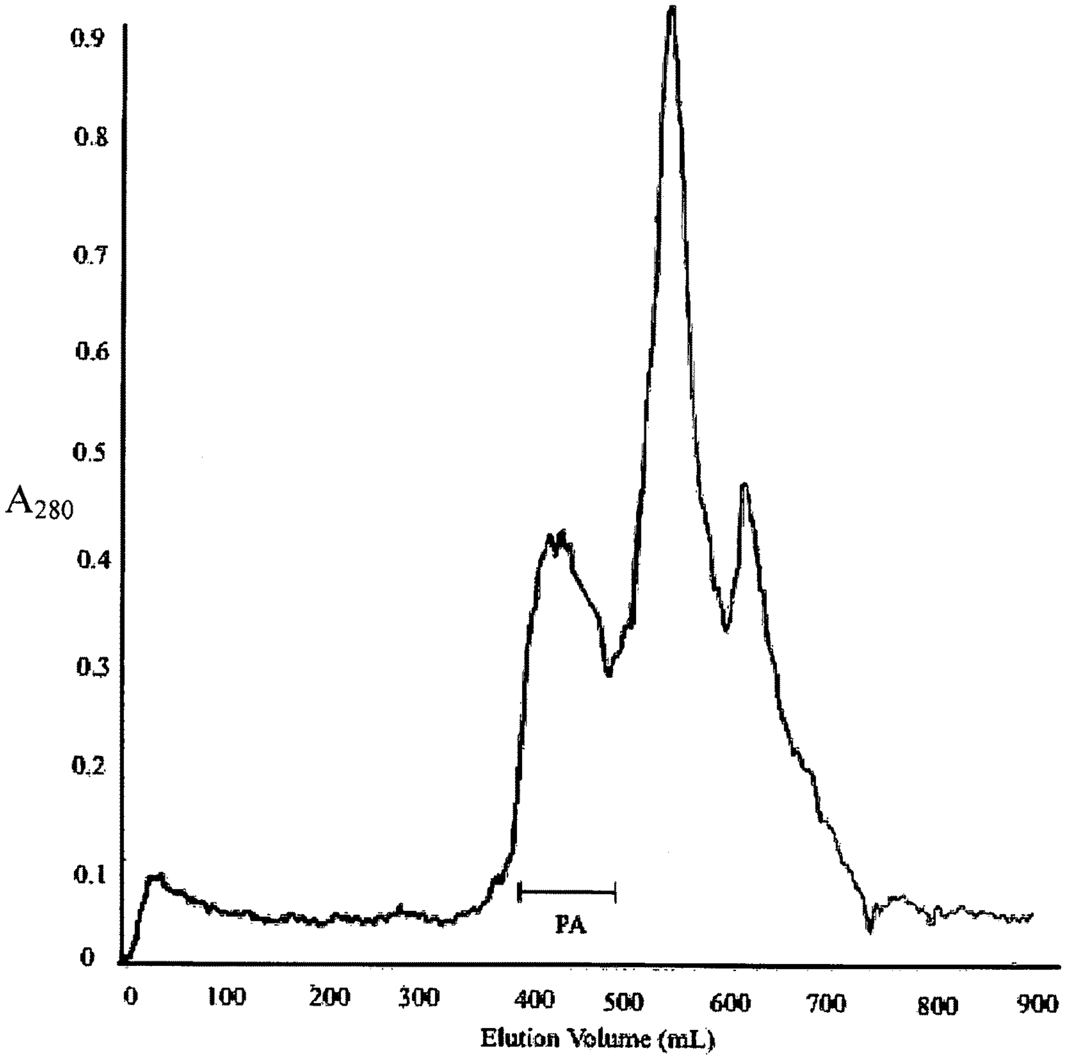
FIG. 1 shows the elution profile in the isolation of ecarin, carinactivase-1, and carinactivase-2 from *E. carinatus* venom using gel filtration on a Superdex 200 column as described in Example 1a. The *E. carinatus* venom (157 mg, 122 $A_{280}$ units) was subjected to gel filtration on Superdex 200 (2.5×95 cm) using of 0.05 M Tris-HCl buffer at pH 8.0. The pooled fractions (28.3 $A_{280}$ units) of the three prothrombin activators (ecarin, carinactivase-1, and carinactivase-2) are indicated by the bar.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference or full-length polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99% of the activity of a reference sequence. Included within the scope of the present invention are biologically active fragments, including those of at least about 18, 19, 20, 21, 22, 23, 24, 25, 26, 27, 28, 29, 30, 40, 50, 60, 70, 80, 90, 100, 120, 140, 160, 180, 200, 250, 300, 400, 500, 600, 700, 800, 900, 1,000, 1,500, 2,000 nucleotides or residues in length, which comprise or encode an activity of a reference polynucleotide or polypeptide. Representative biologically active fragments generally participate in an interaction, e.g. an intramolecular or an inter-molecular interaction. An inter-molecular interaction can be a specific binding interaction or an enzymatic interaction (e.g., the interaction can be transient and a covalent bond is formed or broken). Biologically active fragments of a full-length polypeptide include peptides may comprise amino acid sequences sufficiently similar to or derived from the amino acid sequences of a (putative) full-length polypeptide. Typically, biologically active fragments comprise a domain or motif with at least one activity of a full-length polypeptide. Suitably, the biologically-active fragment has no less than about 1%, 10%, 25% 50% of an activity of the full-length polypeptide from which it is derived.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridisation between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

As used herein, the term "detecting an analyte" means determining the presence, absence, amount or concentration of one or more analytes in a sample.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of nucleic or amino acids that are identical or constitute conservative substitutions. Homology may be determined using sequence comparison programs such as GAP (Devereux et al., 1984) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "isolated" is meant material that is substantially or essentially free from components that normally accompany it in its native state. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

By "obtained from" is meant that the polypeptide or complex, for example, is isolated from, or derived from, a particular source.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient", "subject" and "individual" are used interchangeably and refer to patients, subjects and individuals of human or other mammals and includes any one for whom it is desired to detect analyte levels or to diagnose the presence, absence or severity of a disease or condition using the invention. However, it will be understood that "patient" does not imply that symptoms are present. Suitable mammals that fall within the scope of the invention include, but are not restricted to, primates (e.g. humans, chimpanzees), livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes).

The term "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridise with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "polypeptide variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridise and serve as a site for the initiation of synthesis. By "substantially complementary", it is meant that the primer is sufficiently complementary to hybridise with a target polynucleotide. Preferably, the primer contains no mismatches with the template to which it is designed to hybridise but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridisation conditions. Probes can be labelled directly or indirectly.

The term "reference result" includes a result taken from the same subject at a different time, a result from a normal subject or a group of normal subjects, or a reference standard used in an analytical test.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage, of sequence identity. For the purposes of the present invention, "sequence identity" may be understood to mean the "match percentage" calculated by the DNASIS computer program (Version 2.5 for Windows; available from Hitachi Software Engineering Co., Ltd., South San Francisco, Calif., USA) using standard defaults as used in the reference material accompanying the software.

The term "sequence similarity" refers to the percentage number of amino acids that are identical or constitute conservative substitutions as defined in Table 2 infra. Similarity may be determined using sequence comparison programs such as GAP (Devereux et al., 1984). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997. A detailed discussion of sequence analysis can be found in Unit 19.3 of Ausubel et al., "Current Protocols in Molecular Biology", John Wiley & Sons Inc, 1994-1998, Chapter 15.

"Stringency" as used herein, refers to the temperature and ionic strength conditions, and presence or absence of certain organic solvents, during hybridisation and washing procedures. The higher the stringency, the higher will be the degree of complementarity between immobilized target nucleotide sequences and the labelled probe polynucleotide sequences that remain hybridised to the target after washing. The term "high stringency" refers to temperature and ionic conditions under which only nucleotide sequences having a high frequency of complementary bases will hybridise. The stringency required is nucleotide sequence dependent and depends upon the various components present during hybridisation. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridises to a complementary probe.

The term "transformation" means alteration of the genotype of an organism, for example a bacterium, yeast, mammal, avian, reptile, fish or plant, by the introduction of a foreign or endogenous nucleic acid.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

2. Prothrombin Activators

The present invention is based in part on the discovery that prothrombin activators are suitable clotting agents for preparing serum that is used to detect analytes, despite their known proteolytic activity. Prothrombin activators (sometimes known as prothrombinases) exhibit trypsin-like activity and activate prothrombin (i.e. convert prothrombin to thrombin which in turn converts fibrinogen to fibrin and hence cause clot formation).

In some embodiments, the prothrombin activator is an exogenous prothrombin activator. As used herein, an "exogenous prothrombin activator" means a prothrombin activator obtained from a source other than the blood sample from which the serum sample is to be prepared.

2.1 Wild-type or Naturally-occurring Prothrombin Activators

The prothrombin activators used in the present invention may comprise wild-type or naturally-occurring prothrombin activators including those obtained from any suitable organism, including snake, human, bovine and bacterial prothrombin activator. The prothrombin activator may comprise a full-length wild-type or naturally occurring polypeptide.

In certain embodiments, the prothrombin activator is a snake prothrombin activator. Suitably, the prothrombin activator is a snake venom prothrombin activator. Snake venom prothrombin activators are generally classified in four groups (A, B, C, and D) depending on their structure, function and requirements for co-factors.

Suitably, the snake venom prothrombin activator is a group A prothrombin activator. Group A prothrombin activators are metalloproteinases consisting of three domains: a metalloproteinase, a disintegrin, and a Cys-rich domain. The metalloproteinase domain contains the consensus sequence HEXXHXXGXXH (SEQ ID NO:53), corresponding to the zinc-chelating active site. These prothrombin activators are found at least in several viper venoms, and include ecarin from *Echis carinatus* venom and basparin from *Bothrops asper* venom.

Suitably, the snake venom prothrombin activator is a group B prothrombin activator. Group B prothrombin activators are metalloproteinases consisting of two subunits held non-covalently: a metalloproteinase and a C-type lectin-like disulfide-liked dimer. These prothrombin activators are found in several viper venoms, and include carinactivase-1 and carinactivase-2 from *Echis carinatus* venom and multactivase from *Echis multisquamatus* venom.

Suitably, the snake venom prothrombin activator is a group C prothrombin activator. Group C prothrombin activators are serine proteases and resemble the mammalian factor Xa-factor Va complex. Pseutarin C (or PtPA) and oscutarin C (or OsPA) are group C prothrombin activators from the venoms of *Pseudonaja textilis* and *Oxyuranus scutellatus* respectively. Omicarin C is the prothrombin activator from *Oxyuranus microlepidotus* venom.

Suitably, the snake venom prothrombin activator is a group D prothrombin activator. Group D prothrombin activators are serine proteases and are functionally similar to mammalian factor Xa. Porpharin D (from *Pseudechis porphyriacus*), notecarin D (from *Notechis scutatus scutatus*), trocarin D (from *Tropidechis carinatus*), hopsarin D (from *Hoplocephalus stephensi*), and notenarin D (from *Notechis ater niger*) are all group D prothrombin activators.

A review of snake prothrombin activators is provided in Kini, R. M. (2005), and of those specifically from the venom of Australian Elapids (group C and D prothrombin activators) is in St. Pierre et al. (2005), the contents of each are herein by reference in their entirety. These two reviews use the classification of snake prothrombin activators into groups A-D as described above. This classification supersedes the previous classification system using groups I-III (group I encompasses groups A and B; group II is now group D and group III is now group C), and sometimes additional groups IV (snake venom activators that cleave peptide bonds in prothrombin but do not convert the prothrombin to an enzymatically active product—i.e. thrombin or meizothrombin) and V (bacterial prothrombin activators) as described in earlier review articles, including Rosing, J. et al. (1991) and Rosing, J. et al. (1992), the contents of each being incorporated by reference in their entirety. For an explanation on the change to the classification system, see Kini, R, M., et al. (2001), the contents of which are incorporated by reference in its entirety.

In specific embodiments, the snake prothrombin activator is obtained from the Family Elapidae, illustrative examples of which include species from the genera *Demansia, Hoplocephalus, Notechis, Oxyuranus, Pseudechis, Pseudonaja, Rhinoplocephalus*, and *Tropidechis* including but not limited to *Demansia vestigiata, Hoplocephalus stephensii, Notechis ater humphreysi, Notechis ater niger, Notechis ater serventyi, Notechis flinkders, Notechis humphreysi, Notechis niger, Notechis occidentalis, Notechis scutatus, Notechis scutatus scutatus, Notechis serventyi, Oxyuranus microlepidotus, Oxyuranus scutellatus, Pseudechis porphyriacus, Pseudonaja affinis, Pseudonaja inframaculata, Pseudonaja nuchalis, Pseudonaja textilis, Rhinoplocephalus nigrescens*, and *Tropidechis carinatus*.

In specific embodiments, the snake prothrombin activator is obtained from the Family Viperidae, illustrative examples of which include species from the genera *Botrhops, Echis* and *Trimeresurus*, including but not limited to *Bothrops alternatus, Bothrops asper, Bothrops atrox, Bothrops atrox asper, Bothrops brasili, Bothrops castelnaudi, Bothrops columbiensis, Bothrops erythromelas, Bothrops fonsecai, Bothrops itapetiningae, Bothrops jararaca, Bothrops neuwiedi, Bothrops venezuelensis, Echis carinatus, Echis coloratus, Echis multisquamatus*, and *Trimeresurus okinavensis*.

In specific embodiments, the snake prothrombin activator is obtained from the Family Colubridae, illustrative examples of which include species from the genera *Dispholidus, Rhabdophis* and *Thelotornis*, including but not limited to *Dispholidus typus, Rhabdophis tigrinus tigrinus, Thelotornis kirtlandii*, and *Thelotornis capensis*.

In some embodiments the snake prothrombin activator is from or is obtained from snake venom. The purification and characterisation of PtPA from *P. textilis* snake venom is described in Masci (1986) and Masci et al., (1998), and OsPA from *O. scutellatus* venom is described in Speijer et al., (1986), all of which are incorporated by reference in their entirety. The purification and characterisation of ecarin from *Echis carinatus* venom is described in Morita, T et al. (1981) and Nishida, S et al. (1995), of carinactivase from *Echis carinatus* venom is described in Yamada, D et al. (1996), of multactivase from *Echis multisquamatus* is described in Yamada, D. et al., (1997), and of notecarin from *Notechis scutatus* is described in Tans, G et al., (1985), each of which are incorporated by reference in their entirety.

In certain embodiments, the prothrombin activator is a mammalian prothrombin activator. Mammalian prothrombin activators include those derived from human blood and/or tissue and those derived from bovine blood and/or tissue.

In certain embodiments, the prothrombin activator is a bacterial prothrombin activator. Bacterial prothrombin activators include those from *Staphylococcus aureus, Peptococcus indolicus, Bacteroides melaminogenicus*, and *Pseudomonas aeruginosa* (Rosing, J. et al. (1991).

As will be appreciated by those skilled in the art, the prothrombin activator may comprise, consist essentially of, or consist of one or more polypeptides. In some embodiments, the prothrombin activator comprises, consists essentially of, or consists of a single polypeptide. In other embodiments, the prothrombin activator comprises, consists essentially of, or consists of more than one polypeptide, including but not limited to complexes of polypeptides. Where the prothrombin activator comprises, consists essentially of, or consists of more than one polypeptide, each polypeptide may be from the organisms from the same or different genera, and/or the same or different species.

In certain embodiments, the prothrombin activator comprises an amino acid sequence selected from those set forth in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, and 52 or comprises an amino acid sequence encoded by a nucleotide sequence selected from those set forth in SEQ ID NOs: 5, 6, 9, 10, 14, 15, 17, 19, 20, 21, 22, 23, 24, 25, 31, 33, 35, 37, 39, 41, 43, 45, 47, and 49.

2.2 Chimeric Prothrombin Activators and Fusion Polypeptides

The present invention also contemplates the use of prothrombin activators comprising a chimeric polypeptide. As used herein, a "chimeric polypeptide" includes a first polypeptide component comprising a polypeptide obtained from a first organism linked to a second polypeptide component obtained from a second organism. In some embodiments, the first organism and the second organism are from different genera. In other embodiments, the first organism and the second organism are different species of the same genus. In certain embodiments, the prothrombin activator comprises a chimeric polypeptide that resembles a factor Xa-factor Va complex, wherein the first polypeptide comprises a factor Xa-like polypeptide and the second polypeptide comprises a factor Va-like polypeptide. In certain specific embodiments, the first polypeptide comprises an amino acid sequence selected from those set forth in SEQ ID NOs: 26, 27, 28, 29, 30, 32, 34, 36, 38, 40, 42, 44, 46, 48, and 50, or comprises an amino acid sequence encoded by a nucleotide sequence selected from those set forth in SEQ ID NOs: 19, 20, 21, 22, 23, 24, 25, 31, 33, 35, 37, 39, 41, 43, 45, 47, and 49, and the second polypeptide comprises an amino acid sequence selected from those set forth in SEQ ID NOs: 7, 8, 11, 12, 13, 16, and 18, or comprises an amino acid sequence encoded by a nucleotide sequence selected from those set forth in SEQ ID NOs: 5, 6, 9, 10, 14, 15, and 17.

The present invention also contemplates the use of prothrombin activators comprising a fusion polypeptide. As used herein, a "fusion polypeptide" includes a first polypeptide component linked to a second polypeptide component. The first polypeptide component may be obtained from a first organism and the second polypeptide component may be obtained from a second organism. In some embodiments, the first organism and the second organism are from different genera. In other embodiments, the first organism and the second organism are different species of the same genus. The first polypeptide component or the second polypeptide component of the fusion polypeptide can correspond to all or a portion (e.g., a fragment as described herein) of a wild-type or naturally occurring amino acid sequence. The second polypeptide component can be fused to the N-terminus or C-terminus of the first polypeptide component.

2.3 Fragments of Wild-type or Naturally Occurring Polypeptides

The prothrombin activator may comprise a fragment of a full-length wild-type or naturally occurring polypeptide, wherein the prothrombin activator exhibits prothrombin activating activity.

Typically, fragments of a full-length polypeptide may participate in an interaction, for example an intramolecular or an intermolecular interaction. Such fragments include peptides comprising the amino acid sequences shown in SEQ ID NOs: 2, 3, 4, 51, and 52 and peptides comprising amino acid sequences sufficiently similar to or derived from the amino acid sequences of a (putative) full-length polypeptide, for example, the amino acid sequences shown in SEQ ID NOs: 1, 7, 8, 11, 12, 13, 16, 18, 26, 27, 28, 29, 30, 32, 34, 36, 38, 40, 42, 44, 46, 48, and 50, or the amino acid sequences encoded by a nucleotide sequence selected from those set forth in SEQ ID NOs: 5, 6, 9, 10, 14, 15, 17, 19, 20, 21, 22, 23, 24, 25, 31, 33, 35, 37, 39, 41, 43, 45, 47, and 49, which includes less amino acids than a full-length polypeptide, and exhibit one activity of that polypeptide.

2.4 Variants of Naturally-occurring Prothrombin Activators (Polypeptide)

The present invention also contemplates prothrombin activators comprising polypeptide(s) that is/are variant(s) of the wild-type or naturally-occurring polypeptide(s). Prothrombin activators comprising one or more variant polypeptides encompassed by the present invention are biologically active, that is, they continue to possess prothrombin activating activity.

Such "variant" prothrombin activators include polypeptides derived from the native polypeptide, wherein the polypeptides are derived from the corresponding native polypeptide(s) by deletion (so-called truncation) or addition of one or more amino acids to the N-terminal and/or C-terminal end of the native polypeptide(s); deletion or addition of one or more amino acids at one or more sites in the native polypeptide(s); or substitution of one or more amino acids at one or more sites in the native polypeptide(s). These variant prothrombin activators may result from, for example, genetic polymorphism or human manipulation.

Further non-limiting examples of variant polypeptides include precursor polypeptide or polypeptide in zymogen form processed forms of a full-length or precursor polypeptide or polypeptide in zymogen form.

Variants of a wild-type or naturally-occurring polypeptide will have at least 40%, 50%, 60%, 70%, generally at least 75%, 80%, 85%, usually about 90%, 91%, 92%, 93%, 94%, 95% or more, and typically about 96%, 97%, 98% or more (and all integer percentages in between) sequence similarity or identity with the amino acid sequence for the wild-type or naturally-occurring polypeptide, including but not limited to the sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, and 52, or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, and 49, as determined by sequence alignment programs described elsewhere herein using default parameters. A variant of a wild-type or naturally-occurring polypeptide, which falls within the scope of a variant polypeptide, may differ from that polypeptide generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the corresponding sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, or 52, or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, or 49, by at least 1 but by less than 15, 10 or 5 amino acid residues. In other embodiments, it differs from the corresponding sequences in SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, or 52, or the amino acid sequences encoded by the nucleotide sequences in SEQ ID NOs: 5, 6, 9, 10, 14, 15, 17, 19, 20, 21, 22, 23, 24, 25, 31, 33, 35, 37, 39, 41, 43, 45, 47, or 49, by at least one residue but less than 20%, 15%, 10% or 5% of the residues.

A polypeptide may be altered in various ways including amino acid substitutions, deletions, truncations, and insertions. Methods for such manipulations are generally known in the art. For example, amino acid sequence variants of a polypeptide can be prepared by mutations in the DNA. Methods for mutagenesis and nucleotide sequence alterations are well known in the art. See, for example, Kunkel (1985), Kunkel et al., (1987), U.S. Pat. No. 4,873,192, Watson et al., (1987) and the references cited therein. Guidance as to appropriate amino acid substitutions that do not affect biological activity of the protein of interest may be found in the model of Dayhoff et al. (1978). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of polypeptides. Recursive ensemble mutagenesis (REM), a technique which enhances the frequency of functional mutants in the libraries, can be used in combination with the screening assays to identify polypeptide variants, see for example Arkin et al. (1992) and Delagrave et al. (1993). Conservative substitutions, such as exchanging one amino acid with another having similar properties, may be desirable as discussed in more detail below.

Variant polypeptides may contain conservative amino acid substitutions at various locations along their sequence, as compared to a parent (e.g., naturally-occurring or reference) amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff et al. (1978) and by Gonnet et al. (1992)), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 1.

TABLE 1

| AMINO ACID SUB-CLASSIFICATION | |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants may be screened for biological activity.

TABLE 2

EXEMPLARY AND PREFERRED AMINO ACID SUBSTITUTIONS

| | | |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G. (1993).

Thus, a predicted non-essential amino acid residue in a polypeptide is typically replaced with another amino acid residue from the same side chain family. Alternatively, mutations can be introduced randomly along all or part of a polypeptide gene coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of a polypeptide without abolishing or substantially altering one or more of its activities. Suitably, the alteration does not substantially alter one of these activities, for example, the activity is at least 20%, 40%, 60%, 70% or 80% of wild-type. An "essential" amino acid residue is a residue that, when altered from the wild-type sequence of a reference polypeptide, results in abolition of an activity of the parent molecule such that less than 20% of the wild-type activity is present.

Accordingly, the present invention also contemplates variants of the naturally-occurring polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity to a parent or reference polypeptide sequence as, for example, set forth in SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, or 52, or the parent or reference polypeptide sequence as, for example, encoded by the nucleotide sequence set forth in SEQ ID NO: 5, 6, 9, 10, 14, 15, 17, 19, 20, 21, 22, 23, 24, 25, 31, 33, 35, 37, 39, 41, 43, 45, 47, or 49. Desirably, variants will have at least 30, 40, 50, 55, 60, 65, 70, 75, 80, 85, 90, 91, 92, 93, 94, 95, 96, 97, 98, 99% sequence identity to a parent polypeptide sequence as, for example, set forth in SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, or 52, or the parent polypeptide sequence as, for example, encoded by the nucleotide sequence set forth in SEQ ID NO: 5, 6, 9, 10, 14, 15, 17, 19, 20, 21, 22, 23, 24, 25, 31, 33, 35, 37, 39, 41, 43, 45, 47, or 49. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of the parent polypeptide are contemplated. Polypeptides also include polypeptides that are encoded by polynucleotides that hybridise under stringency conditions as defined herein, especially high stringency conditions, to parent-coding polynucleotide sequences, or the non-coding strand thereof, as described below. Illustrative parent polynucleotide sequences are set forth in SEQ ID NO: 5, 6, 9, 10, 14, 15, 17, 19, 20, 21, 22, 23, 24, 25, 31, 33, 35, 37, 39, 41, 43, 45, 47, and 49.

In some embodiments, variant polypeptides differ from a reference sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NO: 1, 2, 3, 4, 7, 8, 11, 12, 13, 16, 18, 26, 27, 28, 29, 30, 32, 34, 36, 38, 40, 42, 44, 46, 48, 50, 51, or 52, or the amino acid sequences encoded by the nucleotide sequences of SEQ ID NO: 5, 6, 9, 10, 14, 15, 17, 19, 20, 21, 22, 23, 24, 25, 31, 33, 35, 37, 39, 41, 43, 45, 47, or 49, by at least 1% but less than 20%, 15%, 10% or 5% of the residues. (If this comparison requires alignment, the sequences should be aligned for maximum similarity. "Looped" out sequences from deletions or insertions, or mismatches, are considered differences). The differences are, suitably, differences or changes at a non-essential residue or a conservative substitution.

Variants of a protein can be identified by screening combinatorial libraries of mutants, e.g., truncation mutants, of a protein. Libraries or fragments e.g., N terminal, C terminal, or internal fragments, of a protein coding sequence can be used to generate a variegated population of fragments for screening and subsequent selection of variants of a protein.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of proteins.

Some variants of the snake prothrombin activator ecarin are described in U.S. Pat. No. 6,413,737.

2.5 Variants of Naturally-occurring Prothrombin Activators (Nucleotide)

The present invention also contemplates prothrombin activators comprising polypeptide(s) that is/are encoded by variant(s) of the wild-type or naturally-occurring polynucleotide(s) encoding the wild-type or naturally-occurring polynucleotide(s).

Variants of a wild-type or naturally-occurring polynucleotides will have at least 40%, 50%, 60%, 70%, generally at least 75%, 80%, 85%, 86%, 87%, 88%, 89%, usually about 90%, 91%, 92%, 93%, 94%, 95% or more, and typically about 96%, 97%, 98% or more (and all integer percentages in between) sequence similarity or identity with the nucleotide sequence for the wild-type or naturally-occurring polynucleotide, including but not limited to the sequences encoded by the sequences of SEQ ID NOs: 1, 2, 3, 4, 7, 8, 11, 12, 13, 16, 18, 26, 27, 28, 29, 30, 32, 34, 36, 38, 40, 42, 44, 46, 48, 50, 51, or 52 or the sequences of SEQ ID NOs: 5, 6, 9, 10, 14, 15, 17, 19, 20, 21, 22, 23, 24, 25, 31, 33, 35, 37, 39, 41, 43, 45, 47, and 49, or a complement thereof, as determined by sequence alignment programs described elsewhere herein using default parameters.

Exemplary nucleotide sequences that encode the polypeptides encompass full-length genes as well as portions of the full-length or substantially full-length nucleotide sequences of the genes or their transcripts or DNA copies of these transcripts. Portions of a nucleotide sequence may encode polypeptide portions or segments that retain the biological activity of the native polypeptide. A portion of a nucleotide sequence that encodes a biologically active fragment of a polypeptide may encode at least about 20, 21, 22, 23, 24, 25, 30, 40, 50, 60, 70, 80, 90, 100, 120, 150, 300 or 400 contiguous amino acid residues, or almost up to the total number of amino acids present in a full-length polypeptide.

Also contemplated are variants of the nucleotide sequences. Nucleic acid variants can be naturally-occurring, such as allelic variants (same locus), homologs (different locus), and orthologs (different organism) or can be non naturally-occurring. Naturally-occurring variants such as these can be identified with the use of well-known molecular biology techniques, as, for example, with polymerase chain reaction (PCR) and hybridisation techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a polypeptide. Generally, variants of a particular nucleotide sequence will have at least about 30%, 40% 50%, 55%, 60%, 65%, 70%, generally at least about 75%, 80%, 85%, 86%, 87%, 88%, 89%, desirably about 90%, 91%, 92%, 93%, 94%, 95% or more, and more suitably about 96%, 97%, 98% or more sequence identity to that particular nucleotide sequence as determined by sequence alignment programs described elsewhere herein using default parameters.

Nucleotide sequences can be used to isolate corresponding sequences and alleles from other organisms, particularly other snakes. Methods are readily available in the art for the hybridisation of nucleic acid sequences. Coding sequences from other organisms may be isolated according to well known techniques based on their sequence identity with the coding sequences set forth herein. In these techniques all or part of the known coding sequence is used as a probe which selectively hybridises to other coding sequences present in a population of cloned genomic DNA fragments or cDNA fragments (i.e., genomic or cDNA libraries) from a chosen organism (e.g., a snake). Accordingly, the present invention also contemplates polynucleotides that hybridise to reference nucleotide sequences, or to their complements, under stringency conditions described below. As used herein, the term "hybridises under low stringency, medium stringency, high stringency, or very high stringency conditions" describes conditions for hybridisation and washing.

Guidance for performing hybridisation reactions can be found in Ausubel et al., supra, sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridisation in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridisation at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridising in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridisation at 42° C., and about 0.01 M to about 0.02 M salt for washing at 55° C. High stringency conditions also may include 1% BSA, 1 mM EDTA, 0.5 M $NaHPO_4$ (pH 7.2), 7% SDS for hybridisation at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridising in 6×SSC at about 45° C., followed by one or more washes in 0.2×SSC, 0.1% SDS at 65° C.

In certain embodiments, a polypeptide is encoded by a polynucleotide that hybridises to a disclosed nucleotide sequence under low, medium, high, or very high stringency conditions. One embodiment of very high stringency conditions includes hybridising 0.5 M sodium phosphate, 7% SDS at 65° C., followed by one or more washes at 0.2×SSC, 1% SDS at 65° C.

Other stringency conditions are well known in the art and a skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook, J. et al. (2001) at sections 1.101 to 1.104.

While stringent washes are typically carried out at temperatures from about 42° C. to 68° C., one skilled in the art will appreciate that other temperatures may be suitable for stringent conditions. Maximum hybridisation rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8). In general, the $T_m$ of a perfectly matched duplex of DNA may be predicted as an approximation by the formula:

$$T_m=81.5+16.6(\log_{10} M)+0.41\ (\%\ G+C)-0.63\ (\%\ \text{formamide})-(600/\text{length})$$

wherein: M is the concentration of $Na^+$, preferably in the range of 0.01 molar to 0.4 molar; % G+C is the sum of guanine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridisation procedure, a membrane (e.g., a nitrocellulose membrane or a nylon membrane) containing immobilized DNA is hybridised overnight at 42° C. in a hybridisation buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

3. Preparing Prothrombin Activators

Prothrombin activators may be prepared by any suitable procedure known to those of skill in the art.

For example, the prothrombin activators may be produced by any convenient method such as by purifying the polypeptide from naturally-occurring reservoirs, including but not limited to snake venom, blood and blood-derived products (e.g. serum). Methods of purification include affinity chromatography, including lectin (e.g. wheat germ agglutinin) affinity chromatography or other separation. The identity and purity of derived prothrombin activator can be determined for example by SDS-polyacrylamide electrophoresis or chromatographically such as by high performance liquid chromatography (HPLC). For example, the purification and characterisation of pseutarin C (also abbreviated to PtPA) from *P. textilis* snake venom is described in Masci (1986) and Masci et al. (1988), and oscutarin C (OsPA) from *O. scutellatus* venom is described in Speijer et al. (1986), both of which are incorporated by reference in their entirety. The purification of ecarin from *E. carinatus* venom is described in Morita, T et al. (1981), the contents of which is also incorporated by reference in its entirety.

Alternatively, the prothrombin activators may be produced from venom gland cells in culture using methods known in the art, including for example the method described in Yamanouye, N., et al. (2007), which describes the primary culture of secretory cells from the venom gland of *Bothrops jararaca* for in vitro venom production, the contents of which is incorporated by reference in its entirety.

Alternatively, the prothrombin activators may be synthesised by chemical synthesis, e.g. using solution synthesis or solid phase synthesis as described, for example, in Chapter 9 of Atherton and Shephard (1989) and in Roberge et al. (1995).

Alternatively, the prothrombin activators may be prepared by recombinant techniques. For example, the prothrombin activators used in the invention may be prepared by a procedure including the steps of: (a) preparing a construct comprising a polynucleotide sequence that encodes a polypeptide and that is operably linked to a regulatory element; (b) introducing the construct into a host cell; (c) culturing the host cell to express the polypeptide; (d) isolating the polypeptide from the host cell. If the prothrombin activator comprises a complex or two polypeptides, then the prothrombin activator may be prepared by a procedure including the steps of: (a) preparing a construct comprising a polynucleotide sequence that encodes a first polypeptide and that is operably linked to a regulatory element; (b) introducing the construct into a host cell; (c) culturing the host cell to express the first polypeptide; (d) isolating the polypeptide from the host cell; repeating steps (a) to (d) for a second polypeptide; and linking the first polypeptide and the second polypeptide. In illustrative examples, the nucleotide sequence that encodes a polypeptide encodes at least a biologically active portion of the sequences set forth in SEQ ID NO: 5, 6, 9, 10, 14, 15, 17, 19, 20, 21, 22, 23, 24, 25, 31, 33, 35, 37, 39, 41, 43, 45, 47, 49, or a variant thereof.

Recombinant prothrombin activators can be conveniently prepared using standard protocols as described for example in Sambrook, J. et al. (2001), in particular Chapters 16 and 17; Ausubel et al. (1994, supra), in particular Chapters 10 and 16; and Coligan et al., Current Protocols in Protein Science (John Wiley & Sons, Inc. 1995-1997), in particular Chapters 1, 5 and 6. For example, the recombinant production of snake factor V and snake factor X, which can be used to produce group C and group D prothrombin activators, is described in Filippovic, I. et al (2005) and Bos, M. H. A. et al (2009), each of which is incorporated herein in its entirety. An illustrative process for the recombinant production of ecarin and variants of ecarin is provided in Yonemura, H. et al. (2004) and in U.S. Pat. No. 6,413,737, the entire contents of each of which are incorporated herein by reference.

4. Containers

The present invention contemplates any suitable container for preparing a suitable serum sample. Many suitable containers are well known in the art, including those described in U.S. Pat. Nos. 4,227,620; 4,256,120; 6,416,717; 6,592,613; 6,686,204; 7,488,287; 7,699,828; European patent 0 628 816; and commercially available containers including those used in the Examples of the present specification.

In some embodiments, the containers used in accordance with the present invention are tubes, including glass or plastic tubes. Suitable plastics include polyvinyl chloride, polypropylene, polyethylene terephthalate, and polystyrene.

The containers may be evacuated and the end sealed with an appropriate puncturable septum or cap. This allows for a double-ended needle to be used where one end is inserted into a patient's vein and the other end of the needle then punctures the septum or cap covering the end of the tube so that the vacuum in the tube draws the blood sample through the needle into the tube.

The containers may be of any suitable size. In some embodiments, the containers are designed to hold a blood sample of between 50 μL and 10 mL. Suitably, the containers are designed to hold at least 50 μL, 100 μL, 150 μL, 200 μL, 250 μL, 300 μL, 350 μL, 400 μL, 450 μL, 500 μL, 1 mL, 2 mL, 3 mL, 4 mL, 5 mL, 8 mL, or 10 mL of blood sample.

In some embodiments, the containers contain a clotting composition comprising, consisting essentially of, or consisting of 0.01 to 100 gag of prothrombin activator. Suitably, the containers contain a clotting composition comprising, consisting essentially of, or consisting of 0.1 to 10 μg of prothrombin activator. In representative embodiments, the containers contain a clotting composition comprising, consisting essentially of, or consisting of 0.1 to 10 μg of prothrombin activator and hold a 4 mL blood sample providing a final concentration of prothrombin activator in the 4 mL blood sample of 25 ng/mL to 2.5 μg/mL.

In some embodiments, the containers contain a clotting composition comprising, consisting essentially of, or consisting of 0.0005 to 15 μg/mL of prothrombin activator. Suitably, the containers contain a clotting composition comprising, consisting essentially of, or consisting of 0.005 to 10 μg of prothrombin activator.

In some embodiments, the containers contain a clotting composition comprising, consisting essentially of, or consisting of 0.0005 to 15 U/mL of prothrombin activator. Suitably, the containers contain a clotting composition comprising, consisting essentially of, or consisting of 0.0015 to 10 U/mL of prothrombin activator. In some embodiments, a unit measurement is a prothrombin activator unit measurement that is defined as follows: 1 unit will activate prothrombin to produce one unit of amidolytic activity at pH 8.4 at 37° C., and 1 amidolytic unit will hydrolyzs 1.0 μmole of N-p-tosyl-Gly-Pro-Arg-p-nitroanilide per min at pH 8.4 at 37° C.

In some embodiments, the clotting composition may be contained within the container before the blood sample is added to the container. In some embodiments, the clotting composition may be added to the container after the blood sample is added to the container.

Where the clotting composition is contained within the container before the blood sample is added, it may have been added to the container by any suitable method known in the art. In some embodiments, the clotting composition is dissolved into a suitable solvent and is then added to the container and dried onto the inner surface of the container. The solvent may be a neutral buffer. The clotting composition in solution may be dried onto the inner surface of the container by spray-drying or by freeze-drying or by any other suitable method known in the art. In some other embodiments, the clotting composition is dissolved into a suitable solvent and added to the container without drying so that the container contains an aqueous solution comprising the clotting composition. The solvent may be a neutral buffer.

In some embodiments, beads are coated with the clotting composition and these beads are added to the container. The beads may be glass beads or synthetic resinous beads, including polystyrene and propylene beads. The beads may have a spherical shape. In some embodiments, the mean diameter of the beads is between 0.1 mm and 1 mm.

In some embodiments, the container provides for separation of the serum from the clotted cells after clotting has occurred. In some embodiments, the container comprises or contains a gel that provides a barrier between the clotted cells and the serum sample. In some embodiments, the container is a suitable shape and a suitable material to permit centrifugation to separate or assist in maintaining separation of the clotted cells and the serum sample. In some embodiments, the serum sample is removed from the clotted cells, or the clotted cells are removed from the serum sample.

In some embodiments, the container may comprise one or more further components. The other components may include, for example, one or more co-factors, one or more surfactants, and/or one or more clotting agents in addition to the clotting composition.

5. Further Components

The clotting composition described herein consists of, consists essentially of, or comprises a prothrombin activator as herein defined.

As used in the above statement and in similar statements elsewhere in this specification, the term “comprises” (and the like) means the clotting composition includes the prothrombin activator and may also include any one or more further components. Thus, the prothrombin activator is a mandatory component, and any other components are optional and may or may not be present. Other components may include, for example, one or more co-factors, one or more surfactants, and/or one or more additional clotting agents.

As used in the above statement and in similar statements elsewhere in this specification, the term “consists essentially of” (and the like) means that the clotting composition includes the prothrombin activator, and may also include one or more other components, provided those components do not interfere with or contribute to the activity or action of the prothrombin activator. Thus, the prothrombin activator is a mandatory component, and other components are optional and may or may not be present, depending upon whether or not they affect the activity or action of the prothrombin activator.

As used in the above statement and in similar statements elsewhere in this specification, the term “consists of” (and the like) means that the clotting composition includes, and is limited to, the prothrombin activator. Thus, the phrase “consists of” indicates that the prothrombin activator is a mandatory component, and that no other components (such as co-factors or clotting agents) may be present.

Accordingly, in some embodiments, the clotting composition may comprise snake venom, including but not limited to crude snake venom. In some other embodiments, the clotting composition may comprise a preparation of prothrombin activator prepared by partial or full purification of snake venom. Such preparations may be prepared by any suitable method known in the art, including chromatographic and gel filtration methods, including those described herein, and elsewhere. In some other embodiments, the clotting composition may comprise a purified prothrombin activator or isolated prothrombin activator. Purified and isolated prothrombin activators may be prepared by any suitable method known in the art, including those described herein, and elsewhere.

5.1 Co-factors

The ability of prothrombin activators as herein defined to activate prothrombin to thrombin may be improved with the addition of co-factors, including but not limited to calcium, phospholipid(s) and polypeptides comprising FVa activity.

5.2 Surfactants

Suitable surfactants include any suitable surfactant, including but not limited to sodium dodecyl sulphate (SDS), ammonium lauryl sulphate, sodium laureth sulphate, and sodium myreth sulphate.

5.3 Clotting Agents

Clotting agents or coagulants are classified as either intrinsic clotting agents or extrinsic clotting agents according to the blood cascade stimulated (see for example U.S. Pat. No. 6,686,204).

Suitable clotting agents include, but not limited to, diatomaceous earth, microparticles or particles of inorganic silicates, microsilica, glass microparticles, ellagic acid, thrombin, heparinase, thromboplastin, batroxobin, hydroyapitite, kaolin, kaolin particles, prothrombin (including microparticulated prothrombin), fibrinogen, and depolymerised collagen.

6. Serum Samples

As discussed above, the present invention is predicated in part on the discovery that prothrombin activators as defined herein are suitable clotting agents for preparing serum samples that are suitable for detecting analytes. A serum sample that is suitable for detecting analytes is one of suitable quality as discussed herein, and/or one that is prepared within a suitable time as discussed herein.

6.1 Serum Quality

An important factor in the preparation of a serum sample suitable for detecting analytes is the extent to which the clotting process removes fibrinogen from the serum. Serum containing residual fibrinogen or partially degraded fibrinogen, or fibrin as a result of incomplete clotting can lead to analytical accuracy problems because of the formation of precipitates (microdots or strings), latent clotting post-centrifugation and on storage of the serum. Hence complete or substantially complete clotting is pivotal in ensuring highest quality serum and subsequent result accuracy is obtained.

Accordingly, some embodiments of the present invention provide the use of a clotting composition comprising, consisting essentially of, or consisting of a prothrombin activator in the preparation of a serum for detecting an analyte, where the serum comprises ≤30 μg/mL of fibrinogen or fibrinogen/fibrin related products. In more specific embodiments, the serum comprises ≤25 μg/mL, ≤20 μg/mL, ≤15 μg/mL, ≤10 μg/mL, ≤8 μg/mL, or ≤6 μg/mL of fibrinogen or fibrinogen/fibrin related products.

In some embodiments, the serum comprises ≤30%, ≤20%, ≤10%, ≤9%, ≤8%, ≤7%, ≤6%, ≤5%, ≤4%, ≤3%, ≤2%, ≤1%, ≤0.5%, ≤0.2%, ≤0.1% of fibrinogen or fibrinogen/fibrin related products present in the original sample from which the serum was produced.

Levels of fibrinogen and/or fibrinogen/fibrin related products can be detected by any suitable method known in the art, including a sandwich immunoassay using antibodies from MP Biomedicals and standard fibrinogen preparations purchased from NIBSC, Potters Bar, Hertsfordshire, London, UK.

Another important factor in the preparation of a serum sample suitable for detecting analytes is the activity or number of cells or cellular debris that remain in the serum after clotting. The presence of cells can have two effects during storage and analysis of serum or plasma. Firstly, cells may lyse, releasing cellular contents (e.g. potassium, lactate dehydrogenase) into the serum or plasma. This can lead to significant differences between measurements made immediately after centrifugation and measurements after a period of storage. Secondly, cells continue to be metabolically active and may use up significant amounts of nutrients (e.g. glucose) and release metabolic products (e.g. lactate) on storage. Changes can even be observed in the samples of many tubes when the samples are stored for the usual recommended 30 minute clotting time when the samples are from healthy participants. The degree of cellular contamination is therefore an important quality criterion for serum samples and an important advantage of using serum over plasma.

Accordingly, in some embodiments, the serum sample comprises less than 50%, 40%, 30%, 20%, 10%, 5%, or 1% of cells in the blood sample from which it has been prepared.

In some embodiments, the serum sample comprises a change of lactate dehydrogenase activity or phosphate concentration (typically measured in U/L and mmol/L respectively) of <25%, <20%, <15% or <10% over a period of 24 hours, 12 hours, 8 hours, 6 hours, 5 hours, 4 hours, 3 hours, 2 hours, 1 hour or 30 minutes. In some embodiments, the serum sample comprises a change of glucose concentration or potassium concentration (both typically measured in mmol/L) of <5%, <4%, <3%, <2%, <1%, <0.5%, or <0.1% over a period of 24 hours, 12 hours, 8 hours, 6 hours, 5 hours, 4 hours, 3 hours, 2 hours, 1 hour or 30 minutes (for example, from the time of preparing the serum sample). Methods for measuring lactate dehydrogenase activity are well known in the art, see, for example, Dimeski, G., et al. (2004), the contents of which is incorporated by reference in its entirety.

The haemoglobin concentration of a serum sample can also be used to determine whether the serum sample is suitable for detecting analytes. Accordingly, in some embodiments, the serum sample comprises a haemoglobin concentration of <150 mg/L, <100 mg/L, <90 mg/L, <80 mg/L, <70 mg/L, <60 mg/L, <50 mg/L, <40 mg/L, <30 mg/L, <20 mg/L, or <10 mg/L.

6.2 Clotting Time

As a sample for testing, serum is usually preferred over plasma unless urgent results are required and thus the clotting time for a serum tube is considered too long. Another downside to prolonged clotting time is that it can lead to clinically significant analyte concentration changes due to cellular activity in the blood sample, this problem being most pronounced in leukocytosis.

Thus in some embodiments, the present invention provides a method of producing a serum sample for detecting an analyte of interest, the method comprising contacting a blood sample with a clotting composition comprising, consisting essentially of, or consisting of a prothrombin activator as defined herein, where the serum sample is prepared within 25, 20, 15, 10, 8, 6, 5, 4, 3, 2, 1, or 0.5 minutes from contact with the clotting composition.

7. Blood Samples

As discussed herein, there is a desire to provide a clotting composition that is suitable for producing a serum sample from all blood samples, or a container comprising a clotting composition that will clot all blood samples, in a suitable time.

Examples of different types of blood sample for which testing may be desired include blood from healthy individuals, citrated blood, blood with EDTA added, blood from patients on anti-clotting therapy such as heparin, warfarin, citrate, or rivaroxaban, patients taking anti-thrombotic agents including aspirin, thrombocytopenic patients (patients with low platelet counts), and patients with prolonged aPTT.

In some embodiments, the blood sample is a whole blood sample. In some other embodiments, the blood sample is a serum sample derived from a whole blood sample. Exemplary serum samples in this instance include serum samples where a better quality serum sample is desired, including those where the amount of fibrinogen or fibrinogen/fibrin related products and/or the amount of cells or cellular material in the serum sample and/or the amount of haemoglobin is considered too high for the serum sample to be a sample suitable to detect analytes. For example, the serum sample may exhibit microclots or latent clotting. In some other embodiments, the blood sample is a plasma sample derived from a whole blood sample. For example, the plasma sample may exhibit microclots or latent clotting.

8. Detecting Analytes

In some embodiments the present invention further provides methods of detecting an analyte, the method comprising analysing a serum sample prepared by the method of the present invention for the presence or amount of the analyte of interest.

In specific embodiments, the serum sample prepared by the method of the present invention is suitable for more than one analyte test, so that the serum sample can be used to detect more than one analyte. As discussed herein, often a clinician will desire more than one analyte test to be performed on a blood sample from a patient, and it is not uncommon for one serum sample to be used for at least 20 tests, or even more, sometimes between 50-60 or even 70-80 tests. It will be appreciated by those skilled in the art that in specific embodiments the present invention provides for the production of a serum sample where the serum sample is of sufficient volume and quality to enable all desired analyte tests to be performed on the one serum sample. The advantage of this is that both the volume of blood to be taken from the subject and the time taken to perform the analyte tests are reduced.

Illustrative analyte tests are described below. Methods for performing these analyte tests may be performed in a number of ways and are well known in the art.

8.1 Sodium ($Na^+$)

This test measures the amount of sodium in a serum or plasma sample. Sodium plays an important role in salt and water balance in the body. Low sodium levels may indicate too much water intake; heart failure, kidney failure, or loss of sodium from the body due to diarrhea or vomitting. High sodium levels may indicate too much salt intake or insufficient water intake.

8.2 Potassium ($K^+$)

This test measures the amount of potassium in a serum or plasma sample. Levels of potassium that are too high (hyperkalaemia) may be the result of kidney disease, diabetes, ketoacidosis or drugs that decrease the amount of potassium excreted from the body. Levels of potassium that are too low (hypokalaemia) may be caused by dehydration, for example from diarrhoea or vomiting, or excessive sweating. Levels of potassium may also be low as a result of taking drugs that cause the kidneys to lose potassium, for example diuretics.

Potassium levels are often monitored in those patients that take diuretics or heart medications, those with high blood pressure or kidney disease, critical acidosis and alkalosis conditions, and those receiving kidney dialysis or intravenous therapy on a drip.

8.3 Chloride ($Cl^-$)

This test measures the amount of chloride in serum or plasma. Chloride is typically measured to assess whether there is an electrolyte imbalance in the patient. Low chloride and normal sodium can be indicative of vomiting or loss of gastric fluid.

8.4 Bicarbonate ($HCO_3^-$)

This test measures the amount of three forms of carbon dioxide (bicarbonate, carbonic acid, and dissolved carbon dioxide) in serum or plasma. This test is often performed if the patient is having breathing problems. A high level of carbon dioxide may be caused by some diseases including chronic obstructive pulmonary disease, emphysema, pneumonia, Cushing's syndrome or alcoholism, or vomiting. A low level may be caused by some diseases including pneumonia, cirrhosis, hyperventilation, diabetes, dehydration, kidney or heart failure.

8.5 Glucose (Gluc)

This test measures the amount of glucose in serum or plasma. Glucose levels are often tested in those patients exhibiting symptoms of high blood glucose (hyperglycaemia) or hypoglycemia, those who are pregnant, those who have diabetes.

8.6 Urea (Urea)

This test measures the amount of urea in serum or plasma. This test can help evaluate kidney function and monitor the effectiveness of dialysis.

8.7 Creatinine (Creat)

This test measures the amount of creatinine in serum or plasma. This test is pivotal in helping to evaluate kidney function and monitor treatment of kidney disease.

8.8 Urate (Urate)

This test measures the amount of urate (or uric acid) in serum or plasma. High levels of uric acid may be a sign of gout. Uric acid levels are also monitored in patients that are undergoing chemotherapy or radiotherapy to detect tumour lysis syndromes.

8.9 Total Protein (TP or T Prot)

This test measures the total amount of protein in serum or plasma. Although the results of a total protein test will not indicate a specific disease, a high or low protein level often indicates that additional tests are required to determine if there is a problem. Total protein tests are often used to screen for certain liver disorders, kidney disorders, multiple myeloma and hydration status.

8.10 Albumin (Alb)

This test measures the amount of albumin in serum or plasma. Albumin levels are often measured to screen for liver or kidney disease, or to evaluate nutritional status, especially in hospitalised patients.

8.11 Total Bilirubin (T Bili)

This test measures the amount of bilirubin in serum or plasma. Bilirubin levels are measured to screen for and monitor liver disorders, such as jaundice, or liver diseases, such as cirrhosis. Bilirubin levels are also measured in babies to help detect certain rare genetic disorders and to avoid brain damage in those babies with jaundice.

8.12 Alkaline Phosphatase (ALP)

This test measures the amount of alkaline phosphatase in serum or plasma. This test is typically performed to screen for or monitor treatment of a liver or bone disorders.

8.13 Gamma-Glutamyl Transferase (GGT)

This test measures the amount of gamma-glutamyl transferase in serum or plasma. This test is used to screen for liver disease and alcohol abuse. It can also be used to determine if a raised level of ALP is due to liver or bone disease.

8.14 Alanine Aminotransferase (ALT)

This test measures the amount of alanine aminotransferase in serum or plasma. This test is used to screen for liver disease.

8.15 Aspartate Aminotransferase (AST)

This test measures the amount of aspartate aminotransferase in serum or plasma. This test is used to detect liver damage, muscular damage, and other conditions as the enzyme is present in many organs and tissue cells.

8.16 Lactate Dehydrogenase (LD)

This test measures the amount of lactate dehydrogenase in serum or plasma. This test is typically used to identify the cause and location of tissue damage in the body, tissue ischemia, and to monitor its progress.

8.17 Creatine Kinase (CK)

This test measures the amount of creatine kinase in serum or plasma. Creatine kinase is measured in patient's with chest pain or muscle pain or weakness to determine if they have had a heart attack and if other muscles in the body have been damaged.

8.18 Total Calcium (TCa)

This test measures the amount of calcium in serum or plasma. Calcium levels are often measured in patients with kidney, bone or nerve disease, or when symptoms of significantly increased or decreased calcium are present.

8.19 Phosphate (Pi or Phos)

This test measures the amount of phosphate in serum or plasma. Phosphate levels may be measured as a follow-up to a test result of abnormal calcium levels. Phosphate levels may also be measured in patients with kidney disorders, uncontrolled diabetes, or where the patient is taking calcium or phosphate supplements.

8.20 Magnesium ($Mg^{2+}$)

This test measures the amount of magnesium in serum or plasma. This test may be performed if the patient has symptoms of too much or too little magnesium, including weakness, irritability, cardiac arrhythmia, nausea or diarrhoea. Magnesium levels may also be measured if abnormal calcium or potassium levels have been detected.

8.21 Lipase (Lipase)

This test measures the amount of lipase in serum or plasma. This test is typically used to diagnose pancreatitis or other pancreatic diseases.

8.22 Cholesterol (Chol)

This test measures the amount of cholesterol in serum or plasma. Cholesterol levels are measured to screen for risk of developing heart disease.

8.23 Triglycerides (Trig)

This test measures the amount of triglycerides in serum or plasma. As for cholesterol levels, this test is typically used to screen for risk of developing heart disease.

8.24 High-Density Lipoprotein Cholesterol (HDL-C or HDL)

This test measures the amount of HDL cholesterol in serum or plasma. This test is typically used to determine the risk of developing heart disease.

8.25 Iron ($Fe^{2+}$)

This test measures the amount of iron in serum or plasma. Iron is measured to check if a patient has low or high iron levels. Low iron levels can cause anaemia, and is usually due to long-term or heavy bleeding, pregnancy or rapid growth (in children). High iron levels can be due to a genetic condition or extensive blood transfusions.

8.26 Transferrin (Trf)

This test measures the amount of transferrin in serum or plasma. Transferrin is a plasma protein that transports iron through the blood to the liver, spleen and bone marrow. Thus the blood transferrin level is tested to determine the cause of anaemia, to examine iron metabolism (for example, in iron deficiency anaemia) and to determine the iron-carrying capacity of the blood.

8.27 C Reactive Protein (CRP)

This test measures the amount of C reactive protein in serum or plasma. This test is used to identify the presence of inflammation, to determine its severity, and to monitor response to treatment.

8.28 Cortisol (Cortisol)

This test measures the amount of cortisol in serum or plasma. Cortisol levels are measured to help diagnose Cushing's syndrome or Addison's disease.

8.29 Free Thyroxine (fT4)

This test measures the amount of free thyroxine in serum or plasma. The test is typically used to diagnose hypothyroidism or hyperthyroidism.

8.30 Thyroid Stimulating Hormone (TSH)

This test measures the amount of thyroid stimulating hormone in serum or plasma. The test is typically used to screen for, diagnose and monitor thyroid disorders.

8.31 Ferritin

This test is used to measure ferritin in serum or plasma. Low ferritin levels are indicative of iron deficiency. Elevated levels are indicative of iron overload such as in haematochromatosis.

8.32 Troponin (TnI)

This test measures the amount of troponin in serum or plasma. This test, is typically used in a patient with chest pains to determine if the patient has had myocardial damage.

8.33 Haemolytic Index

The haemolytic index test measures the degree of red cell lysis. Haemolysis is the most common interference encountered in a biochemistry laboratory. The test is predominantly used to detect in vitro haemolysis and sample suitability for reporting of certain or all analytes, and in detection of haemolytic anaemias (hereditary spherocytosis, spontaneous haemolysis, RBC enzyme deficiency). Haemolysis or haemolytic index (concentration of free haemoglobin in serum or plasma) is currently estimated by all general chemistry analysers. The value is then used as a guide in determining which analytes and at what haemolysis level may be affected or not reported.

8.34 Icteric Index

The icteric index test returns a value indicating the relative level of bilirubin in a test sample by a purely spectrophotometric method. It is used in determining sample suitability for reporting of certain analytes and cross checking accuracy of bilirubin results in rare cases of interference with the total bilirubin photometric estimation methods. The icteric index has been shown to be of value in detecting cancer paraproteins interference (precipitation and false high total bilirubin) with Roche Total Bilirubin method (Sheppard et al., 2005), where the icteric index has stayed unaffected. Bilirubin can interfere with some creatinine assays at high concentration (e.g. >200 μM/L) as discussed in Dimeski et al., 2008.

8.35 Lipemia Index

The lipemia index has been employed to predict possible interference with assays due to lipaemia.

9. Methods of Diagnosis

The present invention also provides methods of diagnosing the presence, absence or severity of a disease or condition in a subject, wherein the presence, absence or severity of the disease or condition is associated with the presence, absence or an aberrant amount of an analyte of interest in the subject. These methods generally comprise providing a serum sample prepared according to the methods broadly described above; and detecting the presence, absence or aberrant amount of the analyte in the serum sample to thereby determine the presence, absence or severity of the disease or condition in the subject.

In some embodiments, the methods of the present invention involve comparing the result of the analyte test to a reference result in order to obtain the diagnosis.

The disease or condition may be any suitable disease or condition that can be diagnosed using a serum sample, including but not limited to, the diseases or conditions outlined above with reference to different analyte tests.

In some embodiments, the methods may comprise diagnosing the presence or absence of a disease or condition not previously presented by the subject. In other embodiments, the methods may comprise diagnosing the presence, absence or severity of a disease or condition that the subject has previously presented. The methods may comprise reference to a result obtained from the subject at an earlier time. Alternatively, the reference result may be a standard analytical reference.

In some embodiments, the methods are performed in a testing facility such as a pathology laboratory. In some other embodiments, the methods are "point-of-care" methods. As used herein, a "point-of-care method" means that the method is performed at or near the site of patient care. Point-of-care methods are increasingly popular in hospital and other environments where there is a desire to obtain fast results, and is often accomplished through the use of transportable, portable, and hand-held instruments and test kits.

The advantages of point of care testing include the ability to obtain rapid analytical results at the bedside in hospitals, especially in emergency situations and the ability to obtain analytical results at home or in doctors' surgeries (e.g., using droplets of capillary blood obtained by skin puncture).

Devices for point-of-care devices currently available on the market include the immunoassay analyser sold by Siemens called Siemens' DCA Vantage Analyzer, the Retro-STATUS HIV/CD4 350 rapid test device sold by Millenium Biotechnology, Inc. which is used to simultaneously determine a patient's HIV infection status as well as their current immune status, and the Triage PLGF test sold by Alere International which is used for detecting early onset pre-eclampsia.

10. Research Tools

The present invention also contemplates the use of research tools that employ serum samples produced in accordance with the present invention. These methods generally comprise providing a serum sample prepared according to the methods broadly described above; and employing the serum sample in a research tool study, including but not limited to a genomics, proteomics, metabolomics, systems biology, molecular imaging or assay study.

Suitable research tools are well known in the art and include those described in Scaros, O. et al., 2005, the entire contents of which are incorporated by reference. Genomics includes pharmacogenomics which studies the correlation between genetics and gene expression patterns with response to therapeutics. Proteomics permits the analysis of the abundance and distribution of proteins in a system. Metabolomics, or biochemical profiling, is the study of metabolites in a system. Systems biology looks at the entire biological system as a functional unit, producing models of behaviour that can potentially predict hwo that system will respond to stimulus. Molecular imaging technologys have the ability to demonstrate both the level of a specific molecular target and the functional state of that target in vivo, and can be used for diagnostic methods.

In order that the invention may be readily understood and put into practical effect, particular preferred embodiments will now be described by way of the following non-limiting examples.

EXAMPLES

Example 1

Purification and Characterisation of Prothrombin Activators from Snake Venom

Example 1a

Purification and Characterisation of Ecarin, Carinactivase-1 and Carinactivase-2 from *Echis carinatus* Venom This example describes the purification and characterisation of a group A prothrombin activator termed ecarin and two group B prothrombin activators termed carinactivase-1 (CA-1) and carinactivase-2 (CA-2) from the venom of *Echis carinatus.*

Freeze-dried *Echis carinatus* venom (157 mg; Sigma Chemical Co, USA; cat no. V8250) was dissolved in 8 mL of 0.05 M Tris-HCl pH 8.0 buffer and left standing to allow to dissolve for 30 minutes and then centrifuged (1000 g and 10 minutes) to remove insoluble materials. A volume of 7.7 mL of the reconstituted clarified solution was loaded onto a Superdex 200 gel filtration chromatography column (cat no 17-1043-02) (2.5×95 cm) GE Healthcare Bio-Sciences, Sweden) using the same Tris-HCl buffer for the elution. The column flow rate was 20 mL/hr and 4 mL fractions were collected (15 minute fraction). The active fractions were determined by their clotting activity with normal citrated plasma as described in more detail below. The pooled fractions exhibiting prothrombin activator activity contained a total of 100 mL with a total $A_{280}$ of 28.3 units. FIG. 1 shows the elution profile in the isolation of ecarin, carinactivase-1, and carinactivase-2 from *E. carinatus* venom using gel filtration on a Superdex 200 column as described above. The pooled fractions of the three prothrombin activators (ecarin, carinactivase-1, and carinactivase-2) are indicated by the bar in FIG. 1.

Figure 2:
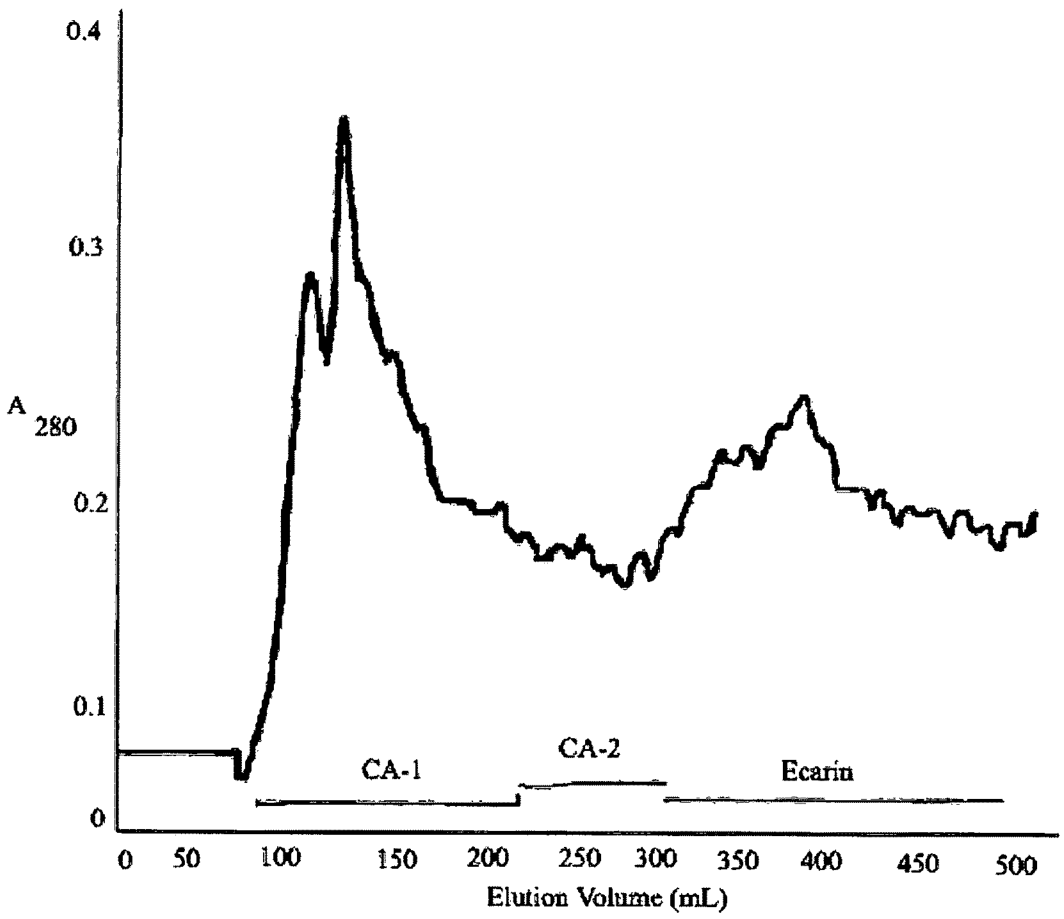
FIG. 2 shows the elution profile of the Blue Sepharose chromatography of the active (procoagulant) fractions from the Superdex 200 gel filtration chromatography described in Example 1a (also shown in FIG. 1). The active fractions were subjected to a column of Blue Sepharose and eluted with a linear gradient of NaCl. Three mL fractions were collected. The fractions indicated by the bars were pooled as carinactivase-1, carinactivase-2, and ecarin, respectively.

These pooled fractions were immediately applied to a column of Blue Sepharose (2.0×12 cm) (Cibacron Blue 3G attached to Sepharose 6 Fast Flow; cat no. 17-0948-01) (GE Healthcare Bio-Sciences, Sweden) pre-equilibrated with the same 0.05 M Tris-HCl buffer pH 8.0. After washing with initial buffer of approximately 2 column volumes, the bound material was eluted with a linear gradient of NaCl in the same buffer (0-1.0 M; 200 mL of each beaker). Carinactivase-1 was recovered in the unbound fractions and carinactivase-2 and ecarin were eluted at 0.2 and 0.5 M NaCl respectively. Prothrombin activator activities were identified by normal citrated plasma clotting assay in the presence of 30 mM calcium and in the absence of added calcium as described in more detail below. Fractions (three mL each) with specific prothrombin activator activities were pooled by their respective specific clotting activity of the clotting times followed by concentrating to 1 mg/mL using a YM 10 membrane in an Amicon stirred cell concentrator Model no. 42. All chromatography was performed at 4° C. using an Gilson peristaltic pump using black to purple chamber set at the required flow rates, an Altex dual wave UV detector set at two attenuation of 280 nm and an LKB 7000 ULTRORAC fraction collector using a time-base fraction collection. FIG. 2 shows the elution profile of this Blue Sepharose chromatography, and the bars indicate the pooled fractions of carinactivase-1, carinactivase-2, and ecarin. The fractions obtained were stored at either 4° C., −20° C. in buffer or −20° C. in 50% glycerol-buffer. These fractions (preparations) containing prothrombin activators were used in all subsequent experiments, except where otherwise indicated.

The prothrombin activator activity was assayed using the method described by Masci et al., 1988. Essentially, this assay method involved coagulation assays performed using a Hyland-Clotek instrument as described by Austen, D. E., et al. 1975. Fresh-pooled citrated plasma from normal volunteers was used for each group of experiments. The clotting time assays for the preparations were performed based on the criteria defined for group A and group B prothrombin activators in Kini, R. M., 2005. The assays were carried in the presence of calcium (30 mM $Ca^{2+}$) to identify the group B prothrombin activators (carinactivase-1 and carinactivase-2) and in the absence of added calcium to identify the group A prothrombin activator (ecarin). The hydrolytic activity against the peptide p-nitroanilide S-2238, measuring the formation of thrombin generation by prothrombin activators, was determined by equilibration of 0.90 mL of 0.02 M Tris-HCl buffer, pH 7.4, with or without 10 mM $CaCl_2$, and 100 μL of S-2238 (3 mM in water) in the cell compartment of a spectrophotometer (Hitachi U2800) at 25° C. The reaction was initiated by addition of a 25 μL aliquot of prothrombin activator preparation to prothrombin (250 nM), and the release of p-nitroaniline was measured at 405 nm. One unit of activity is equivalent to the hydrolysis of 1 pmol of substrate/minute. Assays using other peptide nitroanilides as substrate were performed in the same way, with a final concentration of 100 μM.

Example 1b

Purification and Characterisation of PtPA from *Pseudonaja textilis* Venom and OsPA from *Oxyuranus scutellatus* Venom This example describes the purification and characterisation of group C prothrombin activators from the venom of *Pseudonaja textilis* and *Oxyuranus scutellatus* snakes. These prothrombin activators are abbreviated as PtPA and OsPA respectively.

Figure 3:
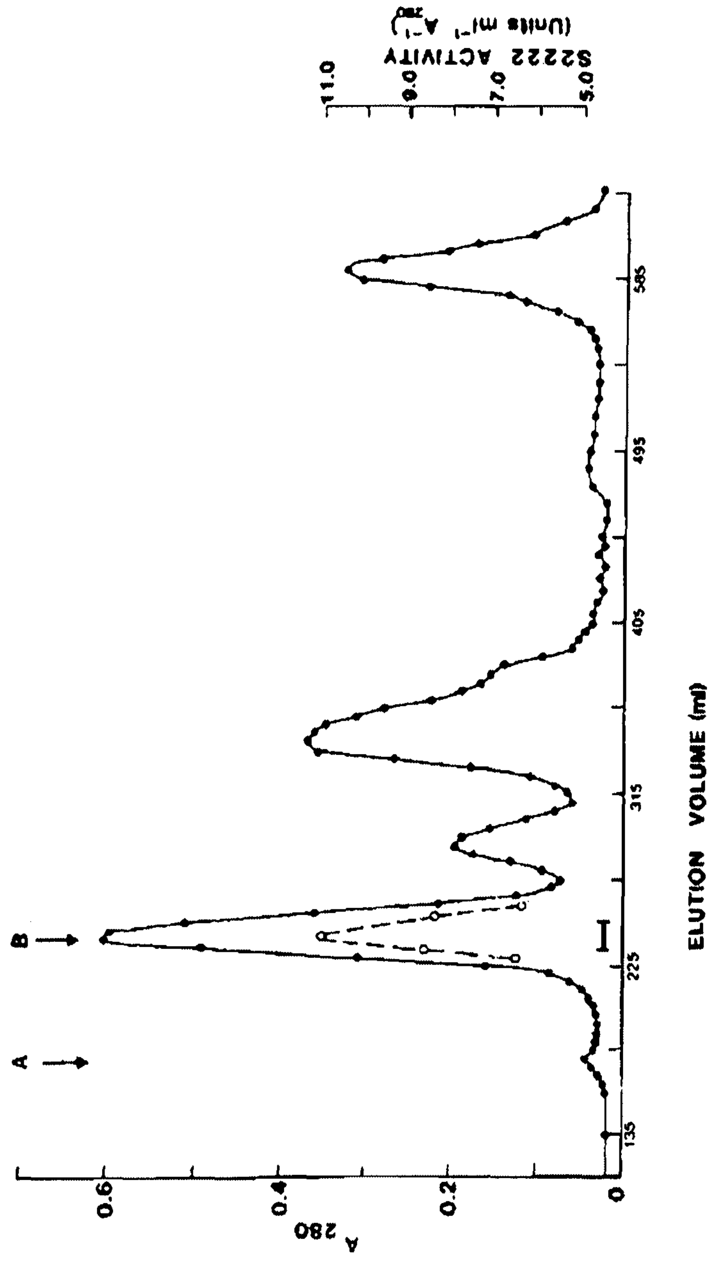
FIG. 3 shows the elution profile for chromatography of reconstituted *P. textilis* venom (50 mg in 5 mL) on a column (2.5×95 cm) of Sephacryl S-300 in 0.05 Tris-HCl buffer, pH 7.4; 4° C.; flow rate, 17 mL/h; $A_{280}$ (●); S-2222 specific activity (○); 'A' and 'B' represent the void volume (167 mL) and the elution volume of the peak of S-2222 activity (250 mL) respectively, as described in Example 1b.

Dried lyophilised *P. textilis* venom was reconstituted in 0.05 M Tris-HCl with a pH of 7.4. FIG. 3 provides an elution profile of the reconstituted *P. textilis* venom on a Sephracryl S-300 column in 0.05 M Tris-HCl buffer at pH 7.4. 'A' refers to void volume and 'B' denotes elution position (Ve) for PtPA which is 250 mL on this column and equates to an approximate molecular mass of 250 kDa. The absorbance at 280 nm ($A_{280}$) under 'B' represents 40% of the total $A_{280}$ units applied to the column. A similar gel filtration experiment with *O. scutellatus* venom showed that approximately 10% of the total $A_{280}$ loaded eluted in the 250 kDa peak (corresponding to the prothrombin activator).

Figure 4:
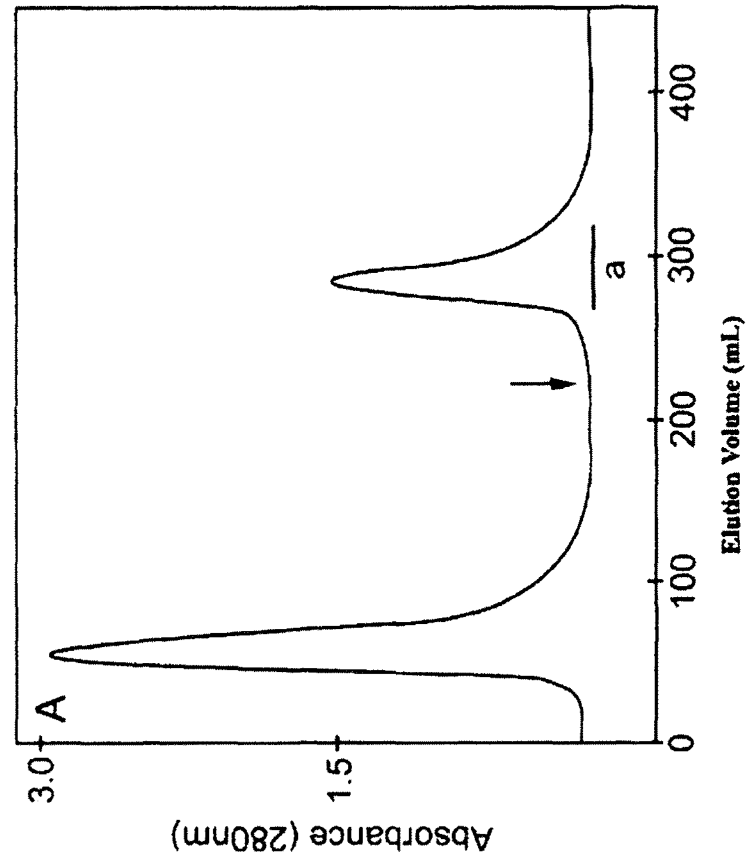
FIG. 4 shows the elution profile of *P. textilis* venom (1 g: 30 mL) using the Con A-Sepharose affinity chromatography method described in Example 1b. The arrow denotes the position of the application of 0.2 M methyl α-D-mannopyranoside to elute PtPA (labelled "a").
Figure 5B:
FIG. 5 shows the results of native PAGE at pH 8.6 of pooled fractions labelled "a" in FIG. 4 where lane A is 25 μg and lane B is 50 μg.
Figure 5A:
Figure 6:
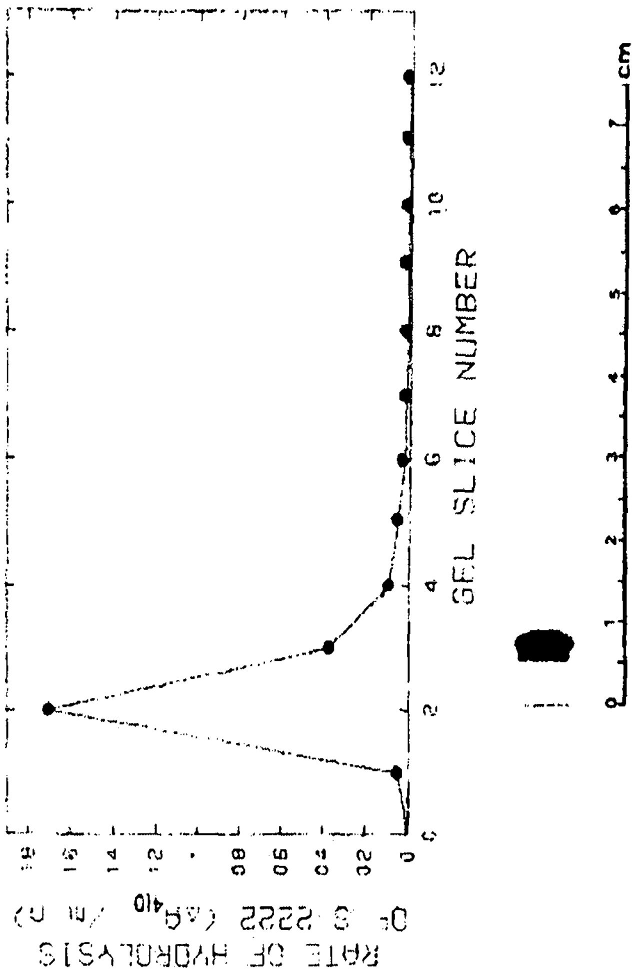
FIG. 6 shows the results of native PAGE at pH 8.6 of purified PtPA where the gel was stained with Coomassie blue and a duplicate gel was cut into 5 mm slices which were each equilibrated with 1 mL of S-2222 assay mixture to locate the activity, as described in Example 1b. The graph shows a plot of S-2222 activity (Y axis reads: "RATE OF HYDROLYSIS OF S-222 ($\Delta A_{410}$/min)) against gel slice number (X axis reads: "GEL SLICE NUMBER").

Affinity chromatography using Con A-Sepharose 4B in 0.05 M Tris-HCl, pH 7.4, was used to purify the prothrombin activator from the crude *P. textilis* and *O. scutellatus* venom. The eluting buffer was 0.2 M methyl α-D-mannopyranoside with 0.01% sodium azide. The elution profile on Con A-Sepharose for PtPA is shown in FIG. 4. The arrow indicates the application of eluting buffer and "a" indicates the fractions pooled to provide prothrombin activator. FIG. 5 shows the results of native PAGE at pH 8.6. Peak "a" from FIG. 4 showed a major protein band and a trace minor band at loadings of 25 μg (A) and 50 μg (B) per lane. The 250 kDa band was excised from the gel in a parallel experiment and shown to have Factor Xa-like activity against the chromogenic substrate S-2222, confirming its identification as PtPA (FIG. 6). A similar pattern of elution was obtained for OsPA.

Figure 7:
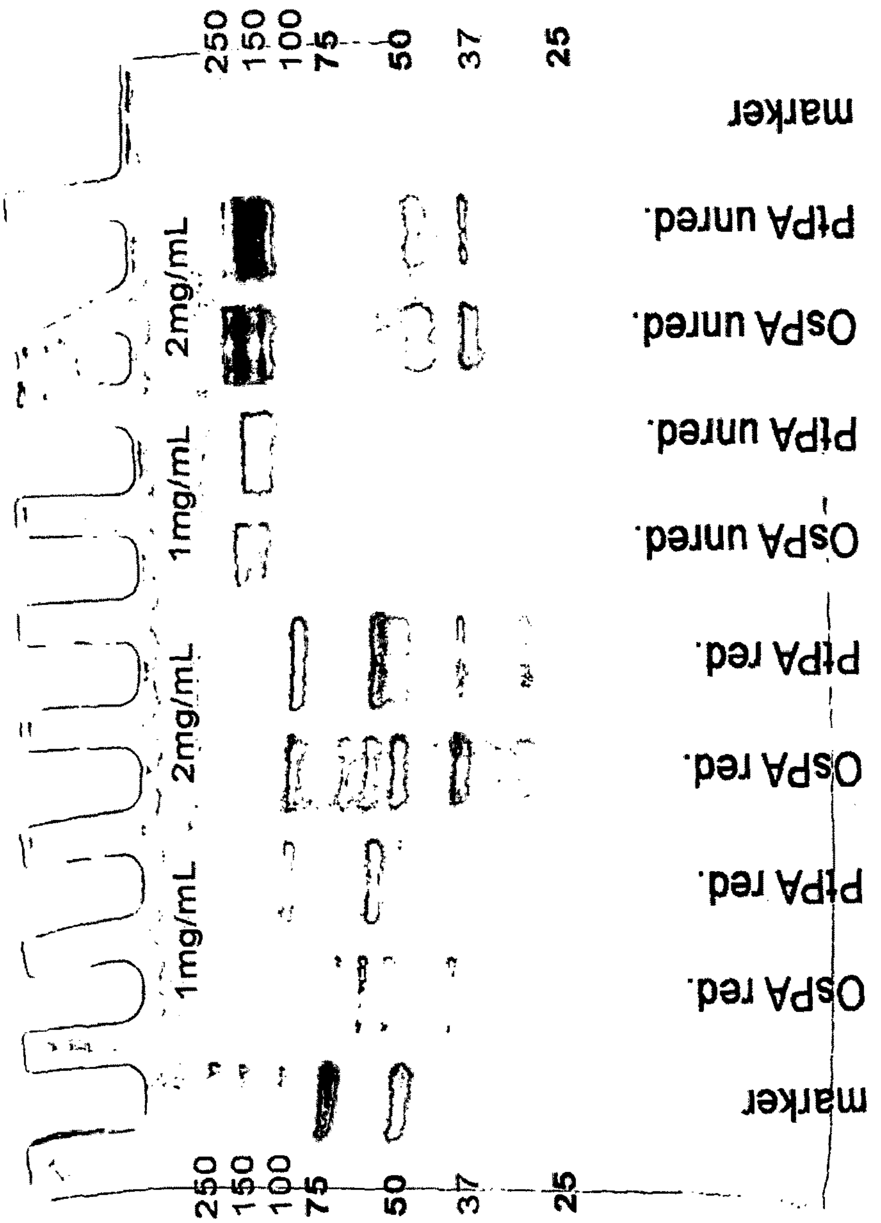
FIG. 7 shows the SDS-PAGE results of the affinity purified preparations of PtPA and OsPA under reducing and non-reducing conditions as described in Example 1b where the lanes are (from left to right): marker; OsPA red. (1 mg/mL); PtPA red. (1 mg/mL); OsPA red. (2 mg/mL); PtPA red. (2 mg/mL); OsPA unred. (1 mg/mL); PtPA unred. (1 mg/mL); OsPA unred. (2 mg/mL); PtPA unred. (2 mg/mL); marker; where "red." designates the components in the presence of β-mercaptoethanol (i.e. reduced) and "unred." designates the components in the absence of β-mercaptoethanol (i.e. unreduced).

PtPA and OsPA were characterised further by SDS-PAGE in the presence (designated "red") and absence ("unred") of β-mercaptoethanol (FIG. 7). It is evident that several bands are present for both PtPA and OsPA representing component polypeptide chains.

PtPA- and OsPA-containing preparations prepared in accordance with this method were used in all subsequent experiments, except where otherwise indicated.

Example 1c

Purification and Characterisation of Notecarin from *Notechis scutatus* Venom

Figure 8:
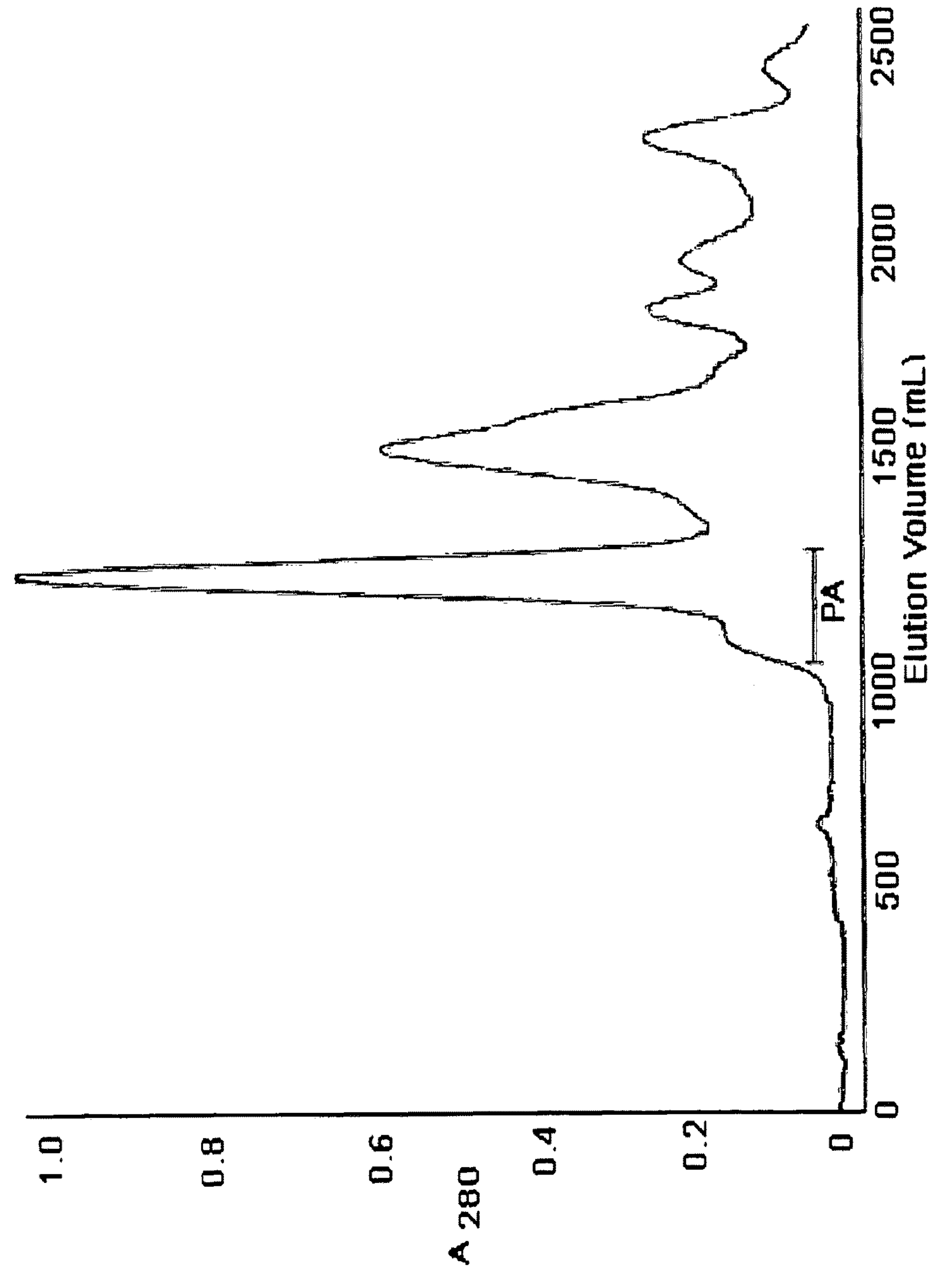
FIG. 8 shows the elution profile in the isolation of notecarin from *N. scutatus* venom using Sephacryl S-300 chromatography as described in Example 1c. The pooled fractions of notecarin are indicated by the bar labelled "PA".

The group D prothrombin activator termed notecarin was purified from the venom of *Notechis scutatus*, using Sephacryl S-300 gel filtration chromatography (5.0×9.5 cm) in a similar manner to that described in Example 1b above for the group C prothrombin activators. The elution profile is shown in FIG. 8, where "PA" refers to the fraction containing notecarin.

Notecarin-containing preparations prepared in accordance with this method were used in all subsequent experiments, except where otherwise indicated.

Example 1d

Further Characterisation of Carinactivase-1, Carinactivase-2, Ecarin, PtPA, OsPA, and Notecarin The prothrombin activator preparations prepared in Examples 1a, 1b, and 1c were further characterised as follows.

Figure 9:
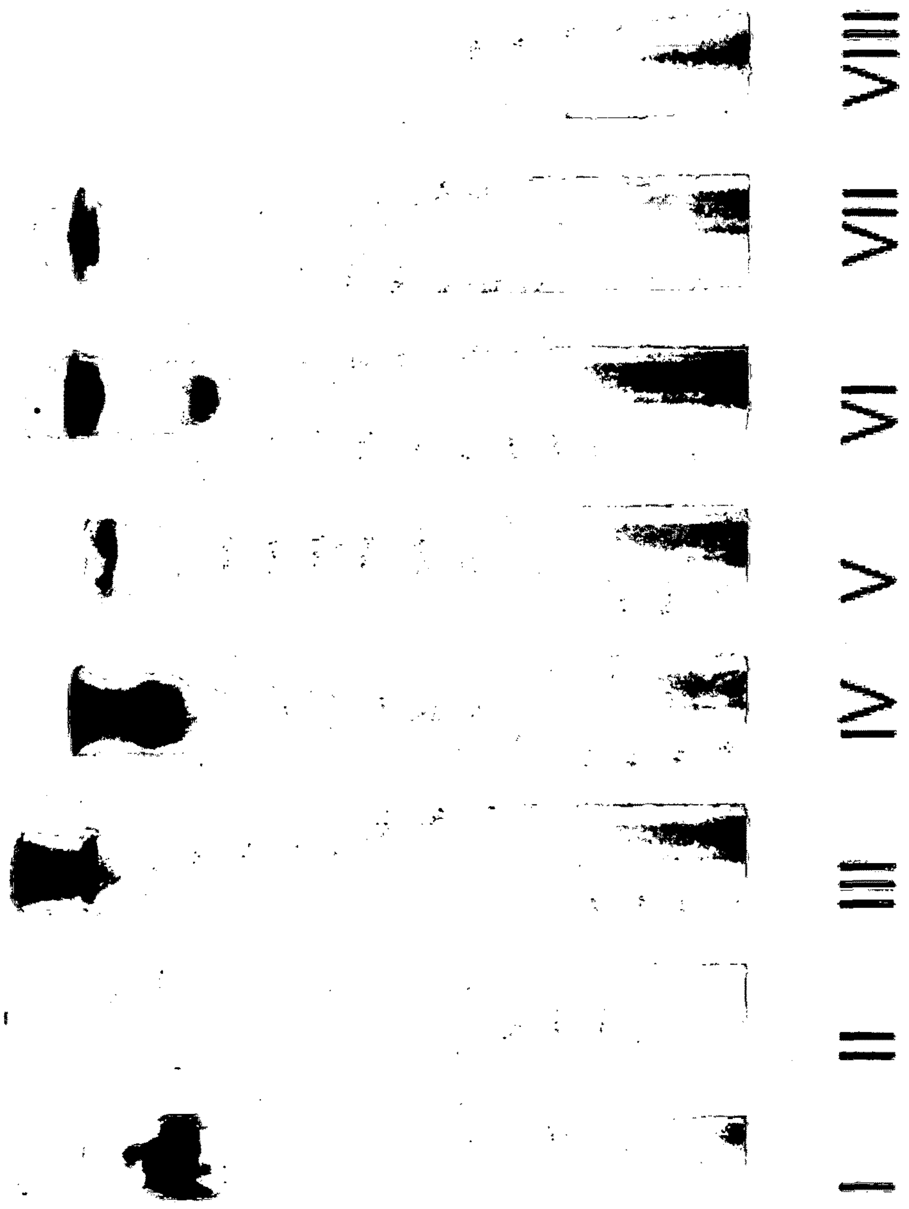
FIG. 9 shows the results of native PAGE at pH 8.9 of the prothrombin activators: carinactivase-1, carinactivase-2, ecarin, PtPA, OsPA, and notecarin, prepared in Examples 1a, 1b, and 1c. In this Figure, the labels represent the following: (I) prothrombin; (II) alpha-thrombin; (III) ecarin; (IV) carinactivase-1; (V) carinactivase-2; (VI) PtPA; (VII) OsPA; (VIII) notecarin (20 μg of each prothrombin activator was loaded).

Native PAGE of prothrombin, alpha-thrombin, and the prothrombin activators at pH 8.9 was performed and the results are shown in FIG. 9, wherein the labels are as follows: (I) prothrombin; (II) alpha-thrombin; (III) ecarin; (IV) carinactivase-1; (V) carinactivase-2; (VI) PtPA; (VII) OsPA; (VIII) notecarin (20 μg of each prothrombin activator was loaded).

Figure 10:
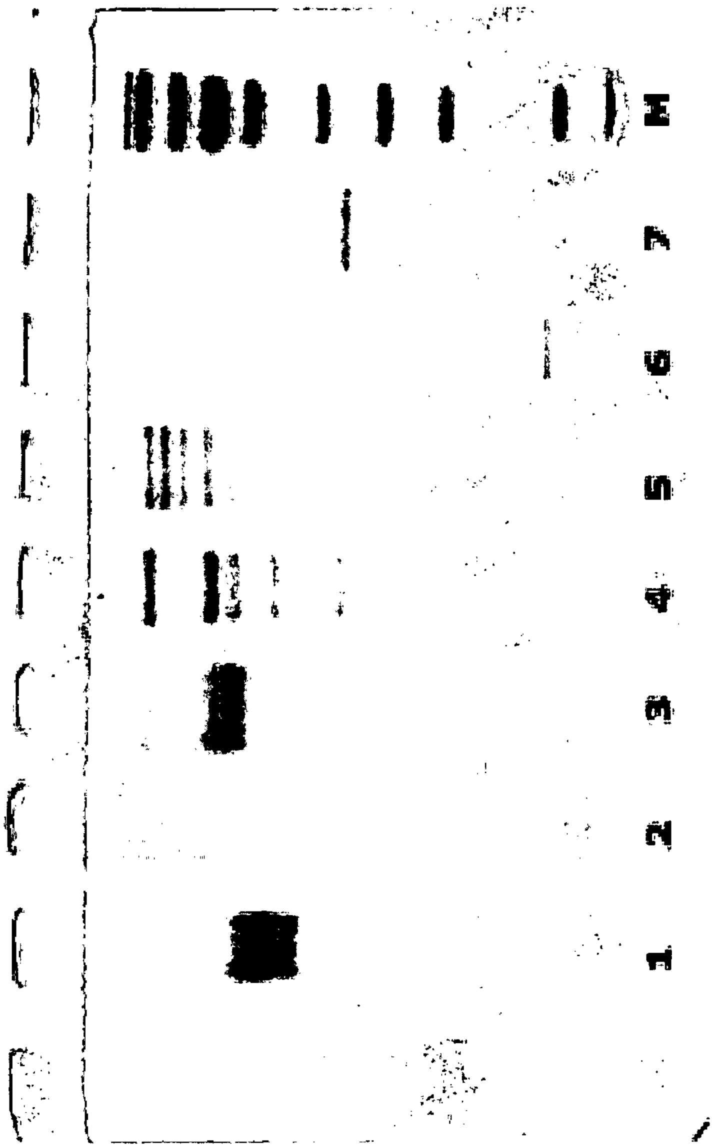
FIG. 10 shows SDS-PAGE characterisation of the prothrombin activators prepared in Examples 1a, 1b, and 1c, in the presence of β-mercaptoethanol, where the lanes are as follows: (1) carinactivase-1; (2) carinactivase-2; (3) ecarin; (4) PtPA; (5) OsPA; (6) notecarin; (7) thrombin; and (M) molecular weight marker.
Figure 11:
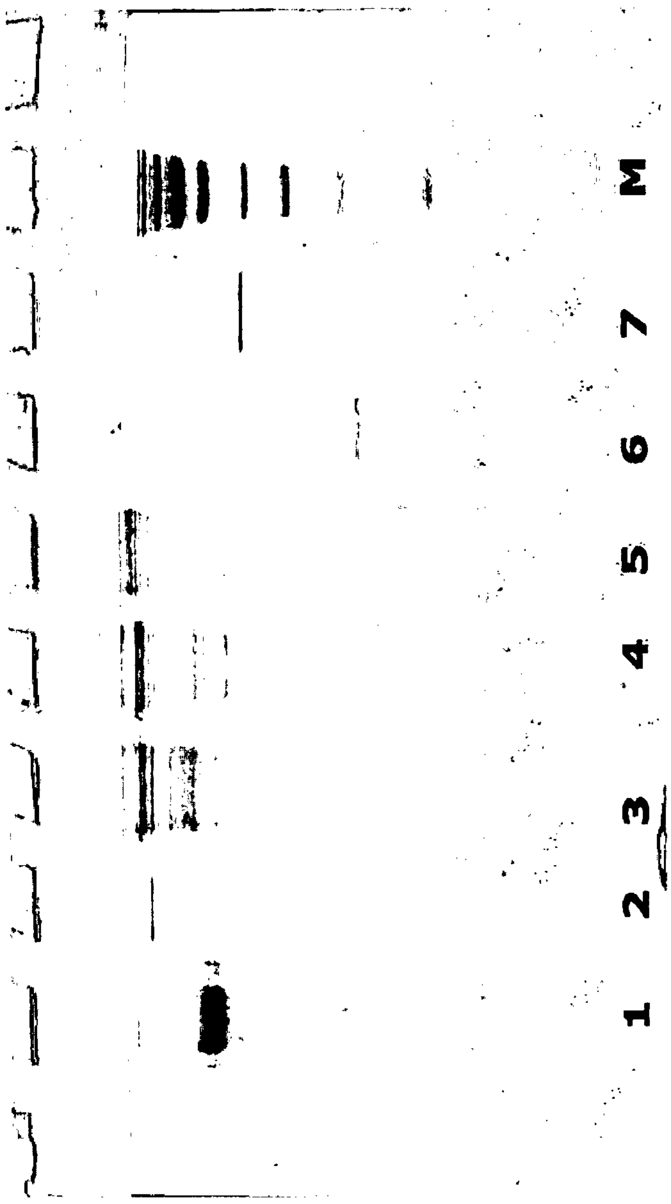
FIG. 11 shows SDS-PAGE characterisation of the prothrombin activators prepared in Examples 1a, 1b, and 1c, in the absence of β-mercaptoethanol, where the lanes are as follows: (1) carinactivase-1; (2) carinactivase-2; (3) ecarin; (4) PtPA; (5) OsPA; (6) notecarin; (7) thrombin; and (M) molecular weight marker.

The prothrombin activator preparations were also characterised further by SDS-PAGE in the presence (FIG. 10) and absence (FIG. 11) of β-mercaptoethanol. In each Figure, the lanes are as follows: (1) carinactivase-1; (2) carinactivase-2; (3) ecarin; (4) PtPA; (5) OsPA; (6) notecarin; (7) thrombin; and (M) molecular weight marker. The PtPA-containing sample in lane (4) and the OsPA-containing sample in lane (5) were the same as those used for the results shown in FIG. 7.

The SDS-PAGE shows that in each case the protein bands in the expected regions are present but also that the preparations are not homogeneous. The protein concentrations of the prothrombin activator preparations were calculated using the relationship that 1 mg/mL solution had an $A_{280}$ of 1, and the molar concentrations were calculated by dividing the protein concentrations by the literature values for the molecular weights. The molar concentrations quoted in subsequent experiments described herein that used these preparations are therefore upper estimates because the preparations are not homogenous.

Example 2

Prothrombin to Thrombin Conversion by Prothrombin Activators

Example 2a

Five-minute Incubation Period

The aim of this experiment was to determine how much prothrombin was converted to thrombin by six different prothrombin activators from snake venom prepared in Example 1, namely preparations containing ecarin, carinactivase-1, carinactivase-2, PtPA, OsPA, and notecarin, after incubation for five minutes at room temperature.

The experiment was performed as follows.

20 mM HEPES Buffer pH 7.4, 150 mM NaCl, 5 mM $CaCl_2$, 0.05% surfactant p20 was prepared.

A solution of human prothrombin in 0.05 M Tris-HCl pH 7.4 was prepared by diluting a stock solution of purified human prothrombin (17.8 mg/mL; #HCP-0200; HTI, USA) 1/50 with distilled water to provide a working solution of 0.36 mg/mL, giving a final concentration in the tube of 72 μg/mL or 0.99 μM. For the gel loading the 0.36 mg/L prothrombin solution was used.

The stock solutions of the prothrombin activator preparations prepared as described earlier were diluted to provide final concentrations of 6 nM.

Stock alpha-thrombin (10 mg/mL, #HCT-0020; HTI, USA) was diluted (1/30) with distilled water containing 0.01% Tween 20 to provide a working thrombin solution of 0.33 mg/L which was used to load on the SDS-PAGE gels.

Samples were then prepared with the volumes shown in Table 3, and incubated for five minutes at room temperature.

TABLE 3

| Volumes in each sample for incubation | | | | | | | | |
|---|---|---|---|---|---|---|---|---|
| Sample | 1 | 2 | 3 | 4 | 5 | 6 | 7 | 8 |
| HEPES buffer (μL) | 80 | 60 | 60 | 60 | 60 | 60 | 60 | 80 |
| Prothrombin (μL) | 20 | 20 | 20 | 20 | 20 | 20 | 20 | 0 |
| Prothrombin activator | 0 | 50 | 50 | 50 | 50 | 50 | 50 | 0 |
| α-thrombin (μL) | 0 | 0 | 0 | 0 | 0 | 0 | 0 | 20 |
| Total volume (μL) | 100 | 100 | 100 | 100 | 100 | 100 | 100 | 100 |

The prothrombin activators in the above samples were as follows: (1) no prothrombin activator (human prothrombin alone in buffer); (2) carinactivase-1; (3) carinactivase-2; (4) ecarin; (5) PtPA; (6) OsPA; (7) notecarin; and (8) highly purified α-thrombin (no prothrombin activator).

SDS PAGE gels used were nUView Precast Mini Gels (#NB10-420, 4-20%) with running buffer Tris-Glycine (#BG-143). Sample buffer (#BG-145) (NuSEP, Australia) was obtained (i.e., non-reducing sample buffer), and a reducing sample buffer of the sample buffer with 5%β-mercaptoethanol (#44143, BDH, UK) was prepared.

After the five minute incubation, a 40 μL aliquot from each sample was transferred into equivalent volume of non-reducing sample buffer or reducing sample buffer. The samples were then incubated for 10 minutes at 100° C. in a heating block. An aliquot of 25 μL of each sample and 12 μL of the pre-stained molecular weight marker (#SM0671 Page Ruler Prestained Protein Ladder, Fermentas, Hanover, Md., USA) were loaded on the gels. The gels were run at 100 V using a Mini-Protein II Cell PAGE apparatus (Bio-Rad) until the dye-front reached the bottom of the gel. The gels were stained with Commassie Brilliant Blue G (#B-0770, Sigma) (0.25% w/v Commassie Brilliant Blue G, 45% methanol, 10% acetic acid), and excess stain was removed by destainer (45% methanol, 45% water and 10% acetic acid).

Figure 12:
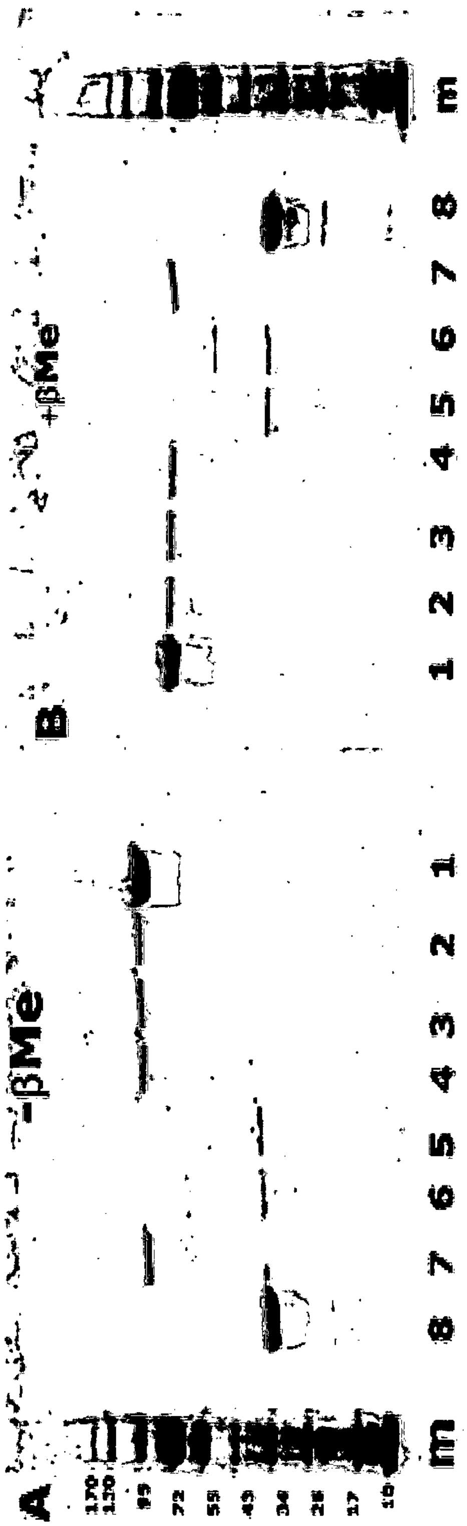

The results are shown in FIG. 12, where FIG. 12A shows the SDS-PAGE gel using the sample buffer without β-mercaptoethanol (non-reducing sample buffer) and FIG. 12B shows the SDS-PAGE gel using the sample buffer containing 5% β-mercaptoethanol (reducing sample buffer). The sample numbers as used in Table 3 above are the same as the lane numbers in the gels in FIG. 12, and "m" represents the molecular weight marker.

This experiment showed complete conversion of prothrombin to thrombin in five minutes by PtPA and OsPA, but very little conversion by the other prothrombin activator preparations under these conditions.

Example 2b

Time Course for Conversion by PtPA and by Notecarin

A time course for conversion of prothrombin (14 μM) to thrombin by PtPA (6 nM) and by notecarin (6 nM) was determined, and the SDS-page gel results are shown in FIG. 13, where each lane is numbered according to the incubation time as shown in Table 4 below, using methodology similar to Example 2a.

TABLE 4

| Incubation time for each lane shown in FIG. 13. | |
|---|---|
| Lane | Time (min) |
| 1 | 0 |
| 2 | 0.5 |
| 3 | 1 |
| 4 | 2 |
| 5 | 4 |
| 6 | 6 |
| 7 | 8 |
| 8 | 10 |
| 9 | 15 |
| 10 | 20 |
| 11 | 25 |
| 12 | 30 |
| 13 | 45 |
| 14 | 150 |

These results show that PtPA is more efficient than notecarin in converting prothrombin to thrombin, but that notecarin still gave complete cleavage of prothrombin after longer reaction times.

Example 2c

N-terminal Sequencing of Selected Bands from the Example 2b Results

Figure 14:
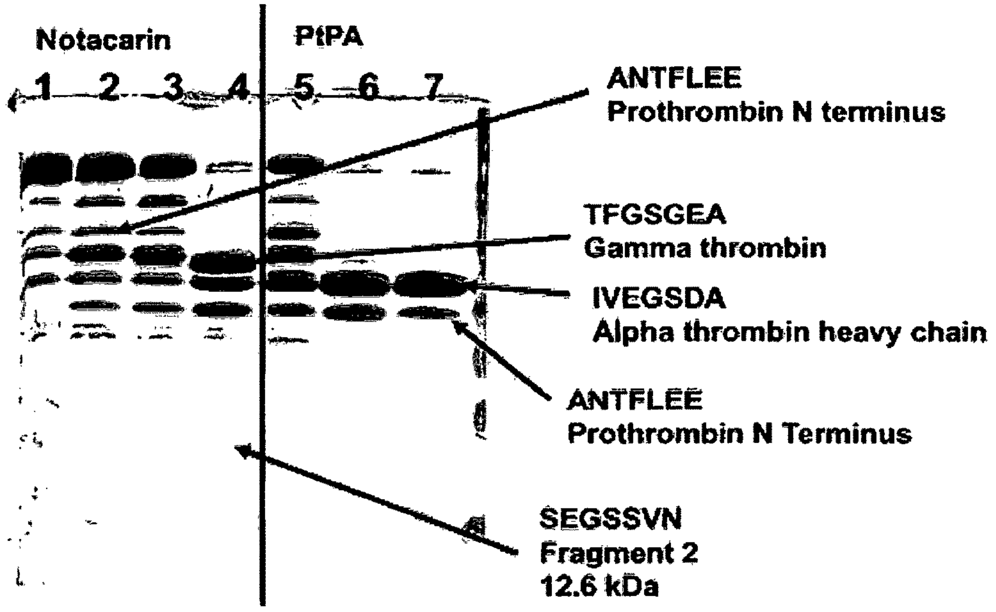
FIG. 14 is an annotated image of part of the SDS-PAGE results in FIG. 13, where selected bands were eluted and subjected to N-terminal sequencing using mass-spectrometry analysis in order to assign to specific molecular domains.

Selected bands from the SDS-PAGE results in Example 2b, produced by the action of PtPA and notecarin on prothrombin (i.e., the fragmentation of prothrombin to thrombin), were eluted and subjected to N-terminal sequencing using mass-spectrometry analysis in order to assign to specific molecular domains. These results are shown in FIG. 14. The SDS-PAGE N-terminal sequencing confirmed conversion of prothrombin to alpha-thrombin by PtPA and notecarin, as shown by the major band with N-terminal sequence IVEGSDA which corresponds to the alpha-thrombin heavy chain.

Example 2d

Estimation of Thrombin Generated by Kinetic Analysis

This experiment was designed to determine the amount of thrombin generated from prothrombin by each of the prothrombin activators: ecarin; carinactivase-1; carinactivase-2; PtPA; OsPA; and notecarin, at 0.6 nM concentration, by way of kinetic analysis.

The absorbance of the p-nitroaniline (pNA) generated from the chromogenic thrombin substrate S-2238 was continuously monitored at 405 nm, for samples containing different concentrations of thrombin and for samples containing one of the prothrombin activators listed above.

Figure 15:
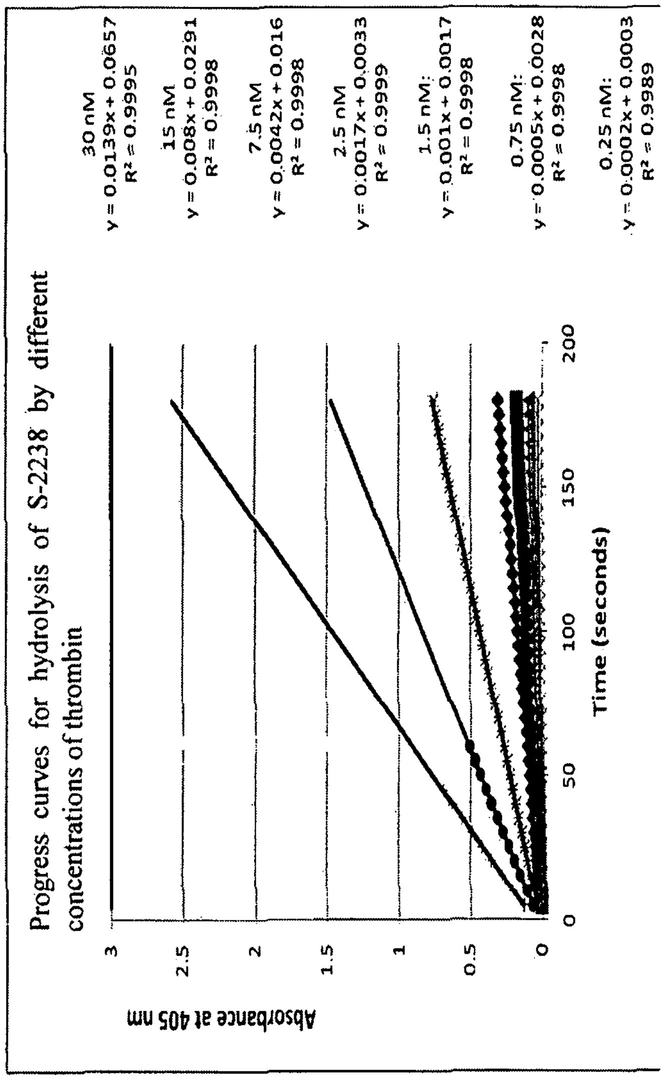

For the thrombin study, each cuvette contained 50 μL of S-2238 substrate (134 μM), 50 μL of thrombin at different concentrations (range of 0.25-30 nM) and 900 μL of HEPES buffer. FIG. 15 shows progress curves for S-2238 hydrolysis by thrombin used to generate the standard curve shown in FIG. 16.

For the study of the prothrombin activators, each cuvette contained 50 μL of prothrombin (247 nM), 10 μL (0.6 nM) of the prothrombin activator (ecarin, carinactivase-1, carinactivase-2, PtPA, OsPA, or notecarin), 1004 (267 μM) S-2238 substrate and 840 μL of HEPES buffer. The reaction slope for each prothrombin activator was determined at 155 seconds and the amount of thrombin generated at 155 seconds read from the standard curve in FIG. 16, as shown in FIG. 17 and Table 5.

TABLE 5

Amount of thrombin generated by 0.6 nM of the prothrombin activators over 155 seconds

Figure 16:
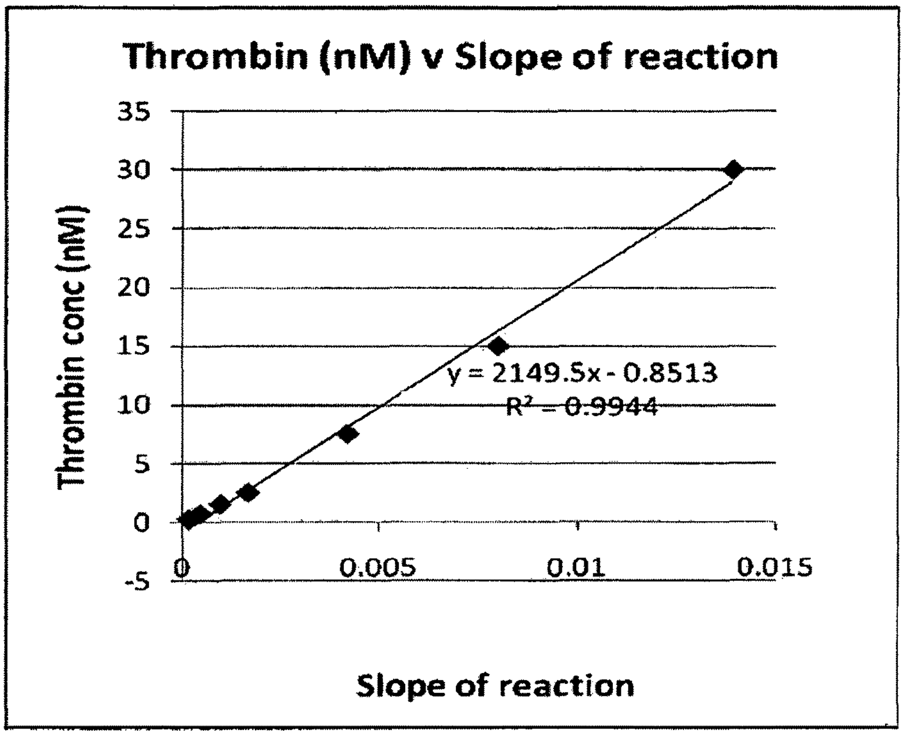
FIG. 16 is a graph of the standard curve derived from the results in FIG. 15, specifically the slopes of the equations for each reaction up to 180 seconds in FIG. 15 were plotted against the thrombin concentration to provide the linear regression equation shown in FIG. 16.
Figure 17:
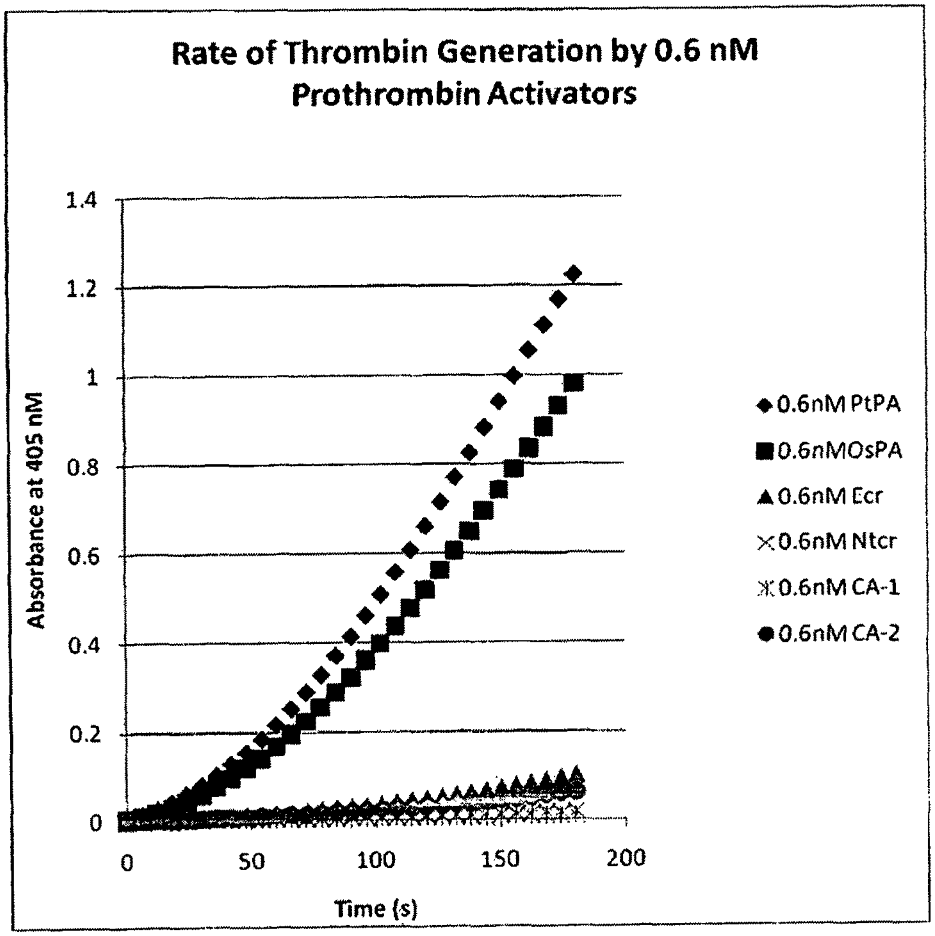
FIG. 17 is a graph showing the rate of thrombin generation by 0.6 nM concentrations of the prothrombin activators: PtPA, OsPA, ecarin (Ecr), notecarin (Ntcr), carinactivase-1 (CA-1), and carinactivase-2 (CA-2) over 180 seconds as described in Example 2d.

| Prothrombin activator (0.6 nM) | Calculated slope from standard curve in FIG. 16 | Amount of thrombin generated (nM) at 155 seconds |
|---|---|---|
| Ecarin | 0.00085 | 1.74 |
| Carinactivase-1 | 0.00007 | 0.07 |
| Carinactivase-2 | 0.0005 | 0.99 |
| PtPA | 0.0094 | 20.12 |
| OsPA | 0.0077 | 16.47 |
| Notecarin | 0.0001 | 0.13 |

All prothrombin activator preparations produced thrombin as expected, but again, the PtPA and OsPA were the most efficient.

These results indicate the group C prothrombin activators (PtPA and OsPA) were the most efficient enzymes in hydrolysing prothrombin to thrombin. This was confirmed by the amount of thrombin formed that was able to hydrolyse the S-2238 substrate to form the colour product pNA. The next most efficient prothrombin activator was ecarin which showed it hydrolysed ~4% of the S-2238, followed by carinactivase-2 (2.5%) then carinactivase-1 and lastly notecarin (<1%) being the least efficient of the prothrombin activators in this purified system. Group D prothrombin activators (e.g., notecarin) require Factor Va, calcium and phospholipid which were absence in the system but all of which are present in blood.

Example 2e

Kinetic Studies on Comparative Rates of Thrombin Generation from Thrombin by Prothrombin Activators This experiment was designed to determine the rate of thrombin formation that is generated from pure prothrombin by each of the prothrombin activator preparations.

Each cuvette contained 50 μL of prothrombin (247 nM), 10 μL of the different prothrombin activators, 100 μL (267 μM) of S-2238 substrate and 840 μL, of HEPES buffer.

The progress curves for S-2238 hydrolysis (thrombin activity) for each prothrombin activator was determined at 3-5 different concentrations ranging from 0.006-6 nM. The data was analysed using DynaFit 4.04.64 Enzyme Kinetic Data Analysis Software (BioKin Ltd, Watertown, Mass., USA) (Kuzmic, P., 1996).

Figure 18:
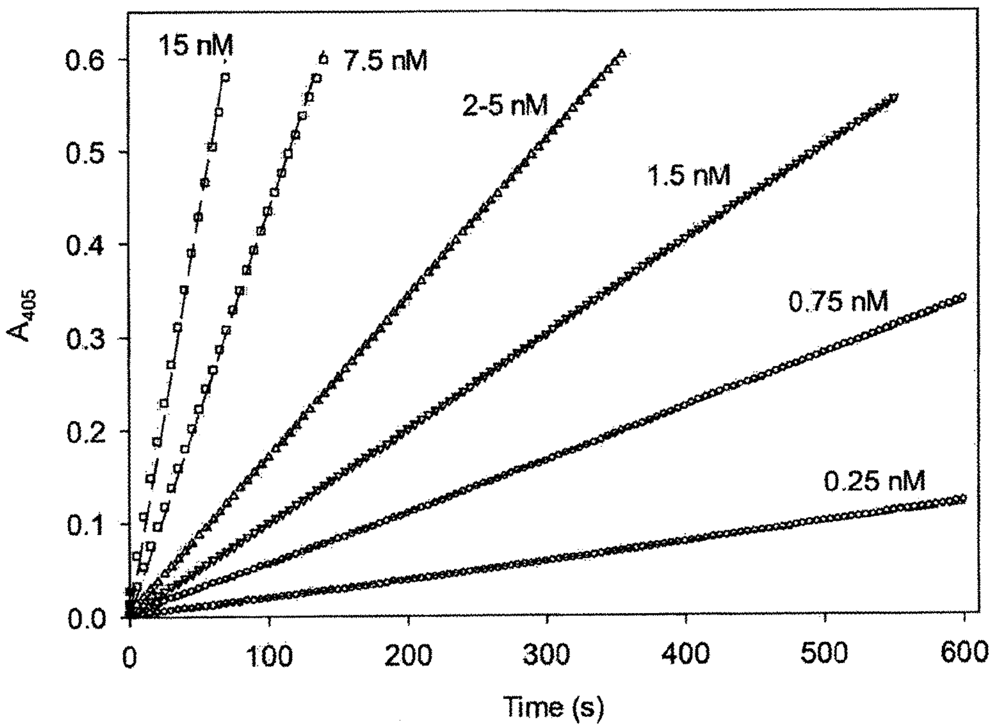
FIG. 18 shows the curve fitting analysis of the thrombin catalysed hydrolysis of S-2238 as described in Example 2e. Thrombin concentrations are indicated on progress curves.

The thrombin catalysed hydrolysis of S-2238 curve fitting analysis is shown in FIG. 18.

Kinetic parameters were then calculated as follows:

Model: $B \rightarrow B + \text{pNA} + P$ (a pseudo first order rate constant for the thrombin hydrolysis of *S*-2238), where:

B=thrombin;

pNA=p-nitroaniline;

P=inhibition product; and

S-2238 is in excess and therefore not included in the reaction.

Differential equations as follows:

$$d[B]/dt = -kb[B] + kb[B];$$

$$d[\text{pNA}]/dt = +kb[B]; \text{ and}$$

$$d[P]/dt = +kb[B].$$

Table 6 shows the estimated kinetic parameters for thrombin.

TABLE 6

Estimated kinetic parameters for thrombin

| Units | Parameter | Initial | Fit | CV % |
|---|---|---|---|---|
| $s^{-1}$ | kb | 61.3 (Sonder, et al., 1986) | 66.2 | 0.4 |

Estimation of rate constant for prothrombin activators:

Model:

$A + Z \rightarrow A + B{:}ka$ (second order rate constant for activation of prothrombin);

$B \rightarrow B + \text{pNA} + P{:}kb$; where

A=prothrombin activator.

Differential equations as follows:

$$d[A]/dt = -ka[A][Z] + ka[A][Z];$$

$$d[Z]/dt = -ka[A][Z];$$

$$d[B]/dt = +ka[A][Z] - kb[B] + kb[B];$$

$$d[\text{pNA}]/dt = +kb[B]; \text{ and}$$

$$d[P]/dt = +kb[B].$$

The kinetic parameters for PtPA were estimated and are shown in Table 7.

TABLE 7

| Estimated kinetic parameters for PtPA | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 6.722e−4 | 1.8 |
| $s^{-1}$ $M^{-1}$ | ka | | $6.72 \times 10^5$ | 1.8 |

The rate of thrombin generation:

$=ka\ (s^{-1}M^{-1}) \times 60\ (s) \times 10^{-6}$

=40.3 μM thrombin/min/M prothrombin/M activator

=40.3 nmol thrombin/mL/min/μmol prothrombin/μmol activator

Figure 19:
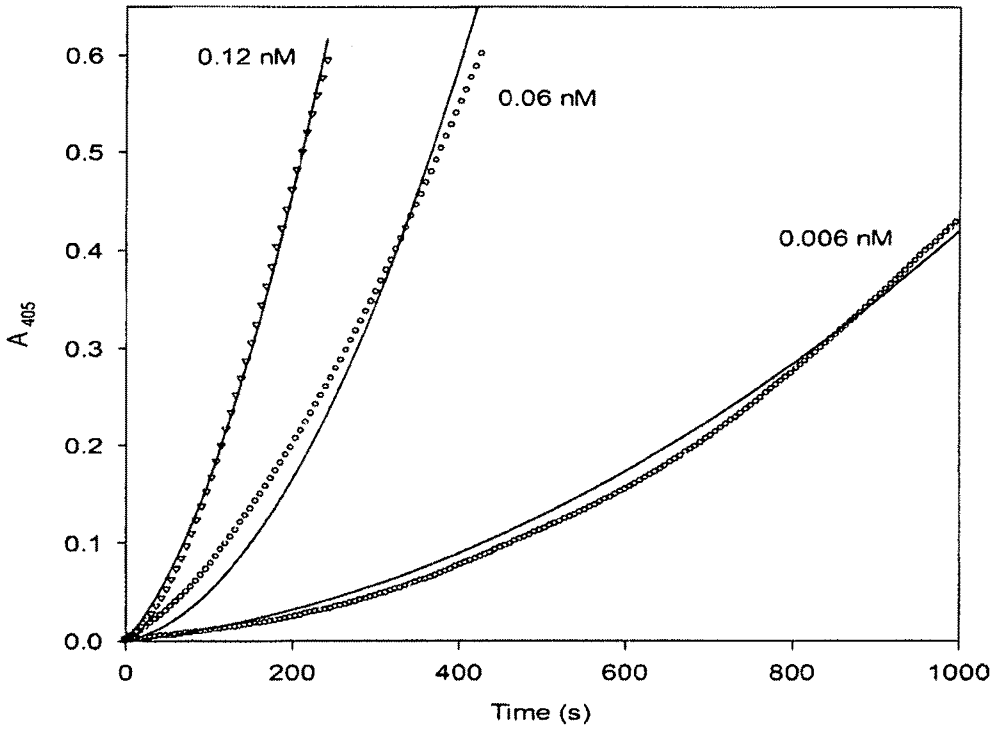
FIG. 19 plots the PtPA activation of prothrombin at the concentrations of PtPA as described in Example 2e.

FIG. 19 plots the PtPA activation of prothrombin, demonstrating the reaction rates of different PtPA concentrations (0.006-0.12 nM) with prothrombin and then the thrombin generated with the chromogenic substrate S-2238, and the best fit curve for PtPA activation of prothrombin. The dotted lines are the experimental results and the continuous lines are those calculated as best fit. These experimental and calculated progress curves show good agreement.

The kinetic parameters for OsPA were then estimated and are shown in Table 8.

TABLE 8

| Estimated kinetic parameters for OsPA | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 7.325e−4 | 3.3 |
| $s^{-1}$ $M^{-1}$ | ka | | $7.33 \times 10^5$ | 3.3 |

The rate of thrombin generation:

=44.0 nmol thrombin/mL/min/μmol prothrombin/μmol activator

Figure 20:
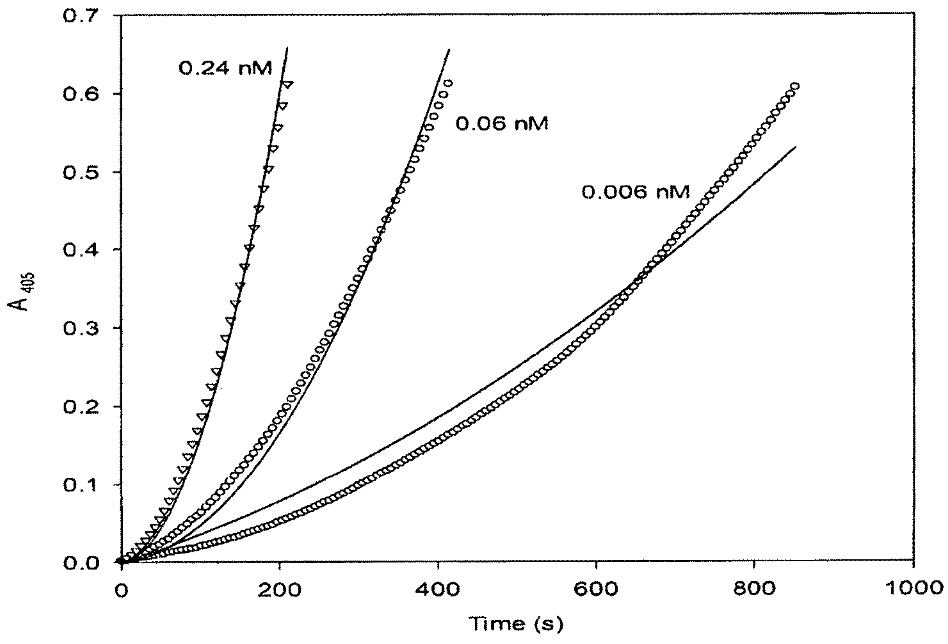
FIG. 20 plots the OsPA activation of prothrombin at the concentrations of OsPA at the concentrations of OsPA as described in Example 2e.

FIG. 20 plots the OsPA activation of prothrombin, demonstrating the reaction rates of different OsPA concentrations (0.006-0.24 nM) with prothrombin and then the thrombin generated with the chromogenic substrate S-2238, and the best fit curve for OsPA activation of prothrombin. The dotted lines are the experimental results and the continuous lines are those calculated as best fit. These experimental and calculated progress curves show good agreement.

The kinetic parameters for ecarin were then estimated and are shown in Table 9.

TABLE 9

| Estimated kinetic parameters for ecarin | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 4.607e−005 | 1.2 |
| $s^{-1}$ $M^{-1}$ | ka | | $4.61 \times 10^4$ | 1.2 |

The rate of thrombin generation:

=2.76 μM thrombin/min/μM prothrombin/μM activator

=2.76 nmol thrombin/mL/min/μmol prothrombin/μmol activator

Figure 21:
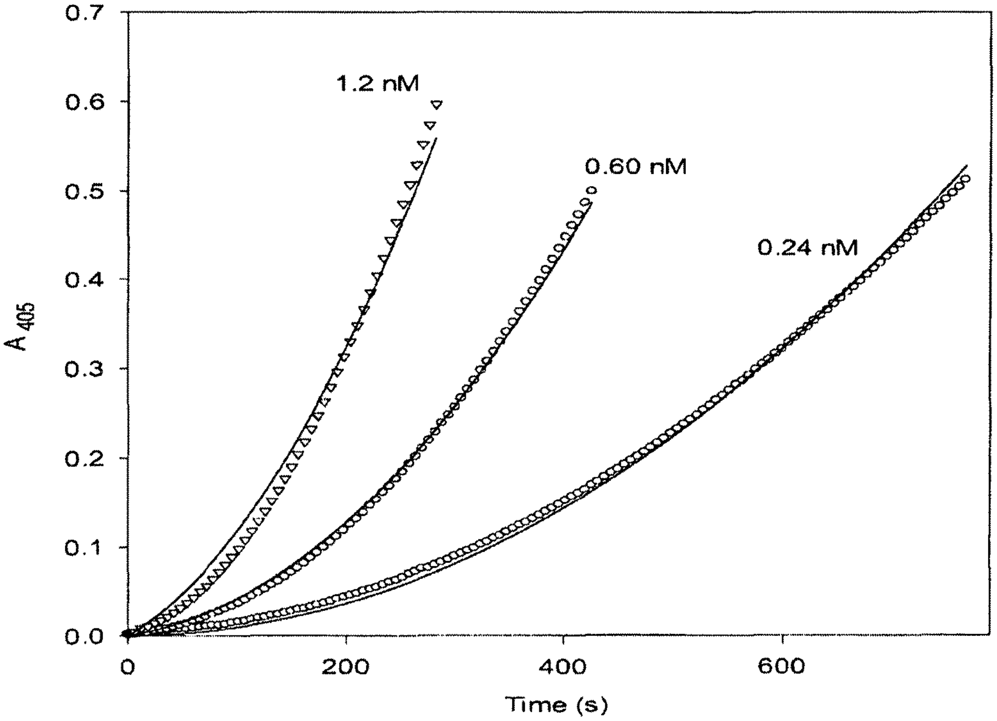
FIG. 21 plots the ecarin activation of prothrombin at the concentrations of ecarin as described in Example 2e.

FIG. 21 plots the ecarin activation of prothrombin, demonstrating the reaction rates of different ecarin concentrations (0.24~1.2 nM) with prothrombin and then the thrombin generated with the chromogenic substrate S-2238, and the best fit curve for ecarin activation of prothrombin. The dotted lines are the experimental results and the continuous lines are those calculated as best fit. These experimental and calculated progress curves show good agreement.

The kinetic parameters for carinactivase-1 were then estimated and are shown in Table 10.

TABLE 10

| Estimated kinetic parameters for carinactivase-1 | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 3.944e−006 | 0.3 |
| $s^{-1}$ $M^{-1}$ | ka | | $3.94 \times 10^3$ | 0.3 |

The rate of thrombin generation:

=0.24 μM thrombin/min/μM prothrombin/μM activator

=0.24 nmol thrombin/mL/min/μmol prothrombin/μmol activator

Figure 22:
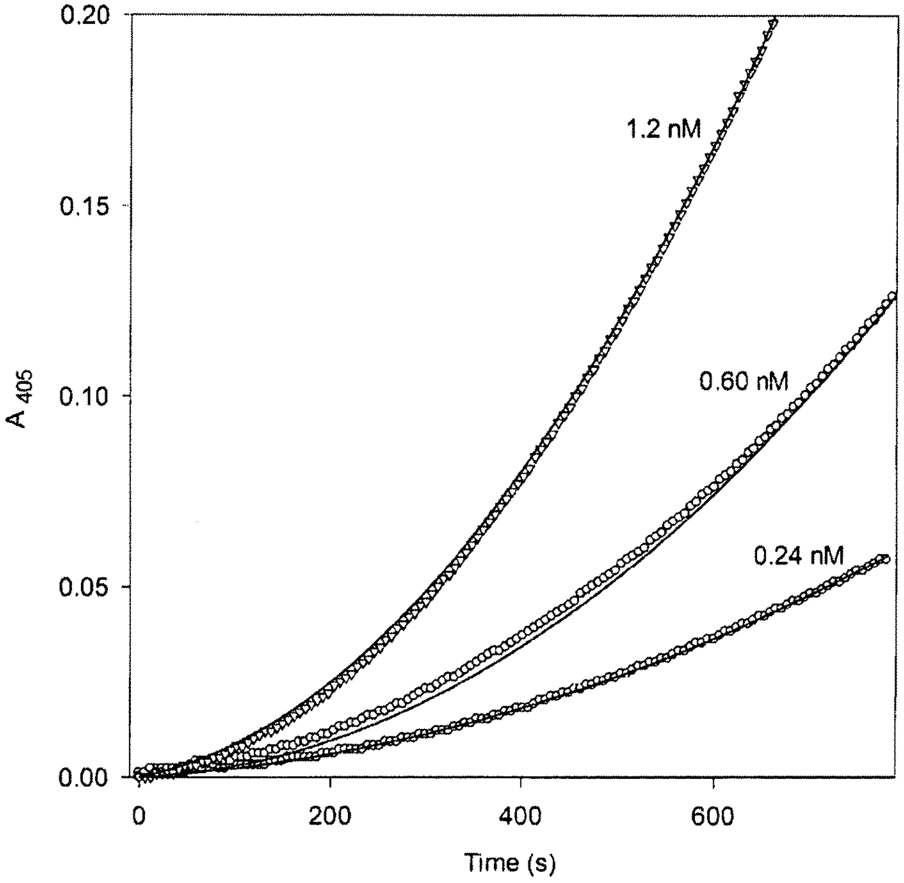
FIG. 22 plots the carinactivase-1 activation of prothrombin at the concentrations of carinactivase-1 as described in Example 2e.

FIG. 22 plots the carinactivase-1 activation of prothrombin, demonstrating the reaction rates of different carinactivase-1 concentrations (0.24-1.2 nM) with prothrombin and then the thrombin generated with the chromogenic substrate S-2238, and the best fit curve for carinactivase-1 activation of prothrombin. The dotted lines are the experimental results and the continuous lines are those calculated as best fit. These experimental and calculated progress curves show good agreement.

The kinetic parameters for carinactivase-2 were then estimated and are shown in Table 11.

TABLE 11

| Estimated kinetic parameters for carinactivase-2 | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 3.183e−005 | 1.8 |
| $s^{-1}$ $M^{-1}$ | ka | | $3.18 \times 10^4$ | 1.8 |

The rate of thrombin generation:

=1.91 μM thrombin/min/μM prothrombin/μM activator

=1.91 nmol thrombin/mL/min/μmol prothrombin/μmol activator

Figure 23:
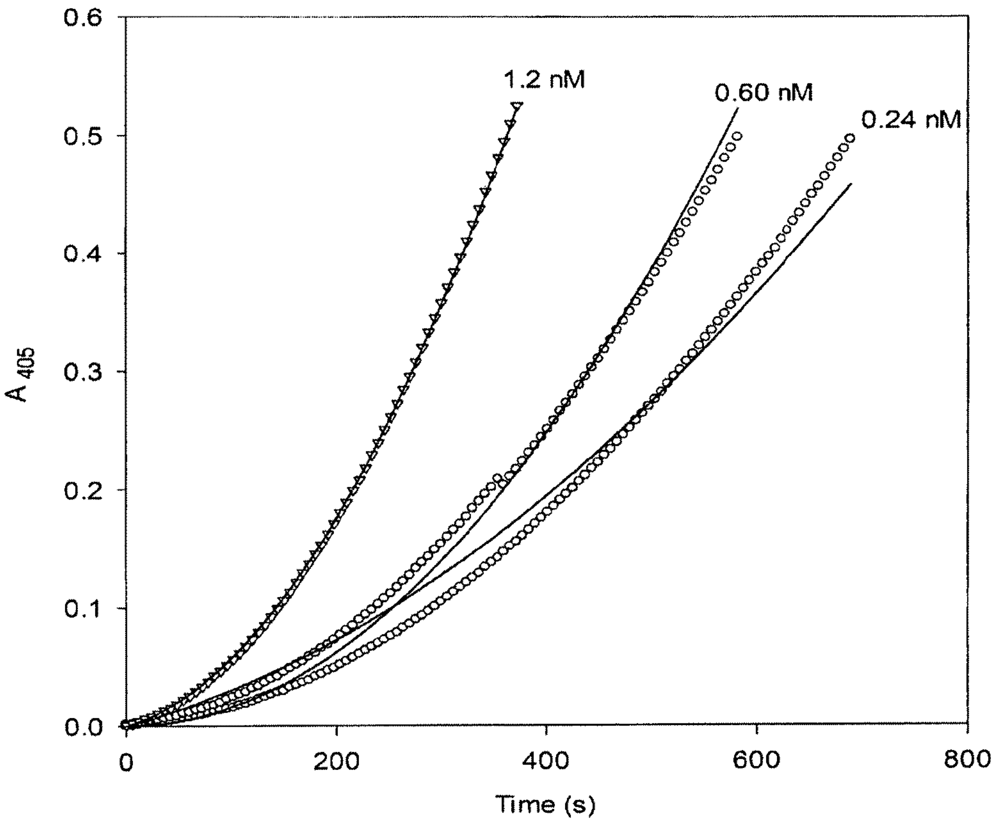
FIG. 23 plots the carinactivase-2 activation of prothrombin at the concentrations of carinactivase-2 as described in Example 2e.

FIG. 23 plots the carinactivase-2 activation of prothrombin, demonstrating the reaction rates of different carinactivase-2 concentrations (0.24-1.2 nM) with prothrombin and then the thrombin generated with the chromogenic substrate S-2238, and the best fit curve for carinactivase-2 activation of prothrombin. The dotted lines are the experimental results and the continuous lines are those calculated as best fit. These experimental and calculated progress curves show good agreement.

The kinetic parameters for notecarin were then estimated and are shown in Table 12.

TABLE 12

| Estimated kinetic parameters for notecarin | | | | |
|---|---|---|---|---|
| Units | Parameter | Initial | Fit | CV % |
| $s^{-1}$ | kb | | 66.2 | |
| $s^{-1}$ $nM^{-1}$ | ka | 0.001 | 7.139e−007 | 0.3 |
| $s^{-1}$ $M^{-1}$ | ka | | $7.14 \times 10^2$ | 0.3 |

The rate of thrombin generation:

=0.043 μM thrombin/min/μM prothrombin/μM activator;

=0.043 nmol thrombin/mL/min/μmol prothrombin/μmol activator.

Figure 24:
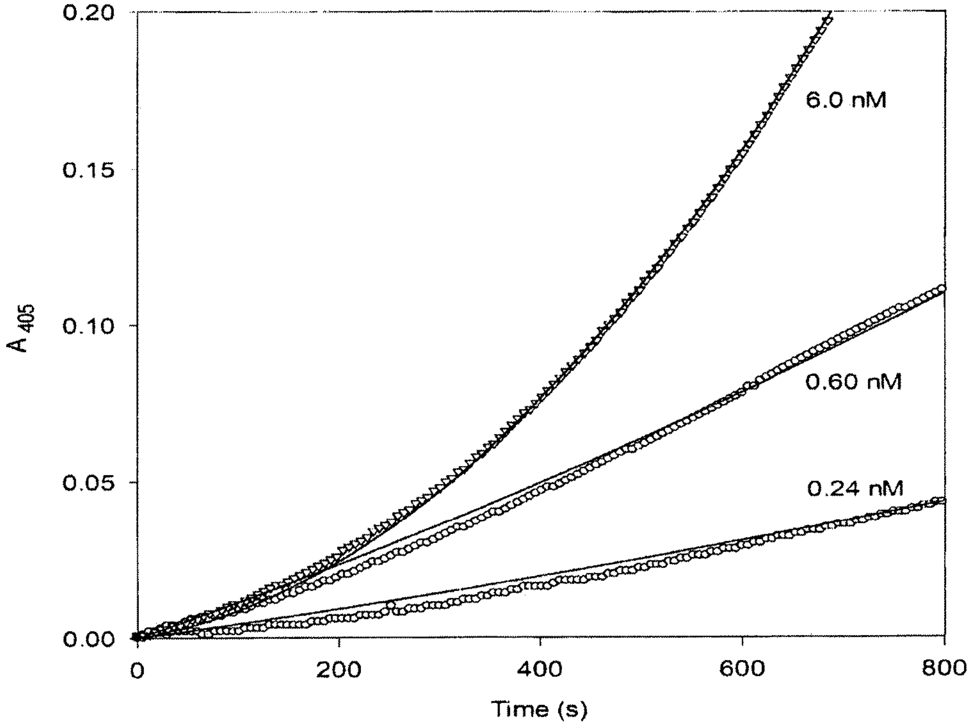
FIG. 24 plots the notecarin activation of prothrombin at the concentrations of notecarin as described in Example 2e.

FIG. 24 plots the notecarin activation of prothrombin, demonstrating the reaction rates of different notecarin concentrations (0.24-6.0 nM) with prothrombin and then the thrombin generated with the chromogenic substrate S-2238, and the best fit curve for notecarin activation of prothrombin. The dotted lines are the experimental results and the continuous lines are those calculated as best fit. These experimental and calculated progress curves show good agreement.

A summary of the estimated activation rate constants and thrombin generation rate for each of the prothrombin activators is provided in Table 13.

TABLE 13

Summary of the estimated activaton rate constants and the thrombin generation rate for the different prothrombin activators

| Prothrombin activator | Activation rate constant ka ($s^{-1}$ $nM^{-1}$) | Thrombin generation rate (nmol thrombin/mL/min/μmol prothrombin/μmol activator) |
|---|---|---|
| PtPA | $6.72 \times 10^5$ | 40.3 |
| OsPA | $7.33 \times 10^5$ | 44.0 |
| ecarin | $4.61 \times 10^4$ | 2.76 |
| carinactivase-1 | $3.94 \times 10^3$ | 0.24 |
| carinactivase-2 | $3.18 \times 10^4$ | 1.91 |
| notecarin | $7.14 \times 10^2$ | 0.043 |

There was no reaction between the different prothrombin activators and the thrombin substrate S-2238, nor was there any reaction by prothrombin with S-2238. The activation rate data constants confirmed the group C prothrombin activators (PtPA and OsPA) are most potent in hydrolysing the prothrombin to thrombin. In fact they were more than 20 times more effective than ecarin and carinactivase-2, more than 200 times then carinactivase-1 and approximately 1000 times more effective than notecarin. The estimated thrombin generation rates equally show the same efficacy ratio, the group C activators were able to generate the largest amount of thrombin, followed by ecarin, carinactivase-2, carinactivase-1 and notecarin being the least efficient. As noted in Example 2d, notecarin requires cofactors for activity.

Materials and Methods as Used in Following Examples

Where indicated in the Examples that follow, the following Materials and Methods were used.

(A) Containers for Preparing Samples

A typical container (e.g. tube) for preparation of a serum sample or a plasma sample contains: (1) a gel barrier to separate cells (and the clot in the case of serum) from plasma or serum during centrifugation and to ensure no subsequent re-mixing; (2) a surfactant coating the inner wall to prevent cell and protein adhesion to the tube wall to minimise subsequent cell lysis; and (3) a procoagulant that enhances the clotting process (e.g. silica particles) for preparation of a serum sample or an anticoagulant (e.g. lithium heparin, citrate, or EDTA) for preparation of a plasma sample.

In the Examples, a number of commercially available tubes were used to prepare serum samples or plasma samples as described below.

Greiner Vacuette™ Plasma Tube. This is a plasma separator tube supplied by Greiner under reference number 456083. The inner wall of the tube is coated with spray-dried lithium heparin (89 IU) that acts as an anticoagulation agent. The tube also contains a separation gel in the base of the tube. Greiner states that this gel acts to form a stable barrier between the plasma and the blood cells allowing parameters to remain stable for up to 48 hours. The fill volume is 5.0 mL.

Becton Dickinson (BD) Vacutainer™ Plasma Tube (BD PST II). This is a plasma separator tube supplied by BD under reference number 367375. Each tube contains 77 IU/mL of lithium heparin (0.2-1.0 mg) as an anticoagulant. The tube contains an acrylic gel (0.8-1.9 g) that forms a barrier between the cells and the plasma during centrifugation. BD state that this gel provides enhanced plasma purity demonstrated by a reduction in fibrin and measurable white blood cells, red blood cells and platelets, and enhanced analyte stability as most analytes are stable in the tube for 24 hours at 25° C. The fill volume is 4.0 mL.

Greiner Vacuette™ Serum Tube. This tube is supplied by Greiner under reference number 456078. The tube contains silica particles as the clot activator. The fill volume is 4.0 mL. The recommended clotting time in this tube is 30 minutes.

Becton Dickinson (BD) Vacutainer™ Serum Tube (BD SST II). This tube is supplied by BD under reference number 367954. This tube is used to obtain and separate a serum sample. Each tube contains 0.20-2.56 mg amorphous (or fused) silica as the coagulation agent, and also a gel (0.90-3.50 g) that forms a barrier between the clot and the serum after centrifugation. BD recommend a clotting time of 30 minutes for this tube. The fill volume is 4.0 mL.

Becton Dickinson (BD) Vacutainer™ Rapid Serum Tube (BD RST). This tube is supplied by BD under reference number 368771. The tube contains a thrombin-based medical clotting agent and gel. BD claims that these tubes will provide a clotted sample within five minutes, (i.e. faster clotting than a standard commercially available serum tube) and will have "minimal fibrin formation". The fill volume is 4.0 mL.

Greiner Vacuette™ No Additive Tube. These are plain plastic tubes supplied by Greiner under reference number 45400 to which prothrombin activators at particular concentrations were added as described in the Examples below.

Sarstedt Serum Tube. This tube is supplied under catalogue number 5092503 with a light brown top and has a fill volume of 4.7 mL. These tubes contain silica particles and a gel barrier.

Terumo Plain Tube. This tube is supplied under the trade mark VENOSAFE under catalogue number VF-076SP and has a fill volume of 6.0 mL. These tubes contain silica particles and a gel barrier.

Terumo Red Top (RT) Tube. This tube is supplied under the trade mark VENOSAFE under catalogue number VF-108SAS and has a fill volume of 8.0 mL. These tubes are internally coated with silica and have a gel barrier.

Greiner Vacuette™ Citrate Tube. This plastic tube contains 3.2% citrate with a 4.0 mL fill volume. The tube is sold under catalogue number 454327.

Greiner Vacuette™ K2EDTA Tube. This plastic tube contains 8 mM EDTA and has a 4.0 mL fill volume. The tube is sold under catalogue number 454023.

(B) Sample Analyses—Clotek Analyser

The Clotek analyser (Hyland, USA) uses a sample tube containing a magnetic ball which oscillates vertically when the tube is inserted into the machine. The magnetic steel ball is held in position by a magnetic field while the tube oscillates. The sample, buffer, ±calcium and procoagulant are added and the timer is triggered. Thrombin converts fibrinogen into clottable fibrin, and the time required to form the detectable clot is the clotting time. At clot formation the steel ball is removed from the magnetic suspension field and the light path, causing the light beam to strike the photocell and stop the timer (Austen, D. E., et al. 1975 and Starr, H., et al., 1980).

(C) Sample Analyses—Thromboelastography

Thromboelastography (TEG) measures clotting of whole blood by determining the rate of blood clot formation and lysis and the elastic properties of the blood clot during its formation and lysis. Where indicated in some Examples below, TEG analysis was performed.

The TEG analysis was performed using a Thrombelastograph® 5000 (TEG, Haemoscope Corporation Pty Ltd, Niles, Ill., USA) with TEG Analytical Software version 4.

The clotting parameters used here for the TEG analysis were as follows:

R—reaction time (seconds/minutes): time from start of the analysis until the TEG tracing amplitude reaches 2 mm, indicating detectable clot formation;

α—angle: measure of the rate of fibrin formation and cross-linking (i.e. clot strengthening);

MA—maximum amplitude (mm): maximum strength of the clot;

TMA—time (seconds/minutes) from start of the analysis until MA is reached; and

K—time (s): time from the start of the clot formation to the time the curve reaches amplitude of 20 mm.

Figure 25:
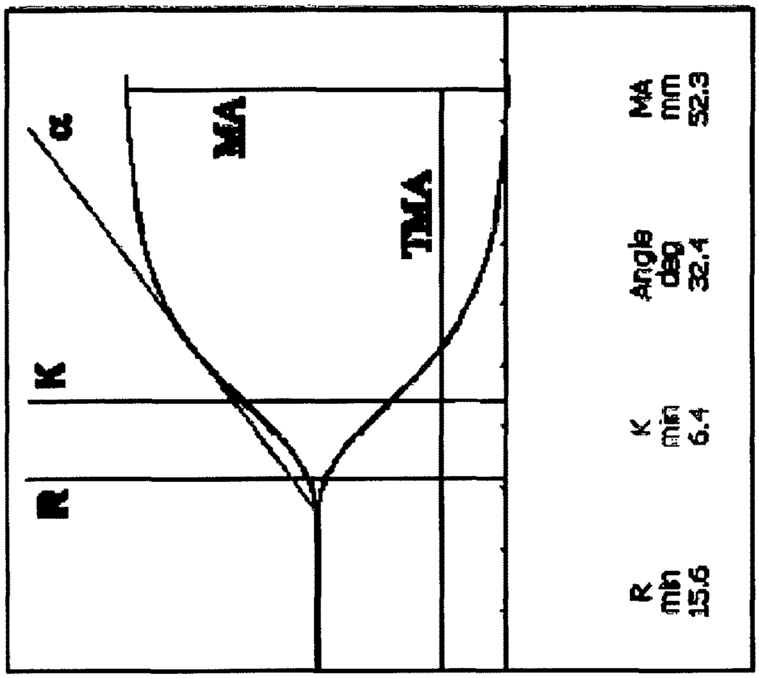
FIG. 25 shows an example of a TEG plot (clot formation part) with the clotting parameters labelled, as discussed in the Examples section.

An example of a TEG plot (clot formation part) with the above clotting parameters labelled is provided in FIG. 25. Only the clotting parameters are presented as the clot lysis parameters were not included.

Example 3

Clotting of Plasma Samples by Venom Prothrombin Activators

Example 3a

Clotting Times of Normal Citrated Plasma by PtPA Versus Bovine Thrombin

The clotting times of pooled citrated plasma (combined plasma from 6 normal participants) by PtPA (prepared as outlined in Example 1d) and bovine α-thrombin (3276 U/mg; Sigma Chemical Co.), with and without added calcium (10 mM), were measured in duplicate samples.

The results are shown in Table 14, where the values are the means of duplicate experiments.

TABLE 14

Clotting times of citrated plasma with PtPA and bovine thrombin, measured in a Hyland-Clotek machine (seconds).

| | Clotting time (seconds) | | | |
|---|---|---|---|---|
| Concentration of enzyme (nM) | PtPA + calcium | PtPA − calcium | thrombin + calcium | thrombin − calcium |
| 100 | 4.2 | 4.7 | 4.8 | 7.9 |
| 50 | 4.2 | 4.8 | 6.4 | 17.9 |
| 30 | 4.3 | 5.0 | **13.3** | 27.2 |
| 10 | 4.5 | 5.4 | 33.2 | 57.2 |
| 3 | 5.0 | 6.2 | **78.6** | >200# |
| 1 | 6.0 | 6.6 | >200# | >200 |
| 0.1 | 8.7 | 8.8 | >200 | >200 |
| 0.001 (1 pM) | **13.5** | 29.0 | >200 | >200 |
| 0.0001 (0.1 pM) | **74.1** | 98.6 | >200 | >200 |
| 0 | >200 | >200 | >200 | >200 |

#Weak clot observed.

The PtPA clotted citrated plasma efficiently at concentrations as low as 0.1 pM with or without recalcification. A concentration of 1 nM gave a clotting time of about 6 seconds, close to the minimum clotting time achieved at 100 nM of 4.2 seconds.

These results also show that PtPA is about $3\times10^4$ times more efficient in the clotting of citrated plasma (with or without re-calcification) on a molar basis than bovine thrombin. For example, in the presence of 10 mM added calcium, 1 pM PtPA gave the same clotting time as 30 nM thrombin and 0.1 pM PtPA had a very similar clotting time to 3 nM thrombin (values in bold in Table 14).

Example 3b

Clotting Times of Normal Citrated Plasma by Prothrombin Activators

This experiment used the same plasma as in Example 3a.

Each Clotek tube contained 100 μL of normal "pooled" citrated plasma, 100 μL of Tris Buffer (150 mM Tris HCl, 150 mM NaCl, pH 7.4), 50 μL 0.2 M $CaCl_2$ or saline, and 50 μL of each procoagulant (either prothrombin activator preparation or thrombin).

The clotting results from each prothrombin activator preparation and thrombin with the normal "pooled" citrated plasma (with and without re-calcification) are shown in Tables 15 and 16. In these tables (and elsewhere), CA-1 is carinactivase-1 and CA-2 is carinactivase-2.

TABLE 15

Clotting times of normal "pooled" citrated plasma with different prothrombin activator preparations and thrombin, with calcium.

| | With $Ca^{2+}$ (seconds) | | | | | | |
|---|---|---|---|---|---|---|---|
| [Procoagulant] (mM) | Ecarin | CA-1 | CA-2 | PtPA | OsPA | Notecarin | Thrombin |
| 100 | 43.0 | 108 | 65.8 | 3.5 | 5.7 | 42.4 | 4.3 |
| 50 | 56.0 | 145 | 85.0 | 4.6 | 6.5 | 52.8 | 6.7 |
| 30 | 69.0 | 181 | 167 | 4.9 | 7.9 | 57.5 | 10.5 |
| 10 | 105 | >300 | >300 | 12.5 | 12.5 | 68.5 | 32.8 |
| 3 | 208 | >300 | >300 | 20.1 | 18.3 | 99.8 | 92.3 |
| 1 | >300 | >300 | >300 | 61 | 30.0 | 144 | >300 |
| 0.1 | >300 | >300 | >300 | 120 | 108 | 284 | ND |
| 0.01 | >300 | >300 | >300 | 212 | >300 | >300 | ND |
| 0.001 | >300 | >300 | >300 | >300 | >300 | >300 | ND |

TABLE 16

Clotting times of normal "pooled" citrated plasma with different prothrombin activator preparations and thrombin, without calcium

| [Procoagulant] (mM) | Without $Ca^{2+}$ (seconds) Ecarin | CA-1 | CA-2 | PtPA | OsPA | Notecarin | Thrombin |
|---|---|---|---|---|---|---|---|
| 100 | 94.0 | >300 | 216 | 3.9 | 7.3 | 51.7 | 5.6 |
| 50 | 129 | >300 | >300 | 5.0 | 8.2 | 67.6 | 9.2 |
| 30 | 167 | >300 | >300 | 6.1 | 8.9 | 76.7 | 14.6 |
| 10 | >300 | >300 | >300 | 9.0 | 14.0 | 115 | 43.6 |
| 3 | >300 | >300 | >300 | 15.5 | 21.5 | 250 | 145 |
| 1 | >300 | >300 | >300 | 24.6 | 34.5 | >300 | >300 |
| 0.1 | >300 | >300 | >300 | 93.0 | 152 | >300 | ND |
| 0.01 | >300 | >300 | >300 | >300 | >300 | >300 | ND |
| 0.001 | >300 | >300 | >300 | >300 | >300 | >300 | ND |

The results show that in the presence of added calcium all the prothrombin activators (representing groups A-D) efficiently clotted normal citrated plasma.

Citrated plasma is not completely calcium depleted. The total calcium concentration in normal citrated plasma is ~1.3 mmol/L and the ionised calcium concentration is unmeasurable (<0.25 mmol/L). However, citrate is a chelator of calcium, binding to the calcium in the sample so that free calcium is not readily available to be used for the clot formation. Calcium is part of the prothrombinase complex and plays an important role in the prothrombin to thrombin catalysis. Citrate also binds other metal ions including magnesium and zinc ions. The amount of citrate present in the tube, 0.109 mol/L is more than sufficient to chelate all the metal ions in the tube.

These results showed that ecarin, the group A prothrombin activator, was more than twice as effective in clotting the plasma in the presence of added calcium, and therefore calcium has a significant enhancement on ecarin's ability to accelerate the clot formation. The group B prothrombin activators, carinactivase-1 and carinactivase-2, were strongly affected by the absence of calcium, with a decrease in activity of ~4-fold, confirming the calcium enhances clotting activity with these prothrombin activators. The activity of notecarin, the group D prothrombin activator, was stimulated by the presence of added calcium, and the requirement for calcium was most evident with the decrease in the notecarin concentration with the addition of calcium increasing its effectiveness by ~30%.

Thrombin itself was affected to a smaller degree by the absence of the added calcium. Thrombin itself generates thrombin formation in the sample via the coagulation cascade of prothrombin which requires calcium. Therefore the amount of thrombin formed from the sample prothrombin decreased with the absence of calcium.

The calcium dependence of the procoagulants was less when they were in high concentrations due to their potency. The results showed that the group C prothrombin activators, PtPA and OsPA, were the most efficient in clotting the normal "pooled" citrate plasma both in the presence or absence of added calcium. In fact, the absence of calcium made minimal difference on the clotting ability of these two procoagulants. With and without the presence of added calcium the group C prothrombin activators required ~0.1 nM to achieve clotting in <5 minutes.

Example 3c

Clotting Times of Citrated Plasma Samples and Fibrinogen by PtPA

The ability of PtPA to clot the following recalcified citrated plasma samples and a sample of purified fibrinogen was determined in the following duplicate samples:

(i) citrated plasma;

(ii) citrated plasma adsorbed by $Al(OH)_3$ (adsorption by $Al(OH)_3$ removes prothrombin and other γ-carboxyglutamate (GLA)-containing proteins);

(iii) citrated plasma from patients on long term warfarin therapy (with International Normalized Ratio (INR) greater than 4.0);

(iv) citrated plasma from patients on long term warfarin therapy (with INR greater than 4.0) adsorbed by $Al(OH)_3$;

(v) citrated Factor X-deficient plasma obtained from congenitally deficient patients;

(vi) citrated Factor V-deficient plasma obtained from congenitally deficient patients; and (vii) purified human fibrinogen (2 mg/mL in isotonic saline), adsorbed with $Al(OH)_3$ (to remove traces of prothrombin).

With respect to (iii) and (iv), warfarin inhibits liver γ-carboxylase, an enzyme which inserts γ-carboxyl groups into 10 N-terminal glutamic acid residues of prothrombin. Warfarin plasma therefore contains an uncarboxylated precursor of prothrombin, descarboxyprothrombin, which is not removed by adsorption with $Al(OH)_3$ With respect to (v) and (vi), Factor Xa and Factor Va are essential components of the human prothrombinase complex. The Factor X-deficient and Factor V-deficient plasmas were supplied by Ortho-Diagnostics, USA.

The results are shown in Table 17.

TABLE 17

Clotting times of citrated plasma samples (i)-(vi) and fibrinogen sample (vii).

| PtPA* (nM) | Clotting time (seconds ± 0.5 seconds) for samples (i) | (ii) | (iii) | (iv) | (v) | (vi) | (vii) |
|---|---|---|---|---|---|---|---|
| 54 | 12.8 | >180 | 15.6 | 18.4 | 16.5 | 12.8 | >180 |
| 26 | 16.4 | >180 | 18.4 | 26.8 | n.d. | n.d. | n.d. |
| 16 | 22.5 | >180 | 24.6 | 28.6 | n.d. | n.d. | n.d. |
| 7.3 | 34.6 | >180 | 38.8 | 42.3 | n.d. | n.d. | n.d. |
| 3.8 | 48.2 | >180 | 55.0 | 59.8 | n.d. | n.d. | n.d. |
| 0# | 10.0 | 10.6 | 7.7 | 8.6 | 14.6 | 10.6 | 5.4 |

*In this experiment, a different preparation of PtPA was used, accounting for the lower clotting activity than in Table 14 above.
n.d. means that the measurements were not determined.
#Where no PtPA was added, 0.1 Units of bovine thrombin (Parke-Davis, now Pfizer, USA) was added to all samples as a positive control. The rapid clotting observed on addition of thrombin confirmed the presence of fibrinogen in all samples.

The results in Table 17 show that:

(1) prothrombin is necessary for clotting by PtPA since $Al(OH)_3$-adsorbed citrated plasma (sample (ii)) was not clotted by PtPA;

(2) PtPA clots warfarin plasma (samples (iii) and (iv)) indicating that descarboxyprothrombin can be converted to α-thrombin by PtPA;

(3) the result for warfarin plasma adsorbed by $Al(OH)_3$ (sample (iv)) confirms that descarboxyprothrombin is converted to α-thrombin, since traces of normal prothrombin in warfarin plasma would be removed by $Al(OH)_3$;

(4) Factor Xa is not required for clotting by PtPA (results for sample (v));

(5) Factor Va is not required for clotting by PtPA (results for sample (vi)); and (6) PtPA is unable to clot a fibrinogen solution and is therefore not functioning as a thrombin-like enzyme.

In summary, these results shows that clotting induced by PtPA is due to prothrombin activation; that descarboxyprothrombin is converted efficiently to thrombin by PtPA; that Factors Xa and Va are not required for prothrombin activation by PtPA; and PtPA does not convert fibrinogen to fibrin under these conditions.

Example 3d

Clotting of EDTA-treated Plasma

A small but significant percentage of samples (serum or lithium heparin plasma samples) received for biochemical analysis is contaminated by EDTA. It is therefore important to determine if the prothrombin activators were effective in clotting EDTA plasma and EDTA whole blood. This example is therefore provided as Example 5b below, so that a comparison of the studies of EDTA plasma and EDTA whole blood could be made.

Example 3e

Clotting of Citrated Plasma from Warfarin Medicated Participants by Prothrombin Activators Warfarin is a commonly used anticoagulant, and therefore the purpose of this experiment was to determine if warfarin therapy affects the ability of the prothrombin activators: ecarin; carinactivase-1; carinactivase-2; PtPA; OsPA; and notecarin, to clot samples from patients medicated with warfarin.

Participant plasma samples with different clotting times (related to warfarin dosage) based on the INR (1.1-7.6) were selected and tested with the different procoagulants (prothrombin activators and thrombin).

The Clotek tubes contained 100 μL of lithium heparin plasma, 100 μL of Tris Buffer (150 mM Tris HCl, 150 mM NaCl, pH 7.4), 504 of 0.2 M $CaCl_2$, and 50 μL of each procoagulant.

The results are shown in Tables 18 and 19. As used in these tables and elsewhere, CA-1 is carinactivase-1 and CA-2 is carinactivase-2.

TABLE 18

Clotting times (seconds) with re-calcified citrated plasma from warfarin medicated patients, by prothrombin activators.

| [Prothrombin activator] | Sample INR | | | | | | |
|---|---|---|---|---|---|---|---|
| 30 nM | 1.1 | 1.2 | 1.5 | 2.0 | 2.9 | 6.4 | 7.6 |
| PtPA | 5.0 | 5.7 | 6.7 | 6.1 | 7.0 | 9.8 | 10.5 |
| OsPA | 9.0 | 9.1 | 12.6 | 16.8 | 17.2 | 17.2 | 19.3 |
| Notecarin | 69.4 | 67.1 | 68.6 | 66.6 | 71.0 | 91.0 | 121 |
| Ecarin | 72.2 | 63.4 | 63.4 | 69.4 | 85.6 | 114 | 111 |
| CA-1 | 231 | 198 | 232 | 229 | >300 | >300 | >300 |
| CA-2 | 115 | 103 | 115 | 109 | 149.2 | 242 | 240 |

TABLE 19

Clotting times (seconds) with re-calcified citrated plasma from warfarin medicated patients by PtPA and thrombin.

| | Sample INR | | | | | |
|---|---|---|---|---|---|---|
| [Procoagulant] 30 nM | 1.1 | 1.7 | 2.3 | 2.8 | 5.8 | 6.4 |
| PtPA | 7.4 | 8.1 | 8.1 | 8.3 | 11.1 | 13.3 |
| Thrombin | 13.4 | 13.7 | 14.7 | 14.0 | 14.7 | 16.3 |

Warfarin leads to a decrease in the synthesis of normal Factor-X (FX) and prothrombin from their active precursors (descarboxyfactor-X and descarboxyprothrombin). Prothrombin and descarboxyprothrombin are the substrates targeted by the prothrombin activators. The decrease in prothrombin means less thrombin was generated by the prothrombin activators, hence the prolonged clotting times observed. Thrombin itself was not inhibited by warfarin thus the clotting times with thrombin are not affected as has been observed in this experiment. The results in this experiment showed that the carinactivase-1 was the only prothrombin activator unable to clot plasma samples with INR ≥2.9. The results showed PtPA and OsPA were the most effective procoagulants for plasma from patients taking warfarin.

Example 3f

Clotting of FV-deficient and FX-deficient Plasma by Prothrombin Activators

The prothrombin activator preparations were tested for their ability to clot commercially available FV-deficient plasma (#0008466150) and FX-deficient plasma (#0008466350) (Instrumentation Laboratory, Lexington, Mass., USA) using the Clotek analyser (Hyland USA).

The Clotek tube contained 100 μL of FV- or FX-deficient plasma, 100 μL of Tris Buffer (150 mM Tris HCl, 150 mM NaCl, pH 7.4), 50 μL 0.2 M $CaCl_2$ and 50 μL of each procoagulant. All procoagulants were at a concentration of 30 nM, and an additional sample containing carinactivase-1 at a concentration of 100 nM was also tested.

The results are shown in Table 20.

TABLE 20

Clotting times (seconds) of FV- or FX-deficient plasma by the prothrombin activator preparations and thrombin

| | Clotting time (seconds) | | |
|---|---|---|---|
| [Procoagulant] 30 nM | Normal "pooled" citrated plasma | FV-deficient plasma | FX-deficient plasma |
| Ecarin | 66.8 | 74.8 | 77.5 |
| CA-1 | 184 | >300 | >300 |
| CA-1 (100 nM) | ND | 216 | 218 |
| CA-2 | 133 | 159 | 159 |
| OsPA | 13.3 | 12.7 | 12.7 |
| PtPA | 9.0 | 7.4 | 7.6 |
| Notecarin | 47.5 | >300 | 71.9 |
| Thrombin | 13.8 | 44.6 | 50.2 |

"ND" means this was not determined.

Notecarin was not able to clot the FV-deficient plasma in 5 minutes, and its clotting efficiency was also diminished in the absence of FX. Furthermore, the clotting activity of the group A and group B prothrombin activators was also diminished in the absence of FV or FX. The group C prothrombin activators, PtPA and OsPA, were clearly the most efficient in clotting the plasma, and have no requirement for FV or FX from plasma.

Thrombin clotting time was significantly increased to be more than 3 times longer in the FV- and FX-deficient plasma compared to the clotting time for the normal "pooled" citrated plasma.

Example 3g

Estimation of Amount of Thrombin Generated by PtPA and OsPA in Normal and Heparinised Citrated Plasma This experiment was designed to provide an estimate of the amount of thrombin that is generated by PtPA and OsPA using different concentrations and in the presence of heparin.

Normal citrated plasma was obtained from a healthy participant into a number of tubes (Greiner citrate) which were immediately centrifuged and the citrated plasma pooled.

The thrombin used was Thrombin-JMI, Topical (Bovine) 5000USP (GenTrac Inc, King Pharmacia, Middleton, Wis., USA). The USP units are equivalent to IU, and one IU is equal to 9 nM. The thrombin substrate used was S-2238 (25 mg stock solution MW 626 Da was dissolved in 15 mL to give 2.67 mM (#820324 Chromogeinix IL Lexington Mass., USA). The heparin used was 5000 IU/5 mL (1000 IU/mL), sodium heparin, Pfizer, NZ. For heparin, 190.9 IU=1 mg (Camenzind, et al 1997); a MWt of ~12000 Da was used to calculate molar concentrations. The buffer used was: 20 mM Hepes buffer; 150 mM NaCl; pH 7.4; 0.05% surfactant p20.

For the plasma incubation the tubes contained 0.5 mL citrated plasma, 50 μL of 0.5 M $CaCl_2$, and 5-40 μL thrombin or a prothrombin activator plus 20 μL of heparin to provide concentrations of 860, 4300, and 8600 nM (2, 10 and 20 IU) or saline. The tubes were incubated for 5 minutes at room temperature. Immediately after this 5 minute period, the clot was ringed using two wood applicator sticks, removed and discarded.

For thrombin activity assays, each spectrophotometric cuvette contained 930 μL of buffer, 50 μL of S-2238 and 20 μL of the clear serum that was remaining after the clot was removed from each tube in the incubation above. The absorbance change was monitored at 405 nm for 5 minutes.

Figure 26:
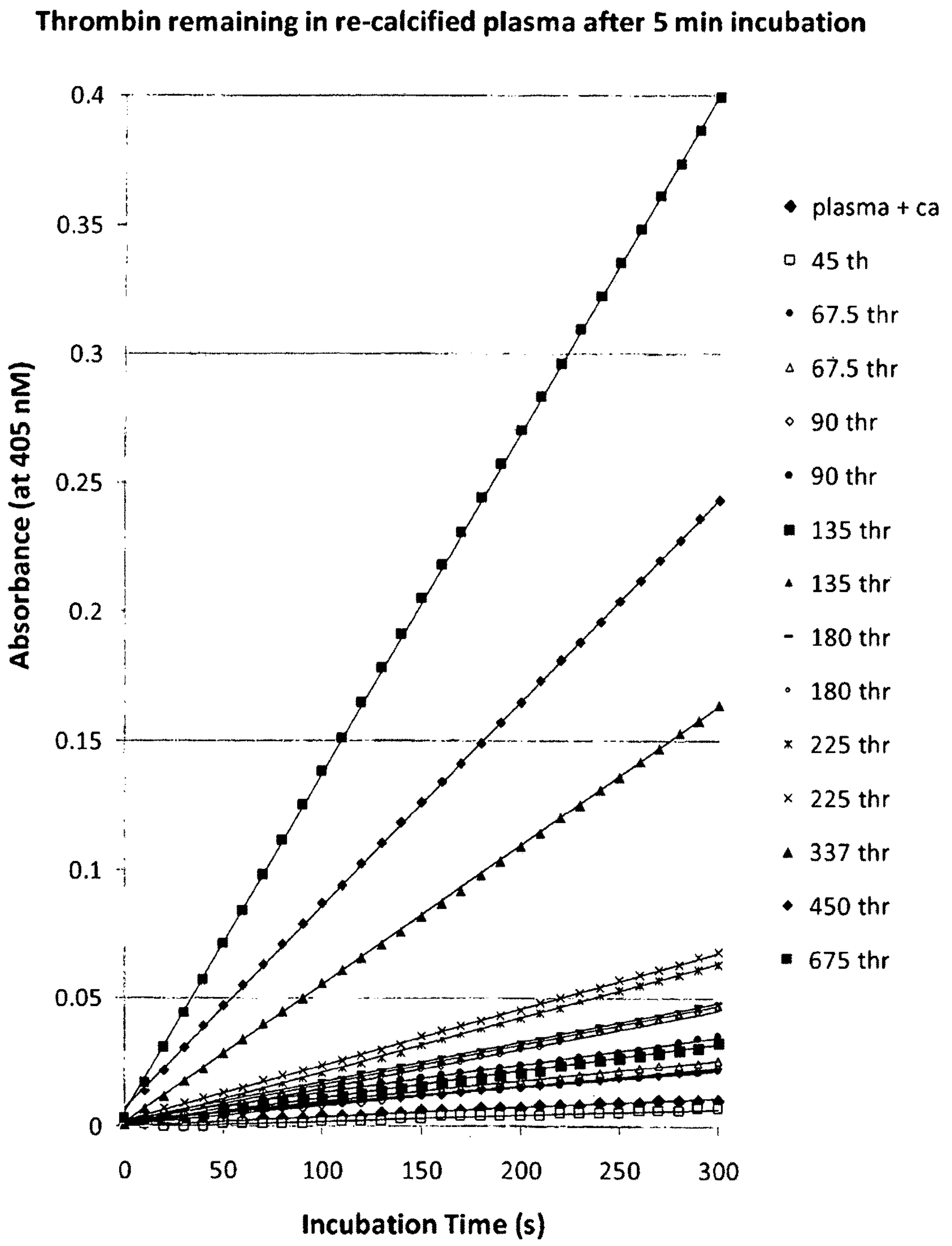
FIG. 26 plots the progress curves for hydrolysis of S-2238 by different thrombin concentrations in duplicate from 45-225 nM over a 5 minute incubation period in normal citrated plasma as described in Example 3g.
Figure 27:
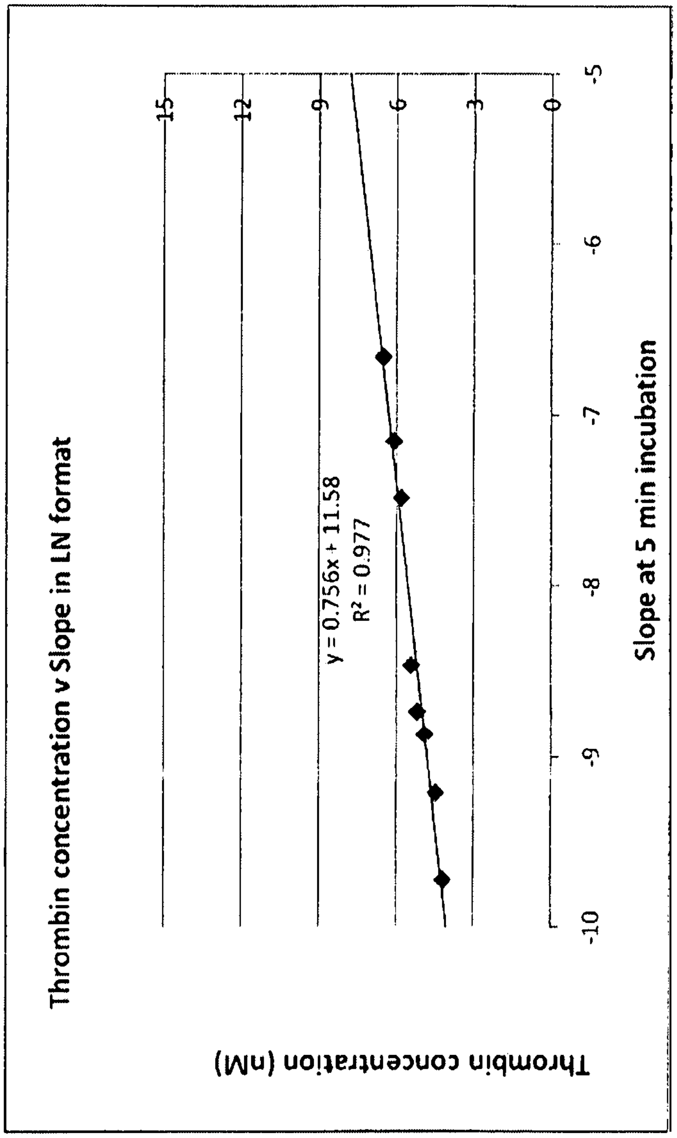
FIG. 27 shows the thrombin standard curve derived from the slope of the reactions in FIG. 26 at the 5 minute incubation mark in logarithmic form, where the x-axis shows the slope ln (absorbance units/minute); and the y-axis shows ln (molar concentration of thrombin).

FIG. 26 shows the activities of remaining thrombin in those tubes to which different concentrations of thrombin had been added. For each curve, the slope at 275 seconds was determined using the time range of 250-300 seconds, and these slopes along with the thrombin concentrations were then used to develop the standard curve in logarithmic format to provide a linear relationship over higher thrombin concentration, as shown in FIGS. 26 and 27.

The re-calcified plasma (no procoagulant) took ~37 minutes to clot at room temperature. All the thrombin containing samples exhibited latent clotting. The lowest concentration of thrombin was the slowest to exhibit latent clotting (~3 minutes). The time to latent clot decreased as the concentration of thrombin increased. The samples with concentrations >200 nM thrombin exhibited latent clotting immediately after the clot was removed as the serum was being aliquoted. At times, a second clot removal was necessary to ensure sufficient sample was obtained from the tube for the photometric analysis.

Figure 28:
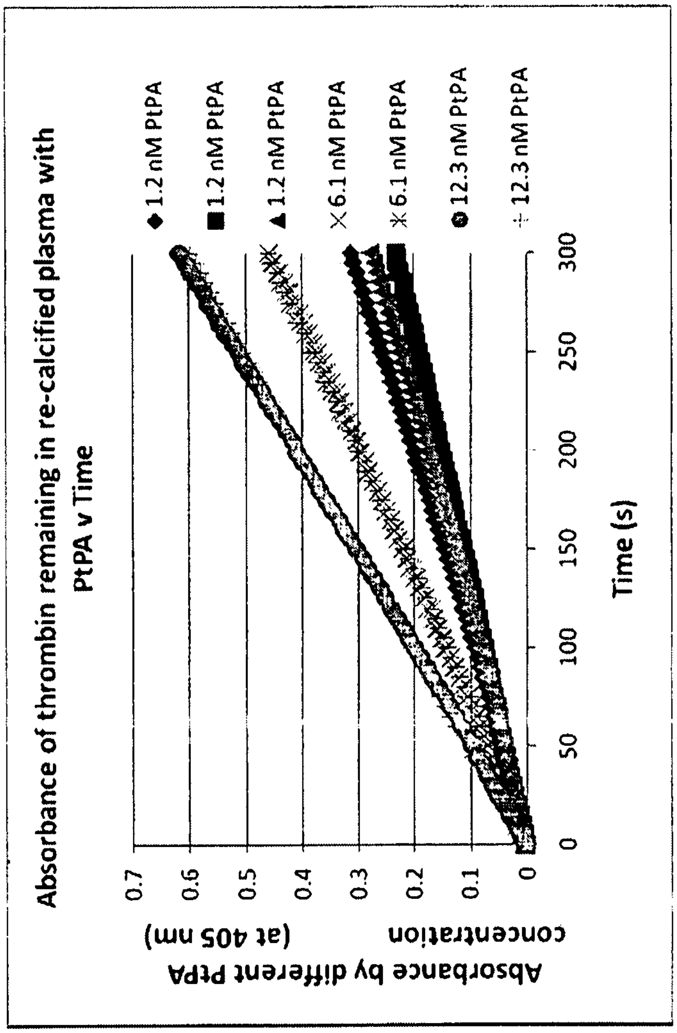
FIG. 28 shows assays of thrombin remaining after clot removal in sera generated by three different PtPA concentrations (in duplicate), as described in Example 3g.
Figure 29:
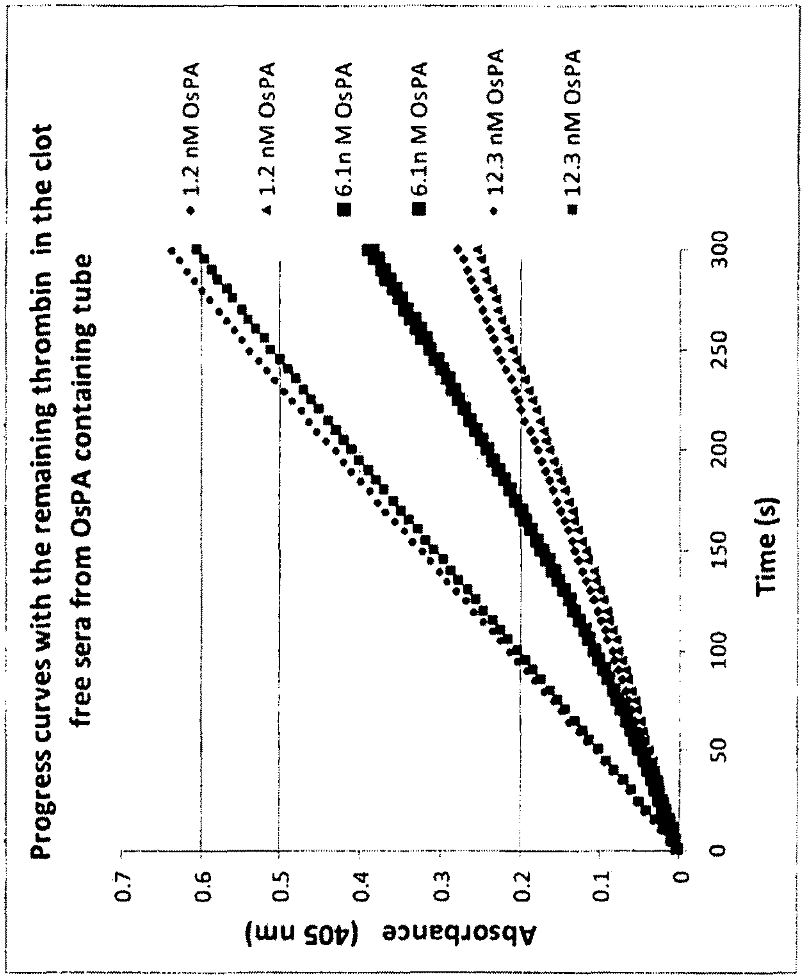
FIG. 29 shows assays of thrombin remaining after clot removal in sera generated by three different OsPA concentrations (in duplicate), as described in Example 3g.

For the samples containing different concentrations of the prothrombin activators PtPA and OsPA, but without heparin, the results were as follows. The spectrophotometric results for the samples containing different concentrations of PtPA are shown in FIG. 28, and for the samples containing different concentrations of OsPA are shown in FIG. 29.

Figure 30:
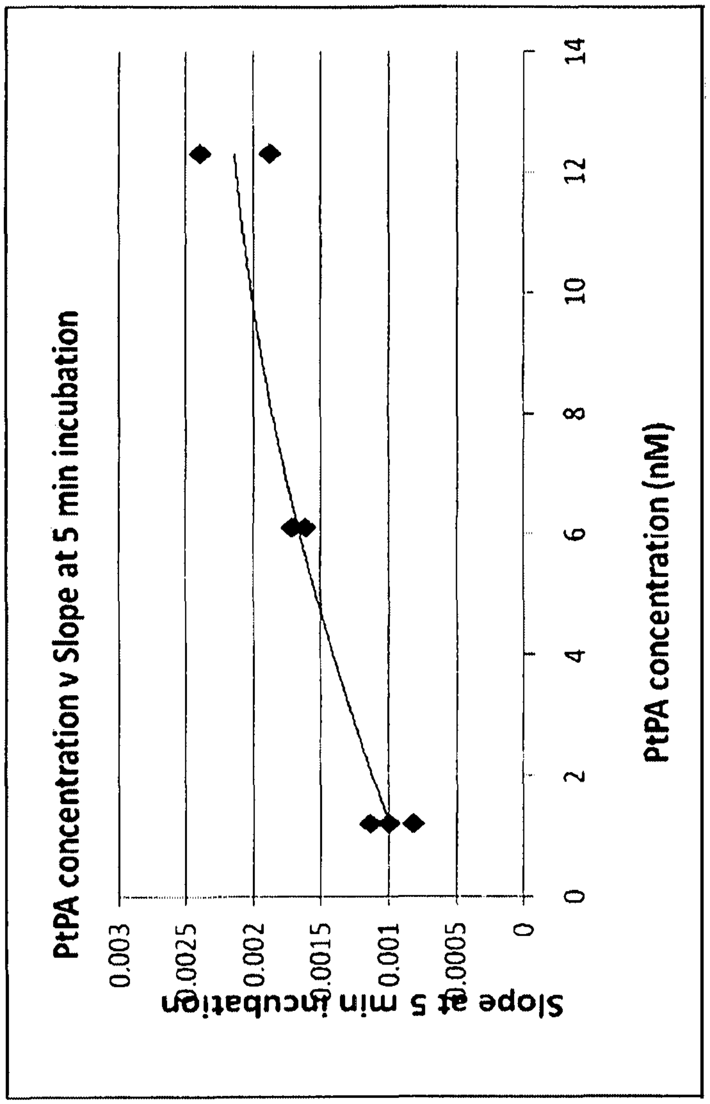
FIG. 30 plots the slopes from FIG. 28 (proportional to thrombin concentrations) against PtPA concentration, as described in Example 3g.
Figure 31:
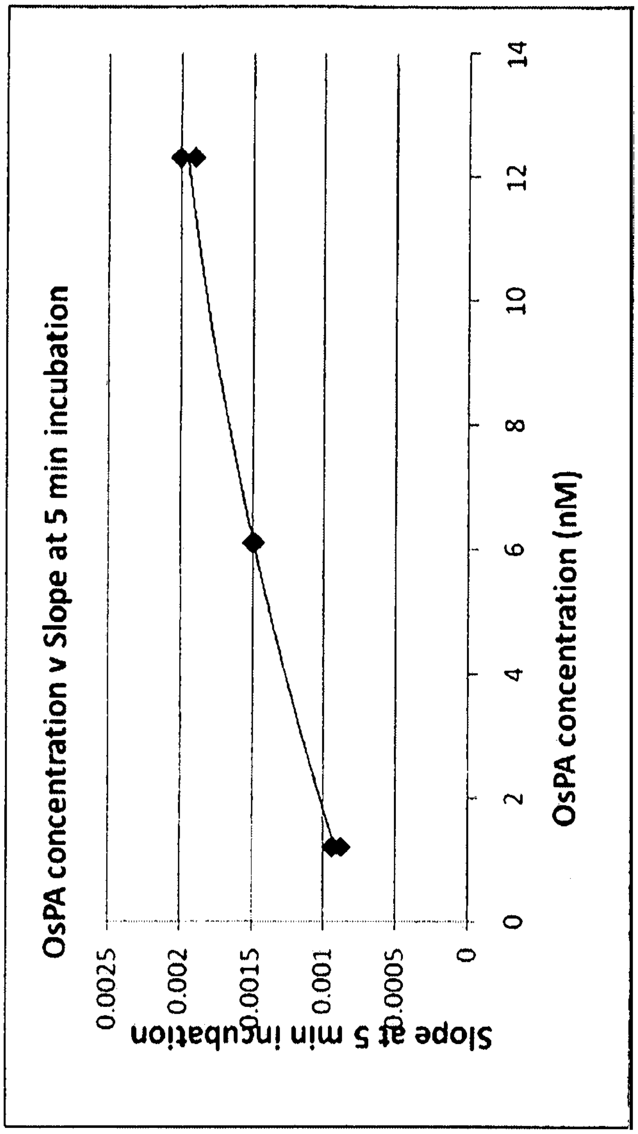
FIG. 31 plots the slopes from FIG. 29 (proportional to thrombin concentrations) against OsPA concentration, as described in Example 3g.

The thrombin concentrations generated by PtPA was then plotted against the slope at 5 minutes, and the results are shown in FIG. 30, and the thrombin concentrations generated by OsPA was then plotted against the slope at 5 minutes with the results are shown in FIG. 31.

The concentration of thrombin generated by the different PtPA and OsPA concentrations remaining active in the serum was estimated and is shown in Table 21.

TABLE 21

Estimation of the active thrombin present in the serum generated by different concentration of PtPA and OsPA determined from the standard curve regression equation, FIG. 27.

| [Prothrombin activator] (nM) | Slope at 5 minutes per second | Estimated concentration of active thrombin (nM) |
|---|---|---|
| PtPA | | |
| 1.2 | 0.00098 | 574 |
| 6.1 | 0.00171 | 869 |
| 12.3 | 0.00196 | 965 |
| OsPA | | |
| 1.2 | 0.00094 | 554 |
| 6.1 | 0.00149 | 784 |
| 12.3 | 0.00195 | 961 |

The results indicated that very significant amounts of thrombin were generated even by 1.2 nM PtPA and OsPA. Very small amounts of PtPA and OsPA were capable of completely clotting the re-calcified normal citrated plasma in <5 minutes. No latent clotting was observed, indicating that the amount of thrombin generated was sufficient to completely catalyse the fibrinogen and prevent latent clotting which would equate to very high quality serum.

For the samples containing different concentrations of heparin, the results were as follows.

Figure 32:
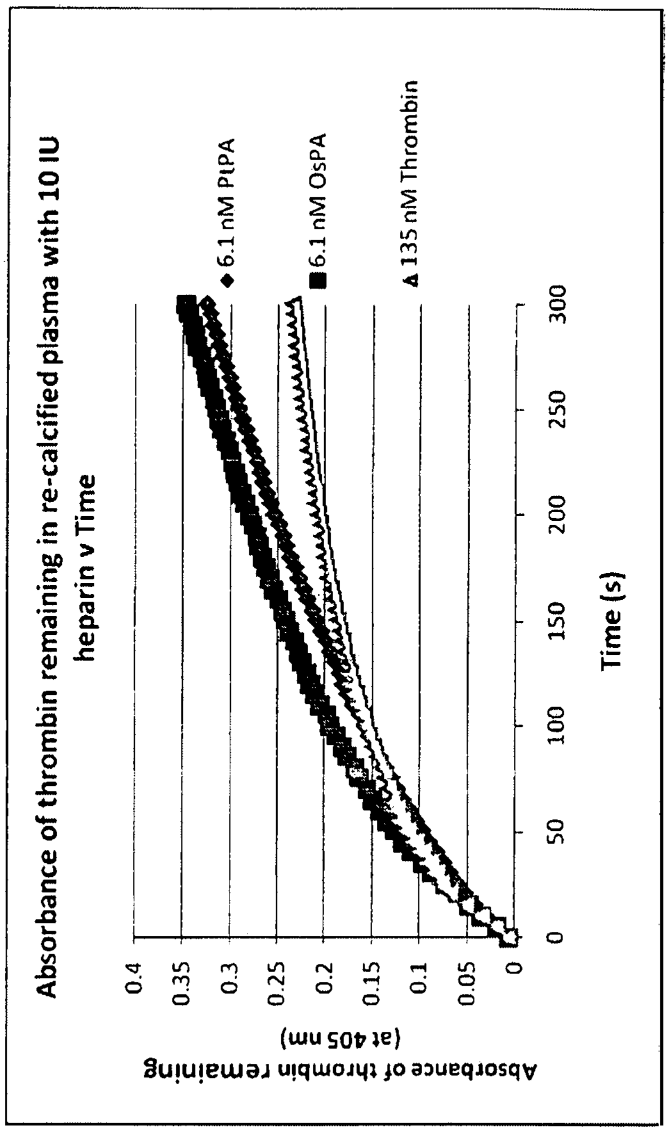
FIG. 32 shows progress curves for the hydrolysis of S-2238 by thrombin remaining in serum after clot removal in the presence of 4300 nM (10 IU) heparin, as described in Example 3g. Thrombin was generated by PtPA and OsPA, or was added.

First, the concentration of thrombin remaining in the serum component from the activity of thrombin, PtPA and OsPA in the presence of 4300 nM (10 IU) heparin was determined and is shown in FIG. 32 (change in $A_{405}$ for S-2238 hydrolysis/minute on the y-axis is proportional to thrombin concentration). The 135 nM thrombin failed to fully clot the plasma sample, with only a minor 2-3 mm "fluff-like" clot observed. The 6.1 nM concentrations of both prothrombin activators clotted the sample containing 4300 nM (10 IU) of heparin in approximately one minute and no latent clotting was observed even after 24 hours storage at room temperature.

Figure 33:
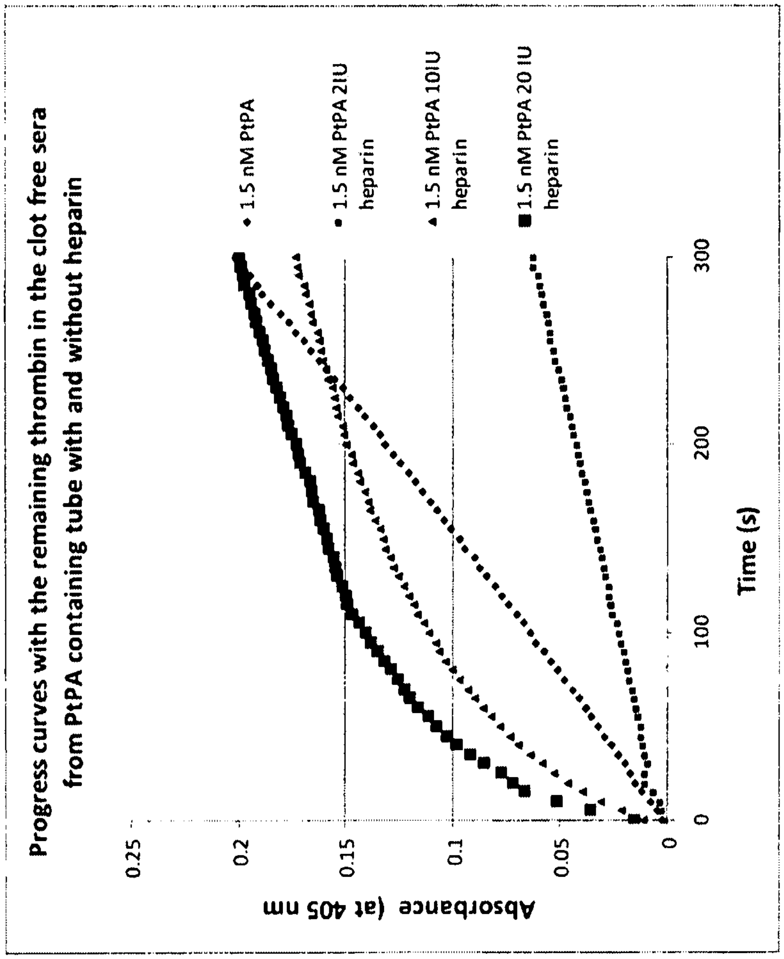
FIG. 33 shows the reaction curves with samples containing different heparin concentrations using 1.5 nM PtPA as described in Example 3g.

It was then investigated whether the reaction was of similar nature with different heparin concentrations. Normal pooled citrated plasma was obtained from the Coagulation Laboratory, Pathology Queensland, Princess Alexandra Hospital as there was insufficient plasma from the normal participant. The results are shown in FIG. 33 (PtPA) and FIG. 34 (OsPA).

The amount of thrombin generated by 1.5 nM PtPA and OsPA concentrations remaining active in the serum was estimated and is shown in Table 22.

TABLE 22

Estimation of the active thrombin present in the serum generated by 1.5 nM of PtPA and OsPA determined from the standard curve regression equation, FIG. 27.

| [Prothrombin activator] (nM) | Heparin nM (IU)/mL | Slope at 5 minutes per second | Estimated concentration of active thrombin (nM) |
|---|---|---|---|
| PtPA | | | |
| 1.5 | 0 | 0.0007 | 443 |
| 1.5 | 860 (2) | 0.00018 | 159 |
| 1.5 | 4300 (10) | 0.00024 | 197 |
| 1.5 | 8600 (20) | 0.00024 | 197 |
| OsPA | | | |
| 1.5 | 0 | 0.0006 | 394 |
| 1.5 | 860 (2) | 0.0002 | 172 |
| 1.5 | 4300 (10) | 0.00022 | 185 |
| 1.5 | 8600 (20) | 0.00020 | 172 |

Figure 34:
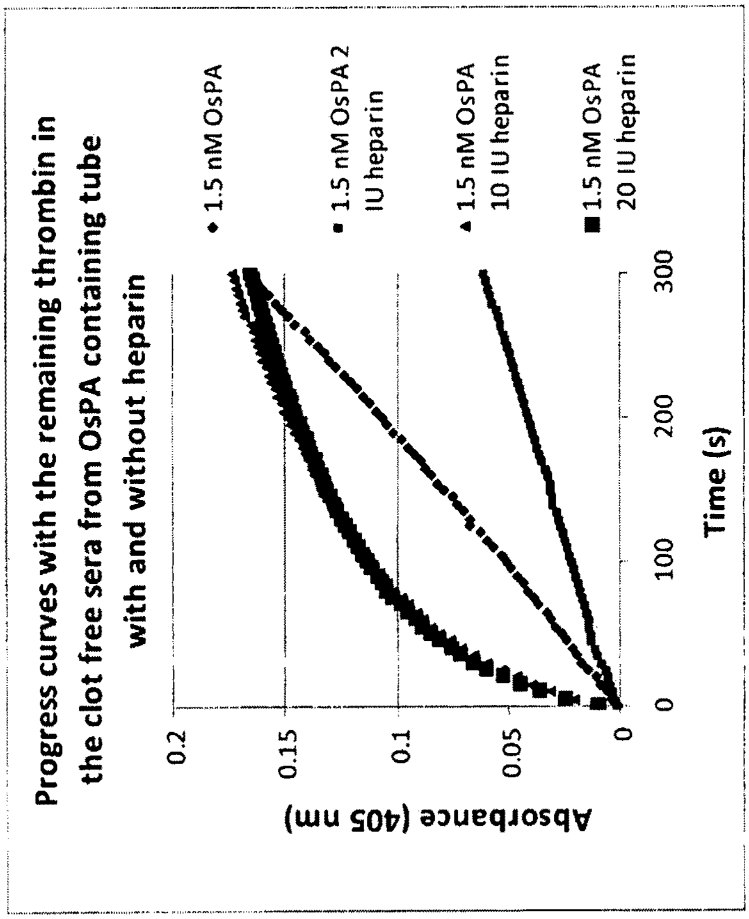
FIG. 34 shows the reaction curves with samples containing different heparin concentrations using 1.5 nM OsPA as described in Example 3g.

The samples containing 860 and 4300 nm (2 and 10 IU) heparin clotted within two minutes and showed no latent clotting. The clot was solid but not as solid as those observed in the samples that did not contain heparin, The 860 nM (2 IU) heparin-containing sample gave a thrombin activity that was about 25% of that of the plasma samples not containing heparin. In contrast, the sample containing 8600 nM (20 IU) heparin produced a "jelly-like" clot (more similar to the clots formed in the thrombin-containing samples) within 3 minutes the sample then exhibited latent clotting within 5 minutes. In FIGS. 33 and 34, the reason for the shape of the progress curves at higher heparin concentrations is unknown.

Example 3h

Estimation of Amount of Thrombin Generated by BD RST Tube Using Normal Pooled Citrated Plasma, and the Effect of Heparin The purpose of this experiment was to provide an estimate of the amount of thrombin generated and present in the active form in the BD RST tube filled with different volumes of plasma. Additionally the effect of heparin on the clotting ability of the BD RST tubes was also studied.

Normal pooled citrated plasma (<24 hours old) was obtained from the Coagulation Laboratory, Pathology Queensland, Princess Alexandra Hospital.

For the standard curve, the BD RST tubes contained 1, 2, 3 and 4 mL of citrated plasma and 50 μL of 0.5 M $CaCl_2$. The tubes were inverted 8-10 times to mix and incubated for 5 minutes. The clot was ringed using two wood applicator sticks, removed and discarded.

Figure 35:
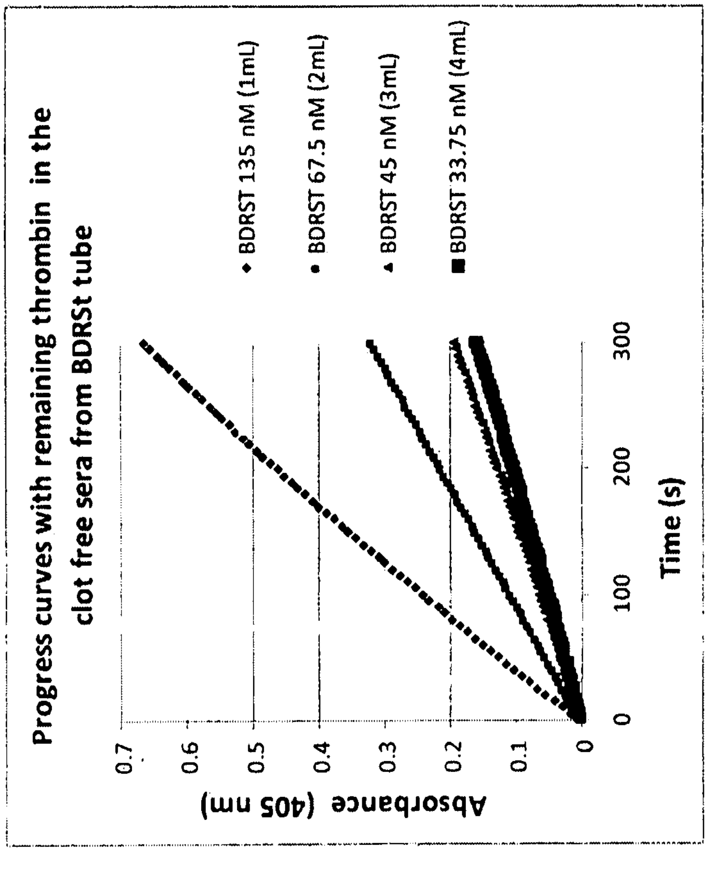
FIG. 35 shows the changes of absorbances over the 5 minute period in pooled "normal" citrated plasma, with each line representating a BD RST tube filled with a different volume of normal pooled citrate plasma, as described in Example 3h.

The spectrophotometric cuvette contained 930 μL of buffer, 50 μL of S-2238 and 20 μL of the clear serum that was remaining after the clot was removed from each BD RST tube above. The absorbance change was monitored at 405 nM for 5 minutes, and the results are shown in FIG. 35. Thrombin concentrations were estimated from the slopes using the standard curve in FIG. 16, and plotted against the slopes from FIG. 35. The original BD RST tube thrombin concentrations and remaining thrombin concentrations in the clot free sera from the four samples were are as follows; 135 versus 4.3; 67.5 versus 1.4; 45 versus 0.5; and 33.8 versus 0.3 nM respectively. It is likely that most of the thrombin was removed during the clot removal as it would be bound to the clot fibrin.

Unlike the samples with pure thrombin described in Example 3g, each sample in each of the BD RST tubes clotted within one minute and no latent clotting was observed. However, the clot strength was much weaker that those observed with PtPA or OsPA described in Example 3g.

Figure 37:
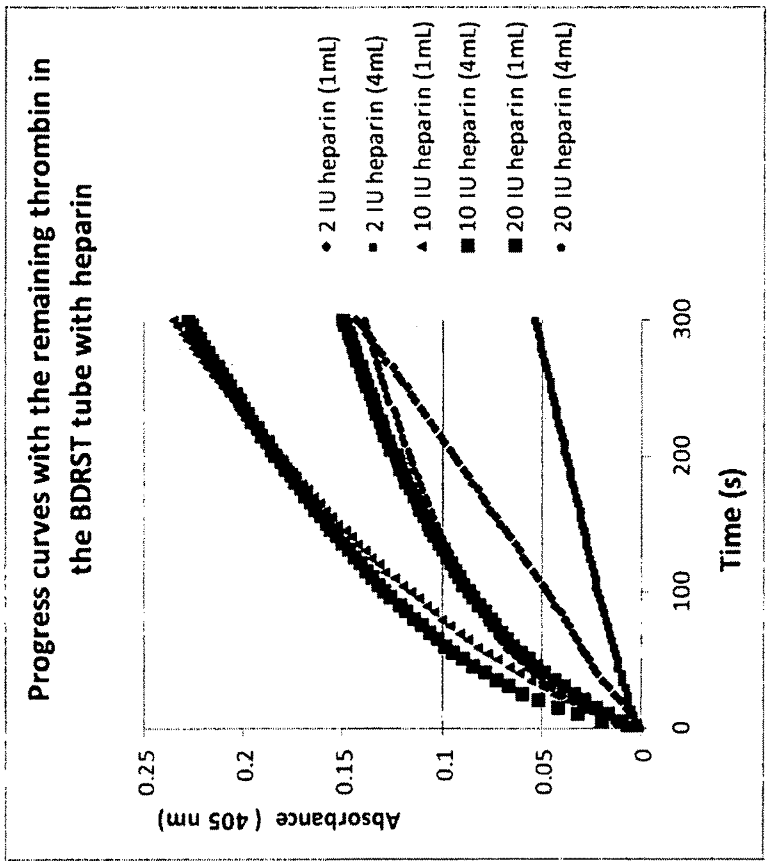
FIG. 37 shows the changes of absorbances over the 5 minute period in pooled "normal" citrated plasma, with each line representating a BD RST tube filled with 1 mL or 4 mL normal pooled citrate plasma and a different concentration of heparin, as described in Example 3h.

For the samples containing different volumes of citrated plasma and different heparin concentrations, the absorance change of each sample was monitored at 405 nM for 5 minutes, and the results are shown in FIG. 37. The reason for the shape of the progress curves at high heparin concentrations is unknown.

There were no samples that produced complete clotting in the presence of any of the three heparin concentrations. The strongest clot was observed with the samples containing 830 nM (2 IU) heparin and one mL of plasma, although the clot was loose by comparison to the solid clots in the absence of heparin. The weakest clots that formed were those in the tube filled with 4 mL of plasma and containing 8600 nM (20 IU) heparin. The clot was "fairy-floss" like and only in part of the sample. All tubes containing heparin showed some latent clotting after 5 minutes. The actual curve shape with the 4300 and 8600 nM (10 and 20 IU) heparin was very similar to the curves observed with PtPA and OsPA.

The slopes and the estimation of active thrombin in the presence of the different heparin concentrations and the different thrombin concentrations are shown in Table 23.

TABLE 23

Figure 36:
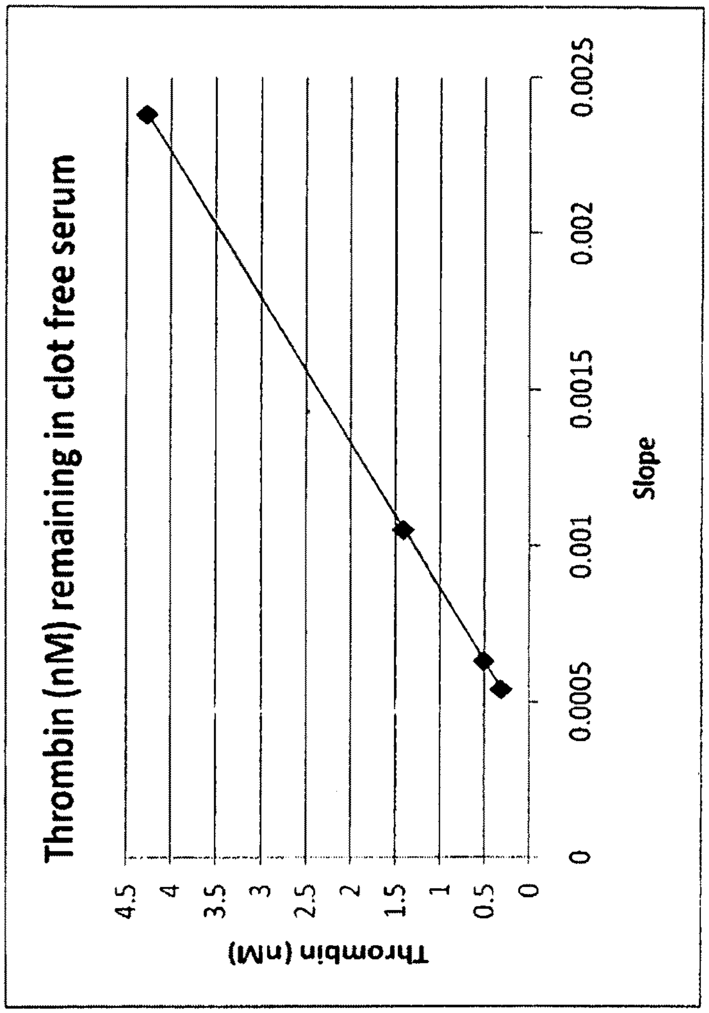
FIG. 36 shows the relationship between the measured slopes from FIG. 35 and the corresponding thrombin concentrations read from the standard curve in FIG. 16, as described in Example 3h.

Estimation of the active thrombin in the presence of different concentrations of heparin and different concentrations of thrombin from BD RST tubes, using the regression equation from the standard curve in FIG. 36.

| [Heparin] (IU) [nM] | [BD RST thrombin] per mL (nM) | Slope | Estimated [active BDRST thrombin] (nM) | Ratio of decrease in presence of heparin (column 2/column 4) |
|---|---|---|---|---|
| 2 [830 nM] | 135 | 0.00050 | 30 | 4.5 |
| 2 [830 nM] | 33.8 | 0.00016 | 6 | 5.6 |
| 10 [2150 nM] | 135 | 0.00050 | 30 | 4.5 |
| 10 [2150 nM] | 33.8 | 0.00024 | 12 | 3.0 |
| 20 [8300 nM] | 135 | 0.00042 | 25 | 5.4 |
| 20 [8300 nM] | 33.8 | 0.00020 | 9 | 3.8 |

The results showed that the same nominal thrombin concentrations (in column 2) produced similar active thrombin concentrations in the presence of different heparin concentrations. Thrombin concentrations measured after clotting were lower by several fold than the nominal concentrations.

Example 4

Clotting of Whole Blood Samples from Healthy Participants by Prothrombin Activators Example 4a Clotting by Ecarin For this experiment, ecarin, purified from *Echis carinatus* venom, was purchased from Sigma (catalogue number EO 504-1VL; batch number 128K 1536). Citrated blood (pool of three samples with normal coagulation profiles) was obtained from Pathology Queensland, Princess Alexandra Hospital, Queensland, Australia.

One vial of ecarin (50 units) was reconstituted in 100 μL of $H_2O$ resulting in a stock concentration of 500 units/mL.

Dilutions of this stock in distilled water (1:100, i.e. 5 units/mL; 1:1000, i.e. 0.5 units/mL; 1:10000, i.e. 0.05 units/mL) were used in TEG assays. Each assay mixture consisted of 310 μL citrated blood, 20 μL 0.2 M $CaCl_2$, and 10 μL saline (control) or ecarin dilution. Therefore, the concentration range of ecarin in the assay mixture was 0 to 0.15 units/mL. All experiments were done in duplicate. The results are shown in Table 24.

TABLE 24

TEG results for clotting of re-calcified citrated blood samples by ecarin.

| Ecarin (units/mL) | R (min) | TMA (min) | α (deg) | MA (mm) |
|---|---|---|---|---|
| control | 6.95 | 26.45 | 52.65 | 65.60 |
| 0.0015 | 7.3 | 27.60 | 59.80 | 65.65 |
| 0.015 | 4.5 | 17.90 | 74.15 | 67.25 |
| 0.15 | 2.1 | 15.75 | 69.25 | 73.80 |

Addition of ecarin to recalcified citrated blood resulted in a concentration dependent decrease in both R-time and TMA, and a small increase in MA. At the highest concentration tested, 0.15 units/mL, ecarin reduced the R-time from 6.95 to 2.1 minutes and the TMA from 26.45 to 15.75 minutes. The lowest concentration of ecarin tested, 0.0015 units/mL, had no significant effect on clotting time and clot strength whereas ecarin at a concentration of 0.015 units/mL had an intermediate effect.

These results suggest that ecarin would also be an effective prothrombin activator to rapidly produce serum for analyte measurements in a clinical laboratory.

Example 4b

Clotting of Normal "Pooled" Re-calcified Citrated Blood by Six Prothrombin Activators Purified preparations of ecarin, carinactivase-1, carinactivase-2, PtPA, OsPA, and notecarin prepared as described in Example 1 were used. Clotting of normal pooled citrated blood (as in Example 4a) by the six prothrombin activators, by thrombin, and in BD RST tubes was studied by TEG, as described in Example 4a.

The results are provided in Table 25.

TABLE 25

TEG clotting study with normal "pooled" re-calcified citrate blood with the different procoagulants.

| Procoagulant (nM) | R (min) | MA (mm) | TMA (min) |
|---|---|---|---|
| Ecarin | | | |
| 32 | 1.2 | 60.5 | 18.2 |
| 9 | 2.2 | 61.6 | 20.1 |
| 3.2 | 3.4 | 59.0 | 21.6 |
| 0.9 | 6.5 | 59.5 | 29.7 |
| Carinactivase-1 | | | |
| 50 | 3.3 | 69.1 | 21.7 |
| 32 | 4.6 | 68.5 | 27.1 |
| 9 | 6.2 | 63.9 | 31.4 |
| 3.2 | 7.4 | 64.9 | 30.3 |
| Carinactivase-2 | | | |
| 50 | 1.8 | 64.9 | 19.9 |
| 32 | 2.1 | 68.2 | 20.0 |
| 9 | 3.3 | 67.8 | 19.7 |
| 3.2 | 4.6 | 68.0 | 23.6 |

TABLE 25-continued

TEG clotting study with normal "pooled" re-calcified citrate blood with the different procoagulants.

| Procoagulant (nM) | R (min) | MA (mm) | TMA (min) |
|---|---|---|---|
| OsPA | | | |
| 0.9 | 0.7 | 63.7 | 18.4 |
| 0.09 | 2.9 | 61.8 | 20.5 |
| 0.009 | 4.2 | 63.5 | 22.5 |
| 0.0009 | 6.2 | 59.3 | 24.8 |
| PtPA | | | |
| 0.9 | 1.5 | 62.4 | 22.1 |
| 0.09 | 2.6 | 63.1 | 23.6 |
| 0.009 | 3.9 | 63.9 | 24.8 |
| 0.0009 | 5.8 | 53.4 | 28.1 |
| Notecarin | | | |
| 3.2 | 1.2 | 62.1 | 20.2 |
| 0.9 | 1.8 | 63.7 | 18.3 |
| 0.09 | 3.7 | 63.2 | 20.3 |
| 0.009 | 7.3 | 59.0 | 26.3 |
| Thrombin | | | |
| 32 | 2.3 | 65.2 | 22.8 |
| 9 | 3.5 | 64.0 | 23.8 |
| 3.2 | 5.5 | 62.4 | 27.6 |
| BD RST | | | |
| 24 | 0.8 | 54.8 | 24.8 |
| 6 | 1.5 | 59.3 | 23.7 |

These results provided further support to the plasma clotting findings (Example 3) that all prothrombin activators clot blood very efficiently; and that the group C prothrombin activators (PtPA and OsPA) were the most effective in clotting the normal "pooled" re-calcified citrated whole blood. For example, 9 μM PtPA and OsPA achieved R times of about 5 minutes, and the maximum clot strength as confirmed by the MA results. The next most effective prothrombin activator was notecarin, the group D prothrombin activator, which was able to produce an R time of 5 minutes and maximum clot strength with a minimum concentration between 0.09 and 0.009 nM. Although notecarin itself does not contain FVa, the FV present in plasma is converted to active form by the small amount of thrombin formed by the notecarin FXa. The next most effective prothrombin activator was ecarin, the group A prothrombin activator, which was able to achieve the desired R time and maximum clot strength with a minimum concentration between 0.9 and 3.2 nM. The least effective prothrombin activators were the group B prothrombin activators, carinactivase-1 and carinactivase-2 which required between ≥9 and ≥3 nM concentrations respectively to achieve R times of <5 minutes and maximum clot strength. The required minimum thrombin concentration to achieve the desired R time and maximum clot strength was ≥3 nM.

Example 4c

Comparison of Commercially Available Serum Tubes and PtPA-containing tubes

Blood from a healthy participant was drawn sequentially into the following tubes using an inline butterfly needle:

(1) a 4.0 mL Greiner Vacuette™ No Additive tube;
(3) Greiner Vacuette™ serum tube;
(4) BD Vacutainer™ serum tube;
(5) Sarstedt serum tube;
(6) Terumo RT tube; and
(7) Terumo plain tube.

The tubes were filled with freshly collected blood to the required fill mark and mixed immediately for 30 seconds by gentle inversion 8-10 times. Then a 340 μL sample was transferred into a TEG cup for immediate analysis. This method of blood collection allowed for rapid transfer of a blood sample for TEG analysis immediately after mixing in the commercially available tube so that no anticoagulant or re-calcification in TEG analysis was required. An aliquot, 330 μL of the blood from the plain tube (1) was immediately transferred to a TEG cup and 10 μL (1.41 μg) of PtPA was added (2), and analysis was immediately started.

All TEG assays were done in duplicate. The TEG parameters (average of the duplicate samples) are shown in Table 26 below.

TABLE 26

TEG results for blood from a healthy participant in different tubes

| Sample | R (min) | TMA (min) | α (deg) | MA (mm) |
|---|---|---|---|---|
| (1) Plain tube | 14.3 | 46.5 | 26.9 | 49.8 |
| (2) PtPA | 0.8 | 12.2 | 70.8 | 54.9 |
| (3) Greiner | 3.0 | 23.5 | 71.2 | 68.2 |
| (4) BD serum | 4.9 | 25.3 | 71.0 | 68.1 |
| (5) Sarstedt | 5.1 | 23.8 | 70.8 | 69.1 |
| (6) Terumo RT | 9.6 | 22.5 | 63.2 | 58.1 |
| (7) Terumo | 13.4 | 31.2 | 38.2 | 54.6 |

Figure 38:
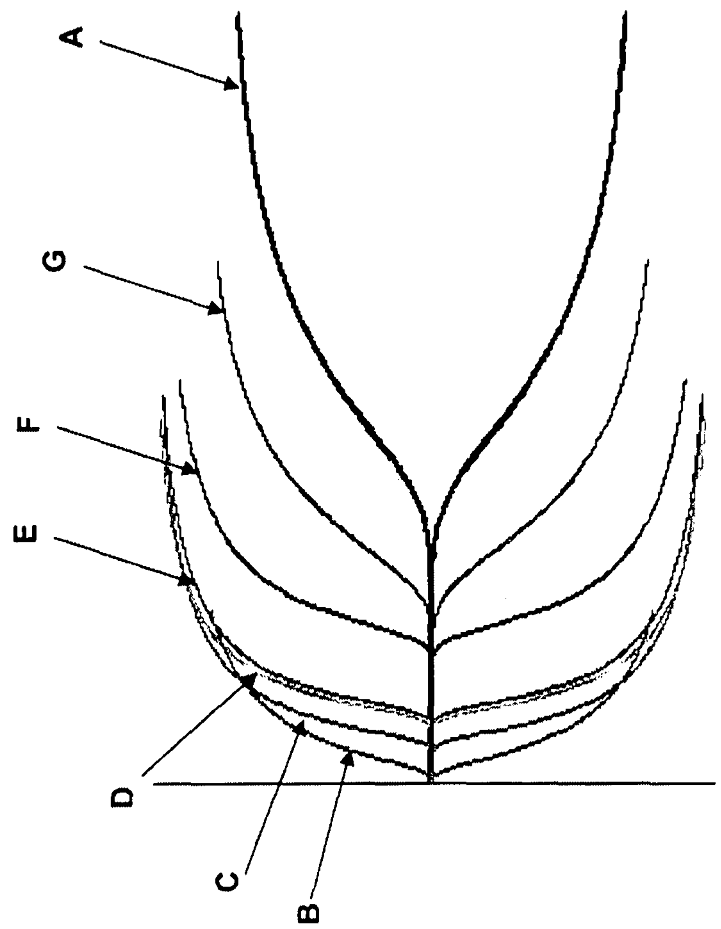
FIG. 38 shows TEG traces for comparison of plain tube, commercially available serum tubes, and PtPA-containing tube as described in Example 4c.
Figure 39A:
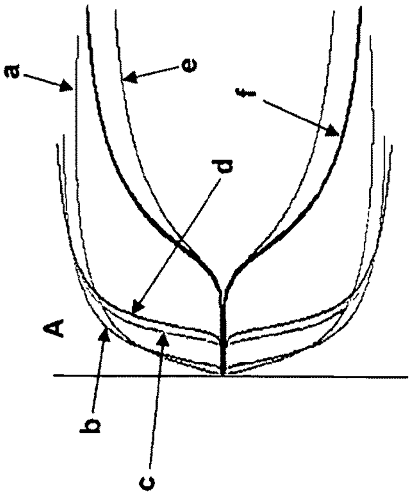
Figure 39B:
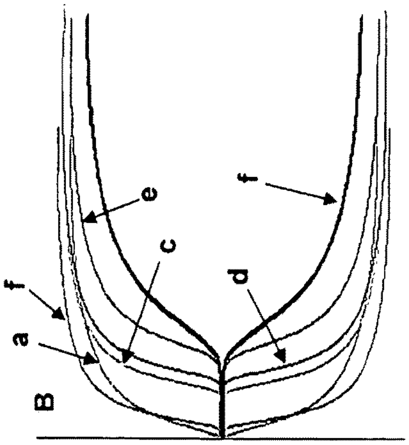
Figure 39C:
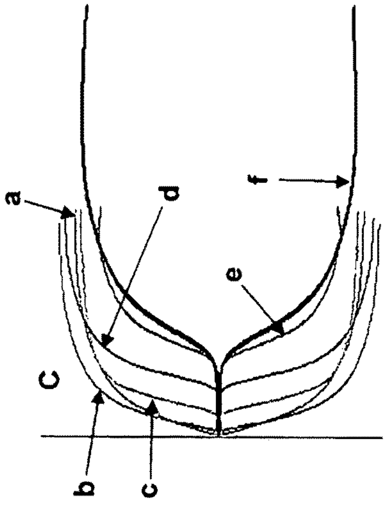
Figure 39D:
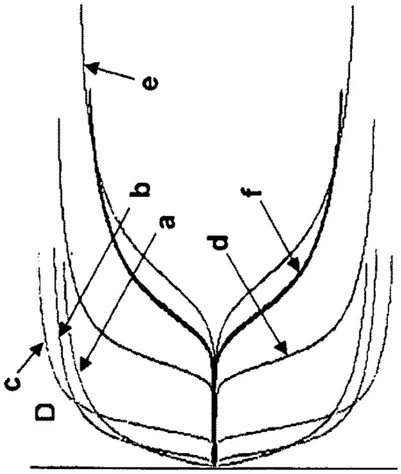

The TEG parameters of Table 26 are shown in the TEG plot in FIG. 38 where: trace A represents the plain plastic tube (1); trace B represents the plain tube with added PtPA (2); trace C represents the Greiner serum tube (3); trace D represents the BD serum tube (4); trace E represents the Sarstedt serum tube (5); trace F represents the Terumo RT tube (6); and trace G represents Terumo serum tube (7).

The blood sample in the PtPA tube (2) clotted most rapidly (R time=0.8 minutes) in the TEG cup. R times for the commercial tubes (3)-(7) varied from 3.0 minutes for the Greiner tube (3) to 13.4 minutes for the Terumo tube (7). These R times can be compared with the R time of 14.3 minutes for the plain tube (1). It is believed that the differences in R times between the commercial tubes reflect the presence of different procoagulants and additives, and/or different amounts of procoagulants or additives in these tubes.

Clot formation in all tubes was also visually observed. The commercially available tubes were allowed to clot for the standard time of 30 minutes. The PtPA specimen was allowed to stand for 5 minutes. The tubes were visually inspected for clot formation prior to loading in the centrifuge. All tubes were centrifuged at 3000 g for 10 minutes at 20° C. The specimens were stored at room temperature, ~21° C. for up to 6 hours and inspected on hourly intervals for latent clot formation. All tubes including the PtPA-containing tube formed solid clots, with the PtPA-containing tube forming a solid immobile clot within 2 minutes. No latent clotting was observed in any of the tubes up to 6 hours after collection.

This example shows that inclusion of a small amount of PtPA led to faster clotting than in any of the commercial tubes tested, demonstrating the potential for rapid production of serum to provide a faster turn-around time for analyte measurements in a clinical laboratory.

Example 4d

Clotting of Normal Citrated Blood by PtPA, OsPA, Ecarin, and Some Commercial Tubes The purpose of this experiment was to investigate how three prothrombin activators: PtPA, OsPA, and ecarin compare to three routinely used commercial clotting tubes: Greiner serum, BD SST II and BD RST.

Blood from a healthy participant was collected into a citrate-containing tube.

For the prothrombin activators, 30 μL of activator (concentration of PtPA and OsPA 0.56 nM; ecarin 5.3 nM in TEG cup), 20 μL of 0.2 M $CaCl_2$ and 290 μL of citrated blood was added to the TEG cup.

For the commercial serum tubes, 1 mL of distilled water was added and allowed to mix on a roller for ~2 hours to dissolve the content of the tube. The BD RST contains 135 nM bovine thrombin (33.8 nM/mL of blood), whereas the concentration used in this experiment in the TEG cup was 53 nM/mL. For the commercial serum tubes 45 μL of the dissolved content, 20 μL of 0.2 M $CaCl_2$ and 275 μL of citrated blood was added to the TEG cup.

The results are shown in Table 27.

TABLE 27

TEG data with PtPA, OsPA, ecarin, and routinely used commercial serum tubes with native blood from a healthy participant.

| Tube | Tube Catalogue # | R time (min) | MA | TMA |
|---|---|---|---|---|
| Greiner Vacuette Serum | 455078 | 2.8 | 62.5 | 20.6 |
| BD SST II | 367958 | 4.3 | 62.8 | 23.5 |
| BD RST (18 nM) | 368771 | 0.5 | 58.8 | 20.2 |
| PtPA (0.53 nM) | | 1.4 | 65.6 | 19.8 |
| OsPA (0.53 nM) | | 1.5 | 64.0 | 19.7 |
| Ecarin (5.3 nM) | | 2.6 | 64.3 | 19.3 |
| Native blood (plain tube) | | 6.4 | 67.6 | 27.8 |

The results demonstrated that the routinely used commercial serum tubes vary in the time at which significant clot formation was detected by the TEG (R time), with the time ranging from 0.5-6.4 minutes for re-calcified citrated blood from a healthy participant. The manufacturers of these tubes recommend a minimum clotting time of 30 minutes prior to centrifugation of the serum tubes. The results also demonstrated that PtPA and OsPA at 0.5 nM gave an R time of <2 minutes with an equivalent clot strength which make them very suitable for evaluation as procoagulant to be used in producing serum rapidly.

Example 5

Clotting of Whole Blood Samples Containing Anticoagulants by Prothrombin Activators Many blood samples are taken from patients being treated with anticoagulants such as heparin, warfarin and citrate. In addition, some blood samples are collected into tubes containing anticoagulants such as EDTA and citrate; or are contaminated with anticoagulants during the collection process. The following experiments were performed to study the clotting of blood samples containing anticoagulants by prothrombin activators.

Example 5a

Concentration Dependent Clotting of Citrated or EDTA Treated Blood from a Healthy Participant TEG analysis was performed where each TEG assay mixture consisted of 310 μL of citrated or EDTA treated blood, 20 μL of $CaCl_2$ (0.2 M) and 10 μL of saline or prothrombin activator solution at a range of concentrations (stock solutions—PtPA, 4.8 mg/mL or OsPA, 2.0 mg/mL). The results are shown in FIG. 39 and in Tables 28 and 29 or PtPA and Tables 30 and 31 for OsPA.

TABLE 28

TEG results for clotting of normal citrated blood with PtPA

| PtPA (μg/mL) | R (min) | TMA (min) | α (deg) | MA (mm) |
|---|---|---|---|---|
| 0 | 10.9 | 40.4 | 23.8 | 55.2 |
| 0.00141 | 10.3 | 39.6 | 26.2 | 44.0 |
| 0.0141 | 4.6 | 22.8 | 54.0 | 67.2 |
| 0.141 | 3.8 | 23.5 | 67.7 | 67.0 |
| 1.41 | 1.0 | 21.2 | 72.4 | 64.8 |
| 14.1 | 0.3 | 20.2 | 74.7 | 59.7 |

TABLE 29

TEG results for clotting of re-calcified EDTA-treated blood with PtPA

| PtPA (μg/mL) | R (min) | TMA (min) | α (deg) | MA (mm) |
|---|---|---|---|---|
| 0 | 9.8 | 39.2 | 25.8 | 54.6 |
| 0.00141 | 9.1 | 31.5 | 34.9 | 60.9 |
| 0.0141 | 6.8 | 27.0 | 62.4 | 64.4 |
| 0.141 | 5.5 | 25.3 | 62.0 | 64.4 |
| 1.41 | 1.3 | 19.8 | 72.1 | 66.3 |
| 14.1 | 0.3 | 21.2 | 70.1 | 60.9 |

TABLE 30

TEG results for clotting of normal citrated blood with OsPA

| OsPA (μg/mL) | R (min) | TMA (min) | α (deg) | MA (mm) |
|---|---|---|---|---|
| 0 | 9.0 | 31.3 | 29.5 | 55.0 |
| 0.000588 | 9.0 | 24.0 | 34.2 | 49.0 |
| 0.00588 | 5.9 | 21.3 | 54.3 | 62.0 |
| 0.0588 | 2.8 | 15.3 | 65.9 | 54.8 |
| 0.588 | 0.8 | 17.9 | 73.6 | 64.2 |
| 5.88 | 0.3 | 19.8 | 72.3 | 58.2 |

TABLE 31

TEG results for clotting of re-calcified EDTA-treated blood with OsPA

| OsPA (μg/mL) | R (min) | TMA (min) | α (deg) | MA (mm) |
|---|---|---|---|---|
| 0 | 13.9 | 40.8 | 31.2 | 50.7 |
| 0.000588 | 16.3 | 45.4 | 29.8 | 53.7 |
| 0.00588 | 9.8 | 30.0 | 36.2 | 62.4 |
| 0.0588 | 3.3 | 18.3 | 64.3 | 70.7 |
| 0.588 | 0.8 | 17.0 | 73.1 | 64.0 |
| 5.88 | 0.3 | 20.8 | 77.0 | 61.1 |

The R time of re-calcified blood without addition of a prothrombin activator was approximately 10 minutes which decreased to 1 minute or 1.3 minutes in the presence of 1.41 μg/mL PtPA (Tables 28 and 29). The rate of clotting was rapid (angle=54-72°) (between 0.0141 and 1.41) and full strength clots with MA values of 60-70 mm were obtained. The R time of re-calcified blood without addition of a prothrombin activator of approximately 10 minutes was decreased to 0.8 minutes in the presence of 0.59 μg/mL OsPA (Tables 30 and 31).

It is believed that the very short R-times and large α observed on addition of the PtPA or OsPA may be explained by generation of a massive burst of thrombin, while downstream reactions (conversion of fibrinogen to fibrin, activation of factor XIII, cross-linking of fibrin monomers) are rate limiting and result in a comparatively smaller improvement of TMA.

The TEG results from Tables 28, 28, 30 and 31 are shown in FIG. 39, where TEG plot A shows the Table 28 results (citrated blood and PtPA); TEG plot B shows the Table 29 results (EDTA treated blood and PtPA); TEG plot C shows the Table 30 results (citrated blood and OsPA) and TEG plot D shows the Table 31 results (EDTA treated blood and OsPA).

In FIG. 39, the traces labelled A in each TEG plot represent 14.1 μg/mL for PtPA and 5.88 μg/mL for OsPA; the traces labelled B represent 1.41 μg/mL for PtPA and 0.588 μg/mL for OsPA; the traces labelled C represent 0.141 μg/mL for PtPA and 0.0588 μg/mL for OsPA; the traces labelled D represent 0.0141 μg/mL for PtPA and 0.00588 μg/mL for OsPA; the traces labelled E represent 0.00141 μg/mL for PtPA and 0.000588 μg/mL for OsPA; and the traces labelled F represent 0 PtPA or 0 μg/mL OsPA.

In summary, PtPA and OsPA both clot re-calcified citrated and EDTA-treated blood in a highly efficient concentration-dependent manner. Thus in practice, blood collected in an EDTA tube could be rapidly clotted to produce serum by adding PtPA or OsPA for biochemical and other laboratory analysis.

Example 5b

Clotting of EDTA Plasma and Blood Obtained from a Healthy Participant

As mentioned in Example 3d above, a small but significant percentage of Samples (serum or lithium heparin plasma samples) received for biochemical analysis is contaminated by EDTA. It is therefore important to determine if prothrombin activators are effective in clotting EDTA plasma and EDTA whole blood. The purpose of this experiment was to do so, and to make a comparison of EDTA plasma and EDTA whole blood.

Blood from a healthy patient was collected into a Greiner EDTA tube containing 1.8 mg/mL (6.2 mmol) EDTA when filled to the fill mark. At this concentration, the EDTA is able to bind all the metal ions (including $Ca^{2+}$, $Mg^{2+}$, $Fe^{2+}$, $Zn^{2+}$, and $Cu^{2+}$) present in the tube. To obtain EDTA plasma, a portion of each sample was centrifuged under standard protocols.

The Clotek tube contained 100 μL of EDTA plasma, 100 μL of Tris Buffer (150 mM Tris HCl, 150 mM NaCl, pH 7.4), 50 μL of 0.2 M $CaCl_2$ or Tris buffer, and 50 μL of each procoagulant.

The TEG cup contained 20 μL of 0.2 M $CaCl_2$ or saline, 60 μL of procoagulant and 260 μL of the EDTA blood.

For the BD RST experiment the contents of two tubes were dissolved with 1 and 4 mL of distilled water respectively, mixed for 5 minutes and 60 μL, of the content used in the TEG cup as the procoagulant.

The results of the plasma clotting study are shown in Table 32 and in Table 33.

TABLE 32

Clotting times for EDTA plasma obtained from a healthy participant with different procoagulants (prothrombin activators and thrombin) at different concentrations, with calcium.

| | With $Ca^{2+}$ (seconds) | | | | | | |
|---|---|---|---|---|---|---|---|
| [Procoagulant] (nM) | Ecarin | CA-1 | CA-2 | PtPA | OsPA | Notecarin | Thrombin |
| 50 | 68.9 | 165.4 | 82.5 | 6.5 | 10.0 | 85.5 | 12.7 |
| 10 | 127 | 232 | 101 | 13.5 | 15.8 | 117 | 43.0 |
| 1 | 224 | >300 | 151 | 35.7 | 42.7 | 206 | >300 |
| 0.1 | ND | ND | ND | 98.6 | 123 | ND | >300 |

"ND" means this was not determined.

TABLE 33

Clotting times for EDTA plasma obtained from a healthy participant with different procoagulants (prothrombin activators and thrombin) at different concentrations, without calcium.

| | Without $Ca^{2+}$ (seconds) | | | | | | |
|---|---|---|---|---|---|---|---|
| [Procoagulant] (nM) | Ecarin | CA-1 | CA-2 | PtPA | OsPA | Notecarin | Thrombin |
| 50 | >300 | >300 | >300 | 31.7 | 56.4 | 132 | 17.9 |
| 10 | >300 | | | 48.7 | 68.2 | 242 | 53.2 |
| 1 | >300 | | | 86.4 | 107 | >300 | >300 |
| 0.1 | | | | 190 | 251 | | >300 |

The results of the BD RST plasma clotting study are shown in Table 34.

TABLE 34

Clotting times for the BD RST tubes, with and without calcium.

| BDRST Tube (nM) | With $Ca^{2+}$ (seconds) | Without $Ca^{2+}$ (seconds) |
|---|---|---|
| 1 mL (23) | 12.3 | 44.9 |
| 4 mL (6) | 34.3 | 101 |

EDTA is a metal chelator which chelates the calcium and in turn prevents the normal clotting process from occurring.

These results show that the calcium-dependent prothrombin activators carinactivase-1 (CA-1) and carinactivase-2 (CA-2) did not clot EDTA plasma even at 50 nM concentration in the pre-requisite time of <5 minutes, although they were able to after re-calcification. The effect on ecarin was significant: without re-calcification the clotting time was more than 5 minutes. The addition of calcium in excess caused only a moderate decrease in clotting time with PtPA and OsPA (for example, PtPA at 0.1 nM, 190 seconds to 98.6 seconds). Although other examples described herein have suggested that notecarin is less effective as a procoagulant than PtPA and OsPA, the results showed it was the prothrombin activator that was the least affected by the absence of calcium. The addition of calcium in excess caused 3-fold increase in the clotting of the plasma with thrombin.

The results from the whole blood clotting study are shown in Table 35.

TABLE 35

TEG results showing the effect of different procoagulants on EDTA blood with and without the presence of calcium.

| Procoagulant (nM) | R (min) | MA (mm) | TMA (min) |
|---|---|---|---|
| Ecarin | | | |
| 53 (re-calcified) | 2.5 | 56.8 | 22.1 |
| 53 (not re-calcified) | 16.9* | ND | ND |
| Carinactivase-1 | | | |
| 53 (re-calcified) | 4.8 | 57.6 | 29.5 |
| 53 (not re-calcified) | 16.9* | ND | ND |
| Carinactivase-2 | | | |
| 53 (re-calcified) | 2.6 | 55.7 | 25.6 |
| 53 (not re-calcified) | 34.8* | ND | ND |
| OsPA | | | |
| 53 (re-calcified) | 1.6 | 41.5 | 21.6 |
| 53 (not re-calcified) | 17.7* | ND | ND |
| PtPA | | | |
| 53 (re-calcified) | 0.5 | 58.2 | 22.9 |
| 53 (not re-calcified) | 17.8* | ND | ND |
| 1 (re-calcified) | 1.6 | 64.0 | 22.9 |
| PtPA | | | |
| 690 nM (Run 1) (not re-calcified) | 50.1* | ND | ND |
| 690 nM (Run 2) (not re-calcified) | 50.3* | ND | ND |
| Notecarin | | | |
| 53 (re-calcified) | 1.9 | 54.2 | 25.8 |
| 53 (not re-calcified) | 17.2* | ND | ND |
| Thrombin | | | |
| 53 (re-calcified) | 2.6 | 49.9 | 31.5 |
| 53 (not re-calcified) | 45.4* | ND | ND |
| BD RST | | | |
| 23 (re-calcified) | 1.6 | 45.4 | 24.0 |
| 23 (re-calcified) | 1.8 | 57.7 | 28.3 |
| 6 (re-calcified) | 30.1* | ND | ND |
| 6 (re-calcified) | 32.5* | ND | ND |
| Re-calcified EDTA blood alone | | | |
| Run 1 | 11.2 | 58.5 | 40.8 |
| Run 2 | 10.6 | 56.7 | 38.5 |

*means measurement was stopped, and ND means this was not determined.

This experiment showed that EDTA whole blood presents a difficult challenge for the procoagulants. Unlike with EDTA plasma, none of the procoagulants were able to clot EDTA blood in the absence of re-calcification. Clotting was not achieved even with very high PtPA concentration (690 nM). However, all procoagulants were able to clot the EDTA blood when it was re-calcified. Rapid and complete clotting was achieved even with a very low PtPA concentration (1 nM). EDTA is the anticoagulant of choice for preserving cellular morphology, and by chelating calcium the EDTA also prevents platelet activation and platelet clumping.

Two additional plasma clotting experiments using 30 nM PtPA were performed. In the first, water was added to the Clotek tube instead of Tris buffer and the sample still clotted in 6.4 seconds. In the second, no buffer was used, only 200 μL EDTA plus 50 μL PtPA and the clotting time was 5.4 seconds. For the TEG study, the following solutions were added to a TEG cup 50 μL Tris buffer, 60 μL PtPA, 230 μL EDTA blood and still no clotting was observed. Additionally, a BD RST tube was filled to the fill mark with EDTA blood and after 60 minutes it showed very partial clotting. It is obvious from these experiments that whenever EDTA may be present, addition of calcium with the procoagulant should be considered in order to achieve clotting.

Example 5c

Clotting of Blood from Warfarin-treated Participants

The effect of PtPA and OsPA on coagulation of blood samples from two participants ("W1" and "W2") on warfarin was determined.

The coagulation parameters of each participant, determined by standard coagulation protocols, are shown in Table 36, where:

aPTT=activated partial thromboplastin time;

PT=prothrombin time;

INR=international normalised ratio; and

Fib-D=prothrombin time derived fibrinogen.

TABLE 36

Coagulation parameters for the participants on anticoagulant treatment

| Participant | aPTT (s) | PT (s) | INR | Fib-D (g/L) |
|---|---|---|---|---|
| W1 | 30.27 | 21.3 | 2.08 | 1.55 |
| W2 | 36.15 | 27.4 | 2.61 | 5.20 |
| Normal plasma | 30-32 | 10-11 | 1.0 | 2.5-4.0 |

The results in Table 36 confirm that the blood from participants W1 and W2 was anticoagulated as expected.

TEG analysis was then performed. Each TEG assay mixture consisted of 310 μL of citrated blood, 20 μL of $CaCl_2$ (0.2 M) and 10 μL of saline or solution of prothrombin activator (PtPA or OsPA) resulting in final assay concentrations of prothrombin activator of between 0 and 14.1 μg/mL.

Figure 40B:
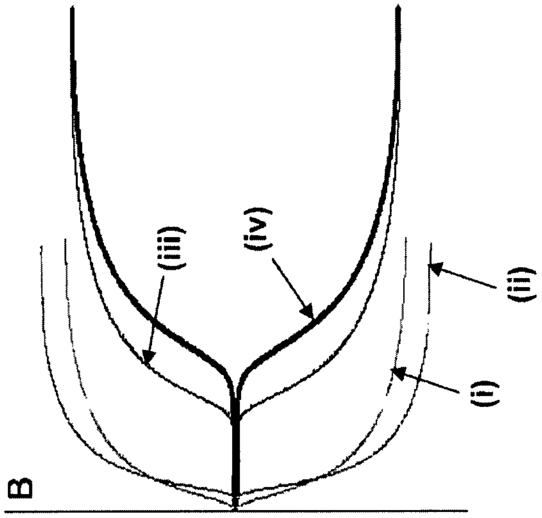
FIG. 40 shows TEG plots of the results for volunteer "W1" in Example 5c.
Figure 40A:
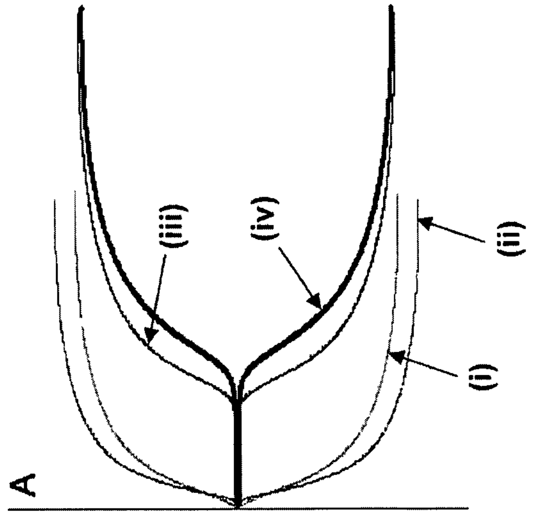
Figure 41:
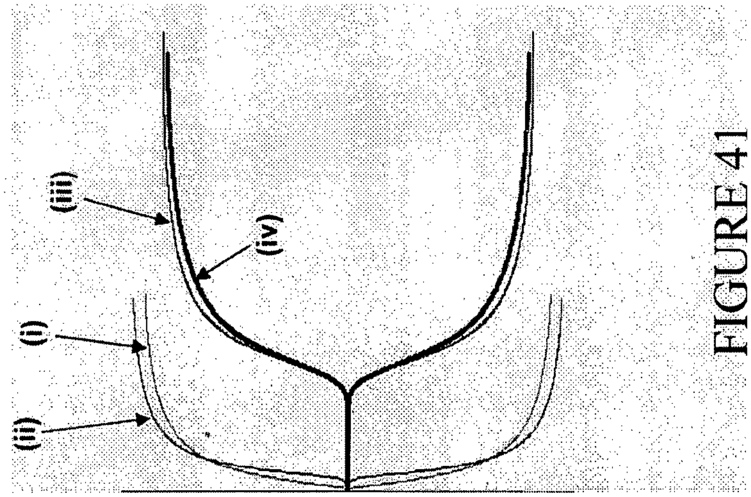
FIG. 41 shows TEG plots of the results for volunteer "W2" in Example 5c.

The TEG results are shown in Tables 37, 38 and 39 below. The values therein are derived from the TEG data as shown in FIGS. 40 and 41.

TABLE 37

TEG results for clotting of citrated blood of W1 with OsPA

| OsPA (μg/mL) | R (min) | TMA (min) | α (deg) | MA (mm) |
|---|---|---|---|---|
| 0 | 12.2 | 35.5 | 23.6 | 50.4 |
| 0.0588 | 4.4 | 22.9 | 68.1 | 59.5 |
| 0.588 | 1.6 | 16.7 | 73.8 | 60.8 |
| 5.88 | 0.6 | 17.8 | 67.5 | 53.0 |

TABLE 38

TEG results for clotting of citrated blood of W1 with PtPA

| PtPA (μg/mL) | R (min) | TMA (min) | α (deg) | MA (mm) |
|---|---|---|---|---|
| 0 | 12.2 | 35.5 | 23.6 | 50.4 |
| 0.0141 | 9.4 | 31.5 | 48.4 | 54.3 |
| 1.41 | 0.8 | 18.8 | 69.7 | 59.6 |
| 14.1 | 0.4 | 20.6 | 65.1 | 53.1 |

TABLE 39

TEG results for clotting of citrated blood of W2 with PtPA

| PtPA (μg/mL) | R (min) | TMA (min) | α (deg) | MA (mm) |
|---|---|---|---|---|
| 0 | 12.3 | 37.6 | 49.1 | 60.8 |
| 0.0141 | 7.7 | 26.1 | 62.9 | 66.4 |
| 1.41 | 1.3 | 17.9 | 77.7 | 73.3 |
| 14.1 | 0.4 | 18.4 | 79.6 | 69.4 |

TEG plots of the results in Tables 37 and 38 are provided in FIG. 40 where TEG plot A shows the results from Table 37 (OsPA) and TEG plot B shows the results from Table 38 (PtPA). In FIG. 40, for the A plot the trace labelled (i) shows the results for 5.88 μg/mL OsPA, the trace labelled (ii) for 0.588 μg/mL OsPA, the trace labelled (iii) for 0.0588 μg/mL OsPA, and the trace labelled (iv) for 0 μg/mL. In FIG. 40, for the B plot the trace labelled (i) shows the results for 14.1 μg/mL PtPA, the trace labelled (ii) for 1.41 μg/mL PtPA, the trace labelled (iii) for 0.0141 μg/mL PtPA, and the trace labelled (iv) for 0 μg/mL.

In FIG. 41, the trace labelled (i) shows the results for 14.1 μg/mL PtPA, the trace labelled (ii) for 1.41 μg/mL PtPA, the trace labelled (iii) for 0.0141 μg/mL PtPA, and the trace labelled (iv) for 0 μg/mL.

In summary, both PtPA and OsPA at low concentrations rapidly clotted blood samples from participants on warfarin therapy, with R times, α values and MA values similar to those in comparable experiments with blood from a healthy participant (see Tables 28-31 above). These results confirm the observation on warfarin plasma in Example 3c.

Example 5d

Clotting of Blood from a High Dose Heparinised Participant with PtPA and OsPA Blood was taken from a participant ("H1") who had been given 35,000 IU of heparin 30 minutes prior to the blood sample being taken. The concentration of heparin was calculated to be approximately 7 IU/mL of blood. Blood was collected in a plain syringe and then transferred to a Greiner Vacuette™ citrate tube.

The coagulation parameters of the participant were measured and are shown in Table 40.

TABLE 40

Coagulation parameters for the heparinised participant.

| Participant | aPTT(s) | PT(s) | INR | TT(s) | PTNH(s) | REPT(s) | Fib-D(g/L) |
|---|---|---|---|---|---|---|---|
| H1 | failed | 41.2 | 3.75 | failed | 17.75 | 15.28 | 2.40 |

All coagulation parameters in Table 40 are known in the art, being: aPTT=activated partial thromboplastin times; PT=prothrombin time; INR=international normalised ratio; TT=thrombin time; PTNH=protamine sulphate time; REPT=repitalise time; Fib-D=prothrombin time derived fibrinogen.

The results in Table 40 are in the range of expected results for a heavily heparinised sample.

TEG analysis was then performed. Each TEG assay mixture consisted of 310 μL of citrated blood, 20 μL of $CaCl_2$ (0.2 M) and 10 μL of saline or solution of prothrombin activator (PA).

The TEG results are shown in Table 41 below and in FIG. 42.

TABLE 41

| TEG results for clotting of blood from a participant on very high doses of heparin. | | | | | |
|---|---|---|---|---|---|
| | PA concentration | Citrated | | | |
| PA | (μg/mL) | R (min) | TMA (min) | α (deg) | MA (mm) |
| | 0 | n.c. | n.c. | n.c. | n.c. |
| PtPA | 14.1 | 0.4 | 20.9 | 72.6 | 64.3 |
| OsPA | 5.9 | 1.3 | 12.8 | 70.6 | 61.3 |

In Table 41 above, "n.c." indicates no clotting.

Figure 42:
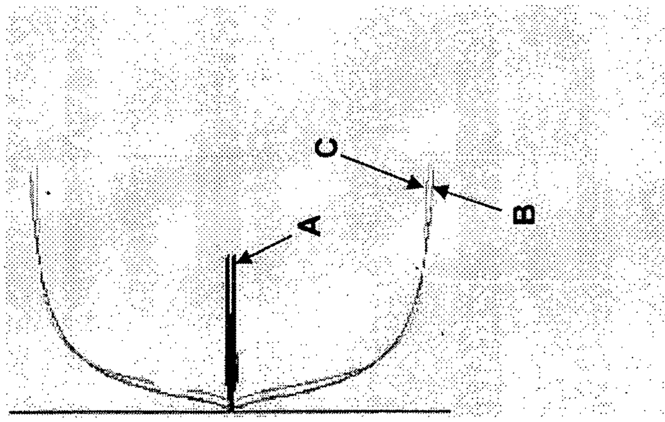
FIG. 42 shows TEG traces for clotting of recalcified citrated blood from a heparinised participant with PtPA or OsPA as described in Example 5d.

TEG traces of the results in Tables 41 are provided in FIG. 42 where the trace labelled A shows the results for no prothrombin activator; the trace labelled B shows the results for 14.1 μg/mL PtPA; and the trace labelled C shows the results for 5.9 μg/mL OsPA.

At the concentration tested both PtPA and OsPA were able to clot citrated blood from the heparinised participant rapidly. The values for the TEG parameters monitored (R-time, TMA, angle, MA) were comparable with the results obtained from blood of a healthy participant, indicating that the activity of the prothrombin activators was not inhibited by the concentration of heparin present in the blood sample.

Example 5e

Clotting of Blood from a Fully Heparinised Participant with a PtPA-containing Tube and a BD RST Tube A 10 mL blood sample was collected from a participant undergoing cardiac surgery who had been given 38,000 IU of heparin 30 minutes before sample collection. The blood was collected in a plain syringe and within 10 minutes delivered to the laboratory for analysis.

The BD RST tube was filled to the fill mark, inverted/mixed for 30 seconds and 340 μL of this blood was transferred to a TEG cup in channel 1.

330 μL of the original heparinised participant blood sample was added to 10 μL of PtPA (final concentration 1.41 μg/mL) in a TEG cup in channel 2.

Figure 43:
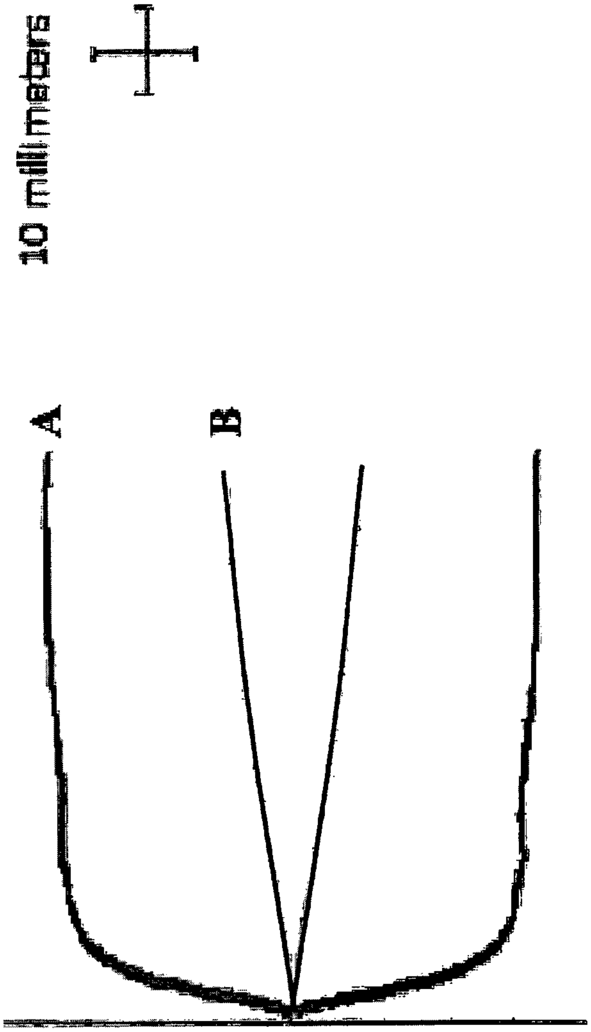
FIG. 43 shows the TEG traces of the Example 5e results.
Figure 44A:
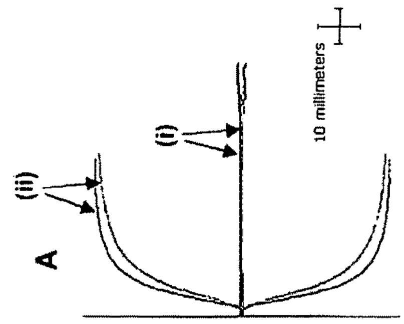
FIG. 44 shows the TEG plots of the Example 6a results.
Figure 44B:
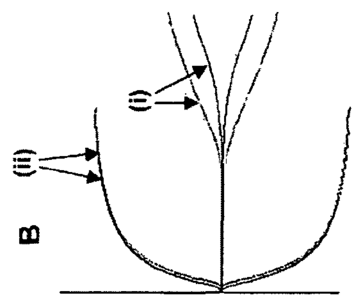
Figure 44C:
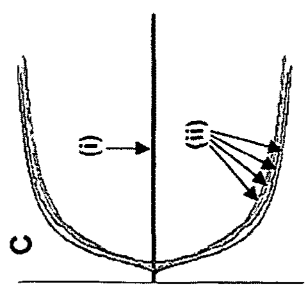
Figure 44D:
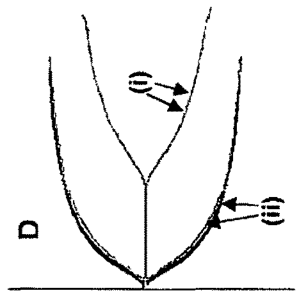
Figure 45A:
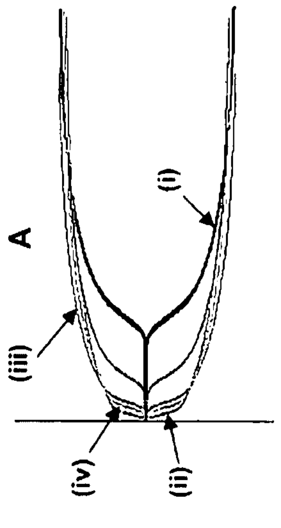
FIG. 45 shows the TEG plots of the Example 6b results.
Figure 45B:
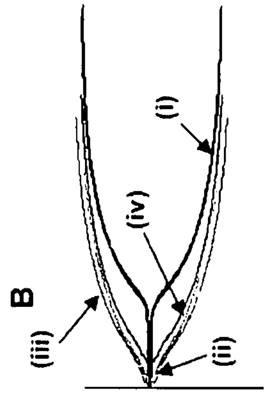
Figure 45C:
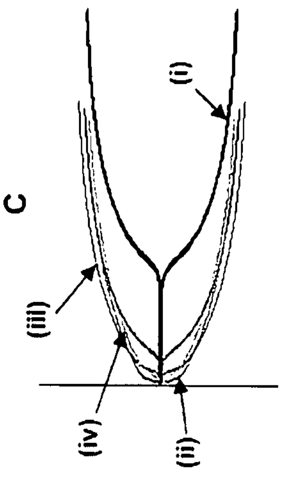
Figure 45D:
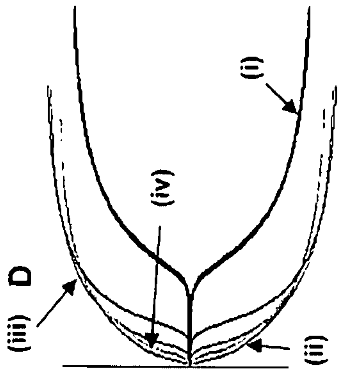

The results of the TEG analysis are shown in Table 42 and in FIG. 43.

TABLE 42

| TEG analysis results for heparinised blood in BD RST tube and with PtPA | | | | | |
|---|---|---|---|---|---|
| Sample | R (min) | K (min) | Angle (deg) | MA (mm) | TMA (min) |
| PtPA (outer trace) | 0.7 | 1.3 | 74.4 | 43.8 | 9.8 |
| BD RST tube (inner trace) | 6.2 | N/A | 7.8 | 11.5 | 24.0 |

For the BD RST tube, the R time was 6.2 minutes with a maximum amplitude (MA) value of 11.5 mm, indicating that only partial clotting was achieved. This clot strength did not increase further during the 2 hour period of the analysis.

With PtPA, the R time was 0.7 minutes, the maximum amplitude (MA) was 43.8 mm and the time to maximum amplitude was 9.8 minutes indicating that a strong and stable clot was achieved quickly.

The results from Table 42 are also shown in FIG. 43 as a TEG plot where trace "A" is the trace of the TEG cup in channel 2 (PtPA) and trace "B" is the trace of the TEG cup in channel 1 (BD RST tube).

The blood collected in the plain syringe, and the blood in the BD RST tube were also monitored visually for clotting. No clotting was observed in the plain syringe for up to 2 days. Blood in the BD RST tube showed partial clotting at 30 minutes and complete clotting within 24 hours.

In summary, the heavily heparinised sample clotted rapidly and completely in a tube containing PtPA but only very slowly and incompletely in a BD RST tube.

Example 5f

Clotting of Blood Samples Containing Heparin by Prothrombin Activators

The ability of venom prothrombin activators to clot blood from a healthy participant collected in a Greiner lithium heparin tube (18 IU heparin per mL of blood) was determined using TEG analysis and the results are shown in Table 43. The citrate sample was collected for the comparison of the MA values.

TABLE 43

| TEG results with blood collected in Greiner lithium heparin tube from a healthy participant. | | | |
|---|---|---|---|
| Procoagulant (nM) | R (min) | MA (mm) | TMA (min) |
| Ecarin | | | |
| 56 (black) | 9.9 | 18.8 | 37.8 |
| 32 (green) | 13.8 | 18.6 | 39.8 |
| Carinactivase - 1 | | | |
| 100 (black) | 35.6* | ND | ND |
| 50 (green) | 34.8* | ND | ND |
| Carinactivase - 2 | | | |
| 56 (black) | 10.4 | 23.0 | 37.8 |
| 34 (green) | 18.0 | 18.5 | 47.5 |
| OsPA (nM) | | | |
| 56 (magenta) | 1.9 | 37.6 | 24.7 |
| 34 (pink) | 2.3 | 36.5 | 26.1 |
| 9 (green) | 2.9 | 29.8 | 25.2 |
| 3 (black) | 10.3 | 6.2 | 20.0 |
| PtPA | | | |
| 56 (magenta) | 2.3 | 33.5 | 26.6 |
| 34 (brown) | 2.3 | 39.8 | 27.2 |
| 9 (green) | 2.8 | 31.3 | 25.7 |
| 3 (black) | 6.8 | 14.7 | 25.8 |
| Notecarin | | | |
| 56 (black) | 2.5 | 34.1 | 30.7 |
| 32 (green) | 7.9 | 18.0 | 28.4 |
| BD RST | | | |
| 25 (black) | 35.6* | ND | ND |
| 6 (green) | 35.8* | ND | ND |
| Re-calcified citrate blood | | | |
| Run 1 | 6.3 | 61.2 | 30.1 |
| Run 2 | 6.5 | 61.5 | 27.1 |

*means measurement was stopped, and
ND means this was not determined.

The results of this experiment with lithium heparin whole blood showed that some of the procoagulants were capable of clotting the heparinised blood at lower procoagulant concentrations, while other procoagulants were unable to clot the blood even at the highest concentration range tested in this experiment. The results show that the group C procoagulants (PtPA and OsPA) were the most effective in clotting the blood collected in Greiner lithium heparin tubes, requiring ≥9 nM for OsPA and PtPA to achieve R time within 5 minutes. This was significantly lower than the MAs (~61) achieved in the recalcified citrated blood. Although not wishing to be bound by theory, it is believed likely that the ATIII-heparin complex inhibits the thrombin formed, and subsequently prevents proper or stronger clot formation. The minimum concentrations required for the other prothrombin activators are >56 nM for ecarin and carinactivase-2, >100 nM for carinactivase-1, and >32 nM of notecarin. The thrombin concentrations of 6 and 25 nM from the BDRST tubes failed to clot the blood at all.

Again, although not wishing to be bound by theory, it is believed likely that the group C prothrombin activators (OsPA and PtPA) produced a much larger and more sustained burst of thrombin to overwhelm the ATIII-heparin complex that inhibits both thrombin and FXa and subsequently the clotting process.

Example 5g

Clotting of Normal "Pooled" Citrated Plasma Spiked with Different Concentrations of Heparin This experiment was performed to determine the required concentrations of the different prothrombin activators to clot plasma spiked with heparin at different concentrations to mimic levels likely to be found in plasma from heparinised patients.

Normal "pooled" citrated plasma had the total calcium adjusted to 2.71 mmol/L and then aliquots of heparin were added to give final heparin concentrations in the Clotek Tube of 0.8, 2.0, 10 and 20 IU/mL which is the range that may be encountered in patient blood samples. Additionally 1 mL aliquots of the citrated plasma were dispensed in Greiner lithium heparin tubes, and then mixed on a roller for 15 minutes to give lithium heparin concentration of 90 IU/mL. The Clotek tube contained 100 μL of sodium or lithium heparin plasma, 100 μL of Tris Buffer (150 mM Tris HCl, 150 mM NaCl, pH 7.4) and 50 μL of each procoagulant.

The clotting results for each prothrombin activator with the heparin spiked plasma samples are shown in Tables 44-49, and for thrombin is shown in Table 50.

TABLE 44

Clotting by PtPA of normal "pooled" citrated plasma spiked with heparin or dispenses in Greiner lithium heparin tubes

| Heparin | PtPA (nM)/Clotting Time (secs) | | | | | |
|---|---|---|---|---|---|---|
| (IU/mL) | 120 nM | 60 nM | 36 nM | 30 nM | 20 nM | 12 nM |
| 0 | 3.3 | 4.3 | 5.2 | 5.5 | 6.4 | 10.1 |
| 0.8 | 3.5 | 5.3 | 7.4 | 7.6 | 10.4 | 14.0 |
| 2.0 | 6.2 | 9.8 | 12.7 | 15.7 | 16.6 | 26.5 |
| 10 | 25.3 | 39.1 | 46.1 | 60.2 | 72.3 | 142 |
| 20 | 38.0 | 47.2 | 68.2 | 80.6 | 232 | >300 |
| 90 (Greiner Li Hep tube) | 17.4 | 27.7 | 53.7 | 69.5 | 228 | >300 |

TABLE 45

Clotting by OsPA of normal "pooled" citrated plasma spiked with heparin or dispenses in Greiner lithium heparin tubes

| Heparin | OsPA(nM)//Clotting Time (secs) | | | | | |
|---|---|---|---|---|---|---|
| (IU/mL) | 120 nM | 60 nM | 36 nM | 30 nM | 20 nM | 12 nM |
| 0 | 6.9 | 7.2 | 8.3 | 8.6 | 8.9 | 9.4 |
| 0.8 | 9.1 | 10.8 | 12.9 | 13.7 | 16.4 | 21.7 |
| 2.0 | 13.8 | 15.2 | 17.6 | 19.1 | 22.6 | 27.9 |
| 10 | 27.3 | 35.2 | 49.2 | 56.5 | 86.1 | 270 |
| 20 | 93.9 | 120 | >300 | >300 | >300 | >300 |
| 90 (Greiner Li Hep tube) | >300 | >300 | >300 | >300 | >300 | >300 |

TABLE 46

Clotting by notecarin of normal "pooled" citrated plasma spiked with heparin or dispenses in Greiner lithium heparin tubes

| Heparin | Notecarin (nM)/Clotting Time (secs) | | | |
|---|---|---|---|---|
| (IU/mL) | 120 nM | 60 nM | 36 nM | 12 nM |
| 0 | 44.3 | 55.1 | 61.6 | 87.0 |
| 0.8 | 49.8 | 65.0 | 78.3 | 126 |
| 2.0 | 57.0 | 92.2 | 129 | 262 |
| 10 | >300 | >300 | >300 | >300 |
| 20 | >300 | >300 | >300 | >300 |
| 90 (Greiner Li Hep tube) | >300 | >300 | >300 | >300 |

TABLE 47

Clotting by ecarin of normal "pooled" citrated plasma spiked with heparin or dispenses in Greiner lithium heparin tubes

| Heparin | Ecarin (nM)/Clotting Time (secs) | | | |
|---|---|---|---|---|
| (IU/mL) | 120 nM | 60 nM | 36 nM | 12 nM |
| 0 | 28.5 | 40.0 | 49.3 | 92.3 |
| 0.8 | 30.1 | 41.3 | 51.8 | 109 |
| 2.0 | 33.1 | 50.9 | 70.7 | 156.6 |
| 10 | 75.7 | 142 | 269 | >300 |
| 20 | 140 | >300 | >300 | >300 |
| 90 (Greiner Li Hep tube) | >300 | >300 | >300 | >300 |

TABLE 48

Clotting by carinactivase-1 of normal "pooled" citrated plasma spiked with heparin or dispenses in Greiner lithium heparin tubes

| Heparin | CA-1(nM)//Clotting Time (secs) | | | |
|---|---|---|---|---|
| (IU/mL) | 120 nM | 60 nM | 36 nM | 12 nM |
| 0 | 170 | 258 | >300 | >300 |
| 0.8 | 215 | 297 | >300 | >300 |
| 2.0 | >300 | >300 | >300 | >300 |
| 10 | >300 | >300 | >300 | >300 |
| 20 | >300 | >300 | >300 | >300 |
| 90 (Greiner Li Hep tube) | >300 | >300 | >300 | >300 |

TABLE 49

Clotting by carinactivase-2 of normal "pooled" citrated plasma spiked with heparin or dispenses in Greiner lithium heparin tubes

| Heparin | CA-2 (nM)/Clotting Time (secs) | | | |
|---|---|---|---|---|
| (IU/mL) | 120 nM | 60 nM | 36 nM | 12 nM |
| 0 | 80.6 | 120 | 168 | 267 |
| 0.8 | 87.8 | 126 | 181 | >300 |
| 2.0 | 130 | 230 | >300 | >300 |
| 10 | >300 | >300 | >300 | >300 |
| 20 | >300 | >300 | >300 | >300 |
| 90 (Greiner Li Hep tube) | >300 | >300 | >300 | >300 |

TABLE 50

Clotting by thrombin of normal "pooled" citrated plasma spiked with heparin or dispenses in Greiner lithium heparin tubes

| Heparin | Thrombin (nM)/Clotting Time (secs) | | | |
|---|---|---|---|---|
| (IU/mL) | 100 | 60 | 30 | 10 |
| 0 | 5.1 | 7.0 | 13.5 | 24.7 |
| 0.8 | 23.2 | >300 | >300 | >300 |
| 2.0 | >300 | >300 | >300 | >300 |
| 10 | >300 | >300 | >300 | >300 |
| 20 | >300 | >300 | >300 | >300 |
| 90 (Greiner Li Hep tube) | >300 | >300 | >300 | >300 |

As was shown in the previous experiment (Example 5f) the presence of heparin (and thrombin inhibition due to the ATIII-heparin complex) presents a major challenge for the procoagulants in preventing partial or complete clotting of blood. The results of this experiment showed the relative effectiveness of the procoagulants in clotting of heparinised plasma.

The results show that PtPA and OsPA were the most effective prothrombin activators in overcoming the anticoagulant effect from the ATIII-heparin complex. PtPA required the lowest concentration (12-20 nM) to clot plasma containing highest heparin concentrations that may be encountered in patient samples. One interesting finding was PtPA was the only prothrombin activator able to effectively clot the heparinised plasma from the Greiner lithium heparin tube in <5 minutes with all but the lowest PtPA concentration of 12 nM even though the heparin concentration was 90 IU/mL compared with the spiked sample containing 20 IU/mL heparin. It was quite possible the PtPA only was aided by the surfactant contained in the Greiner lithium heparin tube. OsPA required >36 nM and ecarin >60 nM to be able to clot the plasma containing 20 IU of heparin, and both were unable to clot the heparinised plasma from the Greiner lithium heparin tube in <5 minutes respectively. Carinactivase-2 and notecarin were unable to clot the plasma containing ≥10 IU of heparin while the carinactivase-1 was unable to clot the plasma containing >0.8 IU of heparin in the pre-requisite time of <5 minutes even when the concentration was 120 nM. The thrombin study showed thrombin concentration of 100 nM was only able to clot the sample spiked with the lowest heparin concentration, 0.8 IU/mL. Thus, when considering the BD RST tube which contains 135 nM of thrombin it is unlikely to clot samples containing heparin >2 IU/mL in the prerequisite time of 5 minutes.

Example 5h

Clotting of Lithium Heparin Plasma from a Healthy Participant

Samples collected in Greiner lithium heparin tubes are likely to be the most highly heparinised samples a laboratory will receive, particularly if the tubes are not filled to the recommended fill volume. The purpose of this experiment was to provide a guide on the minimum concentration required of the procoagulants to clot all other samples that may be received from heparin anticoagulated patients and produce high quality serum.

Greiner lithium heparin tubes were filled to the recommended fill mark, giving a heparin concentration of 18 IU/mL. The Clotek tubes contained 100 μL of lithium heparin plasma, 100 μL of Tris Buffer (150 mM Tris HCl, 150 mM NaCl, pH 7.4) and 50 μL of each procoagulant. The TEG cups contained 60 μL procoagulant and 260 μL of the participant blood collected in Greiner lithium heparin tube.

For the BD RST tube, deionised water was added to two tubes (BDRST1-1 mL; BDRST2-4 mL), allowed to mix on a roller for 30 minutes to dissolve the thrombin and the content was used as with the other procoagulants.

The clotting results for each procoagulant with the lithium heparin plasma are shown in Table 51.

TABLE 51

Clotting study with lithium heparin plasma collected in Greiner Lithium Heparin Tube.

| [Prothrombin activator] (nM) | Clotting Time (s) | | | | | | |
|---|---|---|---|---|---|---|---|
| | Ecarin | CA-1 | CA-2 | PtPA | OsPA | Notecarin | Thrombin |
| 120 | 69.0 | >300 | 100.1 | 7.5 | 15.6 | 47.8 | >300 |
| 60 | 122.6 | >300 | 180.3 | 10.7 | 18.1 | 62.7 | >300 |
| 36 | 175.2 | | 270.6 | 13.1 | 21.0 | 82.4 | >300 |
| 12 | >300 | | >300 | 32.7 | 37.1 | 269.3 | |
| 4 | >300 | | >300 | 78.5 | 102.1 | >300 | |
| 1 | >300 | | >300 | 207.8 | >300 | >300 | |
| 0.1 | >300 | | >300 | >300 | >300 | | |
| 0.01 | >300 | | >300 | >300 | >300 | | |

The experiment design was to show the effectiveness of the procoagulants in clotting heparinised plasma from blood collection tubes. It was found that the minimum required concentration range to achieve clotting of <5 minutes for ecarin and carinactivase-2 was 12 to 36 nM, >120 nM for carinactivase-1, and 4 to 12 nM for notecarin. For the thrombin, concentration of >120 nM was necessary. The BD RST tube was tested as well with 7.7 and 27 nM of thrombin and both concentrations producing clotting time >5 minutes which suggested that the BDRST may be ineffective in clotting samples from patients on high doses of heparin. The results show the group C prothrombin activators (PtPA and OsPA) were easily the most effective in clotting the lithium heparin plasma obtained from blood of a healthy participant collected in Greiner lithium heparin tubes, requiring between 0.1 to 1 nM of PtPA and between 1 to 4 nM of OsPA respectively to achieve clotting in <5 minutes.

Example 5i

Clotting of Blood and Plasma Obtained from a "Fully Heparinised" Cardiac Surgery Participant The highest concentration of heparin given intravenously is in complex surgical procedures such as cardiac surgery. If samples are collected for biochemistry during the maximum heparinisation period the results usually need to be provided in the shortest possible time. If serum is used, this will require the clotting to be completed by the procoagulant by the time these serum samples arrive in the laboratory, say in <10 minutes.

The heparin that is given to patients is sodium heparin while in blood collection tubes or syringes it is lithium heparin. The maximum amount of heparin infused in such patients is ~45000 IU. These patients are also haemodiluted (i.e., there is an increase in blood plasma volume to ~4 L), giving a heparin concentration of ~10 IU per mL of plasma.

This experiment was designed to determine whether the selected procoagulant concentrations were able to clot "fully" heparinised cardiac surgery patient blood and produce high quality serum. The participant had received 37000 IU of heparin and the sample was collected ~30 minutes post heparin infusion, equating to ~9.3 IU of heparin per mL of plasma. A portion of the blood sample was centrifuged to obtain plasma.

For plasma clotting, the Clotek tube contained 100 μL of cardiac participant plasma, 100 μL of Tris Buffer (150 mM Tris HCl, 150 mM NaCl, pH 7.4) and 50 μL of each procoagulant.

For the whole blood clotting, the TEG cup contained 60 μL of procoagulant and 260 μL of the participant blood. Being fully heparinised the blood did not clot on its own.

For the BD RST-1 experiment, the contents of two BDRST tubes were dissolved with 1 and 4 mL of distilled water respectively, and 60 μL of the solution used in the TEG cup as the procoagulant.

For the BDRST-2 experiment, the tubes were filled with 1 and 4 mL of blood respectively, the tubes were inverted 10 times (~30 secs) and 340 μL of the blood was transferred to the TEG cup.

The clotting results for each procoagulant with the patient's plasma are shown in Table 52, and the whole blood results are shown in Table 53.

TABLE 52

Clotting times in seconds of plasma from a "fully heparinised" cardiac surgery participant with the different prothrombin activators, tnrombin and BD RST tube contents at different concentrations.

| Procoagulant conc (nM) | PtPA | OsPA | Ecarin | CA-1 | CA-2 | Notecarin | Thrombin | BDRST |
|---|---|---|---|---|---|---|---|---|
| 120 | 10.0 | ND | 64.8 | 175 | 66.5 | ND | >300 | >300 (27 nM) |
| 60 | 14.8 | 18.7 | 89.7 | >300 | 95.1 | 68.6 | >300 | >300 (6 nM) |
| 36 | 15.9 | 27.3 | >300 | >300 | 124 | 84 | >300 | ND |
| 12 | 36.3 | 35.5 | >300 | >300 | >300 | 163 | ND | ND |
| 6 | 65.9 | ND | ND | ND | ND | ND | ND | ND |
| 4 | 301.6 | 100 | >300 | >300 | >300 | 179 | ND | ND |
| 3 | ND | 123 | ND | ND | ND | ND | ND | ND |
| 1 | ND | >300 | ND | ND | ND | >300 | ND | ND |

ND means this was not determined.

The results from this experiment showed the concentrations of each procoagulant required to clot the plasma in the prerequisite time of <5 minutes. The maximum activator concentration giving clotting time of about 5 minutes were: PtPA 4 nM, OsPA 1-3 nM, notecarin 3 nM, carinactivase-2>12 nM, ecarin >36 nM, carinactivase-1>60 nM, and thrombin >120 nM. It was surprising to note that the notecarin efficacy was comparable to the group C activators.

TABLE 53

Results of the TEG clotting study with blood from a "fully heparinised" cardiac surgery participant with the different procoagulants.

| Procoagulant (nM) | R (min) | MA (mm) | TMA (min) |
|---|---|---|---|
| Ecarin | | | |
| 56 | 2.3 | 47.6 | 19.4 |
| 34 | 3.7 | 49.0 | 25.1 |
| 11 | 16.6 | 35.2* | 53.3* |
| 3 | 28.8* | ND | ND |
| Carinactivase - 1 | | | |
| 112 | 5.3 | 36.9 | 23.7 |
| 56 | 9.8 | 33.1* | 37.7* |
| Carinactivase - 2 | | | |
| 56 | 2.8 | 38.1 | 25.8 |
| 34 | 3.3 | 36.9 | 24.3 |
| 11 | 8.9 | 30.7* | 38.5* |
| OsPA (nM) | | | |
| 56 | 0.2 | 64.2 | 18.6 |
| 3 | 2.9 | 61.4 | 25.8 |
| 2.3 | 4.2 | 54.8 | 28.4 |
| 2 | 11.0 | 29.4* | 37.9* |
| PtPA | | | |
| 56 | 0.4 | 62.9 | 20.1 |
| 6 | 4.4 | 60.9 | 27.9 |
| 3 | 9.7 | 42.8* | 48.6* |
| 2 | 28.7* | ND | ND |
| Notecarin | | | |
| 56 | 0.8 | 51.9 | 23.3 |
| 34 | 1.1 | 51.0 | 19.6 |
| 11 | 2.2 | 46.6 | 22.2 |
| 3 | 7.2 | 39.5 | 33.6 |
| BD RST - 1 | | | |
| 25 | 18.9* | ND | ND |
| 6 | 19.3* | ND | ND |
| BD RST - 2 | | | |
| 135 (1 mL) | 0.4 | 9.9 | 13.3 |
| 34 (4 mL) | 0.3 | 12.7 | 8.1 |

*means measurement was stopped, and ND means this was not determined.

The concentrations determined to achieve an R time of <5 minutes and maximum clot strength from these results for the different prothrombin activators were: PtPA 6 nM, OsPA 2.3 nM, notecarin 3-11 nM, ecarin 11-34 nM, carinactivase-2 11-34 nM, and carinactivase-1 57-112 nM.

Surprisingly, the notecarin produced clots with higher MAs than the group A and B prothrombin activators, and without wishing to be bound by theory, it is postulated that additives within the blood of such patients may have aided clotting efficacy.

The strongest clots formed as indicated by the MA were with the PtPA and OsPA, and the weakest with the carinactivase-1 and carinactivase-2 prothrombin activators.

The thrombin in the BD RST tubes (BDRST-2 experiment with 135 nM of thrombin) produced incomplete clotting and weak clots as indicated by the MA. Such samples are very likely to form latent clotting in the serum post centrifugation.

Example 5j

Clotting of Normal "Pooled" Citrated Plasma Spiked with Rivaroxaban

This experiment was designed to examine the effect of one of the new Factor Xa inhibitor anticoagulants, rivaroxaban, on the clotting ability of the procoagulants.

One rivaroxaban table (10 mg, Mol Wt 435, Xarelto, Bayer Schering Pharm, Germany) tablet was crushed in 5 mL deionised water (2 mg/mL), allowed to mix for 30 minutes, and then centrifuged to remove undissolved particles. The typical therapeutic dose given is 10-40 mg once daily. For a 70 kg person (~3000 mL plasma) the total amount is 0.14-0.57 mg/kg, 0.0033-0.013 mg/mL of plasma. The concentrations prepared and tested in the Clotek tube were: 0.0033, 0.0083, 0.017, 0.033, and 0.17 mg/mL.

The Clotek tubes contained 50 μL of Tris Buffer (150 mM Tris HCl, 150 mM NaCl, pH 7.4), 50 μL 0.2 mM $CaCl_2$, 100 μL normal "pooled" citrated plasma, 50 μL of Tris buffer or anticoagulant of different concentration, and 50 μL of prothrombin activator (30 nM).

The clotting times are shown in Table 54.

TABLE 54

Clotting times (seconds) with normal "pooled" citrated plasma and Rivaroxaban.

| Procoagulant | Anticoagulant concentration | Rivaroxaban concentration (mg/mL) | | | | |
|---|---|---|---|---|---|---|
| (30 nM) | 0 | 0.003 | 0.008 | 0.017 | 0.033 | 0.17 |
| PtPA | 4.8 | 5.8 | 6.2 | 7.7 | 8.8 | 12.0 |
| OsPA | 8.6 | 8.6 | 8.8 | 8.8 | 9.3 | 16.9 |
| Ecarin | 42.6 | 50.7 | 51.6 | 53.9 | 58.9 | 83.9 |
| Notecarin | 41.7 | 42.7 | 44.9 | 46.2 | 47.6 | 67.3 |
| CA-1 | 128 | 133 | 152 | 176 | 194 | 258 |
| CA-2 | 60.9 | 61.1 | 62.8 | 66.1 | 70.6 | 98.0 |
| Thrombin | 7.1 | 7.0 | 7.3 | 7.4 | 8.0 | 9.8 |
| BDRST 23 nM | 5.1 | 5.3 | 5.2 | 5.8 | 5.7 | 7.7 |

The results show that rivaroxaban has minimal effect on the procoagulants in the therapeutic concentration range 0.0033-0.013 mg/mL of plasma that may be encountered in patients. However, at higher concentrations, rivaroxaban had a significant inhibitory effect on clotting in the presence of each of the procoagulants. This effect may be due to inhibition of Factor Xa produced from human FX in the plasma by the thrombin generated by the procoagulants.

Example 5k

Clotting of Blood from a Patient Undergoing Citrate Anticoagulation

In previous experiments, it has been shown that the prothrombin activators are capable of clotting citrated blood collected in Greiner citrate tubes. The purpose of this experiment was to confirm that in vivo citration presented no clotting problems with the prothrombin activators.

In this example, the patient was on 3.0 mmol of citrate per liter of blood flow. The blood was collected in a 50 mL plain syringe (BD Plastipak #300866) for routine pathology testing from which <3 mL was left to perform the very limited study with PtPA only.

The coagulation parameters were: PT 13 s (RR 9-13), INR 1.3, APTT 45 s (RR 24-39), fibrinogen (derived) 7.2 g/L (RR 1.7-4.5), confirming anticoagulation.

The TEG cup contained 20 μL of 0.2 M $CaCl_2$ or saline, 5 μL of PtPA and 320 μL of the citrated blood.

The results are shown in Table 55.

TABLE 55

TEG results for citrated anticoagulated participant.

| Citrated anticoagulated participant | R (min) | MA (mm) | TMA (min) |
|---|---|---|---|
| Re-calcified citrate blood alone | 4.8 | 77.1 | 18.0 |
| 2.8 nM PtPA re-calcified | 0.6 | 74.7 | 15.8 |
| 2.8 nM PtPA non re-calcified | 0.8 | 76.2 | 18.9 |

The results indicated that the citrate concentration used for anticoagulation of patients did not present clotting problems when PtPA was used as the procoagulant in re-calcified and non re-calcified blood. The citrate concentration in blood collected in Greiner Citrate tubes is 3.2% or 109 mM, which is about 36 times the concentration the patient was receiving. Additionally, it was not expected there would be any clotting problems as patients being citrated are continuously monitored for ionised calcium and ionised calcium is replenished as required. The R time in normal "pooled" citrate blood was 6.4 minutes (as shown in Table 43) compared to the 4.8 min in this patient. The re-calcification adds calcium in exceeds to requirement thus theoretically it should not contribute to the difference. It is postulated that the difference is due to higher concentrations of clotting factors including fibrinogen which was 7.2 g/L.

Example 6

Clotting of Whole Blood Samples from Participants with Prolonged Coagulation Profile or Low Platelet Counts Some patients present with prolonged coagulation parameters and/or reduced platelet count as a result of drug treatment or genetic factors (e.g. haemophilia). The following experiments were conducted to determine whether PtPA or OsPA would be able to rapidly clot blood samples from such patients.

Example 6a

Participants with Prolonged Clotting Time

Blood from 4 participants ("A", "B", "C" and "D") with prolonged aPTT indicating a defect in the intrinsic pathway were obtained from Pathology Queensland, Princess Alexandra Hospital, Queensland, Australia. The coagulation parameters of each participant were determined and are shown in Table 56.

TABLE 56

Coagulation parameters* of each participant

| Participant | aPTT(s) | PT(s) | INR | TT(s) | Fib-D(g/L) | plat($\times10^9$/L) |
|---|---|---|---|---|---|---|
| A | 48 | 16 | 1.6 | 19 | 7.1 | 453 |
| B | 44 | 34 | 3.0 | 16 | 4.1 | 97 |
| C | >200 | n.d. | n.d. | n.d. | n.d. | n.d. |
| D | 45 | 16 | 1.5 | 15 | 1.5 | 96 |
| Reference Interval | 25-38 | 8-14 | 0.9-1.3 | 10-15 | 1.5-4.0 | 140-400 |

*aPTT = activated partial thromboplastin times; PT = prothrombin time; INR = international normalised ratio; TT = thrombin time; Fib-D = prothrombin time derived fibrinogen; Plat = platelets, n.d. = not able to be determined. The Reference Intervals were obtained from Pathology Queensland.

TEG analysis was performed. Each TEG assay mixture consisted of 310 μL citrated blood from A-D participant samples, 20 μL of $CaCl_2$ (0.2 M) and 10 μL of saline or PtPA (final concentration 1.41 μg/mL). $CaCl_2$ was added at zero time to initiate clotting.

TEG traces for the four samples are shown in FIG. 44 and TEG parameters from these traces are shown in Table 57.

TABLE 57

TEG results for clotting of blood samples from participants with abnormal coagulation parameters

| | R (min) | TMA (min) | α (deg) | MA (mm) |
|---|---|---|---|---|
| A | >35 | n.d. | n.d. | n.d. |
| A + PtPA | 1.3 | 16.6 | 70.9 | 67.4 |
| B | 23.0 | >39 | 17.0 | n.d. |
| B + PtPA | 0.9 | 21.3 | 70.0 | 59.0 |
| C | >52 | n.d. | n.d. | n.d. |
| C + PtPA | 2.1 | 24.5 | 67.6 | 60.4 |
| D | 16.1 | 43.3 | 26.4 | 31.7 |
| D + PtPA | 1.4 | 19.2 | 52.0 | 40.8 |

"n.d." indicates that this was not measured

TEG plots for the four samples are shown in FIG. 44 where TEG plot A represents participant A and in that plot the two traces labelled (i) represent the saline control with added calcium; the two traces labelled (ii) are the samples with PtPA. TEG plot B represents participant B and in that plot the two traces labelled (i) are saline control with added calcium; the two traces labelled (ii) are the samples with PtPA. TEG plot C represents participant C and in that plot the trace labelled (i) is the saline control; and the four traces labelled (ii) are samples with PtPA added. TEG plot D represents participant D and in that plot the two traces labelled (i) are the saline controls; and the two traces labelled (ii) are the samples with PtPA. Triplicate determinations were carried out for patient C due to grossly abnormal clotting parameters. The data in Table 57 represents averages from the TEG data.

In summary, blood samples from participants A-D show an aPTT time ranging from 44 to >200 seconds indicating a defect in the intrinsic coagulation pathway. Without PtPA the samples did not clot or produced very weak clots. In all cases PtPA (1.41 μg/ml) caused rapid clotting, reducing the clotting time to 1-2 minutes. Thus PtPA is effective in rapidly clotting blood from patients with a deficiency in this coagulation pathway.

Example 6b

Participants with Low Platelet Counts

In participants with low platelet counts, clotting times are significantly increased compared to blood from the healthy population. This is because platelets provide a phospholipid surface for the formation of the prothrombinase complex and accelerate blood clotting.

Blood samples from four participants with low platelet counts ("E", "F", "G" and "H") were obtained from Princess Alexandra Hospital, Queensland, Australia. The coagulation parameters of each participant were determined and are shown in Table 58, confirming the low platelet count.

TABLE 58

Coagulation parameters of each participant

| Participant | aPTT(s) | PT(s) | INR | TT(s) | fib(g/L) | plat($\times10^9$/L) |
|---|---|---|---|---|---|---|
| E | 31 | 10 | 1.1 | n.d. | 4.5 | 10 |
| F | 29 | 14 | 1.4 | n.d. | 1.2 | 29 |
| G | 34 | 12 | 1.2 | n.d. | 2.7 | 18 |
| H | 54 | 11 | 1.2 | 21 | 6.4 | 46 |
| Reference Interval | 25-38 | 8-14 | 0.9-1.3 | 10-15 | 1.5-4.0 | 140-400 |

n.d. indicates that the measurements were not determined.

TEG analysis was performed. Each TEG assay mixture consisted of 310 μL citrated blood from E-H participant samples, 20 μL of $CaCl_2$ (0.2 M) and 10 μL of saline or solution of prothrombin activator (either PtPA at a final concentration of 1.41 μg/mL or 14.1 μg/mL, or OsPA at a final concentration of 0.59 μg/mL or 5.9 μg/mL).

The TEG traces are shown in FIG. 45 and TEG parameters are listed in Tables 59 and 60.

TABLE 59

TEG results for clotting of blood samples from participants with low platelet counts with PtPA

| Participant | μg/mL | R (min) | TMA (min) | α (deg) | MA (mm) |
|---|---|---|---|---|---|
| E | 0 | 10 | 30.3 | 42.3 | 34.6 |
| | 1.41 | 1.5 | 22.5 | 61.6 | 35.3 |
| | 14.1 | 0.4 | 20.3 | 73.2 | 31.1 |
| F | 0 | 9.3 | 29.8 | 15.6 | 28.2 |
| | 1.41 | 1.5 | 24.2 | 29.0 | 31.2 |
| | 14.1 | 0.6 | 24.3 | 38.4 | 28.0 |
| G | 0 | 12.8 | 32.8 | 29.5 | 30.2 |
| | 1.41 | 1.4 | 23.4 | 57.1 | 33.7 |
| | 14.1 | 0.4 | 25.0 | 66.9 | 31.3 |
| H | 0 | 9.1 | 32.0 | 39.3 | 48.2 |
| | 1.41 | 1.7 | 24.2 | 66.3 | 58.8 |
| | 14.1 | 0.3 | 22.2 | 73.7 | 54.7 |

TABLE 60

TEG results for clotting of blood samples from participants with low platelet counts with OsPA

| Participant | μg/mL | R (min) | TMA (min) | α (deg) | MA (mm) |
|---|---|---|---|---|---|
| E | 0 | 10 | 30.3 | 42.3 | 34.6 |
| | 10 | 3.8 | 23.8 | 41.0 | 32.7 |
| | 100 | 0.9 | 21.8 | 63.7 | 32.9 |
| F | 0 | 9.3 | 29.8 | 15.6 | 28.2 |
| | 10 | 3.2 | 25.3 | 27.4 | 28.7 |
| | 100 | 1.6 | 25.6 | 27.5 | 29.3 |

TABLE 60-continued

TEG results for clotting of blood samples from participants with low platelet counts with OsPA

| Participant | μg/mL | R (min) | TMA (min) | α (deg) | MA (mm) |
|---|---|---|---|---|---|
| G | 0 | 12.8 | 32.8 | 29.5 | 30.2 |
| | 10 | 3.3 | 24.6 | 38.8 | 31.7 |
| | 100 | 0.9 | 24.5 | 56.5 | 29.9 |
| H | 0 | 9.1 | 32.0 | 39.3 | 48.2 |
| | 10 | 3.4 | 24.1 | 59.8 | 59.7 |
| | 100 | 0.8 | 22.6 | 66.7 | 54.9 |

The TEG plots are shown in FIG. 45 where plot A shows the results for participant E; plot B shows the results for participant F; plot C shows the results for participant G; and plot D shows the results for participant H. In each plot, the trace labelled (i) represents no PtPA or OsPA; the trace labelled (ii) represents 14.1 μg/mL PtPA; the trace labelled (iii) represents 1.41 μg/mL PtPA; the trace labelled (iv) represents 5.88 μg/mL OsPA; and the blue trace represents 0.588 μg/mL OsPA.

In summary, both PtPA and OsPA clot blood from participants with low platelet counts rapidly to give high strength clots.

Example 7

Comparison of Clotting Activity of Protrhombin Activator-Containing Venoms

Five freshly reconstituted venoms from the snakes *Pseudonaja textilis* (Pt), *Oxyuranus scutellatus* (Os), *Oxyuranus microlepidotus* (Om), *Notchis scutatus* (Ns), and *Echis carinatus* (Ec) were reconstituted in distilled water with a stock concentration of 50 mg/mL. A working stock dilution of 6 mg/mL was freshly prepared and their clotting activity was measured on the clotting of re-calcified citrated plasma. The venoms were serially diluted in duplicates of each concentration in the assay from 2 mg/mL to 500 pg/mL. The results shown are the average of the duplicate measurements. The assay consisted of: 100 μL of 0.02 M Hepes buffer pH 7.4 with added 10 mM calcium, plus 100 μL of citrated plasma and clotting time (in seconds) was measured from the time of the addition of venom dilution.

Figure 46:
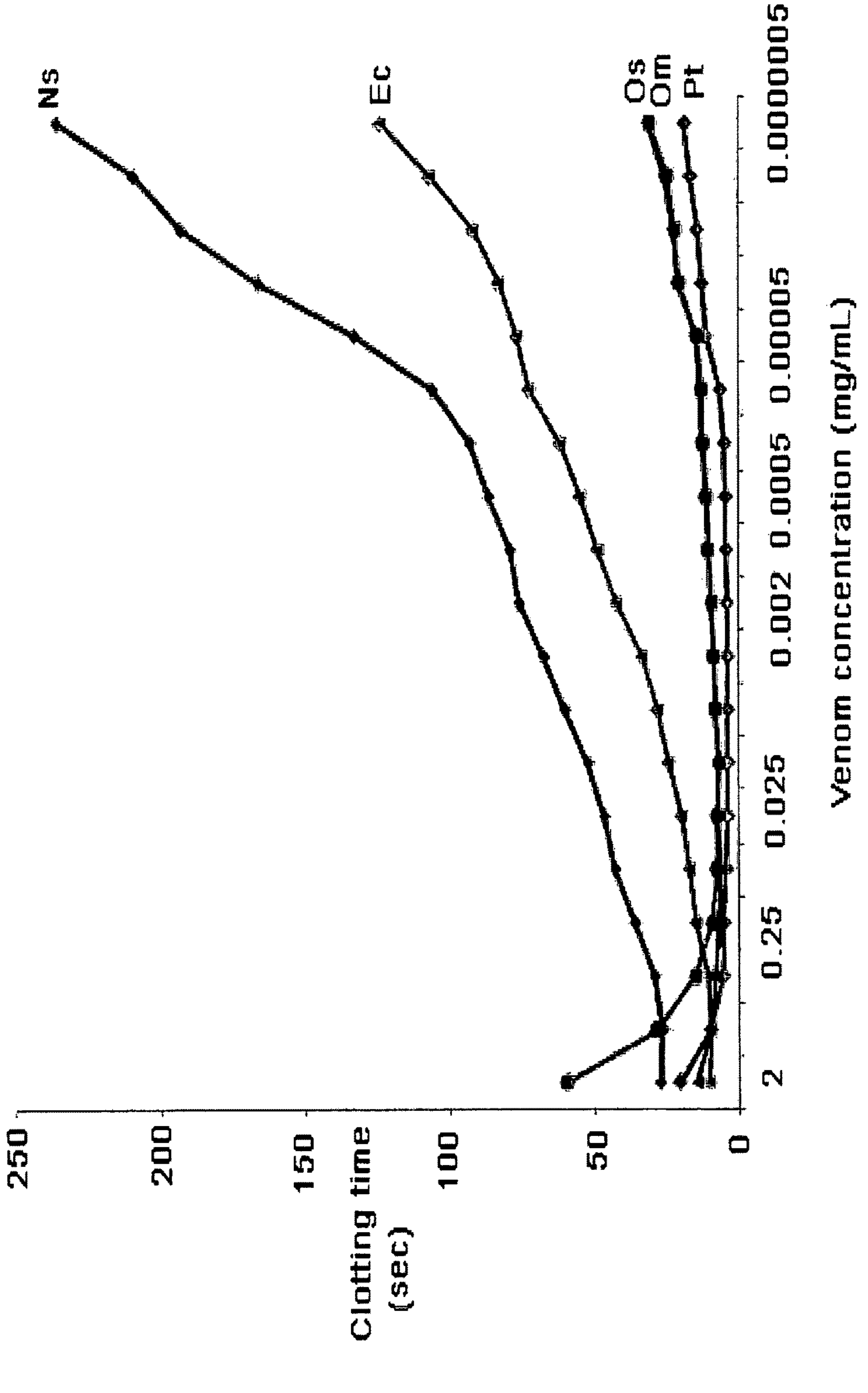
FIG. 46 plots the clotting times of prothrombin activator-containing snake venoms from the species: *Pseudonaja textilis* (Pt), *Oxyuranus scutellatus* (Os), *Oxyuranus microlepidotus* (Om), *Notechis scutatus* (Ns), and *Echis carinatus* (Ec) at different concentrations as described in Example 7.

The results are shown in Table 61 and FIG. 46.

TABLE 61

Clotting times of snake venoms containing prothrombin activators at different concentrations

| Venom | Clotting time (seconds) | | | | |
|---|---|---|---|---|---|
| (mg/mL). | Os | Pt | Om | Ns | Ec |
| 2 | 59.5 | 20.6 | 14.6 | 27.4 | 10.3 |
| 1 | 28.4 | 9.8 | 9.8 | 26.5 | 9.7 |
| 0.5 | 15 | 5.2 | 7.8 | 29.2 | 10.9 |
| 0.25 | 9.3 | 5 | 6.6 | 36 | 14.7 |
| 0.125 | 7.6 | 4.2 | 6.1 | 42.7 | 17.1 |
| 0.063 | 7.4 | 3.6 | 6.8 | 46.4 | 19.8 |
| 0.031 | 6.5 | 3.5 | 6.9 | 52.00 | 24.3 |
| 0.015 | 8.2 | 3.6 | 8.0 | 59.9 | 28.1 |
| 0.0075 | 8.6 | 3.7 | 8.6 | 67.2 | 33.4 |
| 0.0037 | 9.2 | 3.8 | 9.3 | 75.7 | 42.1 |
| 0.002 | 10.6 | 4.0 | 10.7 | 78.8 | 48.6 |
| 0.001 | 11.2 | 4.2 | 11.1 | 86.00 | 54.6 |
| 0.0005 | 12.4 | 4.5 | 12.6 | 92.5 | 61.4 |
| 0.00025 | 12.8 | 6.2 | 13.0 | 105.6 | 72.3 |
| 0.00013 | 14.5 | 11.2 | 14.8 | 132.4 | 76.4 |

TABLE 61-continued

Clotting times of snake venoms containing prothrombin activators at different concentrations

| Venom | Clotting time (seconds) | | | | |
|---|---|---|---|---|---|
| (mg/mL). | Os | Pt | Om | Ns | Ec |
| 0.00006 | 20.4 | 12.6 | 21.1 | 165.5 | 82.5 |
| 0.00003 | 21.8 | 14.3 | 22.4 | 192.6 | 91.3 |
| 0.00001 | 24.6 | 16.5 | 25.6 | 209 | 106.4 |
| 0.0000005 | 30.7 | 18.6 | 31.2 | 235.4 | 123.2 |

As can be seen in both Table 61 and FIG. 46, all five venoms clotted recalcified citrated plasma very efficiently down to concentration of 500 pg/mL. The Group C prothrombin activator-containing venoms (Pt, Os and Om) were the most active achieving clotting times of less 50 seconds at a concentration of 500 pg/mL.

Example 8

Figure 48:
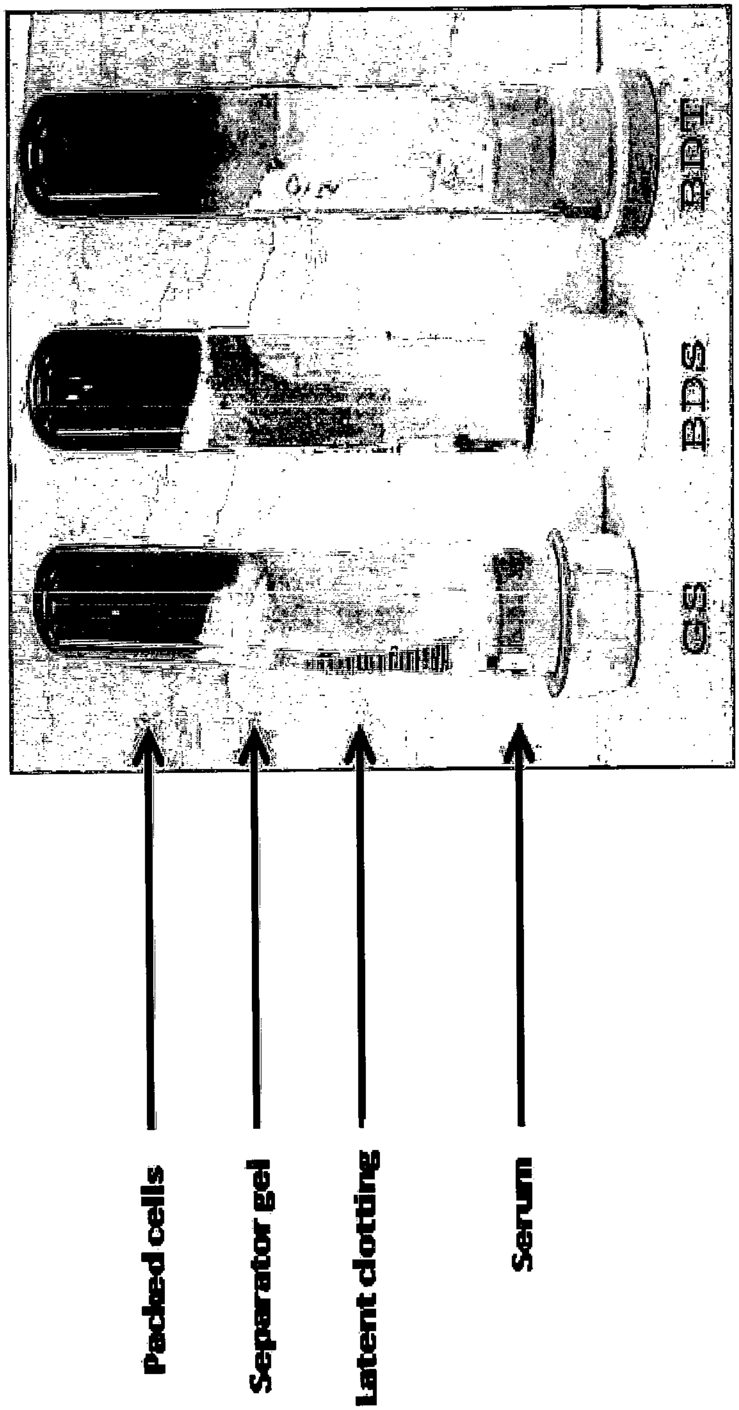
FIG. 48 shows post-centrifugation (latent) clotting in a number of tubes as described in Example 8.
Figure 49:
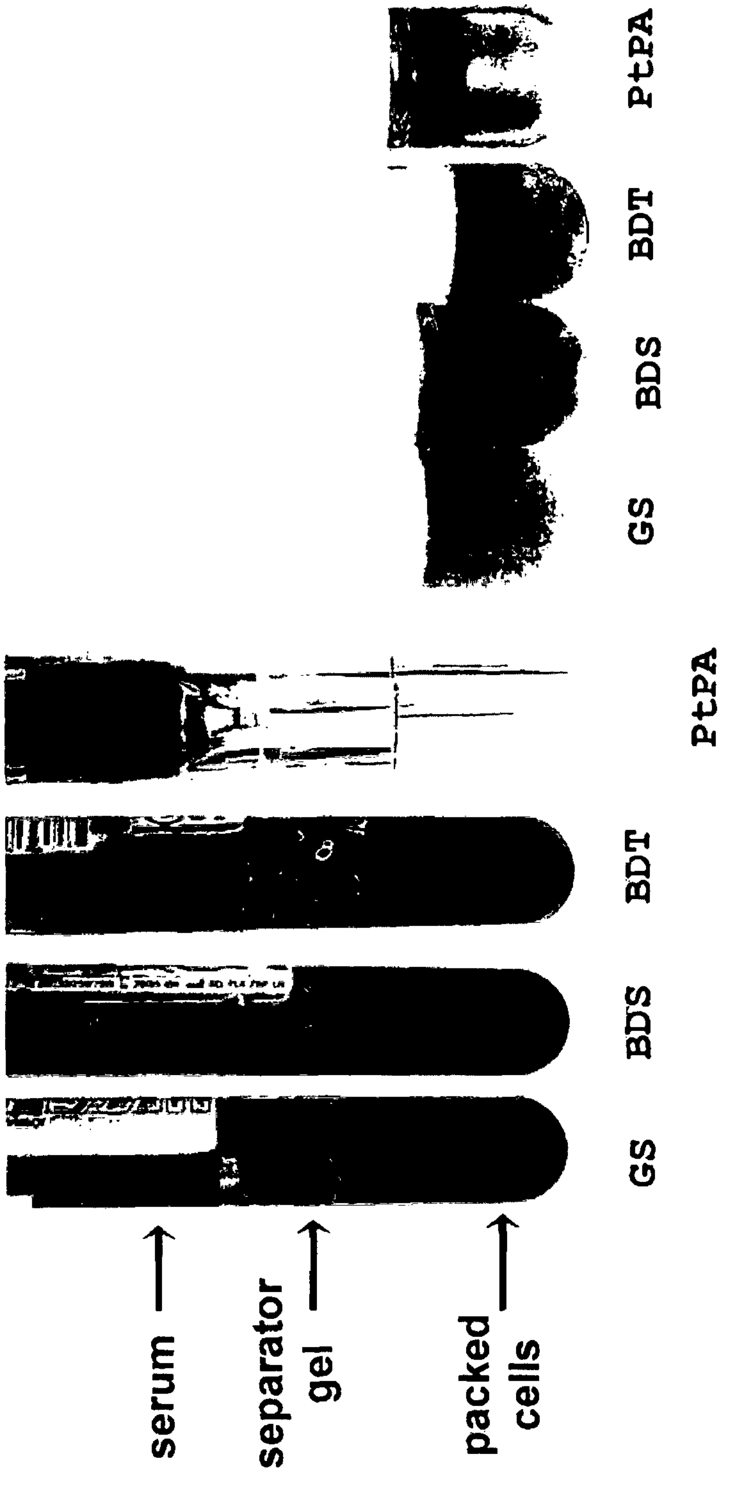
FIG. 49 shows a comparison of serum samples in different tubes as described in Example 8.

Precipitation and Latent Clotting in Plasma and Serum Samples Prepared Using Commercially Available Tubes or Using PTPA and Effects on Troponin I Estimation As discussed in the earlier parts of this specification, a number of problems have been associated with the use of commercial serum and plasma tubes such as latent clotting or no clotting (serum tubes), microclots and fibrinogen strings (serum or plasma tubes), and precipitation of proteins and leakage of cellular material (serum or plasma tubes). To investigate whether a tube containing a prothrombin activator would exhibit some of these problems, blood samples in commercially available tubes were visually inspected and compared against blood samples in PtPA-containing tubes. The results are shown in FIGS. 47-49.

Example 8a

Precipitation and Latent Clotting

Figure 47:
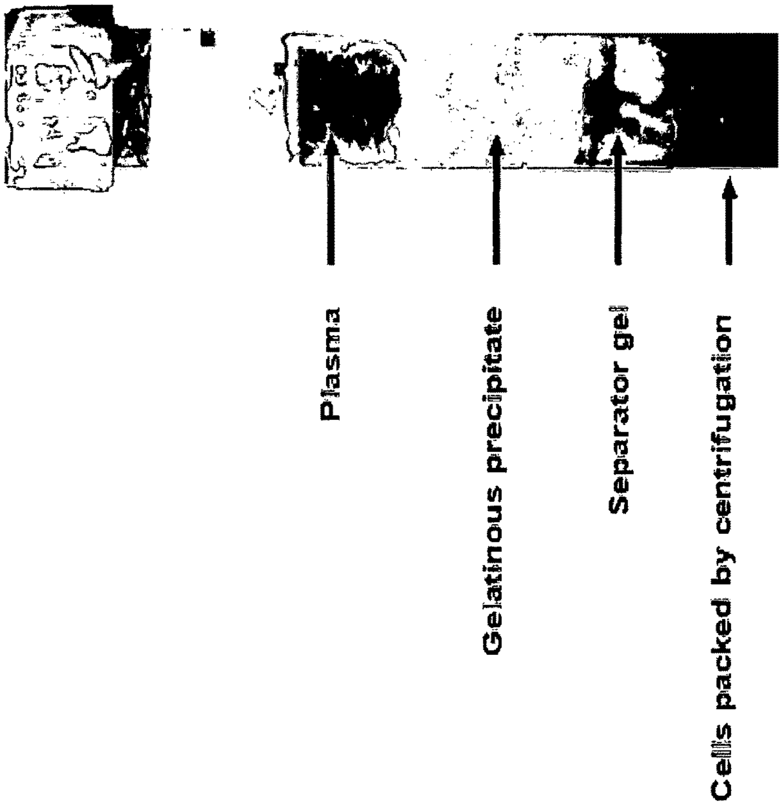
FIG. 47 shows a Greiner plasma tube with gelatinous precipitate as described in Example 8.

FIG. 47 shows the results of plasma preparation from a blood sample collected in a commercially available Greiner plasma (lithium heparin containing) tube. Four sections of the tube are marked (from top to bottom of the Figure): plasma; gelatinous precipitate; separator gel; cells packed by centrifugation. The gelatinous precipitate is composed of fibrinogen and other plasma proteins and forms when the tube is stored at 2-8° C. This precipitate has the potential to interfere with instrument function and analyte determination. Such precipitates occur in ~5% of lithium heparin plasma samples.

FIG. 48 shows the results of serum preparation in three commercially available serum tubes: left tube (GS) is a Greiner serum tube; middle tube (BDS) is a BD serum tube and right tube (BDT) is a BD RST tube. Four sections of the tubes are marked (from top to bottom of the Figure): packed cells; separator gel; latent clotting; serum. Post-centrifugation (latent) clotting is evident in the supernatants or serum component of all three tubes. The tubes are inverted to illustrate the presence of the clots. These latent clots have the potential to interfere with instrumentation and functional assays.

FIG. 49 is in two halves. The left half shows the results of serum preparation from a single blood sample from the same fully heparinised patient in three commercially available tubes (left to right): a Greiner Vacuette™ serum tube (GS), a BD Vacutainer™ serum tube/SST II (BDS) and a BD RST tube (BDT), and also in a Greiner Vacuette™ No Additive tube with PtPA added. Three sections of the tubes are marked (from top to bottom of the Figure): serum; separator gel; packed cells. All four tubes from FIG. 49 were centrifuged then left standing overnight, after which the serum in each tube was transferred to a clear glass tube and photographed as shown in the right half of FIG. 49 (left to right: GS, BDS, BDT and PtPA tubes). The sera from all three commercially available tubes showed evidence of clotting, by clot formation on the side of the tube and observation of fibrin strands, but there was no evidence of precipitation in the serum prepared in the PtPA-containing tube which had a clarity that considerably exceeded that observed with the other samples.

Example 8b

Troponin I Levels

It has been observed that at least some false positive results showing elevated troponin I (one of the most specific markers of cardiac events) are due to precipitation/latent clotting in serum and plasma samples.

Troponin I levels in blood samples from 64 participants were measured using serum and plasma samples prepared in commercially available tubes and PtPA-containing tubes.

Serum and plasma samples were prepared for each participant in five commercially available tubes: Greiner Vacuette™ plasma; BD PST II; Greiner Vacuette™ serum; BD SST II; and BD RST, and in Greiner Vacuette™ No Additive tubes containing PtPA (1.2 μg/4 mL) and analysed for troponin I (TnI) using the Beckman Coulter AccuTnI assay.

Four discrepant results were obtained as indicated in Table 62 for participants 18, 20, 38 and 63. Participants 18 and 38 were healthy, and participants 20 and 63 were both patients undergoing cardiac surgery and on heparin. Three false positive results (participants 18, 20 and 38) were obtained. Re-centrifugation of an aliquot from the primary tube followed by re-assay gave negative results, as expected when compared to results from the other tubes from the same blood sample. A further result was exceptionally high (participant 63). Re-centrifugation of an aliquot and re-assay gave a comparable result with the other tubes.

The fact that centrifugation of samples resolved the discrepancy strongly suggests that the discrepant results were due to latent clotting/precipitate formation causing inaccurate sampling. No discrepant results were obtained with the PtPA serum.

TABLE 62

Troponin I assay results showing discrepancies.

| Participant | Original TnI result (Repeat TnI result) μg/L | | | | | |
|---|---|---|---|---|---|---|
| | PtPA | Greiner plasma | BD PST II | Greiner serum | BD SST II | BD RST |
| 18 | 0.003 | 0.000 | 0.000 | 0.000 | <u>0.053</u> (0.004) | 0.000 |
| 20 | 0.007 | 0.015 | <u>0.093</u> (0.015) | 0.013 | 0.013 | 0.004 |
| 38 | 0.009 | 0.000 | 0.006 | 0.006 | <u>1.334</u> (0.002) | 0.004 |
| 63 | 0.675 (0.690) | 0.665 (0.704) | 0.643 (0.665) | 0.652 (0.650) | 0.542 (0.579) | <u>1.251</u> (0.734) |

In summary, precipitation and latent clotting observed during the preparation of plasma and serum samples in commercially available tubes represent significant problems for analyte determination. No precipitation or evidence of microclot formation was observed when PtPA was used to prepare a serum sample.

Example 9

Fibrinogen, Degraded Fibrinogen and Fibrin Levels in Plasma and Serum Samples Soluble fibrinogen, soluble partially degraded fibrinogen (fdp) and unpolymerised fibrin (FDP) are undesirable components in serum and plasma samples for analyte determination as discussed in the earlier parts of this specification. Briefly, fibrinogen/fdp/FDP should be minimal in a high quality serum sample to avoid further conversion into insoluble fibrin (microclots) after standard serum preparation conditions especially on standing. Microclots or fibrin strands can interfere with instrumentation and affect analyte determination. For serum samples prepared by standard methods, the concentration of fibrinogen/fdp/FDP in the sample is believed to depend on the extent to which the patient/individual is anticoagulated, the health status of the patient (e.g. the presence of liver disease), on the type of sample collection container and in rare cases on inadequate mixing of the sample in the tube. In this example, the concentration of fibrinogen/fdp/FDP in serum and plasma samples prepared using different tubes was investigated to assist in establishing conditions for preparation of a "high quality" serum sample.

Serum and plasma fibrinogen/fdp/FDP concentrations were measured by a sandwich enzyme immunoassay (ELISA) as described below. This assay uses a polyclonal antiserum against fibrinogen which recognises soluble soluble fibrinogen, fdp and FDP.

The ELISA method requires anti-fibrinogen antiserum (as a purified IgG fraction: AHFAS) and anti-fibrinogen antiserum-horseradish peroxidase conjugate (AHFAS-HRP). Preparations of each were purchased from MP Biochemical, USA. International fibrinogen standard was purchased from NIBSC, London, and diluted from a working stock concentration of 1 mg/mL in 50% glycerol/saline.

The wash buffer consisted of 0.05 M phosphate buffer, pH 7.4, 0.5 M NaCl, 0.05% Tween 20 and 1% BSA, while the binding buffer used was 0.1 M bicarbonate buffer, pH 9.6.

Working dilutions of the antibodies were prepared by diluting AHFAS and AHFAS-HRP stocks 1:500 in binding buffer. The HRP substrate solution consisted of 20 mM tetramethylbenzidine, 0.4 mL of 30% $H_2O_2$ and 50 μL of 0.05 M citrate buffer pH 4.0 in a 50 mL reaction solution.

Nunc ELISA IMMUNOSORB 96 well plates (Thermo Fisher Scientific, Rochester, N.Y.) were coated with 100 μL of AHFAS working dilution per well by incubating the plates with AHFAS at 4° C. overnight. The plates were then blocked with 100 μL of 2% bovine serum albumin (Sigma Chemical, Co) in wash buffer at 4° C. overnight and subsequently washed three times with wash buffer.

Blood samples from healthy volunteers (healthy) and patients (cardiac and renal disease) were collected into the following tubes:

Greiner serum tubes (GS or GRS);

BD serum tubes (BDS);

BD RST tubes (BDT or BD RST);

Greiner No Additive tubes with added 1.2 μg PtPA from a PtPA stock solution 4.8 mg/mL (PtPA);

Greiner No Additive tubes with added 0.5 μg OsPA from a OsPA stock solution 2.0 mg/mL (OsPA);

Greiner No Additive tubes with added 0.6 U ecarin;

Greiner No Additive tubes with added 1.2 U ecarin;

Greiner No Additive tubes with added 0.63 U/4 mL ecarin (Example 9b);

Greiner No Additive tubes with added 1.25 U/4 mL ecarin (Example 9c);

Greiner No Additive tubes with added 2.5 U/4 mL ecarin (Example 9c);

Greiner Vacuette™ plasma tubes (GRLH);

BD Vacutainer™ plasma (PST II) tubes (BDLH);

Greiner Vacuette™ citrate tube (3.2% citrate) for plasma (CIT); and

Greiner Vacuette™ K2EDTA tube (1.5-2.2 mg/mL of EDTA) for plasma (EDTA).

Plasma and serum samples prepared in each tube above were prepared under standard Pathology Queensland (Australia) analyte sample preparation procedure where blood was collected into each tube, and the tube was left to stand prior to centrifugation at 3,000 g. The BD RST, PtPA, OsPA and ecarin-containing tubes were left to stand for 5 minutes, while all remaining tubes were left to stand for 30 minutes for normal blood and 60 minutes for anticoagulated blood.

From each tube, 100 μL aliquots of the plasma or serum samples (diluted 1/1,000 dilution and 1/10 dilution, respectively) were plated in triplicate. Serial dilutions of the fibrinogen standard (11 dilutions covering a concentration range of 1,000 ng/mL to 10 ng/mL) were plated out in duplicate. The plates were incubated overnight at 4° C.

The plates were washed six times with wash buffer to remove unbound components and incubated overnight at 4° C. with 100 μL of AHFAS-HRP working solution per well. The plates were again washed 6 times with wash buffer before adding 100 μL HRP substrate solution per well.

Development of a blue colour was monitored in a dark environment until $A_{450}$ nm reached an absorbance of 1.0 at a fibrinogen concentration of 1 μg/mL. The reaction was then stopped by adding 100 μL per well of 1.0 M sulphuric acid solution, yielding a yellow colour. Plates were then read at $A_{450}$ nm in a Thermo Scientific Multiskan Ascent plate reader with Ascent software.

Example 9a

Fibrinogen/fdp/FDP Levels in 48 Serum Samples Collected in Greiner Serum Tubes (GS) from Patients Fibrinogen/fdp/FDP concentration was measured using the ELISA method outlined above in serum samples from Greiner serum (GS) tubes from 48 randomly selected patients requiring analyte determination for their clinical conditions.

Figure 50:
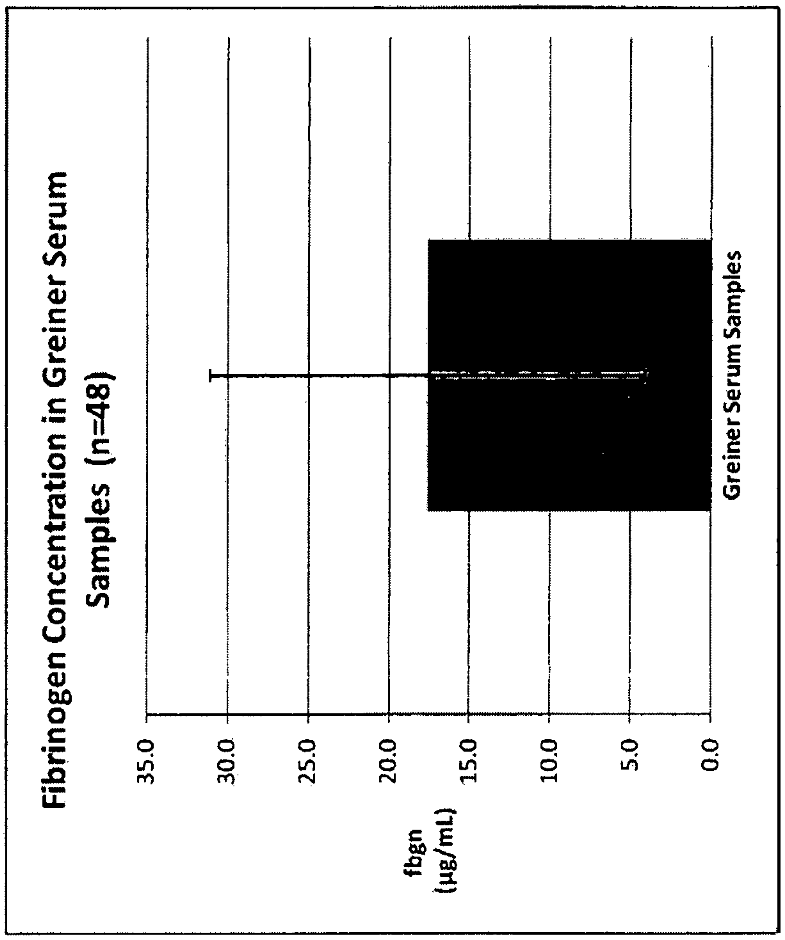
FIG. 50 shows the range of fibrinogen/fdp/FDP concentrations measured in Greiner serum tubes from 48 randomly selected patients requiring analyte determination as described in Example 9a. The bar shows a mean of 17.5 μg/mL and range is 4.4-32 μg/mL.

FIG. 50 shows the results. The concentration of fibrinogen/fdp/FDP in these samples ranged from 4.4-32 μg/mL, compared with fibrinogen concentration in these plasma samples of 2.0-5.0 mg/mL. These data show that greater than or equal to 99% of fibrinogen is removed by the clotting process in standard commercially available serum tubes. These data also provide a reference interval range of fibrinogen in serum preparation in Greiner serum tubes from blood samples from a hospital population.

Example 9b

Fibrinogen/fdp/FDP Levels in Normal Serum and Plasma Samples 36 normal serum samples (as determined by prothrombin time, aPTT and fibrinogen assays) were selected to investigate the effect of PtPA addition (300 ng/mL or 1.2 μg/4 mL tube) on the fibrinogen/fdp/FDP levels. Sera were prepared in Greiner serum tubes (primary tubes) under standard Pathology Queensland procedure prior to aliquoting two equal serum samples of 1 mL from each Greiner serum tube into plain plastic tubes (secondary tubes). PtPA (300 ng/mL or 1.2 μg/4 mL tube) was added to one tube and an equal volume (50 μL) saline to the second to provide matched pairs of secondary tubes.

Figure 51:
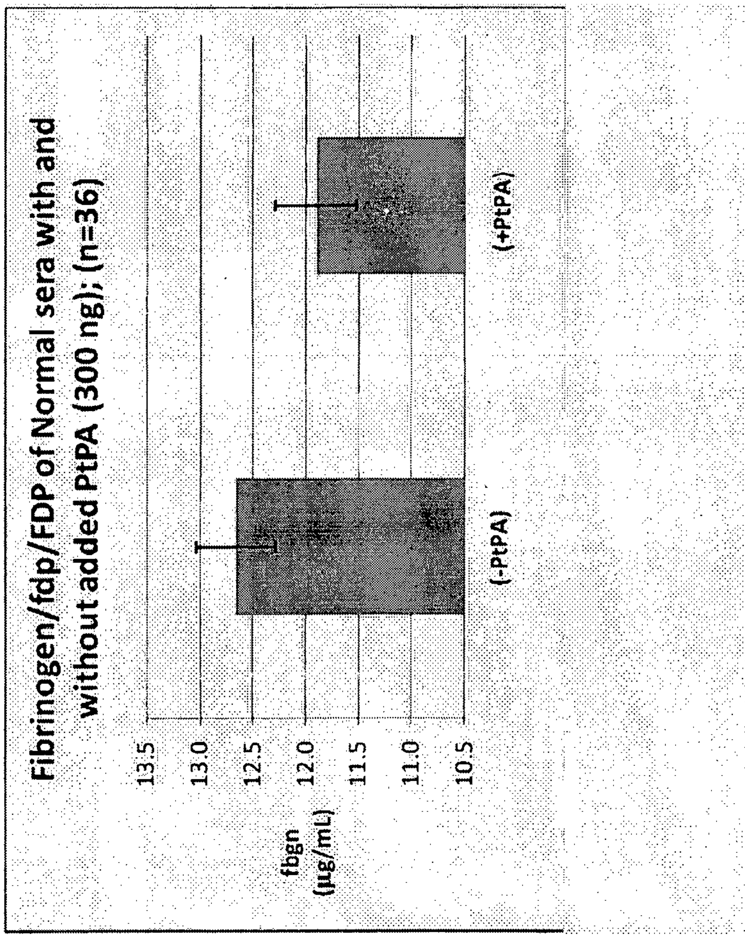
FIG. 51 shows the comparison of the fibrinogen/fdp/FDP concentration measured by ELISA in 36 normal serum samples prepared using Greiner serum (GS) tubes with or without the addition of PtPA as described in Example 9b.

The fibrinogen/fdp/FDP concentration in each secondary tube was measured using the ELISA method outlined above and the results are shown in FIG. 51. In both secondary tubes residual fibrinogen was reduced to less than 1% of that present in blood. However, addition of PtPA further reduced the fibrinogen/fdp/FDP levels from a mean of 12.8 μg/mL to 11.8 μg/mL. This reduction was significant ($p<0.04$) in a paired t-test analysis. Thus the PtPA was capable of further reducing serum fibrinogen/fdp/FDP even in normal individual sera in which residual fibrinogen/fdp/FDP levels were very low. The very small amounts remaining (<1.0%) are likely to be molecules which react with antibody but are not able to polymerise to form insoluble clot.

Figure 52:
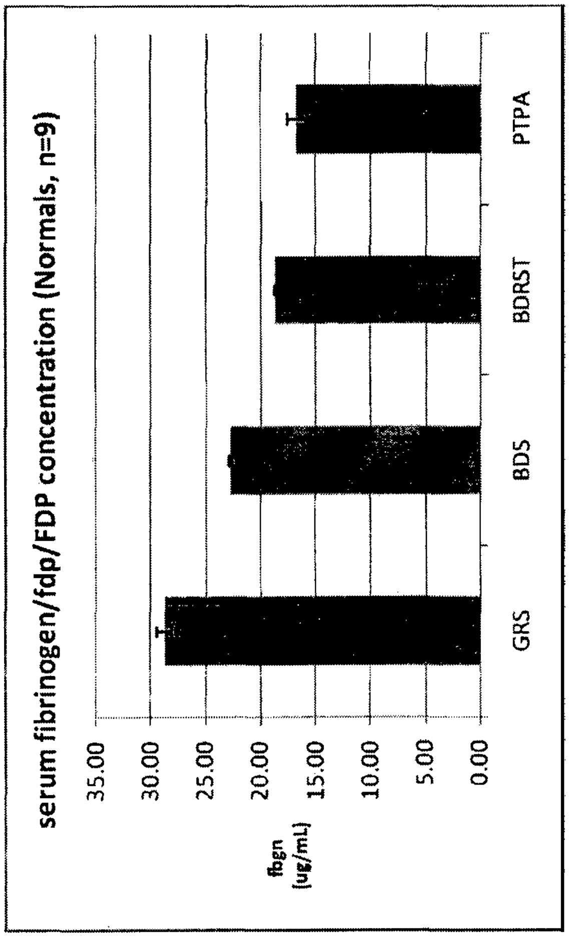
FIG. 52 shows the fibrinogen/fdp/FDP concentrations measured by ELISA in the sera from 9 normal blood samples collected in four different serum tubes: Greiner serum (GRS), BD serum (BDS), BD RST and PtPA (300 ng/mL) as described in Example 9b.

9 normal blood samples were then collected into four different serum tubes: Greiner serum, BD serum, BD RST and PtPA-containing Greiner Vacuette™ No Additive tubes. The fibrinogen/fdp/FDP concentration in each secondary tube was measured using the ELISA method outlined above and the results are shown in FIG. 52. The fibrinogen concentration was considerably lower in the sera prepared in PtPA-containing Greiner Vacuette™ No Additive tube.

Figure 53:
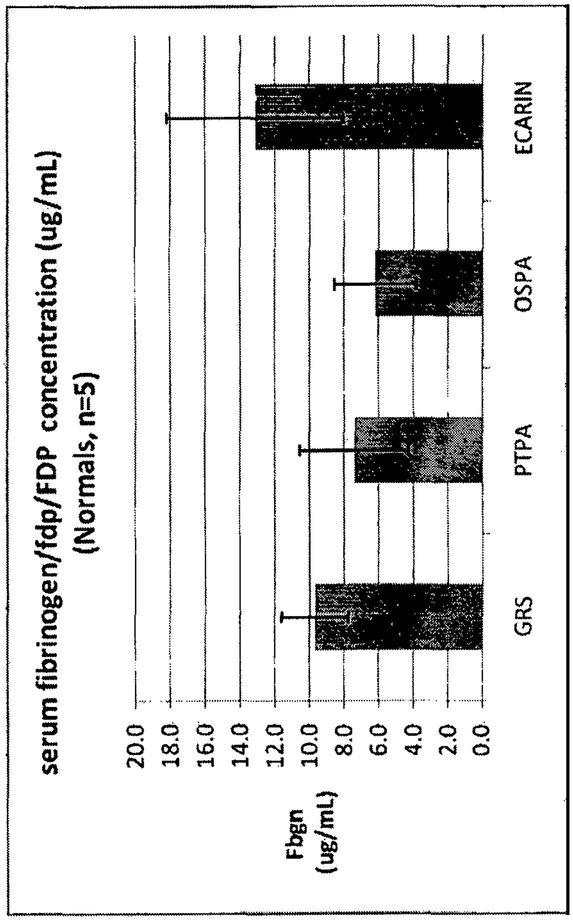
FIG. 53 shows the fibrinogen/fdp/FDP concentrations measured by ELISA in the sera from 5 normal blood samples collected in Greiner serum tubes (GRS), Greiner No Additive tubes with 300 ng/mL of PtPA (PTPA), Greiner No Additive tubes containing 125 ng/mL of OsPA (OSPA) and Greiner No Additive tubes containing 0.16 U/mL of purified ecarin (ECARIN) as described in Example 9b. The bars represent mean±standard deviation.

The concentration of fibrinogen/fdp/FDP in serum produced using OsPA and ecarin was then investigated. Serum samples were prepared from blood of 5 normal participants in Greiner serum tubes (GRS) and in Greiner No Additive tubes containing OsPA (0.50 μg/4 mL tube), ecarin (0.63 units/4 mL tube) and PtPA (1.2 μg/4 mL tube). Fibrinogen/fdp/FDP concentration in the sera of each tube was measured using the ELISA method outlined above. The results are shown in FIG. 53. In all cases residual fibrinogen/fdp/FDP levels were less than 1% that in normal blood or plasma.

Experiment 9c

Fibrinogen/fdp/FDP Levels in Serum Samples Prepared from Heparinised Patients Patients undergoing renal dialysis require moderate levels of heparinisation (1,000-10,000 U of heparin during the treatment period) to avoid prothrombotic events during dialysis. 3 patients from this category were chosen to test the ability of PtPA tubes (1.2 μg/4 mL tube) and BD RST tubes to efficiently clot blood from dialysis patients in a 5 minute incubation time, compared to the clotting of blood taken in Greiner serum (GRS) and BD serum (BD SST II) blood collection tubes in a 30 minute clotting time period. The effectiveness of clotting was determined by measuring the fibrinogen/fdp/FDP concentration in the respective sera using the ELISA method outlined above.

Figure 54:
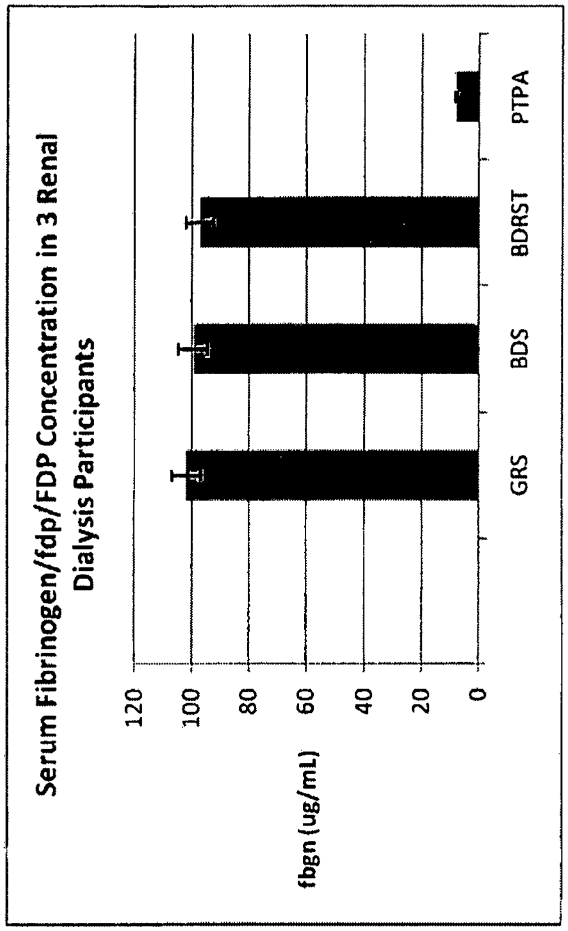
FIG. 54 shows the fibrinogen/fdp/FDP concentrations measured by ELISA of sera from 3 renal dialysis patients collected in Greiner serum tubes (GRS), BD SST II tubes (BDS), BD RST tubes (BDRST) and Greiner No Additive tubes with added 1.2 μg/4 mL tube PtPA (PTPA) as described in Example 9c.

The results are shown in FIG. 54 and reveal that the residual levels of fibrinogen/fdp/FDP in the PtPA-produced sera from the heparinised blood were comparable to those values in the PtPA-produced sera from normal blood (FIGS. 51 and 53). In contrast, residual fibrinogen/fdp/FDP levels in sera produced in the GRS, BDS and BD RST tubes were much higher. At these levels, latent clot formation and microclots are especially likely in the presence of heparin. The values in FIG. 54 for GRS, BDS and BDRST are minimal estimates based on a single dilution of sample.

Blood samples from 2 cardiac surgery patients (treated with 25,000-41,000 Units of heparin) were collected into the following tubes: Greiner plasma tubes, Greiner serum tubes, BD serum tubes, BD RST tubes, Greiner Vacuette™ No Additive tubes with PtPA added (1.2 μg/4 mL tube), Greiner Vacuette™ No Additive tubes with OsPA added (0.50 μg/4 mL tube), Greiner Vacuette™ No Additive tubes with 1.25 units/L of ecarin per 4 mL tube added (EC1), or Greiner Vacuette™ No Additive tubes with 2.5 units/L of ecarin per 4 mL tube added (EC2).

Figure 55:
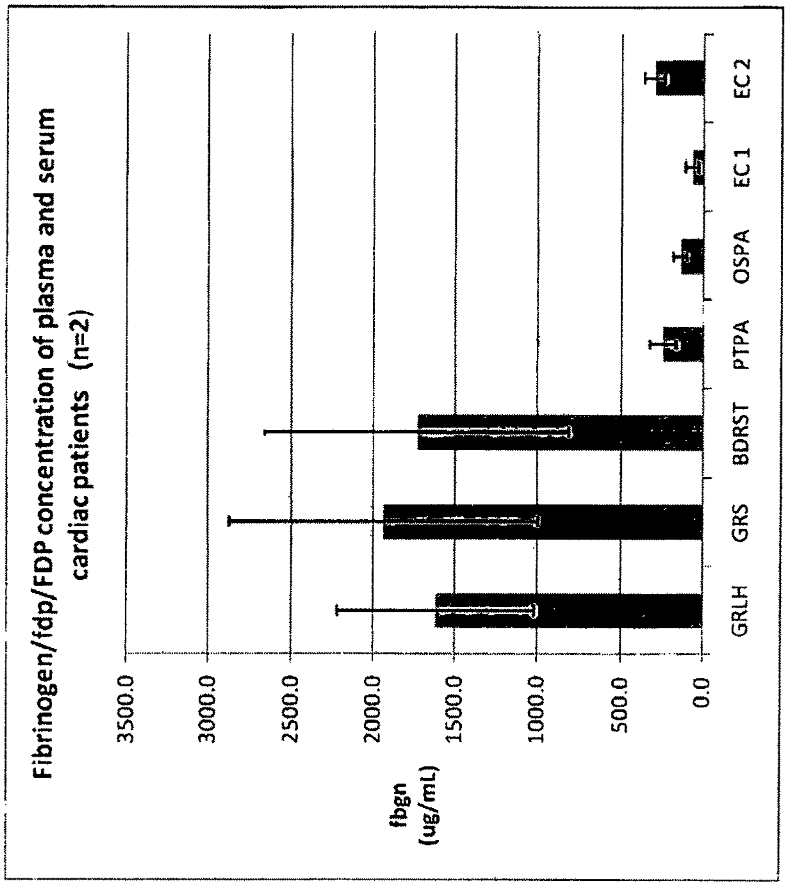
FIG. 55 shows the fibrinogen/fdp/FDP concentrations measured by ELISA of plasma and sera from 2 cardiac patients collected in Greiner plasma tubes (GRLH), Greiner serum tubes (GRS), BD RST tubes (BDRST), Greiner Vacuette™ No Additive tube with added 300 ng/mL PtPA (PTPA), Greiner Vacuette™ No Additive tube with added 125 ng/mL OsPA (OSPA), Greiner Vacuette™ No Additive tube with added 0.31 U/mL of ecarin (EC1) and Greiner Vacuette™ No Additive tube with added 0.63 U/mL of ecarin (EC2) as described in Example 9c.

The fibrinogen/fdp/FDP concentration in the sera and plasma of each tube was determined using the ELISA method outlined above and the results are shown in FIG. 55. The fibrinogen/fdp/FDP concentration was greatly reduced in serum obtained using the prothrombin activator-containing tubes compared to the plasma and other serum tubes. Furthermore, the time allowed for clotting was only five minutes with the prothrombin activator-containing tubes compared to 30 minutes in the other tubes or 60 minutes in the tubes for the anticoagulated blood.

In summary, the tubes containing prothrombin activators were able to produce serum samples with a lower concentration of residual fibrinogen/fdp/FDP than in serum samples produced using commercially available serum or plasma tubes. For normal samples, the effect was relatively small. However, with heparinised samples, the prothrombin activators were able to produce serum with low residual fibrinogen compared to serum prepared in commercial serum tubes. The results suggest that a sufficiently low concentration of residual fibrinogen/fdp/FDP should be achievable by using a prothrombin activator to avoid latent clotting or precipitation in all serum samples. This ability to produce "high quality" serum from patients on high anticoagulant doses (e.g. cardiac care, dialysis) and in "fully heparinised" samples from patients undergoing cardiac surgery is useful.

Example 10

Haemoglobin Concentration in Plasma and Serum Samples

The haemolytic index is used routinely in chemical pathology as a measure of the haemoglobin present in serum and plasma samples and hence the extent of cell lysis. Lysis of all types of blood cells, including erythrocytes, white cells and platelets, can occur in vivo, during blood collection and serum/plasma preparation and on standing. In vitro cell lysis commonly occurs during collection of samples or transfer of samples using small gauge needles or transfer devices which are normally under pressure. In vivo red cell lysis alone may occur in haemolytic anaemias. During the lysis of cells in vitro, cellular content is released into the serum or plasma, falsely altering the results of some analytes; release of cellular content may even cause dilution of other analytes if the haemolysis is extensive. Haemoglobin in plasma or serum may cause spectral problems during analysis and other cellular analytes may cross react. Serum normally contains slightly higher haemoglobin than lithium heparin plasma and this is considered to be due to the clotting process lysing a small number of cells as the clot expands and contracts. A low haemoglobin concentration is therefore an important criterion for a "high quality" serum sample.

The following experiment was performed to compare the haemoglobin content of serum produced in the presence and absence of PtPA and in plasma produced using lithium heparin. Blood samples were collected from 2 patients undergoing citrate anticoagulation therapy and 9 healthy participants. Samples were collected in Greiner plasma tubes, Greiner serum tubes, and Greiner Vacuette™ No Additive tubes containing PtPA (1.2 μg/4 mL of blood). Tubes were centrifuged 5 minutes after collection for the Greiner plasma tubes and Greiner Vacuette™ No Additive tubes with PtPA tubes and 30 minutes for the Greiner Vacuette™ No Additive tubes (without PtPA). The samples were analysed for haemoglobin within 30 minutes after centrifugation. Results are shown in Table 63.

TABLE 63

Haemoglobin concentrations in plasma and serum samples.

| Sample | Haemoglobin concentration (mg/L) Greiner plasma | Greiner serum | Greiner Vacuette ™ No Additive tubes with PtPA |
|---|---|---|---|
| Number of samples (2 citrated and 9 healthy participants) | 11 | 11 | 11 |
| Mean | 55 | 67 | 46 |
| Standard deviation | 26 | 28 | 25 |

The mean haemoglobin concentration in the plasma samples was 55 mg/L, somewhat lower than the 67 mg/L found for the Greiner serum, as expected from the literature. The mean value for the PtPA serum was 46 mg/L, considerably lower than that found for Greiner serum and even lower than that found for plasma. The standard deviations of the mean are large because of the individual variation from person to person. They do not give an estimate of the significance of differences between the three types of tubes for any one person. To check for the significance of these differences, paired two tailed t-tests were performed using the data from the 11 blood samples. The results were as follows:

Greiner plasma v Greiner serum: $p=0.1243$

Greiner serum v Greiner Vacuette™ No Additive tubes with PtPA: $p=0.0188$ (statistically significant $P<0.05$)

Greiner plasma v Greiner Vacuette™ No Additive tubes with PtPA: $p=0.1038$

The conclusions that can be drawn from this Example are that:

(1) The haemoglobin concentration in the plasma samples prepared in the Greiner plasma tubes was lower than that in serum prepared in the Greiner serum tubes, as expected from the literature;

(2) The haemoglobin concentration in the sera prepared in the Greiner Vacuette™ No Additive tubes with PtPA was significantly lower than that in the Greiner serum. The lower level of haemoglobin in these serum samples may reflect the much faster rate of clotting, limiting the amount of cell lysis which occurs during the clotting process; and (3) The mean haemoglobin concentration in the PtPA serum samples was lower than that in the plasma samples and the difference was of borderline significance (p=0.1038).

Thus, the use of the PtPA tube gave sera of higher quality in terms of haemoglobin content than use of the commercial Greiner serum tube.

Example 11

Presence of Cells and Cellular Content in Plasma and Serum Samples

Lithium heparin plasma prepared in commercially available tubes contains residual cells in suspension or in the buffy coat layer on top of the gel barrier in contact with the plasma after centrifugation. Serum prepared from healthy participant samples in commercially available tubes contains fewer cells in contact with the serum (compared with plasma). Storage of plasma and serum for at least 7 days at 2-8° C. is a regulatory requirement in Australia under the National Pathology Laboratory Accreditation Advisory Council (NPACC) in case of re-analysis or requests for additional analyses. The presence of cells can have two effects during storage and analysis of serum or plasma. Firstly, cells may lyse, releasing cellular contents (e.g. $K^+$, lactate dehydrogenase) into the serum or plasma. This can lead to significant differences between measurements made immediately after centrifugation and measurements after a period of storage. Secondly, cells continue to be metabolically active and may use up significant amounts of nutrients (e.g. glucose) and release metabolic products (e.g. lactate) on storage. Changes can even be observed in blood samples of many tubes when the samples are stored for the usual recommended 30 minute clotting time when the samples are from healthy participants.

The degree of cellular contamination is therefore an important quality criterion for serum samples and an important advantage of using serum over plasma.

The following experiments were performed to compare serum prepared using PtPA with serum prepared using Greiner serum tubes and lithium heparin plasma prepared using Greiner plasma tubes. The extent of contamination of serum and plasma samples by cells and cell contents can be assessed using several markers of contamination. Three markers of cellular contamination that were used here are: increase in lactate dehydrogenase (LD) activity on storage; decrease in glucose concentration on storage; and direct observation of cells.

Example 11a

Comparison of PtPA Serum with Lithium Heparin Plasma from Healthy Participants Prepared in Commercially Available Tubes Blood was collected from 10 healthy participants in Greiner plasma tubes, and Greiner serum tubes containing PtPA, prepared as follows. The insides of the Greiner serum tubes were cleaned to remove the Greiner procoagulants/additives by filling the tubes with sterile de-ionized water, inverted ~20 times, allowed to stand 10 minutes, and then the inside wall and inner part of tube cap were scrubbed with sterile cotton swab without disturbing the gel barrier. The content was discarded and the tubes were further filled/inverted/rinsed 3 times with de-ionised water. The cleaned tubes were finally placed in a drying oven at 40° C. to completely dry any water droplets before the PtPA was dispensed (1.2 μg/4 mL of blood). Blood was then collected into the tubes. The two tubes (Greiner plasma and PtPA) from each participant were centrifuged and immediately analysed for lactate dehydrogenase (LD) and glucose (zero time) levels. The samples were allowed to stand at room temperature (21° C.) and re-analysed ~8 hours later on the same analyser. Results are shown in Tables 64 and 65.

TABLE 64

LD activity (U/L) of samples from 10 participants measured at 0 and 8 hours post centrifugation stored at 21° C.

| | A | | | | | | | |
|---|---|---|---|---|---|---|---|---|
| | Greiner plasma | | | | PtPA | | | |
| | 0 hr | 8 hr | 8 − 0 hr* | % 8 − 0 hr* | 0 hr | 8 hr | 8 − 0 hr* | % 8 − 0 hr* |
| Mean | 177 | 199 | 22 | +12.5 | 175 | 173 | 1.3 | −0.6 |
| SD | 14 | 23 | 16 | 9.2 | 19 | 16 | 3.4 | 2.0 |

*= Difference between 8 hours and 0 hours and percent difference between 8 hours and 0 hours.

TABLE 65

Glucose concentration (mmol/L) of samples from 10 participants measured at 0 and 8 hours post-centrifugation stored at 21° C.

| | B | | | | | | | |
|---|---|---|---|---|---|---|---|---|
| | Greiner plasma | | | | PtPA | | | |
| | 0 hr | 8 hr | 8 − 0 hr* | % 8 − 0 hr* | 0 hr | 8 hr | 8 − 0 hr* | % 8 − 0 hr* |
| Mean | 5.1 | 4.7 | 0.5 | −9.1 | 5.2 | 5.1 | 0.08 | −1.5 |
| SD | 0.8 | 0.9 | 0.2 | 5.1 | 0.8 | 0.8 | 0.04 | 0.9 |

*= Difference between 8 hours and 0 hours and percent difference between 8 hours and 0 hours.

In serum samples from the PtPA tubes, the LD and glucose results showed 0.6% and 1.5% change over the 8 hour period compared with the 12.5% and 9.1% change for the Greiner plasma tube samples respectively. In the plasma samples, the presence of cells resulted in glucose consumption, and the LD increased due to leakage from the cells lysed.

The results confirm that clotting of the blood with PtPA removes cells effectively and this prevents any significant changes in the most affected analytes, glucose and LD, for up to 8 hours. Thus, inclusion of PtPA in a serum tube provided high quality stable serum from the healthy participants' blood samples.

Example 11b

Cellular Contamination of Serum and Plasma Prepared from Anticoagulated Patients Blood samples were collected from two participants (P1 and P2) undergoing cardiac surgery who had received in total: P1 —30000, and P2 —35000 units of heparin just prior to blood collection (within 15 minutes post heparin infusion). The samples were collected in 50 mL plain syringes (BD Plastipak REF #300866) filled with ~30 mL blood. The syringes were delivered to the laboratory within 15 minutes of collection. The following tubes were filled with blood: Greiner plasma tube, Greiner serum tube, and Greiner serum tube (cleaned as per the procedure above) containing PtPA (1.2 μg/4 mL of blood). The plasma and PtPA containing tubes were centrifuged immediately on arrival at the laboratory. The Greiner serum tube was allowed to stand for 60 minutes before centrifugation. The samples were analysed, then allowed to stand at room temperature (21° C.) and re-analysed 24 hours later on the same analyser. Results are shown in Tables 66 and 67.

TABLE 66

LD activity (U/L) of samples from 2 cardiac surgery participants measured at 0 and 24 hours post-centrifugation stored at 21° C.

| | A | | | | | | | | | | | |
|---|---|---|---|---|---|---|---|---|---|---|---|---|
| | Greiner Plasma | | | | Greiner Serum | | | | PtPA Serum | | | |
| | 0 hr | 24 hrs | Dfce (24 − 0 hrs) | % Dfce (24 − 0 hrs) | 0 hr | 24 hrs | Dfce (24 − 0 hrs) | % Dfce (24 − 0 hrs) | 0 hr | 24 hrs | Dfce (24 − 0 hrs) | % Dfce (24 − 0 hrs) |
| Mean | 87 | 94 | 8 | +9 | 87 | 98 | 11 | +13 | 84 | 81 | −3 | −3 |
| SD | 11 | 1 | 9 | 12 | 8 | 9 | 1 | 1 | 9 | 10 | 1 | 1 |

TABLE 67

Glucose concentration (mmol/L) of samples from 2 cardiac surgery participants measured at 0 and 24 hours post-centrifugation stored at 21° C.

| | B | | | | | | | | | | | |
|---|---|---|---|---|---|---|---|---|---|---|---|---|
| | Greiner Plasma | | | | Greiner Serum | | | | PtPA Serum | | | |
| | 0 hr | 24 hrs | Dfce (24 − 0 hrs) | % Dfce (24 − 0 hrs) | 0 hr | 24 hrs | Dfce (24 − 0 hrs) | % Dfce (24 − 0 hrs) | 0 hr | 24 hrs | Dfce (24 − 0 hrs) | % Dfce (24 − 0 hrs) |
| Mean | 5.4 | 4.6 | −0.8 | −14.8 | 5.4 | 4.7 | −0.8 | −13.9 | 5.3 | 5.3 | −0.1 | −0.9 |
| SD | 0.1 | 0.1 | 0.0 | 0.4 | 0.1 | 0.1 | 0.1 | 1.0 | 0.1 | 0.1 | 0.1 | 1.3 |

In the PtPA-produced serum samples the LD and glucose results showed a change of −3 and −0.9% at 24 hours compared with the 9%, and −14.8% change in the lithium heparin plasma, and 13% and −13.9% for serum samples respectively. Similar to the healthy participant group of Examples 11a, the presence of cells in plasma resulted in glucose consumption and with cell lysis, the activity of LD was increased. The Greiner serum tubes showed plasma like results, as expected, since the samples never clotted.

In the Greiner serum tube no blood clotting was observed nor was any latent clotting detected visually or by analysers over the 24 hours post-centrifugation. The samples in the PtPA-containing tubes clotted within 3-5 minutes. The 3 tubes of participant P1 were photographed to indicate the presence of cells on top of the gel barrier. In the PtPA tube, very few cells were present above or within the gel barrier, in contrast to the other two tubes where cells were visible throughout and above the gel barrier.

Figure 56:
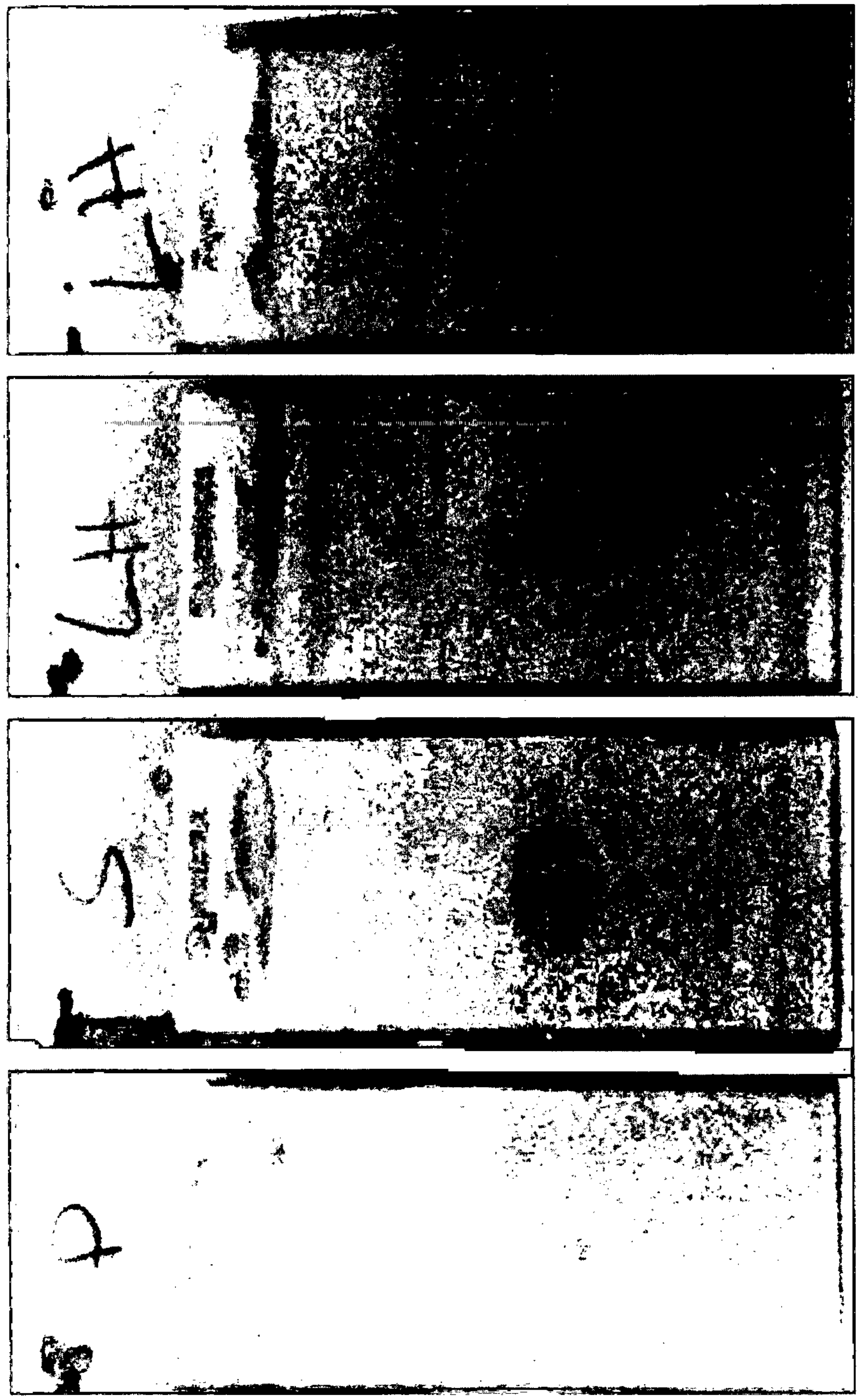
FIG. 56 shows Giemsa-stained Cytospin slides showing cell content above the gel barrier as described in Example 9b where the slides from left to right are: (P)—PtPA serum; (S)—Greiner serum; (LH)—diluted Greiner lithium heparin plasma; and (LH)—undiluted Greiner lithium heparin plasma.

From each of the 3 tubes the majority of the plasma or serum content was gently removed without disturbing the layer on top of the gel barrier, leaving about 0.5 mL of the plasma or serum in the tube. The residual plasma or serum in each tube was re-mixed with the buffy coat and transferred into a slide centrifuge, Cytospin (Shandon-Elliott Cytospin, Shandon-Elliott Instruments Limited) to concentrate the cells and produce a Giemsa-stained slide of the cells, cell stroma, etc for microscopic examination. The slides (shown in FIG. 56) clearly indicate presence of cells in abundance in the plasma, slightly fewer in the Greiner serum and minimal cells in the PtPA-produced serum.

These results confirm clotting of the blood with PtPA was achieved even in so called "fully heparinised" participants, in a very short time, <5 minutes. After centrifugation, the number of residual cells was minimal and insufficient to have an effect on LD activity or glucose concentrations.

Example 11c

Effect of Prolonged Storage of Serum and Plasma Samples from One Cardiac Surgery Participant on Analytes The 3 samples from cardiac surgery participant P2 after 24 hours at room temperature (21° C.) were stored in the primary tubes at 4° C. for 13 additional days, (total of 14 days or 336 hours post collection) and then were re-analysed for $K^+$, glucose, LD and phosphate (Pi). The results are shown in Table 68.

TABLE 68

Concentration of analytes in serum and plasma samples from a cardiac surgery participant measured at 0, 24 and 336 hours post-centrifugation

| Analyte | 0 hr | 24 hrs | 336 hrs | Dfce (24 − 0) | % Dfce (24 − 0) | Dfce (336 − 0) | % Dfce (336 − 0) |
|---|---|---|---|---|---|---|---|
| Greiner Plasma | | | | | | | |
| $K^+$ (mmol/L) | 4.7 | 4.6 | 4.9 | −01 | −2.1 | 0.2 | 4.3 |
| Glucose (mmol/L) | 5.5 | 4.1 | 3.1 | −1.4 | −25.5 | −2.4 | −43.6 |
| LD (U/L) | 79 | 93 | 208 | 14 | 17.7 | 129 | 163.0 |
| Pi (mmol/L) | 0.59 | 0.6 | 0.69 | 0.01 | 1.7 | 0.1 | 16.9 |
| Greiner Serum | | | | | | | |
| $K^+$ (mmol/L) | 4.7 | 4.7 | 5.2 | 0 | 0 | 0.5 | 10.6 |
| Glucose (mmol/L) | 5.5 | 4.7 | 3.8 | −0.8 | −14.5 | −1.7 | −30.9 |
| LD (U/L) | 81 | 91 | 180 | 10 | 12.3 | 99 | 122.2 |
| Pi (mmol/L) | 0.58 | 0.63 | 0.74 | 0.05 | 7.8 | 0.16 | 27.6 |
| PtPA Serum | | | | | | | |
| $K^+$ (mmol/L) | 4.6 | 4.6 | 4.6 | 0 | 0 | 0 | 0 |
| Glucose (mmol/L) | 5.4 | 5.3 | 5.3 | 0.1 | 1.9 | −0.1 | −1.9 |
| LD (U/L) | 77 | 74 | 64 | 3 | 3.9 | −13 | −20.3 |
| Pi (mmol/L) | 0.57 | 0.58 | 0.65 | −0.01 | −1.8 | 0.08 | 12.3 |

Unlike the lithium heparin plasma and "serum" from the Greiner tubes, the PtPA serum sample showed insignificant changes in the $K^+$ and glucose results, while the LD and Pi results showed minimal changes.

In this extreme case scenario, serum produced using PtPA provided easily the most stable sample type that will allow laboratories to provide additional analyte testing at later dates and have confidence the results will be accurate. The 20% fall in LD activity in the PtPA sample was probably due to slow denaturation of existing LD on storage.

Overall Conclusion

PtPA produced serum offers outstanding stability in analyte concentrations that are most likely to be affected by the incomplete removal of cells from the plasma or serum component above the gel barrier during the clotting and/or centrifugation process in all patients. Our results also show by direct observation the relative absence of cells from the PtPA produced sera compared with Greiner lithium heparin plasma prepared from healthy participants or patients on high doses of heparin.

Example 12

Measurement of Biochemical Analytes in Plasma and Serum Samples Prepared in Commercial Tubes and Serum Samples Prepared Using Venom Prothrombin Activators (Ecarin, PtPA, and OsPA)

As discussed in earlier parts of this specification, current commercially available blood collection tubes are unable to produce completely clotted serum from all blood samples in a timely manner to meet the quality and turn-around time expectations from biochemistry laboratories for optimal patient care. The results in the above examples demonstrate that prothrombin activators can be employed to produce a quality serum sample rapidly with low levels of fibrinogen/fdp/FDP and without cellular contaminations (as determined by visual inspection, clarity of the serum and analysis) in blood from a wide variety of patients/individuals.

It was important therefore to determine whether the prothrombin activators might interfere with analysis of analytes commonly used for clinical management of patients. Prothrombin activators are proteolytic enzymes which could in principle cleave serum proteins or proteins involved in analytical methodology, thereby affecting analytical results. Proteins are involved in analytical methods either as the analyte of interest or as reactants (e.g. enzymes, antibodies) used to measure the analytes of interest.

The purpose of this example was to investigate whether serum prepared using prothrombin activators gives the same analytical results as plasma and serum prepared in current commercially available tubes using current commercial methods.

It is not uncommon for more than 30 biochemical analytes to be requested and performed from a single serum or plasma tube. As the range of analytes increases and the analytical volumes per analyte decreases with technological improvements, the number of analyses from a single tube will further increase. Hence it is essential tube additives, specifically procoagulants, be inert and not impose any analytical effect on analytes yet provide highest quality sample for the most accurate estimation of analytes.

Standard analytical test procedures were used in the following experiments for each of the 33 assays which are listed below:

Test 1: Sodium ($Na^+$)
Test 2: Potassium ($K^+$)
Test 3: Chloride ($Cl^-$)
Test 4: Bicarbonate ($HCO_3^-$)
Test 5: Glucose (Gluc)
Test 6: Urea (Urea)
Test 7: Creatinine (Creat)
Test 8: Urate (Urate)
Test 9: Total Protein (TP or T Prot)
Test 10: Albumin (Alb)
Test 11: Total Bilirubin (T Bili)
Test 12: Alkaline Phosphatase (ALP)
Test 13: Gamma-Glutamyl Transferase (GGT)
Test 14: Alanine Aminotransferase (ALT)
Test 15: Aspartate Aminotransferase (AST)
Test 16: Lactate Dehydrogenase (LD)
Test 17: Creatine Kinase (CK)
Test 18: Total Calcium (TCa)
Test 19: Phosphate (Pi or Phos)
Test 20: Magnesium ($Mg^{2+}$)
Test 21: Lipase (Lipase)
Test 22: Cholesterol (Chol)
Test 23: Triglycerides*
Test 24: High-Density Lipoprotein Cholesterol (HDL-C or HDL)
Test 25: Iron ($Fe^{2+}$)
Test 26: Transferrin (Trf)
Test 27: C Reactive Protein (CRP)
Test 28: Cortisol Test (Cortisol)
Test 29: Free Thyroxine (FT4)
Test 30: Thyroid Stimulating Hormone (TSH)
Test 31: Ferritin (Ferritin)
Test 32: Troponin (TnI)
Test 33: Haemolytic Index (Haem index)**

**See also Example 10.

Test 34: Icteric Index*
Test 35: Lipemia Index*

*Triglycerides were not measured in these experiments because of the presence of glycerol in the PtPA preparation. Icteric and Lipaemic indices were also not determined in this study.

Test Analysis

Analysis was performed on Beckman DxC800 general chemistry analysers and a DxI800 immunoassay analyser (Beckman Coulter, Fullerton, Calif., USA). Samples were loaded on the same instruments at the same time and within 1-2 hours post-centrifugation, except where recurrent latent clotting was encountered.

The analytes tested plus semi-quantitative haemolysis levels are listed in the result tables. The upper limit of imprecision of the between-run coefficient of variations (CVs) from the two and three internal quality control concentrations for the 35 analytes tested on the Beckman DxC800 analysers the DxI800 analyser respectively are shown in Table 69. We also measured the activated partial thromboplastin time (aPTT) on an $AC^{TOPS}$. (Instrumentation Laboratory, Lexington Mass., USA) since it was difficult to ascertain the exact anticoagulant concentration in the participants' blood samples at the time of the specimen collection in the cardiac care unit and dialysis participants. In all cases, results were consistent with listed degree of anticoagulation.

Data Analysis

The results of each test were obtained and then data analysis was performed as follows. The mean and standard deviation (SD) were calculated for each test for each type of tube. The difference (actual and %) between each result pair for each test between the different tubes (e.g. PtPA tube result versus Greiner serum result type) was also calculated. The % difference was then compared with the between-run precision values obtained on the analysers (Table 69) to determine if there were analytically significant differences between the different serum tubes and the different serum tubes versus plasma tubes. The participant data was also separated into healthy participants and anticoagulated participants, and the same analysis performed. If a measurement was not obtained for an analyte in any of the three tubes (due to recurrent latent clotting leading to insufficient specimen, insufficient specimen collected, not requested on analyser, or insufficient reagent), the result was not included in the calculation accounting for the variability in the number of specimens analysed per assay.

TABLE 69

Quality Control (QC) imprecision on the Beckman DxC800 and DxI800 analysers (*DxI800)

| | QC Level 1 | | | QC Level 2 | | | QC Level 3 | | |
|---|---|---|---|---|---|---|---|---|---|
| Analyte | Mean | SD | CV % | Mean | SD | CV % | Mean | SD | CV % |
| $Na^+$ | 132 | 1.27 | 1.0 | 150 | 1.33 | 0.9 | | | |
| $K^+$ | 3.9 | 0.06 | 1.4 | 6.0 | 0.07 | 1.2 | | | |
| Cl— | 85 | 1.17 | 1.4 | 100 | 1.19 | 1.2 | | | |
| $HCO_3^-$ | 17 | 0.66 | 3.8 | 29 | 0.85 | 2.9 | | | |
| Gluc | 4.8 | 0.12 | 2.6 | 16.7 | 0.28 | 1.8 | | | |
| Urea | 5.2 | 0.17 | 3.3 | 15.9 | 0.41 | 2.6 | | | |
| Creat | 68 | 3.34 | 4.9 | 491 | 8.93 | 1.8 | | | |
| Urate | 0.23 | 0.001 | 1.9 | 0.49 | 0.01 | 1.5 | | | |
| T Prot | 41 | 0.73 | 1.8 | 67 | 1.07 | 1.6 | | | |
| Alb | 26 | 0.37 | 1.4 | 40 | 0.54 | 1.3 | | | |
| T Bili | 21 | 1.37 | 6.4 | 93 | 1.96 | 2.1 | | | |
| ALP | 106 | 2.79 | 2.6 | 471 | 7.93 | 1.7 | | | |
| GGT | 38.7 | 2.03 | 5.3 | 155 | 2.88 | 1.9 | | | |
| ALT | 25 | 1.52 | 6.2 | 94 | 2.00 | 2.1 | | | |
| AST | 34 | 1.35 | 3.9 | 201 | 2.39 | 1.2 | | | |
| LD | 149 | 3.21 | 2.2 | 408 | 5.65 | 1.4 | | | |
| CK | 139 | 2.53 | 1.8 | 459 | 5.8 | 1.3 | | | |
| TCa | 2.07 | 0.03 | 1.6 | 2.86 | 0.04 | 1.3 | | | |
| Phos | 1.00 | 0.02 | 1.9 | 2.86 | 0.04 | 1.5 | | | |

TABLE 69-continued

Quality Control (QC) imprecision on the Beckman DxC800 and DxI800 analysers (*DxI800)

| Analyte | QC Level 1 | | | QC Level 2 | | | QC Level 3 | | |
|---|---|---|---|---|---|---|---|---|---|
| | Mean | SD | CV % | Mean | SD | CV % | Mean | SD | CV % |
| $Mg^{2+}$ | 0.84 | 0.02 | 2.5 | 1.63 | 0.04 | 2.3 | | | |
| Lipase | 29 | 2.39 | 8.2 | 57 | 4.05 | 7.1 | | | |
| Chol | 3.0 | 0.05 | 1.7 | 6.5 | 0.15 | 2.3 | | | |
| Trig | 1.0 | 0.04 | 3.6 | 2.0 | 0.05 | 2.7 | | | |
| HDL | 1.1 | 0.04 | 3.5 | 1.9 | 0.05 | 2.6 | | | |
| $Fe^{2+}$ | 10 | 0.29 | 2.8 | 34 | 1.93 | 5.7 | | | |
| Trf | 1.0 | 0.04 | 3.5 | 2.3 | 0.08 | 3.5 | | | |
| CRP | 4.6 | 0.36 | 7.9 | 10.0 | 0.55 | 5.4 | | | |
| TnI* | 0.052 | 0.01 | 16.1 | 0.55 | 0.04 | 7.9 | 10.2 | 0.69 | 6.7 |
| Cortisol* | 139 | 8.85 | 6.4 | 552 | 28.48 | 5.2 | 906 | 41.7 | 4.6 |
| fT4* | 7.51 | 0.62 | 8.2 | 23.93 | 0.94 | 4.0 | 50.9 | 1.92 | 3.8 |
| TSH* | 0.71 | 0.05 | 7.1 | 4.17 | 0.26 | 6.3 | 23.1 | 1.53 | 6.6 |
| Ferritin* | 19 | 1.68 | 8.8 | 159 | 9.67 | 6.1 | 358 | 22.42 | 6.3 |

Example 12a

Comparison of PtPA Serum with Serum and Lithium Heparin Plasma Prepared in Commercial Tubes A total of 61 participants were recruited. All 61 participants were adults, >18 years of age, with a mix of males and females. The participants consisted of two groups: 26 healthy volunteers and 35 anticoagulated patients.

Of the 35 anticoagulated patients, 1 was an outpatient on low dose warfarin therapy and 34 were inpatients.

Of the 34 inpatients, 11 were undergoing cardiac surgery, 8 were cardiac care unit patients, and 15 were on dialysis.

The 11 inpatients undergoing cardiac surgery had received in total 25,000-41,000 units of heparin at the time of the blood collection which was within 30 minutes post heparin infusion. The specimens were collected while participants were on bypass (where blood is pumped by machine not by the heart).

The 8 cardiac care unit participants were recruited the night before specimen collection and were receiving heparin by IV infusion, 950-1450 units of heparin per hour. Seven remained on IV heparin infusion (blood collection was ≥12 hours after IV heparin infusion started) at the time of specimens being collected, and the other was due for surgery on the day so had had the infusion stopped approximately three hours prior to the specimen collection (blood collection was >9 hours after IV infusion had started and ~3 hours after IV heparin infusion was stopped). From the information in the patient records the heparin concentration in the infusate and the infusion rate were unchanged for the participants over the period between when IV heparin infusion started and blood was collected.

Of the 15 inpatients on dialysis, 12 were on heparin IV infusion, and 1 was on warfarin/heparin (~1750-7000 units of heparin, initial bolus plus hourly top up dose), and 2 were on clexane. Blood from these patients was collected at least one hour after dialysis commenced.

Blood was drawn using a standardised draw order. The blood was drawn by venipuncture from healthy volunteers, via bypass port from cardiac patients, and via bloodline from dialysis patients. The following tubes were used:

Greiner Vacuette™ citrate tube (for coagulation studies);

Greiner Vacuette™ No Additive tube with PtPA added (1.2 μg/4 mL) (PtPA);

Greiner Vacuette™ plasma tube (GLH);

BD Vacutainer™ plasma/PST II tube (BDLH);

Greiner Vacuette™ serum tube (GRS);

BD serum tube/SST II (BDS); and

BD RST tube (BD RST).

The blood for the PtPA-containing tube was collected in a plain syringe and then transferred from the syringe into the Greiner tube containing the PtPA without a needle to minimise cell lysis.

The Greiner serum and BD SST tubes were allowed to clot for the standard time of 30 minutes for healthy participants and 60 minutes for anticoagulated participants. These tubes were visually inspected for clot formation prior to loading in the centrifuge.

The BD RST and PtPA tubes were visually inspected for clot formation at 5 minutes for all participants at the point of collection (phlebotomy or clinical unit). The BD RST specimens for the healthy participants and for the anticoagulated participants that formed a solid clot at 5 minutes were centrifuged as soon as delivered to the laboratory (<20 minutes). If clotting was incomplete the specimens were re-checked every 10-15 minutes for clotting and left to clot for 60 minutes maximum. The lithium heparin and PtPA tubes were centrifuged immediately on delivery in the laboratory (<20 minutes from collection).

All tubes were centrifuged at 3000 g for 10 minutes at 20° C. in swing bucket centrifuges, and then stored at ~21° C. The tubes were visually inspected for latent clotting immediately after centrifugation and again just prior to loading onto analysers. These tube (primary tubes) were used for analysis except in cases where latent clotting was observed. In tubes where latent clotting was observed, the serum in the primary tubes was transferred to an aliquot tube, re-centrifuged to remove the clots, and the clean serum transferred to another aliquot tube (secondary tube) which was used for analysis. The Greiner No Additive tube does not contain a serum gel barrier, thus the PtPA generated serum was also transferred to a secondary tube for analysis to prevent re-mixing and prolonged contact with the cells.

Results

Figure 57A:
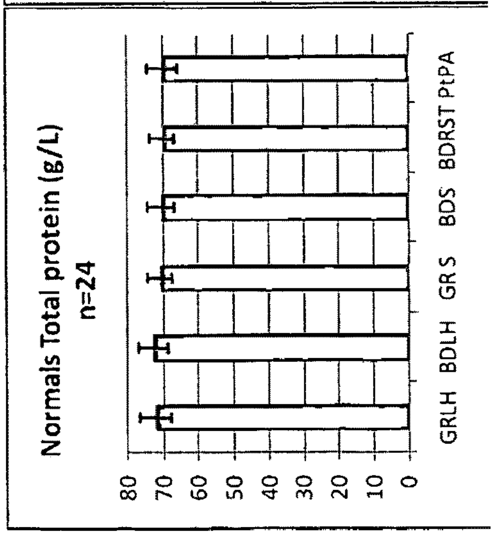
Figure 57B:
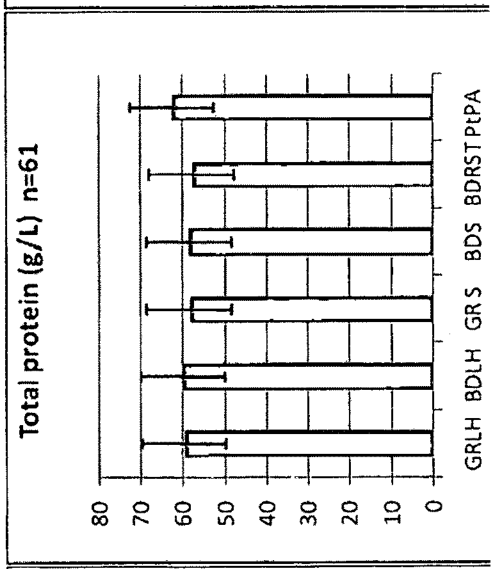
Figure 57C:
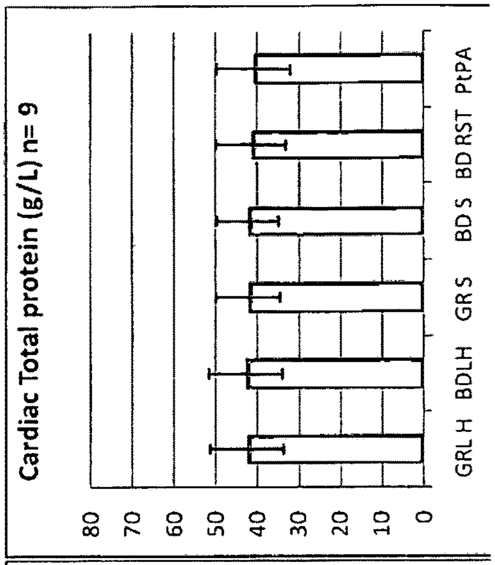

The results are shown in Table 70. Also, an example of results is provided in FIG. 57 for the measurement of total protein (TP). The left graph shows the mean with standard deviation value of all normal patient results (n=26) for each tube type. The centre graph shows the mean value of all patient results (n=61) for each tube type. The right graph shows the mean value of results for cardiac patients (n=11) for each tube type. The units on the y-axis are g/L protein. The error bars are standard deviation.

Comparison of PtPA sera with commercial tube sera from healthy and anticoagulated participants. No significant differences were observed with any of the analytes. This conclusion is based on comparison of the mean test values in Table 70 and a paired-wise statistical analysis described above.

Comparison of PtPA sera with commercial tube lithium heparin plasma from healthy and anticoagulated participants. Significant differences were observed in some analytes ($K^+$, TP, AST and Pi) as expected because of the well established differences between plasma and serum. Sera prepared in the commercially available serum tubes showed similar analytical differences from plasma to those shown with PtPA sera.

TABLE 70

Analytical data for 32 analytes on serum and plasma samples.

| Number of samples | Analyte | Units | Mean ± SD PtPA | GLH | BDLH | GS | BDS | BD RST |
|---|---|---|---|---|---|---|---|---|
| 60 | $Na^+$ | mmol/L | 136.9 ± 2.24 | 137.4 ± 2.44 | 137.2 ± 2.38 | 137.5 ± 2.29 | 137.5 ± 2.34 | 137.4 ± 2.38 |
| 61 | $K^+$ | mmol/L | 4.09 ± 0.59 | 3.91 ± 0.63 | 3.93 ± 0.65 | 4.13 ± 0.62 | 4.15 ± 0.60 | 4.07 ± 0.60 |
| 61 | $Cl^-$ | mmol/L | 104.1 ± 3.8 | 104.6 ± 4.2 | 104.8 ± 4.1 | 104.6 ± 4.0 | 104.8 ± 3.8 | 104.7 ± 3.9 |
| 61 | $HCO_3^-$ | mmol/L | 24.8 ± 2.8 | 25.8 ± 3.0 | 25.3 ± 2.7 | 25.7 ± 3.1 | 25.1 ± 2.9 | 25.0 ± 3.0 |
| 61 | Gluc | mmol/L | 6.2 ± 2.09 | 6.3 ± 2.15 | 6.3 ± 2.11 | 6.2 ± 2.07 | 6.2 ± 2.11 | 6.3 ± 2.08 |
| 61 | Urea | mmol/L | 5.3 ± 2.0 | 5.3 ± 2.0 | 5.4 ± 2.0 | 5.3 ± 2.1 | 5.4 ± 2.1 | 5.3 ± 2.1 |
| 61 | Creat | μmol/L | 134.1 ± 112.8 | 135.1 ± 115.0 | 136.3 ± 114.7 | 137.1 ± 116.0 | 136.7 ± 116.0 | 138.1 ± 116.6 |
| 60 | Urate | mmol/L | 0.27 ± 0.11 | 0.27 ± 0.12 | 0.27 ± 0.12 | 0.28 ± 0.11 | 0.28 ± 0.11 | 0.27 ± 0.12 |
| 61 | TP | g/L | 62.6 ± 13.0 | 65.0 ± 13.2 | 65.5 ± 13.3 | 63.0 ± 12.6 | 63.0 ± 12.5 | 62.8 ± 12.6 |
| 61 | Alb | g/L | 36.1 ± 8.3 | 35.9 ± 8.1 | 35.9 ± 8.1 | 36.1 ± 8.3 | 36.1 ± 8.3 | 36.2 ± 8.3 |
| 58 | T Bili | μmol/L | 13.5 ± 3.8 | 13.6 ± 3.7 | 13.4 ± 3.4 | 13.3 ± 3.6 | 13.4 ± 4.0 | 13.2 ± 3.8 |
| 61 | ALP | U/L | 74.1 ± 26.9 | 68.9 ± 26.5 | 69.4 ± 26.6 | 71.3 ± 26.9 | 71.7 ± 27.5 | 71.4 ± 26.9 |
| 61 | GGT | U/L | 27.9 ± 17.6 | 28.3 ± 17.0 | 28.1 ± 16.9 | 27.3 ± 17.1 | 28.1 ± 17.1 | 27.8 ± 17.5 |
| 61 | §ALT | U/L | 30.4 ± 19.9 | 29.6 ± 18.8 | 29.6 ± 19.1 | 30.4 ± 19.1 | 29.8 ± 19.2 | 30.7 ± 20.1 |
| 59 | §AST | U/L | 34.2 ± 37.7 | 32.5 ± 37.5 | 32.6 ± 36.9 | 32.0 ± 34.9 | 32.6 ± 38.7 | 32.4 ± 39.1 |
| 58 | §LD | U/L | 212.9 ± 110.0 | 215.4 ± 113.1 | 215.3 ± 110.7 | 213.8 ± 106.0 | 222.8 ± 120.0 | 212.5 ± 119.2 |
| 59 | §CK | U/L | 147.1 ± 250.3 | 146.6 ± 250.0 | 145.3 ± 242.8 | 146.0 ± 241.3 | 149.4 ± 259.6 | 147.7 ± 253.3 |
| 61 | TCa | mmol/L | 2.19 ± 0.26 | 2.17 ± 0.24 | 2.17 ± 0.24 | 2.20 ± 0.26 | 2.20 ± 0.26 | 2.19 ± 0.26 |
| 61 | Pi | mmol/L | 1.07 ± 0.28 | 1.02 ± 0.28 | 1.02 ± 0.28 | 1.08 ± 0.30 | 1.08 ± 0.30 | 1.08 ± 0.30 |
| 57 | $Mg^{2+}$ | mmol/L | 0.94 ± 0.19 | 0.95 ± 0.20 | 0.94 ± 0.19 | 0.94 ± 0.18 | 0.94 ± 0.20 | 0.93 ± 0.20 |
| 59 | Lipase | U/L | 28.2 ± 9.0 | 28.3 ± 9.0 | 28.3 ± 8.9 | 28.2 ± 9.0 | 28.6 ± 9.2 | 28.2 ± 9.0 |
| 57 | Chol | mmol/L | 4.2 ± 1.6 | 4.2 ± 1.6 | 4.2 ± 1.6 | 4.3 ± 1.6 | 4.3 ± 1.6 | 4.3 ± 1.6 |
| 58 | HDL-C | mmol/L | 1.17 ± 0.6 | 1.25 ± 0.58 | 1.26 ± 0.60 | 1.20 ± 0.58 | 1.21 ± 0.58 | 1.21 ± 0.59 |
| 59 | $Fe^{2+}$ | μmol/L | 14.6 ± 6.6 | 14.5 ± 6.5 | 14.6 ± 6.7 | 14.7 ± 6.7 | 14.9 ± 6.7 | 14.6 ± 6.6 |
| 59 | Trf | g/L | 2.17 ± 0.74 | 2.13 ± 0.71 | 2.14 ± 0.72 | 2.17 ± 0.73 | 2.19 ± 0.73 | 2.18 ± 0.77 |
| 57 | CRP | μg/L | 14.4 ± 49.3 | 14.5 ± 49.5 | 14.6 ± 50.5 | 14.2 ± 46.8 | 15.0 ± 52.3 | 15.1 ± 52.4 |
| 59 | Cortisol* | nmol/L | 356 ± 247 | 354 ± 241 | 356 ± 254 | 356 ± 249 | 352 ± 248 | 358 ± 250 |
| 60 | FT4* | Pmol/L | 13.6 ± 4.1 | 12.7 ± 3.7 | 12.7 ± 3.6 | 12.7 ± 3.9 | 12.7 ± 3.9 | 12.8 ± 3.7 |
| 61 | TSH* | μIU/mL | 1.81 ± 2.12 | 1.87 ± 2.05 | 1.89 ± 2.12 | 1.83 ± 2.10 | 1.82 ± 2.02 | 1.86 ± 2.08 |
| 43 | Ferritin* | μg/L | 204 ± 191 | 199 ± 191 | 202 ± 192 | 208 ± 203 | 207 ± 198 | 204 ± 187 |
| 60 | §TnI* | μg/L | 0.873 ± 5.33 | 0.994 ± 6.06 | 0.945 ± 5.75 | 0.782 ± 4.77 | 0.869 ± 5.25 | 0.951 ± 5.75 |
| 61 | Haem Index | | 0.2 ± 0.7 | 0.2 ± 0.7 | 0.3 ± 0.7 | 0.3 ± 0.7 | 0.2 ± 0.7 | 0.2 ± 0.7 |

*Analysis performed on a DxI800 immunoassay analyser.

§signifies non-parametric distribution used. The p value was determined by Wilcoxen Matched-Paris Ranks test.

Example 12b

Comparison of PtPA, OsPA and Ecarin Serum with Serum and Plasma Prepared in Commercial Tubes 7 participants were recruited consisting of 5 healthy volunteers with a mix of 4 males and 1 female, and 2 patients undergoing cardiac surgery (all adults >18 years of age). The two cardiac patients had received 34,000 and 43,000 units of heparin within 30 minutes post heparin infusion.

Blood from the healthy participants was drawn by venipuncture using standardized draw order: Greiner citrate plasma tube; Greiner serum tube; Greiner plasma tube; a plain syringe (Thermo 10 mL #CE0197) for the PtPA, OsPA or ecarin containing Greiner No Additive tubes (the concentration of the prothrombin activators in these 4 mL tubes was PtPA 1.2 μg, OsPA 0.5 μg and ecarin 0.625 units for healthy and 1.25 units for cardiac surgery participants). The blood from the syringe was transferred into the Greiner No Additive tubes containing the prothrombin activators without a needle to minimise cell lysis.

For the cardiac participants blood was collected in a plain syringe (30 mL) while on bypass. The blood was delivered to the laboratory within 15 minutes and dispensed into the various tubes listed above.

The Greiner serum tubes were allowed to clot for the standard time of 30 minutes for healthy participants and 60 minutes for the cardiac surgery participants, and then visually inspected prior to loading in the centrifuge for clot formation. The PtPA, OsPA and ecarin specimens were visually inspected for clot formation at 3 and 5 minute mark for all participants at the point of collection (phlebotomy for healthy participants and in the clinical unit for the cardiac surgery participants). The lithium heparin, PtPA, OsPA and ecarin tubes were centrifuged immediately on delivery in the laboratory (<30 minutes from collection).

All tubes were centrifuged at 3000 g for 10 minutes at 20° C. in a swing bucket centrifuge, and then stored at ~21° C. The tubes were visually inspected for latent clotting immediately after centrifugation and again just prior to loading onto analysers. The Greiner primary tubes were used for analysis. The Greiner No Additive tube does not contain a serum gel barrier, thus the serum generated using prothrombin activators was transferred to aliquot (secondary) tubes to prevent re-mixing and prolonged contact with the cells.

Results

Results are shown in Table 71 and support the following conclusions:

1. Comparison of sera produced by the prothrombin activators versus Greiner sera—no significant differences were observed with any of the analytes.

2. Comparison of sera produced by prothrombin activators versus Greiner lithium heparin plasma—significant differences were observed in some analytes ($K^+$, TP, AST and Pi) as expected because of the well established differences between plasma and serum. Sera prepared in commercial serum tubes showed similar analytical differences from plasma to those shown with prothrombin activator sera.

TABLE 71

Data for each analyte from the three different snake procoagulants and the Greiner tubes.

| No of | | | Mean ± SD | | | | |
|---|---|---|---|---|---|---|---|
| Samples | Analyte | Units | GLH | GS | PtPA | OsPA | Ecarin |
| 7 | $Na^+$ | mmol/L | 138.1 ± 1.22 | 138.1 ± 1.46 | 137.3 ± 1.25 | 136.7 ± 2.36 | 137.1 ± 1.57 |
| 7 | $K^+$ | mmol/L | 4.40 ± 0.82 | 4.61 ± 0.71 | 4.53 ± 00.77 | 4.50 ± 0.76 | 4.49 ± 0.79 |
| 7 | $Cl^-$ | mmol/L | 104.0 ± 2.8 | 104.0 ± 2.6 | 103.0 ± 2.6 | 102.9 ± 2.34 | 103.4 ± 2.4 |
| 7 | $HCO_3^-$ | mmol/L | 25.1 ± 3.2 | 25.3 ± 3.5 | 23.9 ± 2.4 | 24.1 ± 2.7 | 23.3 ± 2.2 |
| 7 | Gluc | mmol/L | 5.76 ± 0.88 | 5.69 ± 0.94 | 5.63 ± 0.0.81 | 5.60 ± 0.80 | 5.64 ± 0.0.90 |
| 7 | Urea | mmol/L | 4.63 ± 0.82 | 4.66 ± 0.80 | 4.64 ± 0.85 | 4.54 ± 0.83 | 4.54 ± 0.88 |
| 7 | Creat | μmol/L | 75.1 ± 10.9 | 76.7 ± 12.35 | 75.9 ± 12.10 | 76.29 ± 12.54 | 75.0 ± 12.7 |
| 7 | Urate | mmol/L | 0.33 ± 0.08 | 0.33 ± 0.08 | 0.33 ± 0.08 | 0.32 ± 0.07 | 0.32 ± 0.08 |
| 7 | TP | g/L | 68.5 ± 11.0 | 62.7 ± 11.6 | 63.9 ± 11.8 | 62.4 ± 14.1 | 63.4 ± 13.4 |
| 7 | Alb | g/L | 38.3 ± 5.5 | 38.3 ± 5.5 | 38.6 ± 5.8 | 38.4 ± 6.0 | 38.6 ± 5.8 |
| 7 | T Bili | μmol/L | 15.6 ± 4.6 | 16.6 ± 4.7 | 16.4 ± 4.5 | 16.1 ± 4.6 | 15.7 ± 5.2 |
| 7 | ALP | U/L | 65.7 ± 18.6 | 66.0 ± 18.4 | 66.1 ± 20.7 | 69.3 ± 16.7 | 67.9 ± 18.7 |
| 7 | GGT | U/L | 27.4 ± 15.2 | 25.1 ± 15.0 | 25.4 ± 14.7 | 25.7 ± 15.8 | 24.9 ± 15.8 |
| 7 | §ALT | U/L | 30.4 ± 11.4 | 31.0 ± 11.8 | 32.0 ± 11.4 | 31.7 ± 12.2 | 32.1 ± 11.8 |
| 7 | §AST1 | U/L | 22.6 ± 7.8 | 25.0 ± 8.3 | 24.1 ± 7.2 | 24.9 ± 6.5 | 24.9 ± 6.7 |
| 7 | §LD | U/L | 194.4 ± 23.1 | 193.6 ± 41.6 | 195.6 ± 22.4 | 189.0 ± 18.9 | 192.7 ± 21.2 |
| 7 | §CK | U/L | 98.9 ± 34.9 | 97.9 ± 37.5 | 98.6 ± 36.8 | 97.1 ± 34.0 | 98.0 ± 36.1 |
| 7 | TCa | mmol/L | 2.20 ± 0.236 | 2.23 ± 0.245 | 2.22 ± 0.255 | 2.20 ± 0260 | 2.21 ± 0.25 |
| 7 | Pi | mmol/L | 1.13 ± 0.13 | 1.18 ± 0.14 | 1.19 ± 0.13 | 1.16 ± 0.14 | 1.17 ± 0.13 |
| 7 | $Mg^{2+}$ | mmol/L | 1.04 ± 0.23 | 1.06 ± 0.22 | 1.03 ± 0.20 | 1.03 ± 0.19 | 1.04 ± 0.21 |
| 7 | Chol | mmol/L | 4.3 ± 1.7 | 4.3 ± 1.7 | 4.3 ± 1.7 | 4.3 ± 1.7 | 4.3 ± 1.7 |
| 7 | HDL-C | mmol/L | 1.07 ± 0.27 | 1.04 ± 0.23 | 1.01 ± 0.27 | 1.03 ± 0.28 | 1.01 ± 0.06 |
| 7 | $Fe^{2+}$ | μmol/L | 16.1 ± 5.8 | 16.3 ± 5.9 | 16.4 ± 5.8 | 16.4 ± 5.7 | 16.1 ± 5.8 |
| 7 | Trf | g/L | 2.18 ± 0.51 | 2.18 ± 0.51 | 2.21 ± 0.54 | 2.20 ± 0.53 | 2.21 ± 0.55 |
| 7 | CRP | μg/L | 1.7 ± 1.5 | 1.9 ± 1.6 | 1.7 ± 1.5 | 1.9 ± 1.6 | 1.7 ± 1.5 |
| 7 | Cortisol* | nmol/L | 382.1 ± 251.4 | 379.7 ± 247.2 | 373.6 ± 256.9 | 366.3 ± 241.2 | 359.3 ± 237.7 |
| 7 | FT4* | Pmol/L | 13.53 ± 2.63 | 13.56 ± 3.26 | 13.46 ± 1.2.3 | 13.76 ± 3.17 | 14.23 ± 3.13 |
| 7 | FT3* | Pmol/L | 4.83 ± 0.35 | 4.66 ± 0.43 | 4.91 ± 0.51 | 4.74 ± 0.35 | 4.97 ± 0.48 |
| 7 | TSH* | μIU/mL | 1.86 ± 0.48 | 1.88 ± 0.56 | 1.72 ± 0.30 | 1.75 ± 0.30 | 1.73 ± 0.32 |
| 7 | Ferritin* | μg/L | 236.6 ± 297.2 | 234.9 ± 304.8 | 226.4 ± 280.8 | 207.3 ± 236.5 | 225.3 ± 280.1 |
| 7 | §TnI* | μg/L | 0.079 ± 0.136 | 0.071 ± 0.137 | 0.091 ± 0.165 | 0.092 ± 0.170 | 0.093 ± 0.174 |
| 7 | Haem Index | | 0.4 ± 0.5 | 0.6 ± 0.8 | 0.6 ± 0.5 | 0.4 ± 0.5 | 0.4 ± 0.5 |

§signifies non-parametric distribution used. The p value was determined by Wilcoxen Matched-Paris Ranks test.

*Analysis performed on a DxI800 immunoassay analyser.

Summary of Example 12

The blood of all the healthy and anticoagulated participants ranging from the lowest dose to the highest "fully" heparinised participant clotted within 5 minutes in the PtPA, OsPA and ecarin-containing tubes to give firm immobile clots. No latent clotting was visually observed or detected by the analysers in any of the sera produced by the prothrombin activators. Despite the prothrombin activators being proteolytic enzymes, they did not produce any analytically or clinically significant effect on any of the analytes measured irrespective of whether the analytes were proteins or whether proteins were used as reactive compounds in the analytical methods. There were no significant differences observed in any of the analytes between the sera prepared in the commercial tube and the sera prepared using prothrombin activators. The analytical and clinical differences observed in analytes between lithium heparin plasma prepared in a commercial tube and sera produced using prothrombin activators were in line with published data.

Example 13

Further Measurement of Biochemical Analytes in Plasma and Serum Samples Prepared in Commercial Tubes and Serum Samples Prepared Using Venom Prothrombin Activators (Notecarin and Carinactivase-2)

This Example follows from Example 12 and uses the same methodology described therein.

Example 13a

Analyte Measurement

Blood from 5 healthy participants was collected into Greiner No Additive tubes (Cat No 454001) to which 25 μL of notecarin or carinactivase-2 had been added to give concentrations of 12 nmol/mL and 45 nmol/mL respectively. Greiner Vacuette serum tubes (Cat No 456078; GS) were used as controls. The GS tubes were allowed to clot for 30 minutes as per manufacturer's recommendation prior to centrifugation. The tubes containing the prothrombin activators were observed for clotting immediately upon addition of the blood.

Notecarin and carinactivase-2 tubes clotted within 2 minutes and the tubes were brought to the laboratory and centrifuged within 7 to 15 minutes of collection. The clots formed in the tubes containing the activators were solid, and no latent clot formation was observed or detected.

The samples were then analysed for 31 analytes, and the results are shown in Table 72. For 27 analytes, the values obtained were equal within experimental error, with differences between paired results less than the least significant change (LSC %). The results where the differences were greater than the stated LSC (highlighted) can be explained as follows:

(1) For LD, the slightly lower activities in the two prothrombin activator samples may reflect decreased cellular contamination of these compared to Greiner serum;

(2) The high triglyceride (Trig) level in the Notecarin sample is due to interference by glycerol in which the Notecarin was stored;

(3) Notecarin serum produced higher AST levels, however the differences were clinically insignificant;

(4) Troponin results for the five patients were too low for accurate differentiation.

TABLE 72

Analytical results for serum samples generated by notecarin and carinactivase-2.

| No of | | | Mean ± SD | | | Notec − GS Mean dffce between | CA2 − GS Mean dffce between | | |
|---|---|---|---|---|---|---|---|---|---|
| Samples | Analyte | Units | GS | Notecarin | CA-2 | pairs (%) | pairs (%) | LSC (%) | CAL (%) |
| 5 | $Na^+$ | mmol/L | 138.6 ± 1.5 | 138 ± 1.6 | 138 ± 1.5 | −0.4 | −0.4 | 2.8 | 3 |
| 5 | $K^+$ | mmol/L | 3.94 ± 0.17 | 3.94 ± 0.18 | 3.83 ± 0.18 | 0 | −2.9 | 3.3 | 5 |
| 5 | $Cl^-$ | mmol/L | 104.2 ± 2.4 | 104.2 ± 2.7 | 106.5 ± 2.6 | 0 | 2.2 | 3.3 | 5 |
| 5 | $HCO_3^-$ | mmol/L | 26.8 ± 2.6 | 25.6 ± 2.5 | 25.6 ± 2.2 | −4.5 | −4.5 | 4.8 | 10 |
| 5 | Gluc | mmol/L | 4.86 ± 0.86 | 4.76 ± 0.82 | 4.74 ± 0.65 | −2.1 | −2.4 | 4.4 | 10 |
| 5 | Urea | mmol/L | 5.58 ± 2.49 | 5.56 ± 2.44 | 5.55 ± 2.42 | −0.4 | −0.5 | 5.0 | 10 |
| 5 | Creat | μmol/L | 69.2 ± 25.0 | 69.2 ± 22.9 | 67.2 ± 22.9 | −2.9 | −2.9 | 5.5 | 10 |
| 5 | Urate | mmol/L | 0.242 ± 0.026 | 0.240 ± 0.026 | 0.240 ± 0.023 | −0.8 | −1.2 | 3.8 | 10 |
| 5 | TP | g/L | 66.0 ± 2.0 | 65.0 ± 2.2 | 63.6 ± 2.4 | −1.5 | −3.3 | 3.5 | 5 |
| 5 | Alb | g/L | 40.8 ± 1.9 | 40.2 ± 1.9 | 39.5 ± 1.4 | −1.5 | −3.1 | 3.2 | 5 |
| 5 | T Bili | μmol/L | 11.4 ± 8.8 | 11.6 ± 9.0 | 10.6 ± 6.9 | 1.8 | −7.0 | 7.0 | 10 |
| 5 | ALP | U/L | 60.0 ± 4.1 | 60.4 ± 4.2 | 58.4 ± 4.3 | 0.7 | −2.6 | 4.8 | 10 |
| 5 | GGT | U/L | 14.6 ± 4.9 | 14.4 ± 6.5 | 14.8 ± 5.0 | −1.4 | 1.2 | 7.3 | 10 |
| 5 | ALT | U/L | 22.6 ± 8.0 | 23.2 ± 7.6 | 23.9 ± 7.6 | 2.7 | 5.8 | 6.8 | 10 |
| 5 | AST | U/L | 17.2 ± 3.8 | 19.8 ± 4.4 | 17.3 ± 3.5 | 15.1§ | 0.4 | 6.2 | 10 |
| 5 | LD | U/L | 192.2 ± 17.0 | 184.8 ± 18.3 | 179.9 ± 17.6 | −3.9§ | −6.3§ | 3.7 | 15 |
| 5 | CK | U/L | 81.4 ± 15.9 | 81.0 ± 15.4 | 78.8 ± 14.1 | −0.5 | −3.2 | 3.7 | 15 |
| 5 | TCa | mmol/L | 2.330 ± 0.07 | 2.290 ± 0.07 | 2.267 ± 0.07 | −1.7 | −2.7 | 3.5 | 5 |
| 5 | Pi | mmol/L | 1.314 ± 0.118 | 1.282 ± 0.117 | 1.271 ± 0.099 | −2.4 | −3.3 | 3.8 | 10 |
| 5 | $Mg^{2+}$ | mmol/L | 0.804 ± 0.046 | 0.802 ± 0.051 | 0.792 ± 0.054 | −0.3 | −1.4 | 4.4 | 10 |
| 5 | Chol | mmol/L | 4.84 ± 0.35 | 4.78 ± 0.39 | 4.70 ± 0.34 | −1.2 | −2.9 | 3.6 | 10 |
| 5 | Trig | mmol/L | 1.52 ± 0.55 | 5.61 ± 0.96 | 1.56 ± 0.65 | 269#§ | 2.6 | 5.3 | 10 |
| 5 | HDL-C | mmol/L | 1.420 ± 0.399 | 1.424 ± 0.293 | 1.388 ± 0.277 | 0.3 | −2.6 | 5.2 | 10 |
| 5 | $Fe^{2+}$ | μmol/L | 17.2 ± 3.8 | 16.8 ± 4.1 | 16.6 ± 3.6 | −2.3 | −3.3 | 3.7 | 10 |
| 5 | Trf | g/L | 2.596 ± 0.187 | 2.566 ± 0.188 | 2.508 ± 0.188 | −1.16 | −3.4 | 4.8 | 10 |
| 5 | Cortisol* | nmol/L | 236.0 ± 27.2 | 244.4 ± 21.5 | 231.9 ± 297.7 | 3.6 | −1.7 | 6.4 | 15 |
| 5 | FT4* | Pmol/L | 10.54 ± 1.45 | 11.38 ± 2.05 | 11.08 ± 1.05 | −2.7 | 5.1 | 6.5 | 30 |
| 5 | TSH* | μIU/mL | 1.142 ± 0.783 | 1.142 ± 0.783 | 1.080 ± 0.783 | 1.1 | −4.5 | 7.3 | 15 |
| 5 | Ferritin* | μg/L | 43.6 ± 20 | 43.6 ± 17.5 | 14.2 ± 17.7 | 0.0 | 1.4 | 7.2 | 15 |
| 5 | TnI* | μg/L | 0.009 ± 0.003 | 0.010 ± 0.005 | 0.011 ± 0.002 | 11.6 | 25.6 | 14 | 30 |
| 5 | Haem Index | | 0 ± 0 | 0 ± 0 | 0 ± 0 | 0 | 0 | | |

Analysis performed on Beckman DxC800 and *DxI800 immunoassay analysers.

§= Those results which differ by more than the LSC and/or CAL.

Example 13b

Analyte Stability

Greiner Serum tubes were washed (×5 with distilled water) to remove the surfactant and procoagulant but retain the gel barrier then oven dried. Notecarin and carinactivase-2 (25 μL aliquots) were added to the tubes to give concentrations of 12 nmol/mL and 45 nmol/mL respectively. Blood (5 mL) was collected from a healthy volunteer into one tube containing notecarin and one containing carinactivase-2. The tubes were centrifuged after 5 minutes. $K^+$, glucose, LD and phosphate levels were determined at 3 time intervals after serum preparation. The samples were stored at 23° C. for 5 hours then from 5 to 26.5 hours at 4° C. The level of haemoglobin was also measured.

The results are shown in Table 73.

TABLE 73

Stability of analytes in serum samples generated by Notecarin and Carinactivase-2

| Analyte | Zero time | 5 hrs | 26.5 hrs | Serum Hb mg/L |
|---|---|---|---|---|
| | Notecarin | | | 32 |
| $K^+$ | 4.0 | 4.1 | 4.0 | |
| Glucose | 5.4 | 5.3 | 5.1 | |
| LD | 176 | 175 | 173 | |
| Phosphate | 1.05 | 1.13 | 1.05 | |

TABLE 73-continued

Stability of analytes in serum samples generated by Notecarin and Carinactivase-2

| Analyte | Zero time | 5 hrs | 26.5 hrs | Serum Hb mg/L |
|---|---|---|---|---|
| | Carinactivase 2 | | | 46 |
| $K^+$ | 3.9 | 3.9 | 3.9 | |
| Glucose | 5.3 | 5.0 | 4.9 | |
| LD | 176 | 177 | 170 | |
| Phosphate | 1.03 | 1.04 | 1.06 | |

A haemoglobin level of <50 mg/L is considered clinically insignificant. These results therefore indicate that the serum samples produced by the prothrombin activators were effectively free of haemoglobin (therefore there is very little haemolysis during the clotting process), and free of cellular contamination. If cells or cell debris had been present, the concentration of $K^+$, LD and phosphate would be, expected to increase and the concentration of glucose to decrease on storage. Samples of the sera were taken and analysed for cells using the Cytospin method. Very few cells were detected.

In summary, serum samples prepared by using a group B prothrombin activator (carinactivase-2) and a group D prothrombin activator (notecarin) were of high quality based on completeness of clotting, analytical results and absence of cellular contaminants.

Example 14

Measurement of Biochemical Analytes in Plasma and Serum Samples Prepared in Commercial Tubes and Serum Samples Prepared Using Prothrombin Activator-Containing Venoms This Example uses the same analyte analysis methodology described in Examples 12 and 13.

The discoveries made in the preceding examples surprisingly demonstrated that snake venom prothrombin activators would be suitable for use as procoagulants in clinical environments. This then raised the question whether the crude venoms which contain these prothrombin activators could be used in blood clotting devices without prior purification of the prothrombin activators.

The following experiments were therefore designed and conducted to show whether the venoms could be used to rapidly produce high quality serum from human blood samples. The amount of venom used was approximately four times the amount of purified prothrombin activators used in the preceding experiments, reflecting the fact that the venoms contain other proteins than the prothrombin activators.

Example 14a

Use of Crude *P. Textilis* and *O. scutellatus* Venoms as Procoagulants in Clotting Tubes Blood was collected from 2 healthy volunteers into 10 Greiner No Additive tubes (#454001, Griener Bio-One, Kremsmuster, Austraia) (4 mL capacity) containing 2 and 4 μg (in duplicate for the 4 μg *O. scutellatus* venom) of either *P. textilis* or *O. scutellatus* venom. Blood samples were also collected into Greiner standard serum tubes (#456071, Greiner Bio-One, Kremsmuster, Austraia) for comparison.

Clotting in the venom-containing tubes appeared complete by visual observation in 2 minutes. Samples in the venom-containing tubes were centrifuged after 15 minutes and those in the Greiner serum tubes after 30 minutes. Samples were centrifuged at 3000 g, 10 min and 20° C. (Hereaus 1 S-R centrifuge, Germany). The sera from the Greiner No Additive tubes were immediately transferred into Beckman plain plastic tubes (#448778, Beckman coulter, Brea, Calif., USA) for observation and analysis. Latent clotting was observed in about half (6 out of the 10) of the venom-containing tubes but not in either of the Greiner serum tubes. This indicates that in some tubes, clotting was incomplete at the concentrations of venom used. Samples in the plain plastic tubes were re-centrifuged to remove cells, cell stroma and latent clots and the clear sera obtained analysed within 2 hours for 31 analytes. Sample analysis was performed within two hour post centrifugation for 31 analytes on the Beckman DxC800 general chemistry analyser and DxI800 immuno-analyser (Beckman Coulter, Brea, Calif., USA). There were no clinically significant differences at the concentration levels tested between results obtained for the 12 sera (4 *P. textilis* sera and 6 *O. scutellatus* sera and the 2 Greiner sera).

The results are shown in Table 74.

TABLE 74

Analytical results for serum samples generated by *P. textilis* sera and *O. scutellatus* venom.

| | | | Mean ± SD | | | | | |
|---|---|---|---|---|---|---|---|---|
| No of Samples | Analyte | Units | GS | Brown 2.0 μg | Brown 4.0 μg | Taipan 2.0 μg | Taipan 4.0 μg | Taipan 4.0 μg |
| 2 | $Na^+$ | mmol/L | 136.5 ± 0.71 | 137.0 ± 1.41 | 136.5 ± 0.71 | 137.0 ± 1.41 | 136 ± 0.00 | 136.0 ± 0.00 |
| 2 | $K^+$ | mmol/L | 4.05 ± 0.21 | 4.05 ± 0.07 | 4.00 ± 0.00 | 4.20 ± 0.28 | 4.00 ± 0.00 | 4.25 ± 0.35 |
| 2 | $Cl^-$ | mmol/L | 103.5 ± 0.71 | 103.5 ± 0.71 | 103.5 ± 0.71 | 103.5 ± 0.71 | 104.0 ± 0.00 | 103.5 ± 0.71 |
| 2 | $HCO_3^-$ | mmol/L | 26.0 ± 0.0 | 24.5 ± 0.7 | 24.0 ± 0.0 | 24.5 ± 0.7 | 23.5 ± 0.7 | 24.0 ± 0.0 |
| 2 | Gluc | mmol/L | 5.45 ± 0.35 | 5.20 ± 0.42 | 5.30 ± 0.14 | 5.35 ± 0.50 | 5.2 ± 0.28 | 5.4 ± 0.42 |
| 2 | Urea | mmol/L | 7.45 ± 2.76 | 7.30 ± 2.83 | 7.25 ± 2.90 | 7.30 ± 2.97 | 7.3 ± 2.97 | 7.35 ± 2.90 |
| 2 | Creat | μmol/L | 106.0 ± 2.8 | 101.5 ± 12.0 | 104.0 ± 7.1 | 103.5 ± 6.4 | 107.0 ± 0.00 | 105.0 ± 8.5 |
| 2 | Urate | mmol/L | 0.31 ± 0.13 | 0.30 ± 0.14 | 0.30 ± 0.14 | 0.30 ± 0.14 | 0.30 ± 0.14 | 0.30 ± 0.14 |
| 2 | TP | g/L | 65.0 ± 0.0 | 64.5 ± 0.71 | 65.5 ± 0.71 | 66.0 ± 0.0 | 63.5 ± 0.71 | 65.5 ± 0.71 |
| 2 | Alb | g/L | 39.5 ± 0.7 | 40.5 ± 0.7 | 40.5 ± 0.7 | 40.5 ± 0.71 | 40.0 ± 0.0 | 40.0 ± 0.0 |
| 2 | T Bili | μmol/L | 13.5 ± 5.0 | 1.5 ± 5.0 | 11.0 ± 4.2 | 11.0 ± 5.7 | 12.5 ± 5.0 | 12.5 ± 5.0 |
| 2 | ALP | U/L | 66.5 ± 17.7 | 65.5 ± 20.5 | 69.0 ± 21.2 | 67.5 ± 21.9 | 66.0 ± 21.2 | 68.0 ± 19.8 |
| 2 | GGT | U/L | 14.5 ± 6.4 | 15.0 ± 2.8 | 15.0 ± 7.1 | 16.5 ± 5.0 | 15.5 ± 9.2 | 14.0 ± 7.1 |
| 2 | ALT | U/L | 32.0 ± 2.8 | 30.5 ± 6.4 | 30.5 ± 5.0 | 31.5 ± 3.5 | 31.5 ± 5.0 | 30.5 ± 2.1 |
| 2 | AST | U/L | 23.5 ± 0.7 | 26.5 ± 0.7 | 30.0 ± 0.0 | 29.5 ± 2.1 | 29.5 ± 2.1 | 29.0 ± 0.0 |
| 2 | LD | U/L | 189.5 ± 10.6 | 189.5 ± 20.5 | 193.5 ± 6.4 | 197.5 ± 20.5 | 201.5 ± 14.8 | 201.5 ± 13.4 |
| 2 | CK | U/L | 152.0 ± 83.4 | 154.5 ± 84.0 | 145.5 ± 90.0 | 145.5 ± 89.8 | 147.5 ± 92.6 | 145.5 ± 94.0 |
| 2 | TCa | mmol/L | 2.17 ± 0.06 | 2.18 ± 0.09 | 2.17 ± 0.09 | 2.18 ± 0.06 | 2.15 ± 0.08 | 2.17 ± 0.09 |
| 2 | Pi | mmol/L | 1.22 ± 0.04 | 1.22 ± 0.04 | 1.21 ± 0.07 | 1.21 ± 0.06 | 1.21 ± 0.04 | 1.20 ± 0.04 |
| 2 | $Mg^{2+}$ | mmol/L | 0.915 ± 0.049 | 0.935 ± 0.05 | 0.935 ± 0.049 | 0.930 ± 0.057 | 0.950 ± 0.057 | 0.945 ± 0.049 |
| 2 | Chol | mmol/L | 4.60 ± 0.00 | 4.70 ± 0.00 | 4.70 ± 0.14 | 4.70 ± 0.00 | 4.65 ± 0.07 | 4.70 ± 0.00 |
| 2 | Trig | mmol/L | 2.40 ± 0.28 | 2.50 ± 0.57 | 2.55 ± 0.50 | 2.50 ± 0.57 | 2.50 ± 0.42 | 2.50 ± 0.42 |
| 2 | HDL-C | mmol/L | 1.50 ± 0.42 | 1.35 ± 0.07 | 1.50 ± 0.14 | 1.45 ± 0.07 | 1.50 ± 0.28 | 1.50 ± 0.14 |
| 2 | $Fe^{2+}$ | μmol/L | 13.0 ± 5.7 | 13.0 ± 5.7 | 13.5 ± 5.0 | 13.0 ± 5.7 | 13.0 ± 5.7 | 13.5 ± 5.0 |

TABLE 74-continued

Analytical results for serum samples generated by *P. textilis* sera and *O. scutellatus* venom.

| | | | | | | | | |
|---|---|---|---|---|---|---|---|---|
| 2 | Trf | g/L | 2.59 ± 0.46 | 2.61 ± 0.44 | 2.58 ± 0.35 | 2.62 ± 0.43 | 2.56 ± 0.44 | 2.55 ± 0.36 |
| 2 | Cortisol* | nmol/L | 236.0 ± 27.2 | ± | ± | ± | ± | ± |
| 2 | FT4* | Pmol/L | 11.55 ± 1.34 | 12.80 ± 0.28 | 12.90 ± 2.55 | 12.70 ± 2.12 | 13.25 ± 4.03 | 12.75 ± 1.34 |
| 2 | TSH* | µIU/mL | 2.185 ± 1.011 | 2.135 ± 0.841 | 2.430 ± 1.202 | 2.160 ± 0.834 | 2.070 ± 0.891 | 2.085 ± 0.884 |
| 2 | Ferritin* | µg/L | 50.0 ± 0.0 | 56.0 ± 0.0 | 56.5 ± 2.1 | 51.5 ± 9.2 | 55 ± 9.9 | 51.0 ± 7.1 |
| 2 | TnI* | µg/L | 0.010 ± 0.005 | 0.012 ± 0.008 | 0.010 ± 0.002 | 0.012 ± 0.007 | 0.010 ± 0.003 | 0.007 ± 0.002 |
| 2 | Haem Index | | 0 ± 0 | 0 ± 0 | 0 ± 0 | 0 ± 0 | 0.5 ± 0.7 | 0.5 ± 0.7 |

| No of | Mean difference between pairs (%) | | | | | LSC | CAL |
|---|---|---|---|---|---|---|---|
| Samples | Br2 − GS | BR4 − GS | T2 − GS | T4 − GS | T4R − GS | (%) | (%) |
| 2 | −0.4 | 0.0 | 0.4 | −0.4 | −0.4 | 2.8 | 3 |
| 2 | 0.0 | −1.2 | 3.7 | −1.2 | 4.9 | 3.3 | 5 |
| 2 | 0.0 | 0.0 | 0.0 | 0.5 | 0.0 | 3.3 | 5 |
| 2 | −5.8 | −7.7 | −5.8 | −9.6 | −7.7 | 4.8 | 10 |
| 2 | −4.6 | −2.8 | −1.8 | −4.6 | −0.9 | 4.4 | 10 |
| 2 | −2.0 | −2.7 | −2.0 | −1.3 | −2.0 | 5.0 | 10 |
| 2 | −4.2 | −1.9 | −2.4 | 0.9 | −0.9 | 5.5 | 10 |
| 2 | −3.2 | −3.2 | −3.2 | −3.2 | −3.2 | 3.8 | 10 |
| 2 | −0.8 | 0.8 | 1.5 | −2.3 | 0.8 | 3.5 | 5 |
| 2 | 2.5 | 2.5 | 2.5 | 1.3 | 1.3 | 3.2 | 5 |
| 2 | −14.8 | −18.5 | −18.5 | −7.4 | −7.4 | 7.0 | 20 |
| 2 | −1.5 | 3.8 | 1.5 | −0.8 | 2.3 | 4.8 | 10 |
| 2 | 3.4 | 3.4 | 13.8§ | 6.9 | −3.4 | 7.3 | 10 |
| 2 | −4.7 | −4.7 | −1.6 | −1.6 | −4.7 | 6.8 | 10 |
| 2 | 12.8 | 27.7§ | 25.5§ | 25.5§ | 23.4§ | 6.2 | 15 |
| 2 | 0.0 | 2.1 | 4.2 | 6.3 | 6.3 | 3.7 | 15 |
| 2 | 1.6 | −4.3 | −4.3 | −3.0 | −4.3 | 3.7 | 15 |
| 2 | 0.5 | 0.0 | 0.2 | −1.2 | −0.2 | 3.5 | 5 |
| 2 | 0.0 | −0.8 | −1.2 | −1.2 | −2.0 | 3.8 | 10 |
| 2 | 2.2 | 2.2 | 1.6 | 3.8 | 3.3 | 4.4 | 10 |
| 2 | 2.2 | 2.9 | 2.2 | 1.1 | 2.2 | 3.6 | 10 |
| 2 | 4.2 | 6.2 | 4.2 | 4.2 | 4.2 | 5.3 | 10 |
| 2 | −10.0 | 0.0 | −3.3 | 0.0 | 0.0 | 5.2 | 10 |
| 2 | 0.0 | 3.8 | 0.0 | 0.0 | 3.8 | 3.7 | 10 |
| 2 | 1.0 | −0.2 | 1.2 | −1.0 | −1.5 | 4.8 | 10 |
| 2 | 3.6 | −1.7 | | | | 6.4 | 15 |
| 2 | 10.8 | 11.7 | 10.0 | 14.7 | 10.4 | 6.5 | 30 |
| 2 | −2.3 | 11.2 | −1.1 | −5.3 | −4.6 | 7.3 | 15 |
| 2 | 12.0 | 13.0 | 3.0 | 10.0 | 2.0 | 7.2 | 15 |
| 2 | 26.3 | 0.0 | 26.3 | 5.3 | −31.6 | 14 | 30 |
| 2 | | | | | | | |

§= results differed by more than the CAL.

Analysis was performed on Beckman DxC800 and *DxI800 analysers Br2—Brown snake venom 2.0 µg; Br4—Brown snake venom 4.0 µg; T2—Taipan snake venom 2.0 µg; T4 and T4R—Taipan snake venom 4.0 µg.

In summary, we have shown that crude *P. textilis* and *O. scutellatus* venoms are potential procoagulants for producing serum in blood clotting tubes. The optimal concentrations need to be determined to avoid latent clotting and maintain analytical integrity.

Example 14b

Use of Crude *E. carinatus* Venom as Procoagulant in Clotting Tubes

The following experiments were conducted to show whether *E. carinatus* venom could be used to rapidly produce high quality serum from human blood samples.

Blood was collected from 2 healthy volunteers into 10 Greiner No Additive tubes (#454001, Griener Bio-One, Kremsmuster, Austraia) (4 mL capacity) containing 4 µg of *E. carinatus* venom. At the same time blood was collected into Greiner standard serum tubes (#456071, Greiner Bio-One, Kremsmuster, Austraia) for comparison.

Clotting in the venom-containing tubes appeared complete by visual observation in 3 minutes. Samples in the venom-containing tubes were centrifuged after 10 minutes and those in the Greiner serum tubes after 30 minutes. Samples were centrifuged at 3000 g, 10 min and 20° C. (Hereaus 1 S-R centrifuge, Germany). The sera from the Greiner No Additive tubes were immediately transferred into Beckman plain plastic tubes (#448778, Beckman coulter, Brea, Calif., USA) for observation and analysis. No latent clotting was observed in the venom-containing tubes or in the Greiner serum tubes. Samples in the plain plastic tubes were re-centrifuged to remove any cells during the transfer of serum and the clear sera obtained analysed within 2 hours for 31 analytes. Sample analysis was performed within two hour post centrifugation for 31 analytes on the Beckman DxC800 general chemistry analyser and DxI800 immuno-analyser (Beckman Coulter, Brea, Calif., USA). The results are shown in Table 75. There were clinically significant differences with AST and HDL and no other analyte at the concentration level tested between results obtained for the *E. carinatus* and the Greiner sera.

TABLE 75

Analytical results for serum samples generated by *Echis carinatus* snake venom.

| No of Samples | Analyte | Units | Mean ± SD GS | Mean ± SD *E. carinatus* 4.0 μg | Mean difference between pairs (%) EC4 − GS | LSC (%) | CAL (%) |
|---|---|---|---|---|---|---|---|
| 2 | $Na^+$ | mmol/L | 138.5 ± 0.71 | 137.5 ± 0.71 | −0.7 | 2.8 | 3 |
| 2 | $K^+$ | mmol/L | 4.0 ± 0.14 | 4.0 ± 0.14 | 0.0 | 3.3 | 5 |
| 2 | $Cl^-$ | mmol/L | 103 ± 0.0 | 103.5 ± 0.7 | −0.5 | 3.3 | 5 |
| 2 | $HCO_3^-$ | mmol/L | 27.4 ± 0.92 | 26.1 ± 0.14 | −4.6 | 4.8 | 10 |
| 2 | Gluc | mmol/L | 5.45 ± 0.07 | 5.35 ± 0.07 | −1.8 | 4.4 | 10 |
| 2 | Urea | mmol/L | 7.25 ± 0.64 | 7.30 ± 0.71 | 0.7 | 5.0 | 10 |
| 2 | Creat | μmol/L | 88.5 ± 12.1 | 86.0 ± 17.0 | −2.8 | 5.5 | 10 |
| 2 | Urate | mmol/L | 0.28 ± 0.09 | 0.28 ± 0.09 | 0 | 3.8 | 10 |
| 2 | TP | g/L | 63.5 ± 0.7 | 63.5 ± 0.7 | 0 | 3.5 | 5 |
| 2 | Alb | g/L | 39.5 ± 0.7 | 40.5 ± 0.7 | 2.5 | 3.2 | 5 |
| 2 | T Bili | μmol/L | 13.5 ± 6.4 | 12.0 ± 5.7 | −11.1 | 7.0 | 20 |
| 2 | ALP | U/L | 71.5 ± 23.3 | 70.0 ± 19.8 | −2.1 | 4.8 | 10 |
| 2 | GGT | U/L | 14.0 ± 4.2 | 14.5 ± 7.8 | 3.6 | 7.3 | 10 |
| 2 | ALT | U/L | 34.0 ± 0.0 | 35.5 ± 2.1 | 4.4 | 6.8 | 10 |
| 2 | AST | U/L | 20.5 ± 2.1 | 27.0 ± 00 | 31.7§ | 6.2 | 15 |
| 2 | LD | U/L | 185 ± 5.7 | 193 ± 11.3 | 4.3 | 3.7 | 15 |
| 2 | CK | U/L | 135 ± 50.9 | 133.5 ± 48.8 | −1.1 | 3.7 | 15 |
| 2 | TCa | mmol/L | 2.20 ± 0.014 | 2.17 ± 0.021 | −1.6 | 3.5 | 5 |
| 2 | Pi | mmol/L | 1.215 ± 0.247 | 1.17 ± 0.226 | −3.7 | 3.8 | 10 |
| 2 | $Mg^{2+}$ | mmol/L | 0.91 ± 0.0 | 0.93 ± 0.04 | 1.6 | 4.4 | 10 |
| 2 | Chol | mmol/L | 4.75 ± 0.64 | 4.75 ± 0.64 | 0.0 | 3.6 | 10 |
| 2 | Trig | mmol/L | 1.45 ± 0.50 | 1.50 ± 0.14 | 3.4 | 5.3 | 10 |
| 2 | HDL-C | mmol/L | 1.25 ± 0.21 | 1.80 ± 0.57 | 44.0§ | 5.2 | 10 |
| 2 | $Fe^{2+}$ | μmol/L | 13.5 ± 5.0 | 13.5 ± 5.0 | 0 | 3.7 | 10 |
| 2 | Trf | g/L | 2.62 ± 0.49 | 2.60 ± 0.44 | 1.3 | 4.8 | 10 |
| 2 | Cortisol* | nmol/L | 232 ± 10.6 | 238 ± 7.8 | 2.6 | 6.4 | 15 |
| 2 | FT4* | Pmol/L | 12.2 ± 0.6 | 12.6 ± 0.7 | 3.7 | 6.5 | 30 |
| 2 | TSH* | μIU/mL | 2.16 ± 0.76 | 2.10 ± 0.67 | −3.0 | 7.3 | 15 |
| 2 | Ferritin* | μg/L | 50 ± 2.8 | 47 ± 2.8 | −6.0 | 7.2 | 15 |
| 2 | TnI* | μg /L | 0.024 ± 0.000 | 0.020 ± 0.006 | −18.8 | 14 | 30 |
| 2 | Haem Index | | 0 ± 0 | 0 ± 0 | | | |

§= results were different by more than the CAL.

Analysis was performed on Beckman DxC800 and *DxI800 analysers EC4—*Echis carinatus* venom 4.0 μg.

As these are preliminary results, further investigation is needed to establish why there were clinically significant differences for the AST and HDL results.

In summary, we have shown that use of crude *E. carinatus* venom as procoagulant in blood clotting tubes may be feasible. The optimal concentration and further studies on analyte interference need to be accurately determined to avoid latent clotting and maintain analytical integrity.

Example 15

Stability Studies

For a venom prothrombin activator to be useful as a component of blood collection devices, it must meet three types of stability requirement:

(1) Stability during bulk storage: It needs to be stable for the period after purification before use in manufacture of the tubes. For certainty of supply, this storage period may be for several months. Storage could be as a concentrated aqueous solution or as lyophilized solid. Storage could be under refrigeration if required.

(2) Stability during manufacture: It needs to be stable during the manufacture of the blood collection device. This process is likely to involve addition of an aliquot of a stock solution of the prothrombin activator to tubes which already contain other components such as the separating gel, the surfactant and possible a particulate procoagulant. This would be followed by drying to give a surface layer of prothrombin activator, sealing the tubes under vacuum and sterilization by radiation.

(3) Stability during storage of the device prior to its use: It would be necessary for the activator to retain close to full activity for a period of at least 12 months at room temperature, say 23 C, preferably for a longer period at a higher temperature.

Experiments performed to date suggest that conditions will be found to meet these requirements for at least some of the venom prothrombin activators.

Example 15a

Stability During Bulk Storage

Figure 58:
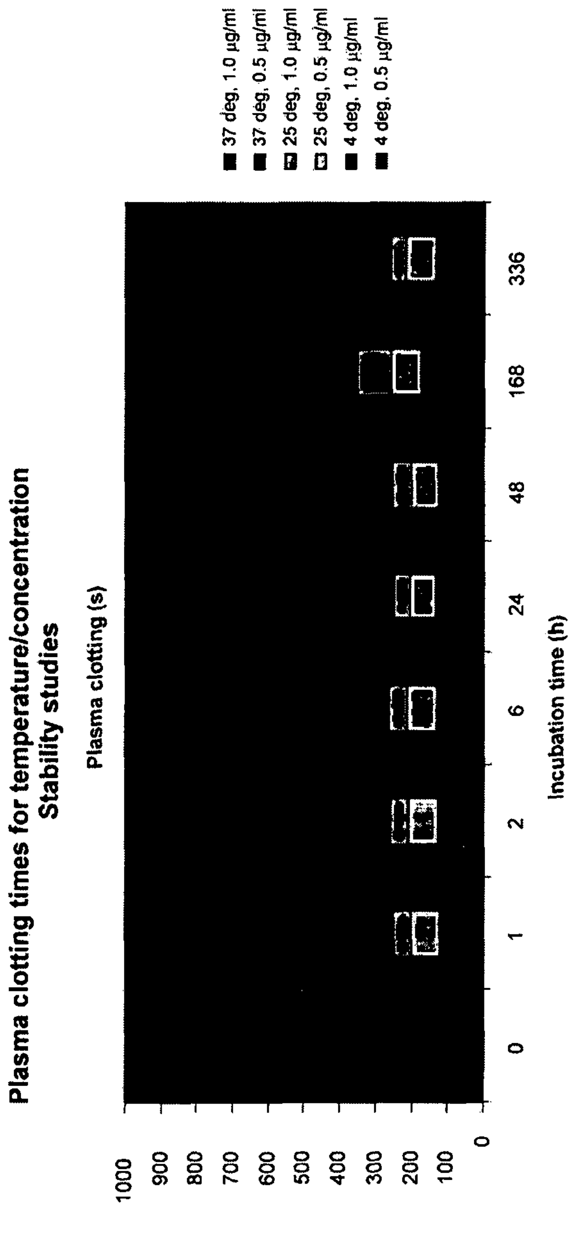

The stability of PtPA when maintained at a range of temperatures as a dilute solution in phosphate buffered saline at pH 7 in plain plastic Eppendorf tubes was determined. Results of plasma clotting assays are shown in FIG. 58. The results show that there was no significant loss of clotting activity after two weeks (336 hours) at 4 or 25° C. Similar results were obtained when the activity of PtPA was measured against the Factor Xa chromogenic substrate S-2222. At 37° C. PtPA lost a significant amount of its activity after 168 hours.

In related experiments, it was demonstrated that pH 7.4 was the optimal temperature for storage and that the addition of calcium ions to the storage buffer stabilized the plasma clotting activity.

These experiments indicate that it should be possible to find conditions for the bulk storage of PtPA and the closely related OsPA so that they retain all or almost all of their activity on storage for extended periods.

Example 15b

Stability During Manufacture

An experiment was performed to determine the effect of gamma radiation on OsPA added to blood collection tubes as a dilute solution.

Stock OsPA (1.089 mg/mL; 4.36 mM) was diluted 1 in 25 with 0.02 M Hepes buffer pH 7.4. 50 μL was added to each of 5 plain blood collection tubes with no other additives were gamma irradiated (16 megaBeq) and to 5 similar tubes which were not irradiated. Similarly, 50 μL of diluted OsPA was added to each of 10 Greiner silica-containing blood collection tubes (Greiner serum tubes) and 5 of these tubes were irradiated.

After gamma irradiation, all tubes were made up to 2.0 mL with 0.02 M Hepes buffer pH 7.4. Aliquots were then taken and tested for hydrolytic activity against S-2765 and clotting activity using normal citrated plasma with added 10 mM calcium.

Figure 59:
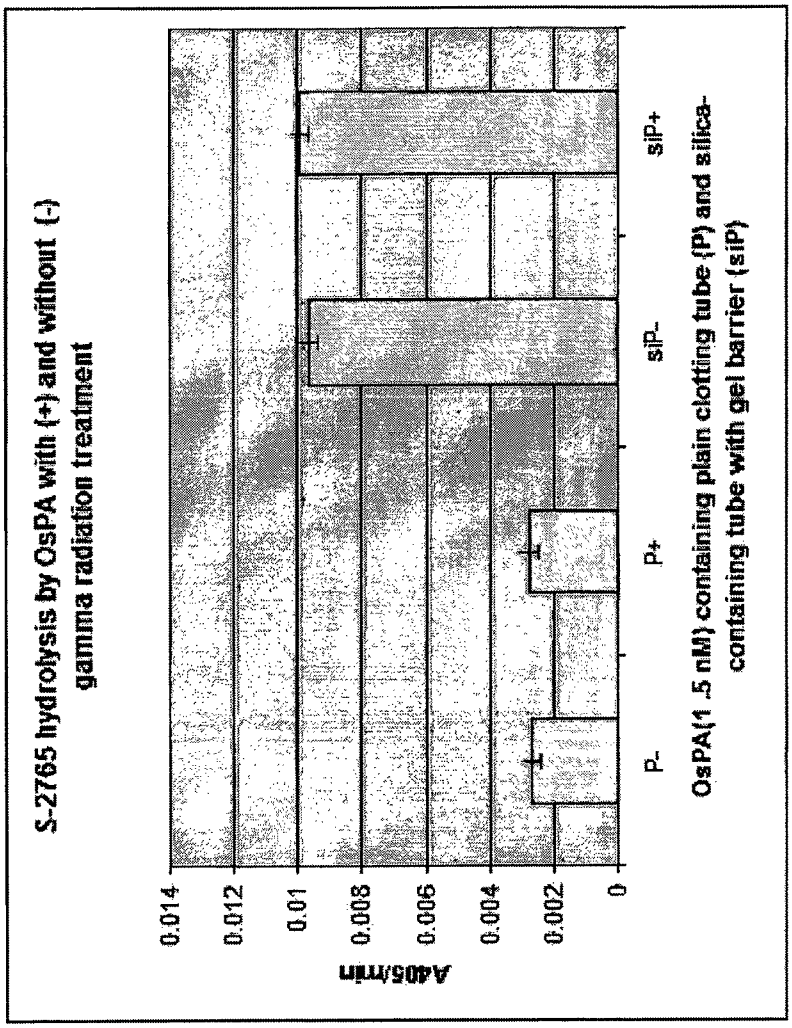
FIG. 59 shows the activity of OsPA against the chromogenic substrate S-2765 after irradiation in Greiner plain tubes (P) and in Greiner serum tubes containing silica and surfactant (siP), as described in Example 15b.
Figure 60:
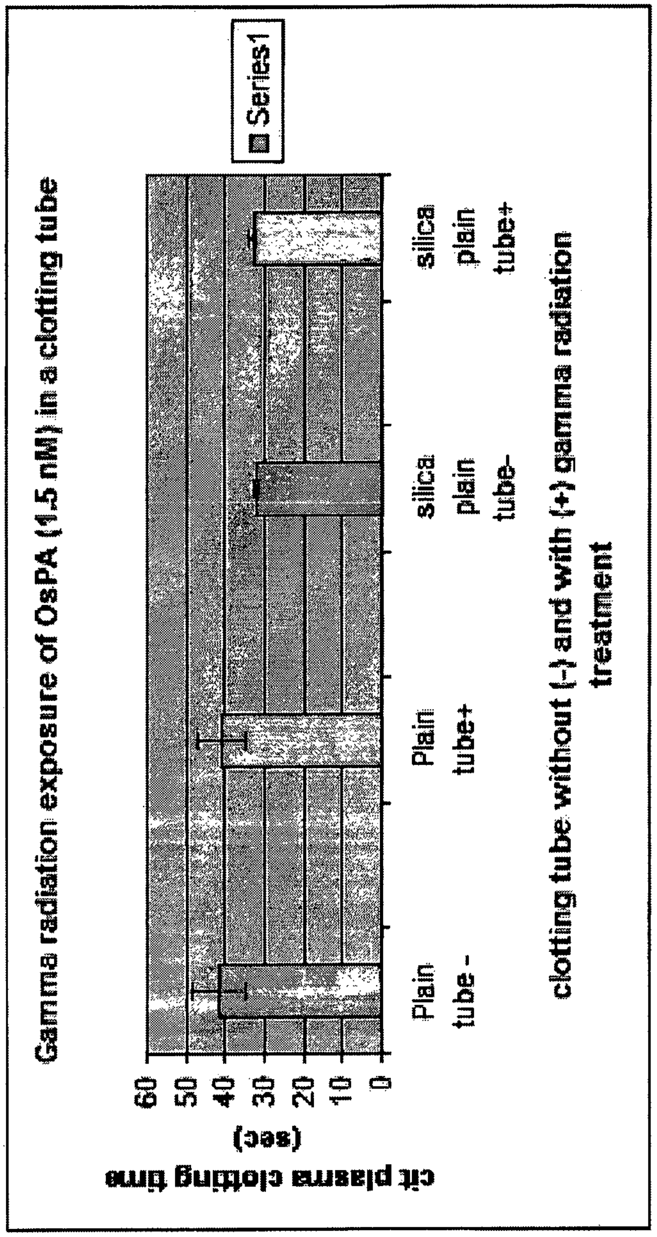
FIG. 60 shows the citrated plasma clotting activity of OsPA in Greiner plain tubes (P) and in Greiner serum tubes containing silica and surfactant, as described in Example 15b.

The results are shown in FIGS. 59 and 60, and show that irradiation had no effect on either clotting activity against recalcified citrated plasma or hydrolytic activity against the chromogenic substrate S-2765.

The addition of OsPA (1.5 nM) to plain blood collection tube showed a significant loss of activity as compared to the freshly diluted OsPA. This can be explained by hydrophobic binding of the OsPA to the plain plastic tube. Adding OsPA to silica-containing blood collection tubes showed recovery of greater than 95% the hydrolytic and clotting activities. Again, no loss activity was observed with gamma irradiation treatment.

In conclusion, gamma irradiation of OsPA in a blood collection tube did not affect either hydrolytic or clotting activity. Adding OsPA to a clotting tube containing silica, gel barrier, and surfactant is the most effective combination determined to date to clot normal blood in less than 1 minute.

Example 15c

Stability During Storage of the Device

Figure 61:
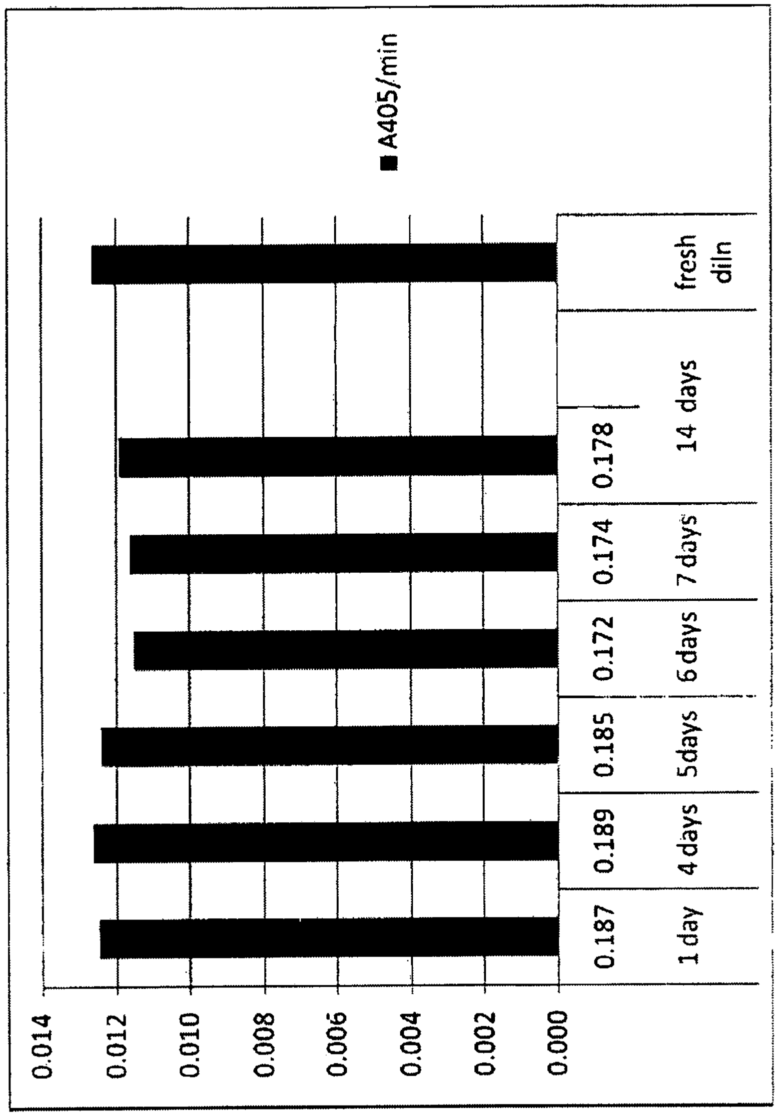
FIG. 61 shows the activity ($A_{405}$/mm) of OsPA against the chromogenic substrate S-2765 over a period of up to 14 days at 23° C. compared to a fresh dilution of stock, as described in Example 15c.

Aliquots (50 μL) of a diluted solution of OsPA in 0.02 M Hepes buffer, pH 7.4 (1.5 nM) were placed in Greiner standard serum tubes. Each tube was rotated to coat the surface with the OsPA and the tubes were placed in a vacuum dessicator and purged by a stream of dry nitrogen before applying a low vacuum for 3 days at 23° C. to dry. The dessicator was opened, flushed with nitrogen and the tubes re-sealed. The tubes were then maintained at room temperature (23° C.). After specified times, three tubes were opened, the contents redissolved in 2 mL water and assayed against the Factor Xa specific substrate S-2222. The results are shown in FIG. 61, and show that the activity (expressed as increase in A405/min) of OsPA towards S-2222 was effectively unchanged by storage at 23° C. as a dry surface layer in the Greiner serum tubes for 14 days. All assays were done in triplicate. In FIG. 61, the right hand bar is the activity of a freshly diluted sample of OsPA stock solution (4.05 uM) and its activity was the same as that found in the tubes, showing that the process used to prepare the tubes did not cause any significant loss of OsPA activity.

Example 16

Preparation of Blood Collection Tube

All commercial serum and plasma tubes are now plastic and contain a number of components which have been developed by the suppliers to enhance the quality of the samples prepared in them. As discussed above, some container (e.g. tube) for preparation of a serum sample or a plasma sample contains:

(1) a gel barrier which aims to separate cells (and clot in the case of serum) from the supernatant (serum or plasma) after centrifugation and to limit re-mixing. The gel is added as a warm liquid which solidifies on cooling to room temperature;

(2) a surfactant sprayed on the inner surface of the plastic tube above the gel barrier to decrease attachment of cells, debris and clot material and cell lysis; and (3) a procoagulant/anticoagulant, usually particulate, sprayed as a suspension onto the inner surface of the tube on top of the surfactant.

The present invention envisages the a serum tube (e.g., a plastic tube) comprising components (1), (2), and (3) as described above, where the tube is prepared by adding components (1) and (2) to the tube first, and subsequently adding component (3) to the tube. Component (3) comprises a procoagulant comprising a clotting composition comprising, consisting essentially of, or consisting of a prothrombin activator as herein defined, for example, component (3) may comprise existing particulate procoagulants used in some commercial serum tubes. The amount of prothrombin activator within each tube can be determined using the experimental results described in detail above, and routine techniques known in the art. The tubes are then evacuated and sterile capped. The tubes are then stored at room temperature.

Also envisaged a serum tube (e.g., a plastic tube) comprising component (3) and optionally comprising components (1) and/or (2). The amount of prothrombin activator within each tube can be determined using the experimental results described in detail above, and routine techniques known in the art. The tubes are evacuated and sterile capped and can be stored at room temperature.

Example 17

Point of Care Embodiment

As discussed above, "point-of-care" testing means that the testing is performed at or near the site of patient care. Point of care testing is becoming increasingly popular in hospital and other environments where there is a need for fast results. It is accomplished using a variety of devices some of which are relatively inexpensive, small, and portable.

In current practice, many point-of-care devices work as follows: a droplet of blood is placed on a membrane which retains blood cells but allows plasma to diffuse through the membrane into a microfluidic device with multiple channels in which a number of analyses are performed. As discussed elsewhere, serum is preferred to plasma as the sample for biochemical or other pathology assays. In this embodiment, the present invention contemplates the use of clotting compositions comprising, consisting essentially of, or consisting of a prothrombin activator to produce serum in devices designed for point of care testing.

In one such device, suitable for hospital and doctors' surgery use, a blood sample obtained by venipuncture is collected into a syringe (or similar) containing a clotting composition comprising, consisting essentially of, or consisting of a prothrombin activator, where composition is achieved in ~30 seconds. The device is designed to allow either filtration or centrifugation to rapidly separate the serum from the clot. The serum so obtained is used in existing microfluidic devices for biochemical or other pathology assays, with the range of analyses increased as the sample being analysed is serum rather than plasma that is used in existing point-of-care devices. Furthermore, a sample of the serum may be retained to allow further analysis in the pathology laboratory.

Figure 62:
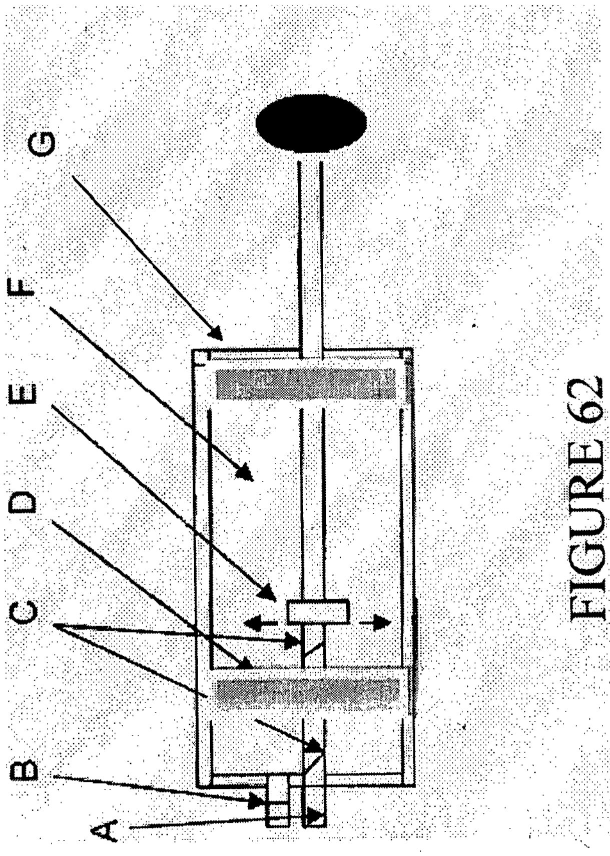
FIG. 62 shows an example of a device (point-of-care device in the form of a syringe) designed to produce high quality serum for analysis, as described in Example 17.

The filtration device in the syringe described above may comprise a filtration mechanism that allows the serum to be pushed through after 5 minutes for analysis. Suitably, the syringe may be divided in compartments as illustrated in FIG. 62, with the syringe labelled as follows:

A—entry port that will have blood collection needle adapter that would unscrew to minimising prodruding component;

B—port for dispensing serum or entry point for point of care sample needles;

C—valves to allow for one way entry of blood and prevent blood being pushed into serum compartment;

D—plunger filter that would allow for serum to be pushed out into the serum compartment (front part of the syringe);

E—opening for blood to enter blood compartment.

F—compartment ion which clotting occurs.

In FIG. 62, G is coated with the clotting composition on the inside to set the clotting process in place. It is then pushed to force the serum across the filter (D).

In another such device, the point-of-care device involves a capillary system, where part of the device is coated with a clotting composition comprising, consisting essentially of, or consisting of a prothrombin activator and an absorbant that can draw the serum into the reaction chamber for analysis.

In another such device, a clotting composition comprising, consisting essentially of, or consisting of a prothrombin activator could be coupled to the membrane of a microfluidic device so as to achieve rapid clotting of a blood droplet placed on the membrane. The serum so formed diffuses into the device and is analysed in place of the plasma currently analysed in such devices.

Summary of Examples

Obtaining a suitable sample for analysis in a timely manner is pivotal in clinical chemistry service provision. Serum is recognised as being the cleaner sample but because of time required for completion of clotting (30 minutes to ensure complete clotting in most currently available commercial tubes plus analysis time in the standard protocols) and an ever-increasing number of patients on anti-coagulant therapy, plasma is commonly used, especially in hospital environments. However, latent clotting (clotting after centrifugation) can occur in plasma samples leading to analytical errors and delays in delivery of critical results. Some of these problems are illustrated in the above examples.

The results in the above examples also show that use of prothrombin activators can produce high quality serum very quickly from blood samples from a wide variety of patients, including patients being treated with anticoagulants. They provide suitable alternatives to lithium heparin plasma and to conventional serum tubes by:

having the clotting process completed in ~5 minutes (time taken to deliver samples to the laboratory) allowing rapid analysis after blood sample collection and hence rapid turn around times comparable to the times for plasma tubes and better than those for most current serum tubes;

at the same time providing high quality serum samples for blood from both healthy and all anticoagulated individuals that may be encountered in a clinical environment with minimal analyte interference from cellular debris and/or latent microclotting; and producing a single serum sample that is suitable for a very wide range of assays typically used in clinical environment, the serum sample being superior to plasma for analyte analysis, and the single sample reducing the burden on scarce resources (blood in critically ill patients, staff time and consumables by needing to collect fewer blood tubes).

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Altschul, S. F., Madden, T. L., Schäffer, A. A., Zhang, J., Zhang, Z., Miller, W., Lipman, D. J., "Gapped BLAST and PSI-BLAST: a new generation of protein database search programs." Nucleic Acids Res. 1997 Sep. 1; 25(17): 3389-402.

Arkin, A. P., Youvan, D. C., "An algorithm for protein engineering: simulations of recursive ensemble mutagenesis" 1992 Proc. Natl. Acad. Sci. USA 89: 7811-7815.

Atherton, E., Shephard, R. C., Solid Phase Peptide Synthesis—A Practical Approach 1989, IRL Press, Oxford England.

Austen, D. E., Rhymes, I. L., "Laboratory manual of blood coagulation" (1975) Blackwell Scientific Publications, London, p37.

Bos, M. H. A., Boltz, M., St Pierre, L., Masci, P. P., de Jersey, J., Lavin, M. F., Camire, R. M., "Venom factor V from the common brown snake escapes hemostatic regulation through procoagulant adaptations" Blood 16 Jul. 2009; 114(3): 686-692.

Camenzind, E., Bakker, W. H., Reijs, A., van Geijlswijk, I. M., Boersma, E., Kutryk, M. J., Krenning, E. P., Roelandt, J. R., Serruys, P. W., "Site-specific intracoronary heparin delivery in humans after balloon angioplasty. A radioisotopic assessment of regional pharmacokinetics." Circulation 1997; 96: 154-65.

Ciuti, R., Rinaldi, G., "Serum and plasma compared for use in 19 common chemical tests performed in the Hitachi 737 analyzer." Clin Chem. 1989; 35: 1562-3.

Cowley, D. M., Nagle, B. A., Chalmers, A. H., Sinton, T. J., "Effects of platelets on collection of specimens for assay of ammonia in plasma." Clin Chem 1985; 31: 332.

Davidson, A. S., Darn, S. M., Sodi, R., "Can lithium heparin plasma be used for protein electrophoresis and paraprotein identification?" Ann Clin Biochem 2006; 43: 31-34.

Dayhoff, M. O., Schwartz, R. M., Orcutt, B. C., et al., "A model of evolutionary change in proteins. Matrices for determining distance relationships" 1978 In Atlas of protein sequence and structure (Dayhoff, M. O. ed.), vol 5, pp 345-358, National Biomedical Research Foundation, Washington D.C.

Delagrave, S., Goldman, E. R., Youvan, D. C., "Recursive ensemble mutagenesis" April 1993 Protein Eng. 6(3): 327-31.

Devereux, J., Haeberli, P., Smithies, O., "A comprehensive set of sequence analysis programs for the VAX." Nucleic Acids Res. 1984 Jan. 11; 12(1 Pt 1): 387-95.

Dimeski, G., Masci, P. P., Trabi, M., Lavin, M. F., de Jersey, J., "Evaluation of the Becton-Dickinson rapid serum tube: does it provide a suitable alternative to lithium heparin plasma tubes?" Clin Chem Lab Med 2010; 48(5): 2111-2120.

Dimeski, G., Badrick, T., Flatman, R., Ormiston, B., "Roche IFCC Methods for Lactate Dehydrogenase Tested for Duplicate Errors with Greiner and Becton-Dickinson Lithium-Heparin and Greiner Serum Samples" Clin Chem 2004; 50(12): 2391-2392.

Dimeski, G., Carter, A., "Rare IgM Interference with Roche/Hitachi Modular Glucose and γ-Glutamyltransferase Methods in Heparin Samples" Clin Chem 2005; 51(11): 2202-2204.

Dimeski, G., Clague, A. E., Hickman, P. E., "Correcting and reporting of potassium results in haemolysed samples" Ann. Clin. Biochem. 2005; 42: 119-123.

Dimeski, G., McWhinney, B., Jones, B., Mason, R., Carter, A., "Extent of bilirubin interference in Beckman-Coulter creatinine methods." Ann Clin Biochem 2008; 45:91-92.

Filippovich, I., Sorokina, N., St Pierre, L., Flight, S., de Jersey, J., Perry, N., Masci, P. P., Lavin, M. F. "Cloning and functional expression of venom prothrombin activator protease from *Pseudonaja textilis* with whole blood procoagulant activity" British Journal of Haematology 2005; 131: 237-246.

Gonnet, G. H., Cohen, M. A., Benner, S. A., "Exhaustive matching of the entire protein sequence database" Jun. 5, 1992 Science 256(5062): 1443-5.

Hartland, A. J., Neary, R. H., "Serum potassium is unreliable as an estimate of in vivo plasma potassium" Clin Chem 1999; 45:1091-1092.

Kini, R. M., Morita, T., Rosing, J., "Classification and Nomenclature of Prothrombin Activators Isolated from Snake Venoms" Thromb. Haemost. 2001 85:710-711.

Kini, R. M., "The intriguing world of prothrombin activators from snake venom" Toxicon (2005) 45: 1133-1145.

Kunkel, T. A., "Rapid and Efficient site-specific mutagenesis without phenotypic selection" 1985 Proc. Natl. Acad. Sci. USA, 82: 488-492.

Kunkel, T. A., Roberts, J. D., Zakour, R. A., "Rapid and Efficient site-specific mutagenesis without phenotypic selection" 1987 Methods in Enzymol. 154: 367-382.

Kuzmic, P., "Program DYNAFIT for the Analysis of Enzyme Kinetic Data: Application to HIV Proteinase" 1996 Anal. Biochem. 237: 260-273.

Lavin, M. F., Masci, P. P., "Prothrombinase complexes with different physiological roles" Thromb Haemost 2009; 102: 421-423.

Masci, P. P., "The Effects of Australian Snake Venoms on Coagulation and Fibrinolysis" Thesis for Masters of Science in the subject of Biochemistry, July 1986, University of Queensland, St Lucia, Brisbane, Australia.

Masci, P. P., Whitaker, A. N., de Jersey, J., "Purification and characterization of a prothrombin activator from the venom of the Australian brown snake, *Pseudonaja textilis* textilis" Biochem. Int. 1988; 17(5):825-835.

Miles, R. R., Roberts, R. F., Putnam, A. R., Roberts, W. L., "Comparison of serum and heparinized plasma samples for measurement of chemistry analytes." Clin Chem 2004; 50: 1704-5.

National Pathology Laboratory Accreditation Advisory Council—Requirements for the Retention of Laboratory Records and Diagnostic Material (Fifth Edition 2009).

Nishida, S., Fujita, T., Kohno, N., Atoda, H., Morita, T., Takeya, H., Kido, I., Paine, M. J. I., Kawabata, S-i., Iwanaga, S. "cDNA Cloning and Deduced Amino Acid Sequence of Prothrombin Activator (Ecarin) from Kenyan *Echis carinatus* venom." Biochemistry 1995; 34: 1771-1778.

Morita, T., Iwanaga, S., "Prothrombin activator from *Echis carinatus* venom" Meth Enzymol 1981; 80-pt. C: 303-311.

Nicholson, J., Mirtschin, P., Madaras, F., Yenning, M., Kokkinn, M., "Digestive properties of the venom of the Australian Coastal Taipan, *Oxyuranus scultellatus* (Peters, 1867)" Toxicon 2006:48:422-428.

O'Keane M. P., Cunningham, S. K., "Evaluation of three different specimen types (serum, plasma lithium heparin and serum gel separator) for analysis of certain analytes: clinical significance of differences in results and efficiency in use." Clin Chem Lab Med. 2006; 44: 662-8.

Parker, H. W., Grandison, A. G. C., "Snakes: A natural history" University of Queensland Press, St. Lucia, Queensland 1977: pp 5, 59 and 87.

Roberge, J. Y., Beebe, X., Danishefsky, S. J., "A strategy for a convergent synthesis of N-linked glycopeptides on a solid support" Science 1995 269(5221); 202-204.

Rosing, J., Tans, G., "Inventory of Exogenous Prothrombin Activators" Thrombosis and Haemostasis (Stuttgart) 1991 65(2): 627-630.

Rosing, J., Tans, G., "Structural and Functional Properties of Snake Venom Prothrombin Activators" Toxicon 30(12): 1515-1527, 1992.

Sambrook, J., Russell, D. W., Molecular cloning. A laboratory manual (third edition) 2001; Cold Spring Harbor Laboratory Press.

Schieck, A., Kornalik, F., Habermann, E. "The prothrombin-activating principle from *Echis carinatus* venom. I. Preparation and biochemical properties" Naunyn-Schmiedeberg's Arch Pharmacol. 1972; 272: 402-416.

Sheppard, C. A., Allen, R. C., Austin, G. E., Young, A. N., Ribeiro, M. A., Fantz, C. R., "Paraprotein interference in automated chemistry analyzers." Clin Chem 2005 June: 51(6): 1077-8.

Smith, G. F., Craft, T. J., "Heparin reacts stoichiometrically with thrombin during thrombin inhibition in human plasma." Biochem. Biophys. Res. Commun. 1976; 71: 738-45.

Sonder, S. A., Fenton, J. W., "Thrombin specificity with tripeptide chromogenic substrates: comparison of human and bovine thrombins with and without fibrinogen clotting activities" Clin. Chem. 1986; 32:934-7.

Speijer, H., Goversriemslag, J. W. P., Zwaal, R. F. A., Rosing, J., "Prothrombin activation by an activator from the venom of *Oxyuranus scutellatus* (Taipan snake)" J. Biol. Chem. 1986; 261(28): 3258-3267.

Starr, H., Rhodes, P., Lam-Po-Tang, P. R., Archer, G. T., "Prothrombin times: an evaluation of four thromboplastins and four machines." Pathology 1980; 12: 567-574.

St Pierre, L., Masci, P., Filippovich, I., Sorokina, N., Marsh, N., Miller, D. J., Lavin, M. F., "Comparative Analysis of Prothrombin Activators from the Venom of Australian Elapids" Mol. Biol. Evol. 2005; 22(9): 1853-1864.

Tans, G., Govers-Riemslag, J. W., van Rijn, J. L., Rosing, J. J., "Purification and properties of a prothrombin activator from the venom of *Notechis scutatus* scutatus" Biol. Chem. 1985 Aug. 5; 260(16): 9366-72.

Thorelli, E., Kaufman, R. J., Dahlbäck, B., "Cleavage requirements of factor V in tissue-factor induced thrombin generation." Thromb. Haemost. 1998 July; 80(1) 92-98.

Wannaslip, N., Sribhen, K., Pussara, N., Hwanpuch, T., Wangchaijaroekit, S., Opartkiattikul, N., "Heparin is unsuitable anticoagulant for the detection of plasma ammonia." Clin Chimica Acta 2006; 371: 196-7.

Watson, J. D., Hopkins, N. H., Roberts, J. W., Steitz, J. A., Weiner, A. M. Molecular Biology of the Gene. fourth edition, 1987 The Benjamin/Cummings Publishing Co., Inc., Menlo Park, Calif.

Yamada, D., Sekiya, F., Morita, T., "Isolation and Characterization of Carinactivase, a Novel Prothrombin Activator in *Echis carinatus* Venom with a Unique Catalytic Mechanism" J. Biol. Chem. 1996; 271(9): 5200-5207.

Yamada, D., Morita, T., "Purification and Characterization of a $Ca^{2+}$-Dependent Prothrombin Activator, Multactivase, from the Venom of *Echis multisquamatus*" J. Biochem. 1997; 122: 991-997.

Yamanouye, N., Kerchove, C. M., Moura-da-Silva, A. M., Carneiro, S. M., Markus, R. P., "Long-term primary culture of secretory cells of *Bothrops jararaca* gland for venom production in vitro" Nature Protocols 2007; 1: 2763-2766.

Yonemura, H., Imamura, T., Soejima, K., Nakahara, Y., Morikawa, W., Ushio, Y., Kamachi, Y., Nakatake, H., Sugawara, K., Nakagaki, T., Nozaki, C., "Preparation of Recombinant α-Thrombin: High-Level Expression of Recombinant Human Prethrombin-2 and Its Activation by Recombinant Ecarin" J. Biochem. 2004; 135: 577-582.

Zubay, G., Biochemistry, third edition Wm. C. Brown Publishers, Oxford (1993).

What is claimed is:

1. A serum preparation container, the container comprising a puncturable septum or cap and being evacuated for drawing blood from a subject into the container, and containing an amount of a surfactant and an amount of a blood clotting composition for preparing a serum sample suitable for detecting an analyte, wherein the blood clotting composition consists essentially of a recombinantly-produced snake venom prothrombin activator, wherein the snake venom prothrombin activator is functional to activate prothrombin without a mammalian factor Xa polypeptide.

2. A method of preparing a serum sample for detecting an analyte of interest, the method comprising collecting a blood sample in a blood collection container, said blood collection container comprising a puncturable septum or cap and being evacuated for drawing blood from a subject into the container, and containing an amount of a surfactant and an amount of a blood clotting composition for preparing a serum sample suitable for detecting an analyte, wherein the blood clotting composition consists essentially of a recombinantly-produced snake venom prothrombin activator that is functional to activate prothrombin without a mammalian factor Xa polypeptide, contacting the blood sample with the blood clotting composition in the container for a time and under conditions sufficient to prepare the serum sample.

3. A method of detecting an analyte of interest, the method comprising providing a serum sample prepared by a serum preparation method and analysing the serum sample for the presence or amount of the analyte of interest, wherein the serum preparation method comprises collecting a blood sample in a blood collection container, said blood collection container comprising a puncturable septum or cap and being evacuated for drawing blood from a subject into the container, and containing an amount of a surfactant and an amount of a blood clotting composition for preparing a serum sample suitable for detecting an analyte, wherein the blood clotting composition consists essentially of a recombinantly-produced purified snake venom prothrombin activator that is functional to activate prothrombin without a mammalian factor Xa polypeptide, contacting the blood sample with the blood clotting composition in the container for a time and under conditions sufficient to prepare the serum sample.

4. The serum preparation container according to claim 1, wherein the snake venom prothrombin activator is a group A prothrombin activator.

5. The serum preparation container according to claim 4, wherein the snake venom prothrombin activator is selected from ecarin and basparin.

6. The serum preparation container according to claim 1, wherein the snake venom prothrombin activator is a group B prothrombin activator.

7. The serum preparation container according to claim 6, wherein the snake venom prothrombin activator is selected from carinactivase-1, carinactivase-2 and multactivase.

8. The serum preparation container according to claim 1, wherein the snake venom prothrombin activator is a group C prothrombin activator.

9. The serum preparation container according to claim 8, wherein the snake venom prothrombin activator is selected from pseutarin C, oscutarin C and Omicarin C.

10. The serum preparation container according to claim 1, wherein the snake venom prothrombin activator is a group D prothrombin activator.

11. The serum preparation container according to claim 10, wherein the snake venom prothrombin activator is selected from porpharin D, notecarin D, trocarin D, hopsarin D and notenarin D.

* * * * *

UNITED STATES PATENT AND TRADEMARK OFFICE

CERTIFICATE OF CORRECTION

PATENT NO. : 10,385,381 B2
APPLICATION NO. : 13/825047
DATED : August 20, 2019
INVENTOR(S) : Paul Masci et al.

It is certified that error appears in the above-identified patent and that said Letters Patent is hereby corrected as shown below:

On the Title Page

(73) Assignee insert: --Q-Sera Pty Ltd, Melbourne (AU)--

Signed and Sealed this
Nineteenth Day of May, 2020

Andrei Iancu
*Director of the United States Patent and Trademark Office*

SEQUENCE LISTING

```
<160> NUMBER OF SEQ ID NOS: 53

<210> SEQ ID NO 1
<211> LENGTH: 609
<212> TYPE: PRT
<213> ORGANISM: Echis carinatus

<400> SEQUENCE: 1

Met Ile Gln Ile Leu Leu Val Ile Ile Cys Leu Ala Val Phe Pro Tyr
1               5                   10                  15

Gln Gly Cys Ser Ile Ile Leu Gly Ser Gly Asn Val Asn Asp Tyr Glu
            20                  25                  30

Val Val Tyr Pro Gln Lys Val Thr Ala Leu Pro Lys Gly Ala Val Gln
        35                  40                  45

Gln Pro Glu Gln Lys Tyr Glu Asp Ala Met Gln Tyr Glu Phe Glu Val
    50                  55                  60

Lys Gly Glu Pro Val Val His Leu Glu Lys Asn Lys Glu Leu Phe Ser
65                  70                  75                  80

Glu Asp Tyr Ser Glu Thr His Tyr Ser Ser Asp Asp Arg Glu Ile Thr
                85                  90                  95

Thr Asn Pro Ser Val Glu Asp His Cys Tyr Tyr His Gly Arg Ile Gln
            100                 105                 110

Asn Asp Ala Glu Ser Thr Ala Ser Ile Ser Ala Cys Asn Gly Leu Lys
        115                 120                 125

Gly His Phe Lys Leu Arg Gly Glu Thr Tyr Phe Ile Glu Pro Leu Lys
    130                 135                 140

Ile Pro Asp Ser Glu His Ala Val Tyr Lys Tyr Glu Asn Ile Glu Asn
145                 150                 155                 160

Glu Asp Glu Ala Pro Lys Met Cys Gly Val Thr Gln Asp Asn Trp Glu
                165                 170                 175

Ser Asp Glu Pro Ile Lys Lys Thr Leu Gly Leu Ile Val Pro Pro His
            180                 185                 190

Glu Arg Lys Phe Glu Lys Lys Phe Ile Glu Leu Val Val Val Val Asp
        195                 200                 205

His Ser Met Val Thr Lys Tyr Asn Asn Asp Ser Thr Ala Ile Arg Thr
    210                 215                 220

Trp Ile Tyr Glu Leu Asn Thr Val Asn Glu Ile Tyr Leu Pro Phe Asn
225                 230                 235                 240
```

```
Ile Arg Val Ala Leu Val Gly Leu Glu Phe Trp Cys Asn Gly Asp Leu
                245                 250                 255

Ile Asn Val Thr Ser Thr Ala Asp Asp Thr Leu His Ser Phe Gly Glu
            260                 265                 270

Trp Arg Ala Ser Asp Leu Leu Asn Arg Lys Arg His Asp His Ala Gln
        275                 280                 285

Leu Leu Thr Asn Val Thr Leu Asp His Ser Thr Leu Gly Ile Thr Phe
    290                 295                 300

Val Tyr Gly Cys Lys Ser Asp Arg Ser Val Glu Leu Ile Leu Asp Tyr
305                 310                 315                 320

Ser Asn Ile Thr Phe Asn Met Ala Tyr Ile Ile Ala His Glu Met Gly
                325                 330                 335

His Ser Leu Gly Met Leu His Asp Thr Lys Phe Cys Thr Cys Gly Ala
            340                 345                 350

Lys Pro Cys Ile Met Phe Gly Lys Glu Ser Ile Pro Pro Pro Lys Glu
        355                 360                 365

Phe Ser Ser Cys Ser Tyr Asp Gln Tyr Asn Lys Tyr Leu Leu Lys Tyr
    370                 375                 380

Asn Pro Cys Ile Leu Asp Pro Pro Leu Arg Lys Asp Ile Ala Ser Pro
385                 390                 395                 400

Ala Val Cys Gly Asn Glu Ile Trp Glu Glu Gly Glu Glu Cys Asp Cys
                405                 410                 415

Gly Ser Pro Ala Asp Cys Arg Asn Pro Cys Cys Asp Ala Ala Thr Cys
            420                 425                 430

Lys Leu Lys Pro Gly Ala Glu Cys Gly Asn Gly Glu Cys Cys Asp Lys
        435                 440                 445

Cys Lys Ile Arg Lys Ala Gly Thr Glu Cys Arg Pro Ala Arg Asp Asp
    450                 455                 460

Cys Val Ala Glu His Cys Thr Gly Gln Ser Ala Glu Cys Pro Arg Asn
465                 470                 475                 480

Glu Phe Gln Arg Asn Gly Gln Pro Cys Leu Asn Asn Ser Gly Tyr Cys
                485                 490                 495

Tyr Asn Gly Asp Cys Pro Ile Met Leu Asn Gln Cys Ile Ala Leu Phe
            500                 505                 510

Ser Pro Ser Ala Thr Val Ala Gln Asp Ser Cys Phe Gln Arg Asn Leu
        515                 520                 525

Gln Gly Ser Tyr Tyr Gly Tyr Cys Thr Lys Glu Ile Gly Tyr Tyr Gly
    530                 535                 540

Arg Phe Pro Cys Ala Pro Gln Asp Val Lys Cys Gly Arg Leu Tyr Cys
545                 550                 555                 560

Leu Asp Asn Ser Phe Lys Lys Asn Met Arg Cys Lys Asn Asp Tyr Ser
                565                 570                 575

Tyr Ala Asp Glu Asn Lys Gly Ile Val Glu Pro Gly Thr Lys Cys Glu
            580                 585                 590

Asp Gly Lys Val Cys Ile Asn Arg Lys Cys Val Asp Val Asn Thr Ala
        595                 600                 605

Tyr
```

<210> SEQ ID NO 2
<211> LENGTH: 63
<212> TYPE: PRT
<213> ORGANISM: Bothrops asper

<400> SEQUENCE: 2

Ser His Asp Asn Ala Gln Leu Leu Thr Ala Ile Lys Ala Tyr Ile Ala
1               5                   10                  15

Thr Met Cys Asp Pro Lys Met Ala Val Ile Met Ala His Glu Ile Gly
            20                  25                  30

His Gly Gly Tyr Tyr Gly Tyr Cys Arg Lys Ile Pro Cys Ala Pro Glu
        35                  40                  45

Asp Val Lys Asp Asp Asp Ile Gly Met Val Leu Pro Gly Thr Lys
    50                  55                  60

<210> SEQ ID NO 3
<211> LENGTH: 32
<212> TYPE: PRT
<213> ORGANISM: Echis carinatus
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 3

Ser Arg Lys Gln Lys Phe Asp Lys Lys Phe Ile Lys Leu Val Ile Val
1               5                   10                  15

Val Asp His Ser Met Val Xaa Lys Xaa Asn Asn Asp Leu Ile Ala Ile
            20                  25                  30

<210> SEQ ID NO 4
<211> LENGTH: 29
<212> TYPE: PRT
<213> ORGANISM: Echis multisquamatus

<400> SEQUENCE: 4

Asp Cys Leu Pro Gly Trp Ser Val Tyr Glu Gly Arg Cys Tyr Lys Val
1               5                   10                  15

Phe Asn Gln Lys Thr Trp Lys Ala Ala Glu Lys Phe Cys
            20                  25

<210> SEQ ID NO 5
<211> LENGTH: 4737
<212> TYPE: DNA
<213> ORGANISM: Pseudonaja textilis

<400> SEQUENCE: 5
gagccacaga atacatttat gtggggaagt ggcaagttgc tgcaggcaga actgactttt 60
gtatatcttt cagcacatta gcctcaatgg gaagatacag tgtgagccct gtccccaaat 120
gtcttctact gatgttcctg ggttggtcag ggctgaagta ttacgaagtg aatgcagctc 180
agctcaggga gtaccatata gctgctcagc tggaagactg ggattacaac ccccaacctg 240
aggagctatc cagattatca gagtcagatc ttacgtttaa aaaaattgtc tatagagaat 300
atgaactaga tttcaaacaa gagaagccaa gagatgagct ctcagggctc ctagggccaa 360
cactacgtgg agaagtggga gacatcctca taatttattt caagaatttt gctactcagc 420
ctgtgagcat tcacccgcag agtgccgtgt acaacaaatg gtcagaaggt tcttcatatt 480
ctgatggaac atcagatgtg gaaagactgg atgatgctgt gcctccaggc cagtcgttca 540
agtatgtgtg gaatatcact gcagaaattg ggccaaagaa agctgatcct ccctgtctca 600
cttatgcgta ctactcacat gtaaacatgg tgcgagactt taattctggt ctcattggtg 660
ctttgctgat atgtaaagaa ggaagcctga atgcaaatgg ttcacaaaaa ttcttcaaca 720

-continued

```
gagaatatgt gctgatgttt tctgtgtttg atgaaagcaa gaactggtac agaaagccct    780
cactacagta cacaattaat gggtttgcca atggaacatt gcctgatgtt caggcttgtg    840
cttatgatca tattagctgg catttgatag gaatgagttc cagtcctgag atcttctctg    900
ttcacttcaa tggacaaacc ttggaacaaa accattacaa agtgtcaacc atcaaccttg    960
tcggaggtgc ctcagtaaca gccaacatgt cagtgagcag gacaggaaaa tggctaatat   1020
cttctctggt tgcaaagcat ctacaagctg ggatgtatgg ttatctaaat atcaaagact   1080
gtggaaatcc agatacttta acaagaaagt tatcctttag agaactgagg aggattatga   1140
actgggaata tttcattgct gcagaagaaa tcacctggga ttatgctcca gaaattccta   1200
gcagtgttga cagaagatac aaagctcagt atctggataa tttttcaaat tttattggca   1260
agaaatacaa aaaggcagtt ttcaggcaat ataaagacag caatttcact aaaccgacct   1320
atgccatttg gcccaaagaa cgtggaattc tgggccccgt tatcagagct aaagtcagag   1380
acacaataag tattgtattc aaaaatctgg ccagtcgacc ttacagcatt tatgtgcatg   1440
gagtttccgt ttcaaaagat gcagaaggag ctatttatcc ttcagatccc aaagagaata   1500
taactcatgg caaagcagtt gaaccaggac aggtctacac atataaatgg actgtgctgg   1560
atacagatga acctacagta aaggattctg agtgcattac taaattatat catagtgctg   1620
tggacatgac aagagatatt gcttcaggac ttattgggcc acttctggtt tgtaaacaca   1680
aggcactcag cgtcaagggc gtacagaata aagctgatgt ggaacagcat gcagtcttcg   1740
cagtgtttga tgaaaacaag agctggtact tggaagacaa tatcaagaaa tactgcagca   1800
atccttccac tgttaagaaa gatgacccta aattttacaa gtccaatgtt atgtacacac   1860
tcaatggcta tgcatcagat agaacagagg ttttggggtt tcatcagtct gaagttgttg   1920
aatggcacct caccagcgta ggtacagtgg atgagattgt tccagtacat ctttctggtc   1980
acaccttctt atccaaggga aaacatcaag atattttaaa tcttttcccc atgagtggtg   2040
aatcggctac tgtaacaatg gacaatctag gaacctggct tctgtcatca tggggctcct   2100
gtgagatgag caatggcatg agattgagat tttggatgc caattatgat gatgaagatg    2160
agggaaatga agaagaggaa gaagatgatg gcgatatttt tgccgacatt ttcattcctc   2220
cagaagtagt aaaaaagaaa gaaaaggacc ccgtaaattt tgtatcagac ccagaatcgg   2280
ataagatagc aaaagaatta ggattattag atgacgagga taatcaagaa gagtcacaca   2340
atgtacagac agaggatgat gaagaacagc taatgatagc tacaatgctt gggtttcgat   2400
catttaaggg gtcagttgct gaagaagaat tgaatctcac agctctagct ttagaagaag   2460
atgcccatgc ttctgatcct cgaattgaca gtaatagtgc acgtaatcct gatgacatag   2520
ctggacgcta cctgcgtact atcaaccgtg gaaataaaag gaggtactac attgcagcag   2580
aagaagtttt gtgggactac tcaccgatcg gaaaaagtca agtgagaagt cgcgcagcca   2640
agaccacatt caaaaaagct attttccgaa gttatcttga tgatactttc cagacaccta   2700
gcactggagg agaatatgaa aagcatcttg gtatactggg tcctatcatt agggctgagg   2760
tggatgatgt aatcgaagtt cagttcagaa atttggcctc cagaccatac tcacttcatg   2820
ctcatggcct tctctatgag aaatcttctg aaggcagaag ctatgatgac aagtctcctg   2880
aattgttcaa aaaggatgat gctatcatgc caaacggcac atacacatat gtctggcaag   2940
tccctccacg gtcaggacca acagacaata cagaaaaatg taaatcatgg gcctattact   3000
ctggtgtaaa tccggaaaaa gatattcact ctggcttaat tggacctatt ttgatctgcc   3060
```

agaaaggcat gattgacaag tacaacagga caatagacat aagggaattt gtcttgtttt 3120
ttatggtctt tgatgaggag aaaagctggt actttccaaa atctgacaaa agcactcgtg 3180
cagagaaact tataggagtc caatctcgcc acacatttcc tgcaattaat gggatccctt 3240
atcagctgca aggcttgacg atgtacaaag atgagaatgt ccactggcat ttgctgaaca 3300
tgggtgggcc caaagatatc catgttgtta attttcatgg tcagacattc actgaagagg 3360
gaagggaaga taatcaactt ggagtccttc ctcttcttcc tggtacattc gcctccatca 3420
aaatgaaacc atccaaaatt ggcacatggc ttttagaaac agaagttggt gaaaatcagg 3480
aaagaggaat gcaggctctc tttactgtca ttgacaaaga ttgtaaatta ccaatgggac 3540
tggcaagtgg gataatacaa gactcacaga tcagtgcttc aggtcatgtt ggatattggg 3600
agcctaagct agcaagactg aataatactg gaaaatataa tgcttggagc atcataaaga 3660
aggaacatga acatccgtgg atccagatag acctacaaag acaagttgtc atcacaggca 3720
ttcagaccca aggagccatg caactactga aacatttgta tactgtggaa tattttttta 3780
cctacagcaa agatgggcaa aactggatta cttttaaagg aagacattcc gaaacacaaa 3840
tgcattttga gggtaattca gatggcacca cagtaaaaga aaaccacatt gatcctccta 3900
ttattgccag atatattagg ctgcatccaa ccaagttcca caacagacct actttccgca 3960
ttgaactgtt aggttgtgaa gttgaaggct gctcagtgcc attgggaatg gaaagtgggg 4020
ctatcaagaa ttcagagatt acagcctctt cttataagaa gacttggtgg agttcatggg 4080
aaccatccct tgcacgactc aatctgaaag gacgaacaaa tgcttggcaa ccaaaggtaa 4140
acaacaaaga tcaatggcta caaattgacc tgcaacatct tacaaaaata acaagcataa 4200
taactcaagg agccacatca atgactacat caatgtatgt gaaaacattc tccatccatt 4260
atactgatga caattcaaca tggaagcctt atttggatgt tcgcacttcc atggaaaagg 4320
ttttcacagg aaatattaac agtgatggtc atgtcaaaca ttttttcaaa ccccctatat 4380
tgtccaggtt cattcgtatc atccctaaaa catggaatca atatattgca ctccggatag 4440
aattgtttgg ttgtgaagtt ttttaaggct tggacagaag actatcaaat caagcaactt 4500
caatgtttca agttttctta ttactaactc tgctttttaa aaggaaacaa aaacaaaagc 4560
ataataaaac tgtcttagca taaaaaagct atccttctca attttcagct atagctttca 4620
aatagctttg aaaatatcaa tcaaaatatc ataactgaag tgactttaca atgattaatt 4680
ctagtgccac tttaatcatg actgtaatcc taatacataa accttatttt ttttgcc 4737

<210> SEQ ID NO 6
<211> LENGTH: 4383
<212> TYPE: DNA
<213> ORGANISM: Pseudonaja textilis

<400> SEQUENCE: 6
atgggaagat acagtgtgag ccctgtcccc aaatgtcttc tactgatgtt cctgggttgg 60
tcagggctga agtattacca agtgaatgca gctcagctca gggagtacca tatagctgct 120
cagctggaag actgggatta caacccccaa cctgaggagc tatccagatt atcagagtca 180
gatcttacgt ttaaaaaaat tgtctataga gaatatgaac tagatttcaa acaagaggag 240
ccaagagatg cgctctcagg gctcctaggg ccaacactac gtggagaagt gggagacagc 300
ctcataattt atttcaagaa ttttgctact cagcctgtga gcattcaccc gcagagtgcc 360
gtgtacaaca aatggtcaga aggttcttca tattctgatg gaacatcaga tgtggaaaga 420
ctggatgatg ctgtgcctcc aggccagtcg ttcaagtatg tgtggaatat cactgcagaa 480

-continued attgggccaa agaaagctga tcctccctgt ctcacttatg cgtactactc acatgtaaac 540
atggtgcgag actttaattc tggtctcatt ggtgctttgc tgatatgtaa agaaggaagc 600
ctgaatgcaa atggttcaca aaaattcttc aacagagaat atgtgctgat gttttctgtg 660
tttgatgaaa gcaagaactg gtacagaaag ccctcactac agtacacaat taatgggttt 720
gccaatggaa cattgcctga tgttcaggct tgtgcttatg atcatattag ctggcatttg 780
ataggaatga gttccagtcc tgagatcttc tctgttcact tcaatggaca aaccttggaa 840
caaaaccatt acaaagtgtc aaccatcaac cttgtcggag gtgcctcagt aacagccgac 900
atgtcagtga gcaggacagg aaaatggcta atatcttctc tggttgcaaa gcatctacaa 960
gctgggatgt atggttatct aaatatcaaa gactgtggaa atccagatac tttaacaaga 1020
aagttatcct ttagagaact gatgaagatt aagaactggg aatatttcat tgctgcagaa 1080
gaaatcacct gggattatgc tccagaaatt cctagcagtg ttgacagaag atacaaagct 1140
cagtatctgg ataatttttc aaattttatt ggcaagaaat acaaaaaggc agttttcagg 1200
caatatgaag acggcaattt cactaaaccg acctatgcca tttggcccaa agaacgtgga 1260
attctgggcc ccgttatcaa agctaaagtc agagacacag taacaattgt attcaaaaat 1320
ctggccagtc gaccttacag catttatgtg catggagttt ccgtttcaaa agatgcagaa 1380
ggagctattt atccttcaga tcccaaagag aatataactc atggcaaagc agttgaacca 1440
ggacaggtct acacatataa atggactgtg ctggatacag atgaacctac agtaaaggat 1500
tctgagtgca ttactaaatt atatcatagt gctgtggaca tgacaagaga tattgcttca 1560
ggacttattg ggccacttct ggtttgtaaa cacaaggcac tcagcgtcaa gggggtacag 1620
aataaagctg atgtggaaca gcatgcagtc ttcgcagtgt ttgatgaaaa caagagctgg 1680
tacttggaag acaatatcaa gaaatactgc agcaatcctt ccgctgttaa gaaagatgac 1740
cctaaatttt acaagtccaa tgttatgtac acactcaatg gctatgcatc agatagaaca 1800
gaggttttga ggtttcatca gtctgaagtt gttcaatggc acctcaccag cgtaggtaca 1860
gtggatgaga ttgttccagt acatctttct ggtcacacct tcttatccaa gggaaaacat 1920
caagatattt taaatctttt ccccatgagt ggtgaatctg ctactgtaac aatggacaat 1980
ctaggaacct ggcttctgtc atcatggggc tcctgtgaga tgagcaatgg catgagattg 2040
agatttttgg atgccaatta tgatgatgaa gatgagggaa atgaagaaga ggaagaagat 2100
gatggtgata tttttgccga cattttcatt ccttcagaag tagtaaaaaa gaaagaagag 2160
gttcccgtaa attttgtacc agacccagaa tcggatgcgc tagcaaaaga attaggatta 2220
atagatgacg agggtaatcc aataatacag ccacgcaggg aacagacaga ggatgatgaa 2280
gaacagctaa tgaaagcttc aatgcttggg cttcgatcat ttaaggggtc agttgctgaa 2340
gaagaattga aacacacagc tctagcttta gaagaagatg cccatgcttc tgatcctcga 2400
attgacagta atagtgcacg taatcctgac gacatagctg gacgctacct gcgtactatc 2460
aaccgtggaa ataaaaggag gtactacatt gcagcagaag aagttttgtg ggactactca 2520
ccgatcggaa aaagtcaagt gagaagtcgc gcagccaaga ccacattcaa aaaagctatt 2580
ttccgaagtt atcttgatga tactttccag acacctagca ctggaggaga atatgaaaag 2640
catcttggta tactgggtcc tatcattagg gctgaggtgg atgatgtaat cgaaattcag 2700
ttcaaaaatt tggcctctag accatactca cttcatgctc atggccttct ctatgagaaa 2760
tcttctgaag gcagaagcta tgacgacaag tctcctgaat tgttcaaaaa ggatgatgct 2820

-continued

```
atcatgccaa atggcacata cacatatgtc tggcaagtcc ctccacggtc aggaccaaca   2880
gacaatacag aaaaatgtaa atcatgggcc tattactctg gtgtaaatcc ggaaaaagat   2940
attcactctg gcttaattgg acctattttg atctgccaga aaggcatgat tgacaagtac   3000
aacaggacaa tagacataag ggaatttgtc ttgtttttta tggtctttga tgaggagaaa   3060
agctggtact ttccaaaatc tgacaaaagc acttgtgaag agaaacttat aggagtccaa   3120
tctctccaca catttcctgc aattaatggg atcccttatc agctgcaagg cttgacgatg   3180
tacaaagatg agaatgtcca ctggcatttg ctgaacatgg gtgggcccaa agatatccat   3240
gttgttaatt ttcatggtca gacattcact gaagagggaa gggaagataa tcaacttgga   3300
gtccttcctc ttcttcctgg tacattcgcc tccatcaaaa tgaaaccatc caaaattggc   3360
acatggcttt tagaaacaga agttggtgaa aatcaggaaa gaggaatgca ggctctcttt   3420
actgtcattg acaaagattg taaattacca atgggactgg caagtgggat aatacaagac   3480
tcacagatca gtgcttcagg tcatgttgga tattgggagc ctaagctagc aagactgaat   3540
aatactggaa aatataatgc ttggagcatc ataaagaagg aacatgaaca tccgtggatc   3600
cagatagacc tacaaagaca agttgtcatc acaggcattc agacccaagg aaccgtgcaa   3660
ctactgcaac attcgtatac tgtggaatat tttgttacct acagcgaaga tgggcaaaac   3720
tggattactt ttaaaggaag acattccgaa acacaaatgc attttgaggg taattcagat   3780
ggcaccacag taaaagaaaa ccacattgat cctcctatta ttgccagata tattagactg   3840
catccaacca agttctacaa cagacctact ttccgcattg aactgttagg ttgtgaagtt   3900
gaaggttgct cagtgccatt gggaatggaa agtggggcta tcaagaattc agagattaca   3960
gcctcttctt ataagaagac ttggtggagt tcatgggaac catcccttgc acgactcaat   4020
ctggaaggag gaacaaatgc ttggcaacca gaggtaaaca acaaagatca atggttacaa   4080
attgacctgc aacatcttac aaaaataaca agcataataa ctcaaggagc cacatcaatg   4140
actacatcaa tgtatgtgaa aacattctcc atccattata ctgatgacaa ttcaacatgg   4200
aagccttatt tggatgttcg cacttccatg gaaaaggttt tcacaggaaa tattaacagt   4260
gatggtcatg tcaaacattt tttcaaaccc cctatattgt ccaggttcat tcgtatcatc   4320
cctaaaacat ggaatcaata tattgcactc cggatagaat tgtttggttg tgaagttttt   4380
taa                                                                 4383
```

<210> SEQ ID NO 7
<211> LENGTH: 1459
<212> TYPE: PRT
<213> ORGANISM: Pseudonaja textilis

<400> SEQUENCE: 7

```
Met Gly Arg Tyr Ser Val Ser Pro Val Pro Lys Cys Leu Leu Leu Met
1               5                   10                  15

Phe Leu Gly Trp Ser Gly Leu Lys Tyr Tyr Glu Val Asn Ala Ala Gln
            20                  25                  30

Leu Arg Glu Tyr His Ile Ala Ala Gln Leu Glu Asp Trp Asp Tyr Asn
        35                  40                  45

Pro Gln Pro Glu Glu Leu Ser Arg Leu Ser Glu Ser Asp Leu Thr Phe
    50                  55                  60

Lys Lys Ile Val Tyr Arg Glu Tyr Glu Leu Asp Phe Lys Gln Glu Lys
65                  70                  75                  80

Pro Arg Asp Glu Leu Ser Gly Leu Leu Gly Pro Thr Leu Arg Gly Glu
                85                  90                  95
```

-continued

```
Val Gly Asp Ile Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ser Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly Asn Pro Asp
                325                 330                 335

Thr Leu Thr Arg Lys Leu Ser Phe Arg Glu Leu Arg Arg Ile Met Asn
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Lys Asp Ser Asn Phe Thr Lys Pro Thr Tyr Ala Ile Trp Pro
                405                 410                 415

Lys Glu Arg Gly Ile Leu Gly Pro Val Ile Arg Ala Lys Val Arg Asp
            420                 425                 430

Thr Ile Ser Ile Val Phe Lys Asn Leu Ala Ser Arg Pro Tyr Ser Ile
        435                 440                 445

Tyr Val His Gly Val Ser Val Ser Lys Asp Ala Glu Gly Ala Ile Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510
```

-continued

```
Asp Met Thr Arg Asp Ile Ala Ser Gly Leu Ile Gly Pro Leu Leu Val
        515                 520                 525

Cys Lys His Lys Ala Leu Ser Val Lys Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Thr Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Leu Gly Phe His Gln Ser
        595                 600                 605

Glu Val Val Glu Trp His Leu Thr Ser Val Gly Thr Val Asp Glu Ile
    610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Glu Glu Asp Asp Gly Asp Ile
    690                 695                 700

Phe Ala Asp Ile Phe Ile Pro Pro Glu Val Val Lys Lys Lys Glu Lys
705                 710                 715                 720

Asp Pro Val Asn Phe Val Ser Asp Pro Glu Ser Asp Lys Ile Ala Lys
                725                 730                 735

Glu Leu Gly Leu Leu Asp Asp Glu Asp Asn Gln Glu Glu Ser His Asn
            740                 745                 750

Val Gln Thr Glu Asp Asp Glu Glu Gln Leu Met Ile Ala Thr Met Leu
        755                 760                 765

Gly Phe Arg Ser Phe Lys Gly Ser Val Ala Glu Glu Glu Leu Asn Leu
    770                 775                 780

Thr Ala Leu Ala Leu Glu Glu Asp Ala His Ala Ser Asp Pro Arg Ile
785                 790                 795                 800

Asp Ser Asn Ser Ala Arg Asn Pro Asp Asp Ile Ala Gly Arg Tyr Leu
                805                 810                 815

Arg Thr Ile Asn Arg Gly Asn Lys Arg Arg Tyr Tyr Ile Ala Ala Glu
            820                 825                 830

Glu Val Leu Trp Asp Tyr Ser Pro Ile Gly Lys Ser Gln Val Arg Ser
        835                 840                 845

Arg Ala Ala Lys Thr Thr Phe Lys Lys Ala Ile Phe Arg Ser Tyr Leu
    850                 855                 860

Asp Asp Thr Phe Gln Thr Pro Ser Thr Gly Gly Glu Tyr Glu Lys His
865                 870                 875                 880

Leu Gly Ile Leu Gly Pro Ile Ile Arg Ala Glu Val Asp Asp Val Ile
                885                 890                 895

Glu Val Gln Phe Arg Asn Leu Ala Ser Arg Pro Tyr Ser Leu His Ala
            900                 905                 910

His Gly Leu Leu Tyr Glu Lys Ser Ser Glu Gly Arg Ser Tyr Asp Asp
        915                 920                 925

Lys Ser Pro Glu Leu Phe Lys Lys Asp Asp Ala Ile Met Pro Asn Gly
```

```
    930                 935                 940

Thr Tyr Thr Tyr Val Trp Gln Val Pro Pro Arg Ser Gly Pro Thr Asp
945                 950                 955                 960

Asn Thr Glu Lys Cys Lys Ser Trp Ala Tyr Tyr Ser Gly Val Asn Pro
                965                 970                 975

Glu Lys Asp Ile His Ser Gly Leu Ile Gly Pro Ile Leu Ile Cys Gln
            980                 985                 990

Lys Gly Met Ile Asp Lys Tyr Asn  Arg Thr Ile Asp Ile  Arg Glu Phe
        995                 1000                 1005

Val Leu  Phe Phe Met Val Phe  Asp Glu Glu Lys Ser  Trp Tyr Phe
    1010                 1015                 1020

Pro Lys  Ser Asp Lys Ser Thr  Arg Ala Glu Lys Leu  Ile Gly Val
    1025                 1030                 1035

Gln Ser  Arg His Thr Phe Pro  Ala Ile Asn Gly Ile  Pro Tyr Gln
    1040                 1045                 1050

Leu Gln  Gly Leu Thr Met Tyr  Lys Asp Glu Asn Val  His Trp His
    1055                 1060                 1065

Leu Leu  Asn Met Gly Gly Pro  Lys Asp Ile His Val  Val Asn Phe
    1070                 1075                 1080

His Gly  Gln Thr Phe Thr Glu  Glu Gly Arg Glu Asp  Asn Gln Leu
    1085                 1090                 1095

Gly Val  Leu Pro Leu Leu Pro  Gly Thr Phe Ala Ser  Ile Lys Met
    1100                 1105                 1110

Lys Pro  Ser Lys Ile Gly Thr  Trp Leu Leu Glu Thr  Glu Val Gly
    1115                 1120                 1125

Glu Asn  Gln Glu Arg Gly Met  Gln Ala Leu Phe Thr  Val Ile Asp
    1130                 1135                 1140

Lys Asp  Cys Lys Leu Pro Met  Gly Leu Ala Ser Gly  Ile Ile Gln
    1145                 1150                 1155

Asp Ser  Gln Ile Ser Ala Ser  Gly His Val Gly Tyr  Trp Glu Pro
    1160                 1165                 1170

Lys Leu  Ala Arg Leu Asn Asn  Thr Gly Lys Tyr Asn  Ala Trp Ser
    1175                 1180                 1185

Ile Ile  Lys Lys Glu His Glu  His Pro Trp Ile Gln  Ile Asp Leu
    1190                 1195                 1200

Gln Arg  Gln Val Val Ile Thr  Gly Ile Gln Thr Gln  Gly Ala Met
    1205                 1210                 1215

Gln Leu  Leu Lys His Leu Tyr  Thr Val Glu Tyr Phe  Phe Thr Tyr
    1220                 1225                 1230

Ser Lys  Asp Gly Gln Asn Trp  Ile Thr Phe Lys Gly  Arg His Ser
    1235                 1240                 1245

Glu Thr  Gln Met His Phe Glu  Gly Asn Ser Asp Gly  Thr Thr Val
    1250                 1255                 1260

Lys Glu  Asn His Ile Asp Pro  Pro Ile Ile Ala Arg  Tyr Ile Arg
    1265                 1270                 1275

Leu His  Pro Thr Lys Phe His  Asn Arg Pro Thr Phe  Arg Ile Glu
    1280                 1285                 1290

Leu Leu  Gly Cys Glu Val Glu  Gly Cys Ser Val Pro  Leu Gly Met
    1295                 1300                 1305

Glu Ser  Gly Ala Ile Lys Asn  Ser Glu Ile Thr Ala  Ser Ser Tyr
    1310                 1315                 1320

Lys Lys  Thr Trp Trp Ser Ser  Trp Glu Pro Ser Leu  Ala Arg Leu
    1325                 1330                 1335
```

```
Asn Leu  Lys Gly Arg Thr Asn  Ala Trp Gln Pro Lys  Val Asn Asn
    1340                 1345                 1350

Lys Asp  Gln Trp Leu Gln Ile  Asp Leu Gln His Leu  Thr Lys Ile
    1355                 1360                 1365

Thr Ser  Ile Ile Thr Gln Gly  Ala Thr Ser Met Thr  Thr Ser Met
    1370                 1375                 1380

Tyr Val  Lys Thr Phe Ser Ile  His Tyr Thr Asp Asp  Asn Ser Thr
    1385                 1390                 1395

Trp Lys  Pro Tyr Leu Asp Val  Arg Thr Ser Met Glu  Lys Val Phe
    1400                 1405                 1410

Thr Gly  Asn Ile Asn Ser Asp  Gly His Val Lys His  Phe Phe Lys
    1415                 1420                 1425

Pro Pro  Ile Leu Ser Arg Phe  Ile Arg Ile Ile Pro  Lys Thr Trp
    1430                 1435                 1440

Asn Gln  Tyr Ile Ala Leu Arg  Ile Glu Leu Phe Gly  Cys Glu Val
    1445                 1450                 1455

Phe
```

<210> SEQ ID NO 8
<211> LENGTH: 1460
<212> TYPE: PRT
<213> ORGANISM: Pseudonaja textilis

<400> SEQUENCE: 8

```
Met Gly Arg Tyr Ser Val Ser Pro Val Pro Lys Cys Leu Leu Leu Met
1               5                   10                  15

Phe Leu Gly Trp Ser Gly Leu Lys Tyr Tyr Gln Val Asn Ala Ala Gln
            20                  25                  30

Leu Arg Glu Tyr His Ile Ala Ala Gln Leu Glu Asp Trp Asp Tyr Asn
        35                  40                  45

Pro Gln Pro Glu Glu Leu Ser Arg Leu Ser Glu Ser Asp Leu Thr Phe
    50                  55                  60

Lys Lys Ile Val Tyr Arg Glu Tyr Glu Leu Asp Phe Lys Gln Glu Glu
65                  70                  75                  80

Pro Arg Asp Ala Leu Ser Gly Leu Leu Gly Pro Thr Leu Arg Gly Glu
                85                  90                  95

Val Gly Asp Ser Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ser Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240
```

-continued

```
Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asp Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly Asn Pro Asp
                325                 330                 335

Thr Leu Thr Arg Lys Leu Ser Phe Arg Glu Leu Met Lys Ile Lys Asn
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Glu Asp Gly Asn Phe Thr Lys Pro Thr Tyr Ala Ile Trp Pro
                405                 410                 415

Lys Glu Arg Gly Ile Leu Gly Pro Val Ile Lys Ala Lys Val Arg Asp
            420                 425                 430

Thr Val Thr Ile Val Phe Lys Asn Leu Ala Ser Arg Pro Tyr Ser Ile
        435                 440                 445

Tyr Val His Gly Val Ser Val Ser Lys Asp Ala Glu Gly Ala Ile Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510

Asp Met Thr Arg Asp Ile Ala Ser Gly Leu Ile Gly Pro Leu Leu Val
        515                 520                 525

Cys Lys His Lys Ala Leu Ser Val Lys Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Ala Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Leu Arg Phe His Gln Ser
        595                 600                 605

Glu Val Val Gln Trp His Leu Thr Ser Val Gly Thr Val Asp Glu Ile
    610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655
```

-continued

```
Thr Met Asp Asn Leu Gly Thr Trp Leu Leu Ser Ser Trp Gly Ser Cys
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Glu Glu Asp Asp Gly Asp Ile
    690                 695                 700

Phe Ala Asp Ile Phe Ile Pro Ser Glu Val Val Lys Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Ile Asp Asp Glu Gly Asn Pro Ile Ile Gln Pro Arg
            740                 745                 750

Arg Glu Gln Thr Glu Asp Asp Glu Glu Gln Leu Met Lys Ala Ser Met
        755                 760                 765

Leu Gly Leu Arg Ser Phe Lys Gly Ser Val Ala Glu Glu Glu Leu Lys
    770                 775                 780

His Thr Ala Leu Ala Leu Glu Glu Asp Ala His Ala Ser Asp Pro Arg
785                 790                 795                 800

Ile Asp Ser Asn Ser Ala Arg Asn Pro Asp Asp Ile Ala Gly Arg Tyr
                805                 810                 815

Leu Arg Thr Ile Asn Arg Gly Asn Lys Arg Arg Tyr Tyr Ile Ala Ala
            820                 825                 830

Glu Glu Val Leu Trp Asp Tyr Ser Pro Ile Gly Lys Ser Gln Val Arg
        835                 840                 845

Ser Arg Ala Ala Lys Thr Thr Phe Lys Lys Ala Ile Phe Arg Ser Tyr
    850                 855                 860

Leu Asp Asp Thr Phe Gln Thr Pro Ser Thr Gly Gly Glu Tyr Glu Lys
865                 870                 875                 880

His Leu Gly Ile Leu Gly Pro Ile Ile Arg Ala Glu Val Asp Asp Val
                885                 890                 895

Ile Glu Ile Gln Phe Lys Asn Leu Ala Ser Arg Pro Tyr Ser Leu His
            900                 905                 910

Ala His Gly Leu Leu Tyr Glu Lys Ser Ser Glu Gly Arg Ser Tyr Asp
        915                 920                 925

Asp Lys Ser Pro Glu Leu Phe Lys Lys Asp Asp Ala Ile Met Pro Asn
    930                 935                 940

Gly Thr Tyr Thr Tyr Val Trp Gln Val Pro Pro Arg Ser Gly Pro Thr
945                 950                 955                 960

Asp Asn Thr Glu Lys Cys Lys Ser Trp Ala Tyr Tyr Ser Gly Val Asn
                965                 970                 975

Pro Glu Lys Asp Ile His Ser Gly Leu Ile Gly Pro Ile Leu Ile Cys
            980                 985                 990

Gln Lys Gly Met Ile Asp Lys Tyr  Asn Arg Thr Ile Asp  Ile Arg Glu
        995                 1000                1005

Phe Val  Leu Phe Phe Met Val  Phe Asp Glu Glu Lys  Ser Trp Tyr
    1010                1015                1020

Phe Pro  Lys Ser Asp Lys Ser  Thr Cys Glu Glu Lys  Leu Ile Gly
    1025                1030                1035

Val Gln  Ser Leu His Thr Phe  Pro Ala Ile Asn Gly  Ile Pro Tyr
    1040                1045                1050

Gln Leu  Gln Gly Leu Thr Met  Tyr Lys Asp Glu Asn  Val His Trp
    1055                1060                1065

His Leu  Leu Asn Met Gly Gly  Pro Lys Asp Ile His  Val Val Asn
```

-continued

```
    1070                1075                1080

Phe His  Gly Gln Thr Phe Thr  Glu Glu Gly Arg Glu  Asp Asn Gln
    1085                1090                1095

Leu Gly  Val Leu Pro Leu Leu  Pro Gly Thr Phe Ala  Ser Ile Lys
    1100                1105                1110

Met Lys  Pro Ser Lys Ile Gly  Thr Trp Leu Leu Glu  Thr Glu Val
    1115                1120                1125

Gly Glu  Asn Gln Glu Arg Gly  Met Gln Ala Leu Phe  Thr Val Ile
    1130                1135                1140

Asp Lys  Asp Cys Lys Leu Pro  Met Gly Leu Ala Ser  Gly Ile Ile
    1145                1150                1155

Gln Asp  Ser Gln Ile Ser Ala  Ser Gly His Val Gly  Tyr Trp Glu
    1160                1165                1170

Pro Lys  Leu Ala Arg Leu Asn  Asn Thr Gly Lys Tyr  Asn Ala Trp
    1175                1180                1185

Ser Ile  Ile Lys Lys Glu His  Glu His Pro Trp Ile  Gln Ile Asp
    1190                1195                1200

Leu Gln  Arg Gln Val Val Ile  Thr Gly Ile Gln Thr  Gln Gly Thr
    1205                1210                1215

Val Gln  Leu Leu Gln His Ser  Tyr Thr Val Glu Tyr  Phe Val Thr
    1220                1225                1230

Tyr Ser  Glu Asp Gly Gln Asn  Trp Ile Thr Phe Lys  Gly Arg His
    1235                1240                1245

Ser Glu  Thr Gln Met His Phe  Glu Gly Asn Ser Asp  Gly Thr Thr
    1250                1255                1260

Val Lys  Glu Asn His Ile Asp  Pro Pro Ile Ile Ala  Arg Tyr Ile
    1265                1270                1275

Arg Leu  His Pro Thr Lys Phe  Tyr Asn Arg Pro Thr  Phe Arg Ile
    1280                1285                1290

Glu Leu  Leu Gly Cys Glu Val  Glu Gly Cys Ser Val  Pro Leu Gly
    1295                1300                1305

Met Glu  Ser Gly Ala Ile Lys  Asn Ser Glu Ile Thr  Ala Ser Ser
    1310                1315                1320

Tyr Lys  Lys Thr Trp Trp Ser  Ser Trp Glu Pro Ser  Leu Ala Arg
    1325                1330                1335

Leu Asn  Leu Glu Gly Gly Thr  Asn Ala Trp Gln Pro  Glu Val Asn
    1340                1345                1350

Asn Lys  Asp Gln Trp Leu Gln  Ile Asp Leu Gln His  Leu Thr Lys
    1355                1360                1365

Ile Thr  Ser Ile Ile Thr Gln  Gly Ala Thr Ser Met  Thr Thr Ser
    1370                1375                1380

Met Tyr  Val Lys Thr Phe Ser  Ile His Tyr Thr Asp  Asp Asn Ser
    1385                1390                1395

Thr Trp  Lys Pro Tyr Leu Asp  Val Arg Thr Ser Met  Glu Lys Val
    1400                1405                1410

Phe Thr  Gly Asn Ile Asn Ser  Asp Gly His Val Lys  His Phe Phe
    1415                1420                1425

Lys Pro  Pro Ile Leu Ser Arg  Phe Ile Arg Ile Ile  Pro Lys Thr
    1430                1435                1440

Trp Asn  Gln Tyr Ile Ala Leu  Arg Ile Glu Leu Phe  Gly Cys Glu
    1445                1450                1455

Val Phe
    1460
```

<210> SEQ ID NO 9
<211> LENGTH: 4380
<212> TYPE: DNA
<213> ORGANISM: Oxyuranus scutellatus

<400> SEQUENCE: 9
atgggaagat acagtgtgag ccctgtcccc aaatgtcttc tactgatgtt cctgggttgg 60
tcagggctga agtattacca agtgaatgca gctcagctca gggagtaccg tttagctgct 120
cagctggaag actgggatta caacccccaa cctgaggagc tatccagatt atcagagtca 180
gatcttacgt ttaaaaaaat tgtctataga gaatatgaac tagatttcaa acaagagaag 240
ccaagagatg agctctcagg gctcctaggg ccaacactac gtggagaagt gggagacagc 300
ctcataattt atttcaagaa ttttgctact cagcctgtga gcattcaccc gcagagtgcc 360
gtgtacaaca aatggtcaga aggttcttca tattctgatg gaacatcaga tgtggaaaga 420
ctggatgatg ctgtgcctcc aggccagtcg ttcaagtatg tgtggaatat cactgcagaa 480
attgggccaa agaaagctga tcctccctgt ctcacttatg cgtactactc acatgtaaac 540
atggtgcgag actttaattc tggtctcatt ggtgctttgc tgatatgtaa agaaggaagc 600
ctgaatgcag atggtgcaca aaaattcttc aacagagaat atgtgctgat gttttctgtg 660
tttgatgaaa gcaagaactg gtacagaaag ccctcattac agtacacaat taatgggttt 720
gccaatggaa cattgcctga tgttcaggct tgtgcttatg atcatattag ctggcatttg 780
ataggaatga gttccagtcc tgagatcttc tctgttcact tcaatggaca aaccttggaa 840
caaaaccatt acaaagtgtc aaccatcaac cttgtcggag gtgcctcagt aacagccaac 900
atgtcagtga gcaggacagg aaaatggcta atatcttctc tggttgcaaa gcatctacaa 960
gctgggatgt atggttatct aaatatcaaa gactgtggaa atccagatac tttaacaaga 1020
aagttatcct ttagagaacg gaggaggatt atgaaatggg aatatttcat tgctgcagaa 1080
gaaatcacct gggattatgc tccagaaatt cctagcagtg ttgacagaag atacaaagct 1140
cagtatctgg ataatttttc aaattttatt ggcaagaaat acaaaaaggc agttttcagg 1200
caatatgaag acagcaattt cactaaaccg acctatgcca tttggcccaa agaacgtgga 1260
attctgggcc ccgttatcaa agctaaagtc agagacacag taacaattgt attcaaaaat 1320
ctggccagtc gaccttacag catttatgtg catggagttt ccgtttcaaa agatgcagaa 1380
ggagctgttt atccttcaga tcccaaagag aatataactc atggcaaagc agttgaacca 1440
ggacaggtct acacatataa atggactgtg ctggatacag atgaacctac agtaaaggat 1500
tctgagtgca ttactaaatt atatcatagt gctgtggaca tgacaagaga tattgcttca 1560
ggacttattg ggccacctct ggtttgtaaa cgcaaggcac tcagcatcag gggggtacag 1620
aataaagctg atgtggaaca gcatgcagtc ttcgcagtgt ttgatgaaaa caagagctgg 1680
tacttggaag acaatatcaa gaaatactgc agcaatcctt ccagtgttaa gaaagatgac 1740
cctaaatttt acaagtccaa tgttatgtac acactcaatg gctatgcatc agatagaaca 1800
gaggtttggg ggtttcatca gtctgaagtt gttgaatggc acctcaccag cgtaggtaca 1860
gtggatgaga ttgttccagt acatctttct ggtcacacct tcttatccaa gggaaaacat 1920
caagatattt taaatctttt tcccatgagt ggtgaatcgg ctactgtaac aatggacaat 1980
ctaggaacct ggcttctgtc atcatggggc tcctgtgaga tgagcaatgg catgagattg 2040
agatttttgg atgccaatta tgatgatgaa gatgagggaa atgaagaaga ggaagaagat 2100

-continued

```
gatggtgata tttttgccga cattttcaat cctccagaag tagtaataaa gaaagaagag   2160
gttcccgtaa attttgtacc agacccagaa tcggatgcgc tagcaaaaga attaggatta   2220
tttgatgacg aggataatcc aaaacagtca cgcagtgaac agacagagga tgatgaagaa   2280
cagctaatga tagcttcaat gcttgggctt cgatcattta aggggtcagt tgctgaagaa   2340
gaattgaaac acacagctct agctttagaa gaagatgccc atgcttctga tcctcgaatt   2400
gacagtaata gtgcacataa ttctgacgac atagctggac gctacctgcg tactatcaac   2460
cgcagaaata aaaggaggta ctacattgca gcagaagaag ttttgtggga ctactcaccg   2520
atcggaaaaa gtcaagtgag aagtctccca gccaagacca cattcaaaaa agctattttc   2580
cgaagttatc ttgatgatac tttccagaca cctagcactg gaggagaata tgaaaagcat   2640
cttggtatac tgggtcctat cattagggct gaggtggatg atgtaatcga agttcagttc   2700
agaaatttgg cctctagacc atactcactt catgctcatg gccttctcta tgagaaatct   2760
tctgaaggca gaagctatga cgacaactct cctgaattgt tcaaaaaaga tgatgctatc   2820
atgccaaacg gcacatacac atatgtctgg caagtccctc cacggtcagg accaacagac   2880
aatacagaaa aatgtaaatc atgggcctat tactctggtg taaatccgga aaaagatatt   2940
cactctggct taattggacc tattttgatc tgccagaaag gcatgattga caagtacaac   3000
aggacaatag acataaggga atttgtcttg ttttttatgg tctttgatga ggagaaaagc   3060
tggtactttc caaaatctga caaaagcact tgtgaagaga aacttatagg agtccaatct   3120
cgccacacat ttcctgcaat taatgggatc ccttatcagc tgcaaggctt gatgatgtac   3180
aaagatgaga atgtccactg gcatttgctg aacatgggtg ggcccaaaga tgtccatgtt   3240
gttaattttc atggtcagac attcactgaa gagggaaggg aagataatca acttggagtc   3300
cttcctcttc ttcctggtac attcgcctcc atcaaaatga aaccatccaa aattggcaca   3360
tggcttttag aaacagaagt tggtgaaaat caggaaagag gaatgcaggc tctctttact   3420
gtcattgaca aagattgtaa attaccaatg ggactggcaa gtgggataat acaagactca   3480
cagatcagtg cttcaggtca tgttggatat tgggagccta agctagcaag actgaataat   3540
actggaatgt ttaatgcttg gagcatcata aagaaggaac atgaacatcc gtggatccag   3600
atagacctac aaagacaagt tgtcatcaca ggcattcaga cccagggaac cgtgcaacta   3660
ctgaaacatt cgtatactgt ggaatatttt gttacctaca gcaaagatgg gcaaaactgg   3720
attactttta aaggaagaca ttccaaaaca caaatgcatt ttgagggtaa ttcagatggc   3780
accacagtaa aagaaaacca cattgatcct cctattattg ccagatatat taggctgcat   3840
ccaaccaagt tctacaacac acctactttc cgcattgaac tgttaggttg tgaagttgaa   3900
ggttgctcag tgccattggg aatggaaagt ggggctatca aggattcaga gattacagcc   3960
tcttcttata aaaagacttg gtggagttca tgggaaccat tccttgcacg actcaatctg   4020
aaaggacgaa caaatgcttg gcaaccaaag gtaaacaaca aagatcaatg gctacaaatt   4080
gacctgcaac atcttacaaa aataacaagc ataataactc aaggagccac atcaatgact   4140
acatcaatgt atgtgaaaac attctccatc cattatactg atgacaattc aacatggaag   4200
ccttatttgg atgttcgcac ttccatggaa aaggttttca caggaaatat taacagtgat   4260
ggtcatgtca aacatttttt caaccccccct atattgtcca ggttcattcg tatcatccct   4320
aaaacatgga atcaatatat tgcactccgg atagaattgt ttggttgtga agtttttttaa   4380
```

<210> SEQ ID NO 10
<211> LENGTH: 4675

```
<212> TYPE: DNA
<213> ORGANISM: Oxyuranus scutellatus scutellatus

<400> SEQUENCE: 10

atgggaagat acagtgtgag ccctgtcccc aaatgtcttc tactgatgtt cctgggttgg     60

tcagggctga agtattacca agtgaatgca gctcagctca gggagtaccg tatagctgct    120

cagctggaag actgggatta caaccccaa cctgaggagc tatccagatt atcagagtca    180

gatcttacgt ttaaaaaaat tgtctataga gaatatgaac tagatttcaa acaagagaag    240

ccaagagatg agctctcagg gctcctaggg ccaacactac gtggagaagt gggagacagc    300

ctcataattt atttcaagaa ttttgctact cagcctgtga gcattcaccc gcagagtgcc    360

gtgtacaaca aatggtcaga aggttcttca tattctgatg gaacatcaga tgtggaaaga    420

ctggatgatg ctgtgcctcc aggccagtcg ttcaagtatg tgtggaatat cactgcagaa    480

attgggccaa agaaagctga tcctccctgt ctcacttatg cgtactactc acatgtaaac    540

atggtgcgag actttaattc tggtctcatt ggtgctttgc tgatatgtaa agaaggaagc    600

ctgaatgcag atggtgcaca aaaattcttc aacagagaat atgtgctgat gttttctgtg    660

tttgatgaaa gcaagaactg gtacagaaag ccctcattac agtacacaat taatgggttt    720

gccaatggaa cattgcctga tgttcaggct tgtgcttatg atcatattag ctggcatttg    780

ataggaatga gttccagtcc tgagatcttc tctgttcact tcaatggaca aaccttggaa    840

caaaaccatt acaaagtgtc aaccatcaac cttgtcggag gtgcctcagt aacagccaac    900

atgtcagtga gcaggacagg aaaatggcta atatcttctc tggttgcaaa gcatctacaa    960

gctgggatgt atggttatct taatatcaaa gactgtggaa atccagatac tttaacaaga   1020

aagttatcct ttagagaatg gaggaggatt atgaaatggg aatatttcat tgctgcagaa   1080

gaaatcacct gggattatgc tccagaaatt cctagcagtg ttgacagaag atacaaagct   1140

cagtatctgg atttttcaaa ttttattggc aagaaataca aaaaggcagt tttcaggcaa   1200

tatgaagaca gcaatttcac taaaccgacc tatgccattt ggcccaaaga acgtggaatt   1260

ctgggccccg ttatcaaagc taaagtcaga gacacagtaa caattgtatt caaaaatctg   1320

gccagtcgac cttacagcat ttatgtgcat ggagtttccg tttcaaaaga tgcagaagga   1380

gctgtttatc cttcagatcc caaagagaat ataactcatg gcaaagcagt tgaaccagga   1440

caggtctaca catataaatg gactgtgctg gatacagatg aacctacagt aaaggattct   1500

gagtgcatta ctaaattata tcatagtgct gtggacatga caagagatat tgcttcagga   1560

cttattgggc cacttctggt ttgtaaacgc aaggcactca gcatcagggg ggtacagaat   1620

aaagctgatg tggaacagca tgcagtcttc gcagtgtttg atgaaaacaa gagctggtac   1680

ttggaagaca atatcaagaa atactgcagc aatccttcca gtgttaagaa agatgaccct   1740

aaattttaca agtccaatgt tatgtacaca ctcaatggct atgcatcaga tagaacagag   1800

gtttgggggt ttcatcagtc tgaagttgtt gaatggcacc tcaccagcgt aggtacagtg   1860

gatgagattg ttccagtaca tctttctggt cacaccttct tatccaaggg aaaacatcaa   1920

gatattttaa atctttttcc catgagtggt gaatccgcta ctgtaacaat ggacaatcta   1980

ggaacctggc ttctgtcatc atggggctcc tgtgagatga gcaatggcat gagattgaga   2040

tttttggatg ccaattatga tgatgaagat gagggaaatg aagaagagga agaagatgat   2100

ggtgatattt ttgccgacat tttcaatcct ccagaagtag taataaagaa agaagaggtt   2160

cccgtaaatt ttgtaccaga cccagaatcg gatgcgctag caaaagaatt aggattattt   2220
```

-continued

```
gatgacgagg ataatccaaa acagtcacgc agtgaacaga cagaggatga tgaagaacag   2280
ctaatgatag cttcaatgct tgggcttcga tcatttaagg ggtcagttgc tgaagaagaa   2340
ttgaaacaca cagctctagc tttagaagaa gatgcccatg cttctgatcc tcgaattgac   2400
agtaatagtg cacataattc tgacgacata gctggacgct acctgcgtac tatctaccgc   2460
agaaataaaa ggaggtacta cattgcagca gaagaagttt tgtgggacta ctcaccgatc   2520
ggaaaaagtc aagtgagaag tctcccagcc aagaccacat tcaaaaaagc tattttccga   2580
agttatcttg atgatacttt ccagacacct agcactggag gagaatatga aaagcatctt   2640
ggtatactgg gtcctatcat tagggctgag gtggatgatg taatcgaagt tcagttcaga   2700
aatttggcct ctagaccata ctcacttcat gctcatggcc ttctctatga gaaatcttct   2760
gaaggcagaa gctatgacga caactctcct gaattgttca aaaaggatga tgctatcatg   2820
ccaaacggca catacacata tgtctggcaa gtccctccac ggtcaggacc aacagacaat   2880
acagaaaaat gtaaatcatg ggcctattac tctggtgtaa atccggaaaa agatattcac   2940
tctgggctta ttggacctat tttgatctgc cagaaaggca tgattgacaa gtacaacagg   3000
acaatagaca taagggaatt tgtcttgttt tttatggtct ttgatgagga gaaaagctgg   3060
tactttccaa aatctgacaa aagcacttgt gaagagaaac ttataggagt ccaatctcgc   3120
cacacatttc ctgcaattaa tgggatccct tatcagctgc aaggcttgat gatgtacaaa   3180
gatgagaatg tccactggca tttgctgaac atgggtgggc ccaaagatgt ccatgttgtt   3240
aattttcatg gtcagacatt cactgaagag ggaagggaag ataatcaact tggagtcctt   3300
cctcttcttc ctggtacatt cgcctccatc aaaatgaaac catccaaaat tggcacatgg   3360
cttttagaaa cagaagttgg tgaaaatcag gaaagaggaa tgcaggctct ctttactgtc   3420
attgacaaag attgtaaatt accaatggga ctggcaagtg ggataataca agactcacag   3480
atcagtgctt caggtcatgt tggatattgg gagcctaagc tagcaagact gaataatact   3540
ggaatgttta atgcttggag catcataaag aaggaacatg aacatccgtg gatccagatc   3600
gacctacaaa gacaagttgt catcacaggc attcagaccc agggaaccgt gcacctactg   3660
aaacattcgt atactgtgga atattttgtt acctacagca aagatgggca aaactggatt   3720
acttttaaag gaagacattc caaaacacaa atgcattttg agggtaattc agatggcacc   3780
acagtaaaag aaaaccacat tgatcctcct attattgcca gatatattag gctgcatcca   3840
accaagttct acaacacacc tactttccgc attgaactgt taggttgtga agttgaaggt   3900
tgctcagtgc cattgggaat ggaaagtggg gctatcaagg attcagagat tacagcctct   3960
tcttataaaa agacttggtg gagttcatgg gaaccattcc ttgcacgact caatctgaaa   4020
ggacgaacaa atgcttggca accaaaggta aacaacaaag atcaatggct acaaattgac   4080
ctgcaacatc ttacaaaaat aacaagcata ataactcaag gagccacatc aatgactaca   4140
tcaatgtatg tgaaaacatt ctccatccat tatactgatg acaattcaac atggaagcct   4200
tatttggatg ttcgcacttc catggaaaag gttttcacag gaaatattaa cagtgatggt   4260
catgtcaaac attttttcaa ccccccctata ttgtccaggt tcattcgtat catccctaaa   4320
acatggaatc aatatattgc actccggata gaattgtttg gttgtgaagt tttttaaggc   4380
ttggacagaa gactgtcaaa tcaagcaact tcaatgtttc aagttttctt attactaact   4440
ctgcttttta aaaggaaaca aaaacaaaag cataataaaa ctgtcttagc ataaaaaaaa   4500
ctatccttct caattttcag ccatagcttt caaatagctt tgaaaatatc aatcaaaata   4560
tcataactga agtgacgttt acaatgatta attcgtagtg ccacgtttaa tcatgaatgt   4620
```

aatcctaata caataaaatc gttattgttt ttgccccaaa aaaaaaaaaa aaaaa 4675

<210> SEQ ID NO 11
<211> LENGTH: 1458
<212> TYPE: PRT
<213> ORGANISM: Oxyuranus scutellatus scutellatus

<400> SEQUENCE: 11

Met Gly Arg Tyr Ser Val Ser Pro Val Pro Lys Cys Leu Leu Leu Met
1 5 10 15

Phe Leu Gly Trp Ser Gly Leu Lys Tyr Tyr Gln Val Asn Ala Ala Gln
20 25 30

Leu Arg Glu Tyr Arg Ile Ala Ala Gln Leu Glu Asp Trp Asp Tyr Asn
35 40 45

Pro Gln Pro Glu Glu Leu Ser Arg Leu Ser Glu Ser Asp Leu Thr Phe
50 55 60

Lys Lys Ile Val Tyr Arg Glu Tyr Glu Leu Asp Phe Lys Gln Glu Lys
65 70 75 80

Pro Arg Asp Glu Leu Ser Gly Leu Leu Gly Pro Thr Leu Arg Gly Glu
85 90 95

Val Gly Asp Ser Leu Ile Ile Tyr Phe Lys Asn Phe Ala Thr Gln Pro
100 105 110

Val Ser Ile His Pro Gln Ser Ala Val Tyr Asn Lys Trp Ser Glu Gly
115 120 125

Ser Ser Tyr Ser Asp Gly Thr Ser Asp Val Glu Arg Leu Asp Asp Ala
130 135 140

Val Pro Pro Gly Gln Ser Phe Lys Tyr Val Trp Asn Ile Thr Ala Glu
145 150 155 160

Ile Gly Pro Lys Lys Ala Asp Pro Pro Cys Leu Thr Tyr Ala Tyr Tyr
165 170 175

Ser His Val Asn Met Val Arg Asp Phe Asn Ser Gly Leu Ile Gly Ala
180 185 190

Leu Leu Ile Cys Lys Glu Gly Ser Leu Asn Ala Asp Gly Ala Gln Lys
195 200 205

Phe Phe Asn Arg Glu Tyr Val Leu Met Phe Ser Val Phe Asp Glu Ser
210 215 220

Lys Asn Trp Tyr Arg Lys Pro Ser Leu Gln Tyr Thr Ile Asn Gly Phe
225 230 235 240

Ala Asn Gly Thr Leu Pro Asp Val Gln Ala Cys Ala Tyr Asp His Ile
245 250 255

Ser Trp His Leu Ile Gly Met Ser Ser Ser Pro Glu Ile Phe Ser Val
260 265 270

His Phe Asn Gly Gln Thr Leu Glu Gln Asn His Tyr Lys Val Ser Thr
275 280 285

Ile Asn Leu Val Gly Gly Ala Ser Val Thr Ala Asn Met Ser Val Ser
290 295 300

Arg Thr Gly Lys Trp Leu Ile Ser Ser Leu Val Ala Lys His Leu Gln
305 310 315 320

Ala Gly Met Tyr Gly Tyr Leu Asn Ile Lys Asp Cys Gly Asn Pro Asp
325 330 335

Thr Leu Thr Arg Lys Leu Ser Phe Arg Glu Trp Arg Arg Ile Met Lys
340 345 350

Trp Glu Tyr Phe Ile Ala Ala Glu Glu Ile Thr Trp Asp Tyr Ala Pro
355 360 365

-continued

```
Glu Ile Pro Ser Ser Val Asp Arg Arg Tyr Lys Ala Gln Tyr Leu Asp
    370                 375                 380

Phe Ser Asn Phe Ile Gly Lys Lys Tyr Lys Lys Ala Val Phe Arg Gln
385                 390                 395                 400

Tyr Glu Asp Ser Asn Phe Thr Lys Pro Thr Tyr Ala Ile Trp Pro Lys
                405                 410                 415

Glu Arg Gly Ile Leu Gly Pro Val Ile Lys Ala Lys Val Arg Asp Thr
            420                 425                 430

Val Thr Ile Val Phe Lys Asn Leu Ala Ser Arg Pro Tyr Ser Ile Tyr
        435                 440                 445

Val His Gly Val Ser Val Ser Lys Asp Ala Glu Gly Ala Val Tyr Pro
    450                 455                 460

Ser Asp Pro Lys Glu Asn Ile Thr His Gly Lys Ala Val Glu Pro Gly
465                 470                 475                 480

Gln Val Tyr Thr Tyr Lys Trp Thr Val Leu Asp Thr Asp Glu Pro Thr
                485                 490                 495

Val Lys Asp Ser Glu Cys Ile Thr Lys Leu Tyr His Ser Ala Val Asp
            500                 505                 510

Met Thr Arg Asp Ile Ala Ser Gly Leu Ile Gly Pro Leu Leu Val Cys
        515                 520                 525

Lys Arg Lys Ala Leu Ser Ile Arg Gly Val Gln Asn Lys Ala Asp Val
    530                 535                 540

Glu Gln His Ala Val Phe Ala Val Phe Asp Glu Asn Lys Ser Trp Tyr
545                 550                 555                 560

Leu Glu Asp Asn Ile Lys Lys Tyr Cys Ser Asn Pro Ser Ser Val Lys
                565                 570                 575

Lys Asp Asp Pro Lys Phe Tyr Lys Ser Asn Val Met Tyr Thr Leu Asn
            580                 585                 590

Gly Tyr Ala Ser Asp Arg Thr Glu Val Trp Gly Phe His Gln Ser Glu
        595                 600                 605

Val Val Glu Trp His Leu Thr Ser Val Gly Thr Val Asp Glu Ile Val
    610                 615                 620

Pro Val His Leu Ser Gly His Thr Phe Leu Ser Lys Gly Lys His Gln
625                 630                 635                 640

Asp Ile Leu Asn Leu Phe Pro Met Ser Gly Glu Ser Ala Thr Val Thr
                645                 650                 655

Met Asp Asn Leu Gly Thr Trp Leu Leu Ser Ser Trp Gly Ser Cys Glu
            660                 665                 670

Met Ser Asn Gly Met Arg Leu Arg Phe Leu Asp Ala Asn Tyr Asp Asp
        675                 680                 685

Glu Asp Glu Gly Asn Glu Glu Glu Glu Glu Asp Asp Gly Asp Ile Phe
    690                 695                 700

Ala Asp Ile Phe Asn Pro Pro Glu Val Val Ile Lys Lys Glu Glu Val
705                 710                 715                 720

Pro Val Asn Phe Val Pro Asp Pro Glu Ser Asp Ala Leu Ala Lys Glu
                725                 730                 735

Leu Gly Leu Phe Asp Asp Glu Asp Asn Pro Lys Gln Ser Arg Ser Glu
            740                 745                 750

Gln Thr Glu Asp Asp Glu Glu Gln Leu Met Ile Ala Ser Met Leu Gly
        755                 760                 765

Leu Arg Ser Phe Lys Gly Ser Val Ala Glu Glu Glu Leu Lys His Thr
    770                 775                 780
```

-continued

```
Ala Leu Ala Leu Glu Glu Asp Ala His Ala Ser Asp Pro Arg Ile Asp
785                 790                 795                 800

Ser Asn Ser Ala His Asn Ser Asp Asp Ile Ala Gly Arg Tyr Leu Arg
                805                 810                 815

Thr Ile Tyr Arg Arg Asn Lys Arg Arg Tyr Tyr Ile Ala Ala Glu Glu
            820                 825                 830

Val Leu Trp Asp Tyr Ser Pro Ile Gly Lys Ser Gln Val Arg Ser Leu
        835                 840                 845

Pro Ala Lys Thr Thr Phe Lys Lys Ala Ile Phe Arg Ser Tyr Leu Asp
    850                 855                 860

Asp Thr Phe Gln Thr Pro Ser Thr Gly Gly Glu Tyr Glu Lys His Leu
865                 870                 875                 880

Gly Ile Leu Gly Pro Ile Ile Arg Ala Glu Val Asp Asp Val Ile Glu
                885                 890                 895

Val Gln Phe Arg Asn Leu Ala Ser Arg Pro Tyr Ser Leu His Ala His
            900                 905                 910

Gly Leu Leu Tyr Glu Lys Ser Ser Glu Gly Arg Ser Tyr Asp Asp Asn
        915                 920                 925

Ser Pro Glu Leu Phe Lys Lys Asp Asp Ala Ile Met Pro Asn Gly Thr
    930                 935                 940

Tyr Thr Tyr Val Trp Gln Val Pro Pro Arg Ser Gly Pro Thr Asp Asn
945                 950                 955                 960

Thr Glu Lys Cys Lys Ser Trp Ala Tyr Tyr Ser Gly Val Asn Pro Glu
                965                 970                 975

Lys Asp Ile His Ser Gly Leu Ile Gly Pro Ile Leu Ile Cys Gln Lys
            980                 985                 990

Gly Met Ile Asp Lys Tyr Asn Arg  Thr Ile Asp Ile Arg  Glu Phe Val
        995                 1000                1005

Leu Phe  Phe Met Val Phe Asp  Glu Glu Lys Ser Trp  Tyr Phe Pro
    1010                1015                1020

Lys Ser  Asp Lys Ser Thr Cys  Glu Glu Lys Leu Ile  Gly Val Gln
    1025                1030                1035

Ser Arg  His Thr Phe Pro Ala  Ile Asn Gly Ile Pro  Tyr Gln Leu
    1040                1045                1050

Gln Gly  Leu Met Met Tyr Lys  Asp Glu Asn Val His  Trp His Leu
    1055                1060                1065

Leu Asn  Met Gly Gly Pro Lys  Asp Val His Val Val  Asn Phe His
    1070                1075                1080

Gly Gln  Thr Phe Thr Glu Glu  Gly Arg Glu Asp Asn  Gln Leu Gly
    1085                1090                1095

Val Leu  Pro Leu Leu Pro Gly  Thr Phe Ala Ser Ile  Lys Met Lys
    1100                1105                1110

Pro Ser  Lys Ile Gly Thr Trp  Leu Leu Glu Thr Glu  Val Gly Glu
    1115                1120                1125

Asn Gln  Glu Arg Gly Met Gln  Ala Leu Phe Thr Val  Ile Asp Lys
    1130                1135                1140

Asp Cys  Lys Leu Pro Met Gly  Leu Ala Ser Gly Ile  Ile Gln Asp
    1145                1150                1155

Ser Gln  Ile Ser Ala Ser Gly  His Val Gly Tyr Trp  Glu Pro Lys
    1160                1165                1170

Leu Ala  Arg Leu Asn Asn Thr  Gly Met Phe Asn Ala  Trp Ser Ile
    1175                1180                1185

Ile Lys  Lys Glu His Glu His  Pro Trp Ile Gln Ile  Asp Leu Gln
```

-continued 1190 1195 1200

Arg Gln Val Val Ile Thr Gly Ile Gln Thr Gln Gly Thr Val His
1205 1210 1215

Leu Leu Lys His Ser Tyr Thr Val Glu Tyr Phe Val Thr Tyr Ser
1220 1225 1230

Lys Asp Gly Gln Asn Trp Ile Thr Phe Lys Gly Arg His Ser Lys
1235 1240 1245

Thr Gln Met His Phe Glu Gly Asn Ser Asp Gly Thr Thr Val Lys
1250 1255 1260

Glu Asn His Ile Asp Pro Pro Ile Ile Ala Arg Tyr Ile Arg Leu
1265 1270 1275

His Pro Thr Lys Phe Tyr Asn Thr Pro Thr Phe Arg Ile Glu Leu
1280 1285 1290

Leu Gly Cys Glu Val Glu Gly Cys Ser Val Pro Leu Gly Met Glu
1295 1300 1305

Ser Gly Ala Ile Lys Asp Ser Glu Ile Thr Ala Ser Ser Tyr Lys
1310 1315 1320

Lys Thr Trp Trp Ser Ser Trp Glu Pro Phe Leu Ala Arg Leu Asn
1325 1330 1335

Leu Lys Gly Arg Thr Asn Ala Trp Gln Pro Lys Val Asn Asn Lys
1340 1345 1350

Asp Gln Trp Leu Gln Ile Asp Leu Gln His Leu Thr Lys Ile Thr
1355 1360 1365

Ser Ile Ile Thr Gln Gly Ala Thr Ser Met Thr Thr Ser Met Tyr
1370 1375 1380

Val Lys Thr Phe Ser Ile His Tyr Thr Asp Asp Asn Ser Thr Trp
1385 1390 1395

Lys Pro Tyr Leu Asp Val Arg Thr Ser Met Glu Lys Val Phe Thr
1400 1405 1410

Gly Asn Ile Asn Ser Asp Gly His Val Lys His Phe Phe Asn Pro
1415 1420 1425

Pro Ile Leu Ser Arg Phe Ile Arg Ile Ile Pro Lys Thr Trp Asn
1430 1435 1440

Gln Tyr Ile Ala Leu Arg Ile Glu Leu Phe Gly Cys Glu Val Phe
1445 1450 1455

<210> SEQ ID NO 12
<211> LENGTH: 1459
<212> TYPE: PRT
<213> ORGANISM: Oxyuranus scutellatus

<400> SEQUENCE: 12

Met Gly Arg Tyr Ser Val Ser Pro Val Pro Lys Cys Leu Leu Leu Met
1 5 10 15

Phe Leu Gly Trp Ser Gly Leu Lys Tyr Tyr Gln Val Asn Ala Ala Gln
20 25 30

Leu Arg Glu Tyr Arg Leu Ala Ala Gln Leu Glu Asp Trp Asp Tyr Asn
35 40 45

Pro Gln Pro Glu Glu Leu Ser Arg Leu Ser Glu Ser Asp Leu Thr Phe
50 55 60

Lys Lys Ile Val Tyr Arg Glu Tyr Glu Leu Asp Phe Lys Gln Glu Lys
65 70 75 80

Pro Arg Asp Glu Leu Ser Gly Leu Leu Gly Pro Thr Leu Arg Gly Glu
85 90 95

```
Val Gly Asp Ser Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asp Gly Ala Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240

Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly Asn Pro Asp
                325                 330                 335

Thr Leu Thr Arg Lys Leu Ser Phe Arg Glu Arg Arg Arg Ile Met Lys
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Glu Asp Ser Asn Phe Thr Lys Pro Thr Tyr Ala Ile Trp Pro
                405                 410                 415

Lys Glu Arg Gly Ile Leu Gly Pro Val Ile Lys Ala Lys Val Arg Asp
            420                 425                 430

Thr Val Thr Ile Val Phe Lys Asn Leu Ala Ser Arg Pro Tyr Ser Ile
        435                 440                 445

Tyr Val His Gly Val Ser Val Ser Lys Asp Ala Glu Gly Ala Val Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510

Asp Met Thr Arg Asp Ile Ala Ser Gly Leu Ile Gly Pro Pro Leu Val
```

```
        515                 520                 525

Cys Lys Arg Lys Ala Leu Ser Ile Arg Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Ser Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Trp Gly Phe His Gln Ser
        595                 600                 605

Glu Val Val Glu Trp His Leu Thr Ser Val Gly Thr Val Asp Glu Ile
    610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Glu Glu Asp Asp Gly Asp Ile
    690                 695                 700

Phe Ala Asp Ile Phe Asn Pro Pro Glu Val Val Ile Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Phe Asp Asp Glu Asp Asn Pro Lys Gln Ser Arg Ser
            740                 745                 750

Glu Gln Thr Glu Asp Asp Glu Glu Gln Leu Met Ile Ala Ser Met Leu
        755                 760                 765

Gly Leu Arg Ser Phe Lys Gly Ser Val Ala Glu Glu Glu Leu Lys His
    770                 775                 780

Thr Ala Leu Ala Leu Glu Glu Asp Ala His Ala Ser Asp Pro Arg Ile
785                 790                 795                 800

Asp Ser Asn Ser Ala His Asn Ser Asp Asp Ile Ala Gly Arg Tyr Leu
                805                 810                 815

Arg Thr Ile Asn Arg Arg Asn Lys Arg Arg Tyr Tyr Ile Ala Ala Glu
            820                 825                 830

Glu Val Leu Trp Asp Tyr Ser Pro Ile Gly Lys Ser Gln Val Arg Ser
        835                 840                 845

Leu Pro Ala Lys Thr Thr Phe Lys Lys Ala Ile Phe Arg Ser Tyr Leu
    850                 855                 860

Asp Asp Thr Phe Gln Thr Pro Ser Thr Gly Gly Glu Tyr Glu Lys His
865                 870                 875                 880

Leu Gly Ile Leu Gly Pro Ile Ile Arg Ala Glu Val Asp Asp Val Ile
                885                 890                 895

Glu Val Gln Phe Arg Asn Leu Ala Ser Arg Pro Tyr Ser Leu His Ala
            900                 905                 910

His Gly Leu Leu Tyr Glu Lys Ser Ser Glu Gly Arg Ser Tyr Asp Asp
        915                 920                 925

Asn Ser Pro Glu Leu Phe Lys Lys Asp Asp Ala Ile Met Pro Asn Gly
    930                 935                 940
```

-continued

Thr Tyr Thr Tyr Val Trp Gln Val Pro Pro Arg Ser Gly Pro Thr Asp
945 950 955 960

Asn Thr Glu Lys Cys Lys Ser Trp Ala Tyr Tyr Ser Gly Val Asn Pro
965 970 975

Glu Lys Asp Ile His Ser Gly Leu Ile Gly Pro Ile Leu Ile Cys Gln
980 985 990

Lys Gly Met Ile Asp Lys Tyr Asn Arg Thr Ile Asp Ile Arg Glu Phe
995 1000 1005

Val Leu Phe Phe Met Val Phe Asp Glu Glu Lys Ser Trp Tyr Phe
1010 1015 1020

Pro Lys Ser Asp Lys Ser Thr Cys Glu Glu Lys Leu Ile Gly Val
1025 1030 1035

Gln Ser Arg His Thr Phe Pro Ala Ile Asn Gly Ile Pro Tyr Gln
1040 1045 1050

Leu Gln Gly Leu Met Met Tyr Lys Asp Glu Asn Val His Trp His
1055 1060 1065

Leu Leu Asn Met Gly Gly Pro Lys Asp Val His Val Val Asn Phe
1070 1075 1080

His Gly Gln Thr Phe Thr Glu Glu Gly Arg Glu Asp Asn Gln Leu
1085 1090 1095

Gly Val Leu Pro Leu Leu Pro Gly Thr Phe Ala Ser Ile Lys Met
1100 1105 1110

Lys Pro Ser Lys Ile Gly Thr Trp Leu Leu Glu Thr Glu Val Gly
1115 1120 1125

Glu Asn Gln Glu Arg Gly Met Gln Ala Leu Phe Thr Val Ile Asp
1130 1135 1140

Lys Asp Cys Lys Leu Pro Met Gly Leu Ala Ser Gly Ile Ile Gln
1145 1150 1155

Asp Ser Gln Ile Ser Ala Ser Gly His Val Gly Tyr Trp Glu Pro
1160 1165 1170

Lys Leu Ala Arg Leu Asn Asn Thr Gly Met Phe Asn Ala Trp Ser
1175 1180 1185

Ile Ile Lys Lys Glu His Glu His Pro Trp Ile Gln Ile Asp Leu
1190 1195 1200

Gln Arg Gln Val Val Ile Thr Gly Ile Gln Thr Gln Gly Thr Val
1205 1210 1215

Gln Leu Leu Lys His Ser Tyr Thr Val Glu Tyr Phe Val Thr Tyr
1220 1225 1230

Ser Lys Asp Gly Gln Asn Trp Ile Thr Phe Lys Gly Arg His Ser
1235 1240 1245

Lys Thr Gln Met His Phe Glu Gly Asn Ser Asp Gly Thr Thr Val
1250 1255 1260

Lys Glu Asn His Ile Asp Pro Pro Ile Ile Ala Arg Tyr Ile Arg
1265 1270 1275

Leu His Pro Thr Lys Phe Tyr Asn Thr Pro Thr Phe Arg Ile Glu
1280 1285 1290

Leu Leu Gly Cys Glu Val Glu Gly Cys Ser Val Pro Leu Gly Met
1295 1300 1305

Glu Ser Gly Ala Ile Lys Asp Ser Glu Ile Thr Ala Ser Ser Tyr
1310 1315 1320

Lys Lys Thr Trp Trp Ser Ser Trp Glu Pro Phe Leu Ala Arg Leu
1325 1330 1335

```
Asn Leu  Lys Gly Arg Thr Asn  Ala Trp Gln Pro Lys  Val Asn Asn
    1340                 1345                 1350

Lys Asp  Gln Trp Leu Gln Ile  Asp Leu Gln His Leu  Thr Lys Ile
    1355                 1360                 1365

Thr Ser  Ile Ile Thr Gln Gly  Ala Thr Ser Met Thr  Thr Ser Met
    1370                 1375                 1380

Tyr Val  Lys Thr Phe Ser Ile  His Tyr Thr Asp Asp  Asn Ser Thr
    1385                 1390                 1395

Trp Lys  Pro Tyr Leu Asp Val  Arg Thr Ser Met Glu  Lys Val Phe
    1400                 1405                 1410

Thr Gly  Asn Ile Asn Ser Asp  Gly His Val Lys His  Phe Phe Asn
    1415                 1420                 1425

Pro Pro  Ile Leu Ser Arg Phe  Ile Arg Ile Ile Pro  Lys Thr Trp
    1430                 1435                 1440

Asn Gln  Tyr Ile Ala Leu Arg  Ile Glu Leu Phe Gly  Cys Glu Val
    1445                 1450                 1455

Phe


<210> SEQ ID NO 13
<211> LENGTH: 1460
<212> TYPE: PRT
<213> ORGANISM: Oxyuranus scutellatus

<400> SEQUENCE: 13

Met Gly Arg Tyr Ser Val Ser Pro Val Pro Lys Cys Leu Leu Leu Met
1               5                   10                  15

Phe Leu Gly Trp Ser Gly Leu Lys Tyr Tyr Gln Val Asn Ala Ala Gln
            20                  25                  30

Leu Arg Glu Tyr Arg Ile Ala Ala Gln Leu Glu Asp Trp Asp Tyr Asn
        35                  40                  45

Pro Gln Pro Glu Glu Leu Ser Arg Leu Ser Glu Ser Glu Leu Thr Phe
    50                  55                  60

Lys Lys Ile Val Tyr Arg Glu Tyr Glu Leu Asp Phe Lys Gln Glu Lys
65                  70                  75                  80

Pro Arg Asp Glu Leu Ser Gly Leu Leu Gly Pro Thr Leu Arg Gly Glu
                85                  90                  95

Val Gly Asp Ile Leu Ile Ile Tyr Phe Lys Asn Phe Ala Thr Gln Pro
            100                 105                 110

Val Ser Ile His Pro Gln Ser Ala Val Tyr Asn Lys Trp Ser Glu Gly
        115                 120                 125

Ser Ser Tyr Ser Asp Gly Thr Ser Asp Val Glu Arg Leu Asp Asp Ala
    130                 135                 140

Val Pro Pro Gly Gln Ser Phe Lys Tyr Val Trp Asn Ile Thr Ala Glu
145                 150                 155                 160

Ile Gly Pro Lys Lys Ala Asp Pro Pro Cys Leu Thr Tyr Ala Tyr Tyr
                165                 170                 175

Ser His Val Asn Met Val Arg Asp Phe Asn Ser Gly Leu Ile Gly Ala
            180                 185                 190

Leu Leu Ile Cys Lys Glu Gly Ser Leu Asn Ala Asn Gly Ala Gln Lys
        195                 200                 205

Phe Phe Asn Arg Glu Tyr Val Leu Met Phe Ser Val Phe Asp Glu Ser
    210                 215                 220

Lys Asn Trp Tyr Arg Lys Pro Ser Leu Gln Tyr Thr Ile Asn Gly Phe
225                 230                 235                 240
```

-continued

```
Ala Asn Gly Thr Leu Pro Asp Val Gln Ala Cys Ala Tyr Asp His Ile
                245                 250                 255

Ser Trp His Leu Ile Gly Met Ser Ser Ser Pro Glu Ile Phe Ser Val
            260                 265                 270

His Phe Asn Gly Gln Thr Leu Glu Gln Asn His Tyr Lys Val Ser Thr
        275                 280                 285

Ile Asn Leu Val Gly Gly Ala Ser Val Thr Ala Asn Met Ser Val Ser
    290                 295                 300

Arg Thr Gly Lys Trp Leu Ile Ser Ser Leu Val Ala Lys His Leu Gln
305                 310                 315                 320

Ala Gly Met Tyr Gly Tyr Leu Asn Ile Lys Asp Cys Gly His Pro Asn
                325                 330                 335

Thr Leu Thr Arg Lys Leu Ser Phe Arg Glu Leu Arg Arg Ile Met Asn
            340                 345                 350

Trp Glu Tyr Phe Ile Ala Ala Glu Glu Ile Thr Trp Asp Tyr Ala Pro
        355                 360                 365

Glu Ile Pro Ser Ser Val Asp Arg Arg Tyr Lys Ala Gln Tyr Leu Asp
    370                 375                 380

Asn Phe Ser Asn Phe Ile Gly Lys Lys Tyr Lys Lys Ala Val Phe Arg
385                 390                 395                 400

Gln Tyr Glu Asp Gly Asn Phe Thr Lys Pro Thr Tyr Ala Ile Trp Pro
                405                 410                 415

Lys Glu Arg Gly Ile Leu Gly Pro Val Ile Lys Ala Lys Val Arg Asp
            420                 425                 430

Thr Val Thr Ile Val Phe Lys Asn Leu Ala Ser Arg Pro Tyr Ser Ile
        435                 440                 445

Tyr Val His Gly Val Ser Val Ser Lys Asp Ala Glu Gly Ala Ile Tyr
    450                 455                 460

Pro Ser Asp Pro Lys Glu Asn Ile Thr His Gly Lys Ala Val Glu Pro
465                 470                 475                 480

Gly Gln Val Tyr Thr Tyr Lys Trp Thr Val Leu Asp Thr Asp Glu Pro
                485                 490                 495

Thr Val Lys Asp Ser Glu Cys Ile Thr Lys Leu Tyr His Ser Ala Val
            500                 505                 510

Asp Met Thr Arg Asp Ile Ala Ser Gly Leu Ile Gly Pro Leu Leu Val
        515                 520                 525

Cys Lys Leu Lys Ala Leu Ser Val Lys Gly Val Gln Asn Lys Ala Asp
    530                 535                 540

Val Glu Gln His Ala Val Phe Ala Val Phe Asp Glu Asn Lys Ser Trp
545                 550                 555                 560

Tyr Leu Glu Asp Asn Ile Lys Lys Tyr Cys Ser Asn Pro Ser Ser Val
                565                 570                 575

Lys Lys Asp Asp Pro Lys Phe Tyr Lys Ser Asn Val Met Tyr Thr Leu
            580                 585                 590

Asn Gly Tyr Ala Ser Asp Arg Thr Glu Val Leu Gly Phe His Gln Ser
        595                 600                 605

Glu Val Val Gln Trp His Leu Thr Ser Val Gly Thr Val Asp Glu Ile
    610                 615                 620

Val Pro Val His Leu Ser Gly His Thr Phe Leu Ser Lys Gly Lys His
625                 630                 635                 640

Gln Asp Ile Leu Asn Leu Phe Pro Met Ser Gly Glu Ser Ala Thr Val
                645                 650                 655

Thr Met Asp Asn Leu Gly Thr Trp Leu Leu Ser Ser Trp Gly Ser Cys
```

```
            660                 665                 670

Glu Met Ser Asn Gly Met Arg Leu Arg Phe Leu Asp Ala Asn Tyr Asp
        675                 680                 685

Asp Glu Asp Glu Gly Asn Glu Glu Glu Glu Glu Asp Asp Gly Asp Ile
    690                 695                 700

Phe Ala Asp Ile Phe Ser Pro Pro Glu Val Val Lys Lys Lys Glu Glu
705                 710                 715                 720

Val Pro Val Asn Phe Val Pro Asp Pro Glu Ser Asp Ala Leu Ala Lys
                725                 730                 735

Glu Leu Gly Leu Leu Asp Asp Glu Asp Asn Pro Glu Gln Ser Arg Ser
            740                 745                 750

Glu Gln Thr Glu Asp Asp Glu Glu Gln Leu Met Ile Ala Ser Val Leu
        755                 760                 765

Gly Leu Arg Ser Phe Lys Gly Ser Val Ala Glu Glu Glu Leu Lys His
    770                 775                 780

Thr Ala Leu Ala Leu Glu Glu Asp Ala His Ala Ser Asp Pro Arg Ile
785                 790                 795                 800

Asp Ser Asn Ser Ala Arg Asn Ser Asp Asp Ile Ala Gly Arg Tyr Leu
                805                 810                 815

Arg Thr Ile Asn Arg Arg Asn Lys Arg Arg Tyr Tyr Ile Ala Ala Glu
            820                 825                 830

Glu Val Leu Trp Asp Tyr Ser Pro Ile Gly Lys Ser Gln Val Arg Ser
        835                 840                 845

Leu Pro Ala Lys Thr Thr Phe Lys Lys Ala Ile Phe Arg Ser Tyr Leu
    850                 855                 860

Asp Asp Thr Phe Gln Thr Pro Ser Thr Gly Gly Glu Tyr Glu Lys His
865                 870                 875                 880

Leu Gly Ile Leu Gly Pro Ile Ile Arg Ala Glu Val Asp Asp Val Ile
                885                 890                 895

Glu Val Gln Phe Arg Asn Leu Ala Ser Arg Pro Tyr Ser Leu His Ala
            900                 905                 910

His Gly Leu Leu Tyr Glu Lys Ser Ser Glu Gly Arg Ser Tyr Asp Asp
        915                 920                 925

Asn Ser Pro Glu Leu Phe Lys Lys Asp Asp Ala Ile Met Pro Asn Gly
    930                 935                 940

Thr Tyr Thr Tyr Val Trp Gln Val Pro Pro Arg Ser Gly Pro Thr Asp
945                 950                 955                 960

Asn Thr Glu Lys Cys Lys Ser Trp Ala Tyr Tyr Ser Gly Val Asn Pro
                965                 970                 975

Glu Lys Asp Ile His Ser Gly Leu Ile Gly Pro Ile Leu Ile Cys Gln
            980                 985                 990

Lys Gly Met Ile Asp Lys Tyr Asn  Arg Thr Ile Asp Ile  Arg Glu Phe
        995                 1000                1005

Val Leu  Phe Phe Met Val Phe  Asp Glu Glu Lys Ser  Trp Tyr Phe
    1010                1015                1020

Pro Lys  Ser Asp Lys Ser Thr  Cys Glu Glu Lys Leu  Ile Gly Val
    1025                1030                1035

Gln Ser  Ser His His Thr Phe  Pro Ala Ile Asn Gly  Ile Pro Tyr
    1040                1045                1050

Gln Leu  Gln Gly Leu Met Met  Tyr Lys Asp Glu Asn  Val His Trp
    1055                1060                1065

His Leu  Leu Asn Met Gly Gly  Pro Lys Asp Ile His  Val Val Asn
    1070                1075                1080
```

```
Phe His  Gly Gln Thr Phe Thr  Glu Glu Gly Arg Glu  Asp Asn Gln
    1085                 1090                 1095

Leu Gly  Val Leu Pro Leu Leu  Pro Gly Thr Phe Ala  Ser Ile Lys
    1100                 1105                 1110

Met Lys  Pro Ser Lys Ile Gly  Thr Trp Leu Leu Glu  Thr Glu Val
    1115                 1120                 1125

Gly Glu  Asn Gln Glu Arg Gly  Met Gln Ala Leu Phe  Thr Val Ile
    1130                 1135                 1140

Asp Lys  Asp Cys Lys Leu Pro  Met Gly Leu Ala Ser  Gly Ile Ile
    1145                 1150                 1155

Gln Asp  Ser Gln Ile Ser Ala  Ser Gly His Val Glu  Tyr Trp Glu
    1160                 1165                 1170

Pro Lys  Leu Ala Arg Leu Asn  Asn Thr Gly Met Phe  Asn Ala Trp
    1175                 1180                 1185

Ser Ile  Ile Lys Lys Glu His  Glu His Pro Trp Ile  Gln Ile Asp
    1190                 1195                 1200

Leu Gln  Arg Gln Val Val Ile  Thr Gly Ile Gln Thr  Gln Gly Thr
    1205                 1210                 1215

Val Gln  Leu Leu Lys His Ser  Tyr Thr Val Glu Tyr  Phe Val Thr
    1220                 1225                 1230

Tyr Ser  Lys Asp Gly Gln Asn  Trp Ile Thr Phe Lys  Gly Arg His
    1235                 1240                 1245

Ser Glu  Thr Gln Met His Phe  Glu Gly Asn Ser Asp  Gly Thr Thr
    1250                 1255                 1260

Val Lys  Glu Asn His Ile Asp  Pro Pro Ile Ile Ala  Arg Tyr Ile
    1265                 1270                 1275

Arg Leu  His Pro Thr Lys Phe  Tyr Asn Thr Pro Thr  Phe Arg Ile
    1280                 1285                 1290

Glu Leu  Leu Gly Cys Glu Val  Glu Gly Cys Ser Val  Pro Leu Gly
    1295                 1300                 1305

Met Glu  Ser Gly Ala Ile Lys  Asn Ser Glu Ile Thr  Ala Ser Ser
    1310                 1315                 1320

Tyr Lys  Lys Thr Trp Trp Ser  Ser Trp Glu Pro Phe  Leu Ala Arg
    1325                 1330                 1335

Leu Asn  Leu Glu Gly Gly Thr  Asn Ala Trp Gln Pro  Glu Val Asn
    1340                 1345                 1350

Asn Lys  Asp Gln Trp Leu Gln  Ile Asp Leu Gln His  Leu Thr Lys
    1355                 1360                 1365

Ile Thr  Ser Ile Ile Thr Gln  Gly Ala Thr Ser Met  Thr Thr Ala
    1370                 1375                 1380

Met Tyr  Val Lys Thr Phe Ser  Ile His Tyr Thr Asp  Asp Asn Ser
    1385                 1390                 1395

Thr Trp  Lys Pro Tyr Leu Asp  Val Arg Thr Ser Met  Glu Lys Val
    1400                 1405                 1410

Phe Thr  Gly Asn Ile Asn Ser  Asp Gly His Val Lys  His Phe Phe
    1415                 1420                 1425

Lys Pro  Pro Ile Leu Ser Arg  Phe Ile Arg Ile Ile  Pro Lys Thr
    1430                 1435                 1440

Trp Asn  Gln Tyr Ile Ala Leu  Arg Ile Glu Leu Phe  Gly Cys Glu
    1445                 1450                 1455

Val Phe
    1460
```

<210> SEQ ID NO 14
<211> LENGTH: 4383
<212> TYPE: DNA
<213> ORGANISM: Oxyuranus microlepidotus

<400> SEQUENCE: 14
atgggaagat acagtgtgag ccctgtcccc aaatgtcttc tactgatgtt cctgggttgg 60
tcagggctga agtattacca agtgaatgca gctcagctca gggagtaccg tatagctgct 120
cagctggaag actgggatta caacccccaa cctgaggagc tatccagatt atcagagtca 180
gagcttacgt ttaaaaaaat tgtctataga gaatatgaac tagatttcaa acaagagaag 240
ccaagagatg agctctcagg gctcctaggg ccaacactac gtggagaagt gggagacatc 300
ctcataattt atttcaagaa ttttgctact cagcctgtga gcattcaccc gcagagtgcc 360
gtgtacaaca aatggtcaga aggttcttca tattctgatg gaacatcaga tgtggaaaga 420
ctggatgatg ctgtgcctcc aggccagtcg ttcaagtatg tgtggaatat cactgcagaa 480
attgggccaa agaaagctga tcctccctgt ctcacttatg cgtactactc acatgtaaac 540
atggtgcgag actttaattc tggtctcatt ggtgctttgc tgatatgtaa agaaggaagc 600
ctgaatgcaa atggtgcaca aaaattcttc aacagagaat atgtgctgat gttttctgtg 660
tttgatgaaa gcaagaactg gtacagaaag ccctcactac agtacacaat taatgggttt 720
gccaatggaa cattgcctga tgttcaggct tgtgcttatg atcatattag ctggcatttg 780
ataggaatga gttccagtcc tgagatcttc tctgttcact tcaatggaca aaccttggaa 840
caaaaccatt acaaagtgtc aaccatcaac cttgtcggag gtgcctcagt aacagccaac 900
atgtcagtga gcaggacagg aaaatggcta atatcttctc tggttgcaaa gcatctacaa 960
gctgggatgt atggttatct aaatatcaaa gactgtggac atccaaatac tttaacaaga 1020
aagttatcct ttagagaact gaggaggatt atgaactggg aatatttcat tgctgcagaa 1080
gaaatcacct gggattatgc tccagaaatt cctagcagtg ttgacagaag atacaaagct 1140
cagtatctgg ataatttttc aaattttatt ggcaagaaat acaaaaaggc agttttcagg 1200
caatatgaag acggcaattt cactaaaccg acctatgcca tttggcccaa agaacgtgga 1260
attctgggcc ccgttatcaa agctaaagtc agagacacag taacaattgt attcaaaaat 1320
ctggccagtc gacccttacag catttatgtg catggagttt ccgtttcaaa agatgcagaa 1380
ggagctattt atccttcaga tcccaaagag aatataactc atggcaaagc agttgaacca 1440
ggacaggtct acacatataa atggactgtg ctggatacag atgaacctac agtaaaggat 1500
tctgagtgta ttactaaatt atatcatagt gctgtggaca tgacaagaga tattgcttca 1560
ggacttattg ggccacttct ggtttgtaaa ctcaaggcac tcagcgtcaa gggggtacag 1620
aataaagctg atgtggaaca gcatgcagtc ttcgcagtgt ttgatgaaaa taagagctgg 1680
tacttggaag acaatatcaa gaaatactgc agcaatcctt ccagtgttaa gaaagatgac 1740
cctaaatttt acaagtccaa tgttatgtac acactcaatg gctatgcatc agatagaaca 1800
gaggttttgg ggtttcatca gtctgaagtt gttcaatggc acctcaccag cgtaggtaca 1860
gtggatgaga ttgttccagt acatctttct ggtcacacct tcttatccaa gggaaaacat 1920
caagatattt taaatctttt tcccatgagt ggtgaatcgg ctactgtaac aatggacaat 1980
ctaggaacct ggcttctgtc atcatggggc tcctgtgaga tgagcaatgg catgagattg 2040
agatttttgg atgccaatta tgatgatgaa gatgagggaa atgaagaaga ggaagaagat 2100
gatggtgata tttttgccga cattttcagt cctccagaag tagtaaaaaa gaaagaagag 2160

-continued

```
gttcccgtaa attttgtacc agacccagaa tcggatgcgc tagcaaaaga attaggatta   2220
ttagatgacg aggataatcc agaacagtca cgcagtgaac agacagagga tgatgaagaa   2280
cagctaatga tagcttcagt gcttgggctt cgatcattta aggggtcagt tgctgaagaa   2340
gaattgaaac acacagctct agctttagaa gaagatgccc atgcttctga tcctcgaatt   2400
gacagtaata gtgcacgtaa ttctgacgac atagctggac gctacctgcg tactatcaac   2460
cgcagaaata aaaggaggta ctacattgca gcagaagaag ttttgtggga ctactcaccg   2520
atcggaaaaa gtcaagtgag aagtctccca gccaagacca cattcaaaaa agctattttc   2580
cgaagttatc ttgatgatac tttccagaca cctagcactg gaggagaata tgaaaagcat   2640
cttggtatac tgggtcctat cattagggct gaggtggatg atgtaatcga agttcagttc   2700
agaaatttgg cctctagacc atactcactt catgctcatg gccttctcta tgagaaatct   2760
tctgaaggca gaagctatga cgacaactct cctgaattgt tcaaaaagga tgatgctatc   2820
atgccaaacg gcacatacac atatgtctgg caagtccctc cacggtcagg accaacagac   2880
aatacagaaa aatgtaaatc atgggcctat tactctggtg taaatccgga aaaagatatt   2940
cactctggct taattggacc tattttgatc tgccagaaag gcatgattga caagtacaac   3000
aggacaatag acataaggga atttgtcttg tttttatgg tctttgatga ggagaaaagc   3060
tggtactttc ccaaatctga caaaagcact tgtgaagaga aacttatagg agtccaatct   3120
tctcaccaca catttcctgc aattaatggg atcccttatc agctgcaagg cttgatgatg   3180
tacaaagatg agaatgtcca ctggcatttg ctgaacatgg gtgggcccaa agatatccat   3240
gttgttaatt ttcatggtca gacattcact gaagagggaa gggaagataa tcaacttgga   3300
gtccttcctc ttcttcctgg tacattcgcc tccatcaaaa tgaaaccatc caaaattggc   3360
acatggcttt tagaaacaga agttggtgaa aatcaggaaa gaggaatgca ggctctcttt   3420
actgtcattg acaaagattg taaattacca atgggactgg caagtgggat aatacaagac   3480
tcacagatca gtgcttcagg tcatgttgaa tattgggagc ctaagctagc aagactgaat   3540
aatactggaa tgtttaatgc ttggagcatc ataaagaagg aacatgaaca tccgtggatc   3600
cagatagacc tacaaagaca agttgtcatc acaggcattc agacccaggg aaccgtgcaa   3660
ctactgaaac attcgtatac tgtggaatat tttgttacct acagcaaaga tgggcaaaac   3720
tggattactt ttaaaggaag acattccgaa acacaaatgc attttgaggg taattcagat   3780
ggcaccacag taaaagaaaa ccacattgat cctcctatta ttgccagata tattaggctg   3840
catccaacca agttctacaa cacacctact ttccgcattg aactgttagg ttgtgaagtt   3900
gaaggttgct cagtgccatt gggaatggaa agtggggcta tcaagaattc agagattaca   3960
gcctcttctt ataagaagac ttggtggagt tcatgggaac cattccttgc acgactcaat   4020
ctggaaggag gaacaaatgc ttggcaacca gaggtaaaca acaaagatca atggctacaa   4080
attgacctgc aacatcttac aaaaataaca agcataataa ctcaaggagc cacatcaatg   4140
actacagcaa tgtatgtgaa aacattctcc atccattata ctgatgacaa ttcaacatgg   4200
aagccttatt tggatgttcg cacttccatg gaaaaggttt tcacaggaaa tattaacagt   4260
gatggtcatg tcaaacattt tttcaaaccc cctatattgt ccaggttcat tcgtatcatc   4320
cctaaaacat ggaatcaata tattgcactc cggatagaat tgtttggttg tgaagttttt   4380
taa                                                                 4383
```

<210> SEQ ID NO 15

<211> LENGTH: 9179
<212> TYPE: DNA
<213> ORGANISM: Homo sapiens

<400> SEQUENCE: 15
gcaagaactg caggggagga ggacgctgcc acccacagcc tctagagctc attgcagctg 60
ggacagcccg gagtgtggtt agcagctcgg caagcgctgc ccaggtcctg gggtggtggc 120
agccagcggg agcaggaaag gaagcatgtt cccaggctgc ccacgcctct gggtcctggt 180
ggtcttgggc accagctggg taggctgggg gagccaaggg acagaagcgg cacagctaag 240
gcagttctac gtggctgctc agggcatcag ttggagctac cgacctgagc ccacaaactc 300
aagtttgaat ctttctgtaa cttcctttaa gaaaattgtc tacagagagt atgaaccata 360
ttttaagaaa gaaaaaccac aatctaccat ttcaggactt cttgggccta ctttatatgc 420
tgaagtcgga gacatcataa aagttcactt taaaaataag gcagataagc ccttgagcat 480
ccatcctcaa ggaattaggt acagtaaatt atcagaaggt gcttcttacc ttgaccacac 540
attccctgcg gagaagatgg acgacgctgt ggctccaggc cgagaataca cctatgaatg 600
gagtatcagt gaggacagtg gacccaccca tgatgaccct ccatgcctca cacacatcta 660
ttactcccat gaaaatctga tcgaggattt caactcgggg ctgattgggc ccctgcttat 720
ctgtaaaaaa gggaccctaa ctgagggtgg gacacagaag acgtttgaca agcaaatcgt 780
gctactattt gctgtgtttg atgaaagcaa gagctggagc cagtcatcat ccctaatgta 840
cacagtcaat ggatatgtga atgggacaat gccagatata acagtttgtg cccatgacca 900
catcagctgg catctgctgg gaatgagctc ggggccagaa ttattctcca ttcatttcaa 960
cggccaggtc ctggagcaga accatcataa ggtctcagcc atcacccttg tcagtgctac 1020
atccactacc gcaaatatga ctgtgggccc agagggaaag tggatcatat cttctctcac 1080
cccaaaacat ttgcaagctg ggatgcaggc ttacattgac attaaaaact gcccaaagaa 1140
aaccaggaat cttaagaaaa taactcgtga gcagaggcgg cacatgaaga ggtgggaata 1200
cttcattgct gcagaggaag tcatttggga ctatgcacct gtaataccag cgaatatgga 1260
caaaaaatac aggtctcagc atttggataa tttctcaaac caaattggaa aacattataa 1320
gaaagttatg tacacacagt acgaagatga gtccttcacc aaacatacag tgaatcccaa 1380
tatgaaagaa gatgggattt tgggtcctat tatcagagcc caggtcagag acacactcaa 1440
aatcgtgttc aaaaatatgg ccagccgccc ctatagcatt taccctcatg gagtgacctt 1500
ctcgccttat gaagatgaag tcaactcttc tttcacctca ggcaggaaca acaccatgat 1560
cagagcagtt caaccagggg aaacctatac ttataagtgg aacatcttag agtttgatga 1620
acccacagaa aatgatgccc agtgcttaac aagaccatac tacagtgacg tggacatcat 1680
gagagacatc gcctctgggc taataggact acttctaatc tgtaagagca gatccctgga 1740
caggcgagga atacagaggg cagcagacat cgaacagcag gctgtgtttg ctgtgtttga 1800
tgagaacaaa agctggtacc ttgaggacaa catcaacaag ttttgtgaaa atcctgatga 1860
ggtgaaacgt gatgacccca agttttatga atcaaacatc atgagcacta tcaatggcta 1920
tgtgcctgag agcataacta ctcttggatt ctgctttgat gacactgtcc agtggcactt 1980
ctgtagtgtg gggacccaga atgaaatttt gaccatccac ttcactgggc actcattcat 2040
ctatggaaag aggcatgagg acaccttgac cctcttcccc atgcgtggag aatctgtgac 2100
ggtcacaatg gataatgttg gaacttggat gttaacttcc atgaattcta gtccaagaag 2160
caaaaagctg aggctgaaat tcagggatgt taaatgtatc ccagatgatg atgaagactc 2220
atatgagatt tttgaacctc cagaatctac agtcatggct acacggaaaa tgcatgatcg 2280
tttagaacct gaagatgaag agagtgatgc tgactatgat taccagaaca gactggctgc 2340
agcattagga atcaggtcat tccgaaactc atcattgaat caggaagaag aagagttcaa 2400
tcttactgcc ctagctctgg agaatggcac tgaattcgtt tcttcaaaca cagatataat 2460
tgttggttca aattattctt ccccaagtaa tattagtaag ttcactgtca ataaccttgc 2520
agaacctcag aaagcccctt ctcaccaaca agccaccaca gctggttccc cactgagaca 2580
cctcattggc aagaactcag ttctcaattc ttccacagca gagcattcca gcccatattc 2640
tgaagaccct atagaggatc ctctacagcc agatgtcaca gggatacgtc tactttcact 2700
tggtgctgga gaattcaaaa gtcaagaaca tgctaagcat aagggaccca aggtagaaag 2760
agatcaagca gcaaagcaca ggttctcctg gatgaaatta ctagcacata aagttgggag 2820
acacctaagc caagacactg gttctccttc cggaatgagg ccctgggagg accttcctag 2880
ccaagacact ggttctcctt ccagaatgag gccctggaag gaccctccta gtgatctgtt 2940
actcttaaaa caaagtaact catctaagat tttggttggg agatggcatt tggcttctga 3000
gaaaggtagc tatgaaataa tccaagatac tgatgaagac acagctgtta acaattggct 3060
gatcagcccc cagaatgcct cacgtgcttg ggggagaaagc acccctcttg ccaacaagcc 3120
tggaaagcag agtggccacc caaagtttcc tagagttaga cataaatctc tacaagtaag 3180
acaggatgga ggaaagagta gactgaagaa aagccagttt ctcattaaga cacgaaaaaa 3240
gaaaaaagag aagcacacac accatgctcc tttatctccg aggacctttc accctctaag 3300
aagtgaagcc tacaacacat tttcagaaag aagacttaag cattcgttgg tgcttcataa 3360
atccaatgaa acatctcttc ccacagacct caatcagaca ttgccctcta tggattttgg 3420
ctggatagcc tcacttcctg accataatca gaattcctca aatgacactg gtcaggcaag 3480
ctgtcctcca ggtctttatc agacagtgcc cccagaggaa cactatcaaa cattccccat 3540
tcaagaccct gatcaaatgc actctacttc agaccccagt cacagatcct cttctccaga 3600
gctcagtgaa atgcttgagt atgaccgaag tcacaagtcc ttccccacag atataagtca 3660
aatgtcccct tcctcagaac atgaagtctg gcagacagtc atctctccag acctcagcca 3720
ggtgaccctc tctccagaac tcagccagac aaacctctct ccagacctca gccacacgac 3780
tctctctcca gaactcattc agagaaacct ttccccagcc ctcggtcaga tgcccatttc 3840
tccagacctc agccatacaa ccctttctcc agacctcagc catacaaccc tttctttaga 3900
cctcagccag acaaacctct ctccagaact cagtcagaca aacctttctc cagccctcgg 3960
tcagatgccc ctttctccag acctcagcca tacaaccctt tctctagact tcagccagac 4020
aaacctctct ccagaactca gccatatgac tctctctcca gaactcagtc agacaaacct 4080
ttccccagcc ctcggtcaga tgcccatttc tccagacctc agccatacaa ccctttctct 4140
agacttcagc cagacaaacc tctctccaga actcagtcaa acaaaccttt ccccagccct 4200
cggtcagatg cccctttctc cagaccccag ccatacaacc ctttctctag acctcagcca 4260
gacaaacctc tctccagaac tcagtcagac aaacctttcc ccagacctca gtgagatgcc 4320
cctctttgca gatctcagtc aaattcccct taccccagac ctcgaccaga tgacactttc 4380
tccagacctt ggtgagacag atctttcccc aaactttggt cagatgtccc tttccccaga 4440
cctcagccag gtgactctct ctccagacat cagtgacacc acccttctcc cggatctcag 4500
ccagatatca cctcctccag accttgatca gatattctac ccttctgaat ctagtcagtc 4560

-continued

```
attgcttctt caagaattta atgagtcttt tccttatcca gaccttggtc agatgccatc   4620
tccttcatct cctactctca atgatacttt tctatcaaag gaatttaatc cactggttat   4680
agtgggcctc agtaaagatg gtacagatta cattgagatc attccaaagg aagaggtcca   4740
gagcagtgaa gatgactatg ctgaaattga ttatgtgccc tatgatgacc cctacaaaac   4800
tgatgttagg acaaacatca actcctccag agatcctgac aacattgcag catggtacct   4860
ccgcagcaac aatggaaaca gaagaaatta ttacattgct gctgaagaaa tatcctggga   4920
ttattcagaa tttgtacaaa gggaaacaga tattgaagac tctgatgata ttccagaaga   4980
taccacatat aagaaagtag tttttcgaaa gtacctcgac agcactttta ccaaacgtga   5040
tcctcgaggg gagtatgaag agcatctcgg aattcttggt cctattatca gagctgaagt   5100
ggatgatgtt atccaagttc gttttaaaaa tttagcatcc agaccgtatt ctctacatgc   5160
ccatggactt tcctatgaaa aatcatcaga gggaaagact tatgaagatg actctcctga   5220
atggtttaag gaagataatg ctgttcagcc aaatagcagt tatacctacg tatggcatgc   5280
cactgagcga tcagggccag aaagtcctgg ctctgcctgt cgggcttggg cctactactc   5340
agctgtgaac ccagaaaaag atattcactc aggcttgata ggtcccctcc taatctgcca   5400
aaaaggaata ctacataagg acagcaacat gcctatggac atgagagaat ttgtcttact   5460
atttatgacc tttgatgaaa agaagagctg gtactatgaa aagaagtccc gaagttcttg   5520
gagactcaca tcctcagaaa tgaaaaaatc ccatgagttt cacgccatta atgggatgat   5580
ctacagcttg cctggcctga aaatgtatga gcaagagtgg gtgaggttac acctgctgaa   5640
cataggcggc tcccaagaca ttcacgtggt tcactttcac ggccagacct tgctggaaaa   5700
tggcaataaa cagcaccagt taggggtctg gccccttctg cctggttcat ttaaaactct   5760
tgaaatgaag gcatcaaaac ctggctggtg gctcctaaac acagaggttg gagaaaacca   5820
gagagcaggg atgcaaacgc catttcttat catggacaga gactgtagga tgccaatggg   5880
actaagcact ggtatcatat ctgattcaca gatcaaggct tcagagtttc tgggttactg   5940
ggagcccaga ttagcaagat taaacaatgg tggatcttat aatgcttgga gtgtagaaaa   6000
acttgcagca gaatttgcct ctaaaccttg gatccaggtg gacatgcaaa aggaagtcat   6060
aatcacaggg atccagaccc aaggtgccaa acactacctg aagtcctgct ataccacaga   6120
gttctatgta gcttacagtt ccaaccagat caactggcag atcttcaaag ggaacagcac   6180
aaggaatgtg atgtatttta atggcaattc agatgcctct acaataaaag agaatcagtt   6240
tgacccacct attgtggcta gatatattag gatctctcca actcgagcct ataacagacc   6300
tacccttcga ttggaactgc aaggttgtga ggtaaatgga tgttccacac ccctgggtat   6360
ggaaaatgga aagatagaaa acaagcaaat cacagcttct tcgtttaaga aatcttggtg   6420
gggagattac tgggaaccct tccgtgcccg tctgaatgcc cagggacgtg tgaatgcctg   6480
gcaagccaag gcaaacaaca ataagcagtg gctagaaatt gatctactca agatcaagaa   6540
gataacggca attataacac agggctgcaa gtctctgtcc tctgaaatgt atgtaaagag   6600
ctataccatc cactacagtg agcagggagt ggaatggaaa ccatacaggc tgaaatcctc   6660
catggtggac aagatttttg aaggaaatac taataccaaa ggacatgtga agaacttttt   6720
caaccccccca atcatttcca ggtttatccg tgtcattcct aaaacatgga atcaaagtat   6780
tgcacttcgc ctggaactct ttggctgtga tatttactag aattgaacat tcaaaaaccc   6840
ctggaagaga ctctttaaga cctcaaacca tttagaatgg gcaatgtatt ttacgctgtg   6900
ttaaatgtta acagttttcc actatttctc tttcttttct attagtgaat aaaattttat   6960
```

acaagaagct tttataatgt aactccttgc taccagtaag taagataatg gctattactt 7020
ctgcattaat ttgaatacag gtaggaaaat atcaagaacc aacaagaaaa gggcttatct 7080
ttcttaatga ttgaaaatgc tatgaagtaa tatttatgta gttaaaatgc ttcattataa 7140
ctcttttaaa tcctttacac actagtaaaa cagatattac tttaaataat aattgataga 7200
cctggataac tttcacaaac acatgatttt ttaatggttt ttcttgagtg aagagaaaaa 7260
caatattatc aaatgaaata agtacttaaa atatcctgtc tttcccatat aacaatgatt 7320
tttctgactt tccatgagta aaaaaacagc caagcatctt tccagtagcc ccattgaaat 7380
tgtgaatccg tcctggtctc cctaaggact gcacacattg atattcaagg ttggtggtca 7440
ttagatatgg aacagaactg aaataaccat ggtagaactg aatgtgtaat gttggcttta 7500
ttctagctgg tactacatgg cacacagttt caaaacataa tttcacctac tggaaagctc 7560
agacctgtaa aacagagcat gggaactgct ggtctaaatg cagttgttcc tgctcaaaga 7620
gacctctggc caaactggca agcagttaaa gttttctttc agggccttcc tctctatggc 7680
ctcaacttcc tcctctctct tcttccagca acttcccctt tcatcattcc tttccctggg 7740
gacttggcat tcagtgatcc tgtagatatt gcacaactgg ggaaccttta gacatcctta 7800
aaatcacatg agatagacag tcatttgggg tgtctgaaat aaaccacccc aaaacttagt 7860
gttaaaagag caaccaaaaa aaatttatgt gagattatgg atttgttact tagcttgatt 7920
taatcatcct gtaacgtgta catatatcaa aatgttatgt ataccataaa tatataaaat 7980
tttatcaacg aaattcataa caatctctca gaccacagag aaatcaaatt agaactgagg 8040
actaagaaac tcactcgaaa ccacacaact acatggaaac tgaacaacct gctcctgaat 8100
gactactggg taaataatga aattaaggca gaaataaata agttccttaa aaccaatgag 8160
aacaaagaga caacatacca gaatctctag gagacagggc tttgcttttg ctgcattcta 8220
ttcgttgtga acacaaatta caggccagtc tcgattcagt gtagaaggga actgcataag 8280
gaccacatac caggaggcat aattcactgg gagcatcttt agaaactacc agagttacct 8340
gttgcccata ccagtggggt aagccctatg aatgtatatg agagtttcaa acatccacaa 8400
aacattggct ttctaatatt cgtattccca ctattccttt cttttcatga ttcatgtcat 8460
tgtcccatca acatttctaa gatttccatt ccgttaagag caaaagagaa tgttggaagg 8520
tgggggaaaa catttctttg ttttctacag ggccagcttc ttggatgtgt gtgatctgtt 8580
cagttgcaaa gggtcacatg ctcagaagga ccgcatgcta aatttaatgc tttgcagtta 8640
ccctcttgaa atcctttatt ttttaagaag gaattcgaca tttccatttt tcaatgagcc 8700
ccacaaatta cgcagctagt cctgggcttc tctactctga aattgggcag gatctctctt 8760
gatctagaat ttactaaggc ataatagggg caagaaaatc ttatgaaata atggggggta 8820
gggaagagat gggaatggag catgagatcc agcttcgtta ttctctactt gagaaaaata 8880
aggccccaaa gattaaacaa cttgcccaag gatattgctt gttagtgtca gaactgaaac 8940
cagaaaccaa atgatcatat ccctagactt ttagtctgct ttctcttcca taaaatgaaa 9000
cttataatgt ttctaatcca ttgctcagac aggtagacat gaatattaat tgataatgac 9060
tattaattga tctggaaaat acttgtttgg ggatcaataa tatgtttggg ctattatcta 9120
atgctgtgta gaaatattaa aacccctgtt attttgaaat aaaaaagata cccactttt 9179

<210> SEQ ID NO 16
<211> LENGTH: 2224
<212> TYPE: PRT

<213> ORGANISM: Homo sapiens

<400> SEQUENCE: 16

```
Met Phe Pro Gly Cys Pro Arg Leu Trp Val Leu Val Val Leu Gly Thr
1               5                   10                  15

Ser Trp Val Gly Trp Gly Ser Gln Gly Thr Glu Ala Ala Gln Leu Arg
            20                  25                  30

Gln Phe Tyr Val Ala Ala Gln Gly Ile Ser Trp Ser Tyr Arg Pro Glu
        35                  40                  45

Pro Thr Asn Ser Ser Leu Asn Leu Ser Val Thr Ser Phe Lys Lys Ile
    50                  55                  60

Val Tyr Arg Glu Tyr Glu Pro Tyr Phe Lys Lys Glu Lys Pro Gln Ser
65                  70                  75                  80

Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
        115                 120                 125

Leu Asp His Thr Phe Pro Ala Glu Lys Met Asp Asp Ala Val Ala Pro
    130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
        195                 200                 205

Lys Gln Ile Val Leu Leu Phe Ala Val Phe Asp Glu Ser Lys Ser Trp
    210                 215                 220

Ser Gln Ser Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
                245                 250                 255

Leu Leu Gly Met Ser Ser Gly Pro Glu Leu Phe Ser Ile His Phe Asn
            260                 265                 270

Gly Gln Val Leu Glu Gln Asn His His Lys Val Ser Ala Ile Thr Leu
        275                 280                 285

Val Ser Ala Thr Ser Thr Thr Ala Asn Met Thr Val Gly Pro Glu Gly
    290                 295                 300

Lys Trp Ile Ile Ser Ser Leu Thr Pro Lys His Leu Gln Ala Gly Met
305                 310                 315                 320

Gln Ala Tyr Ile Asp Ile Lys Asn Cys Pro Lys Lys Thr Arg Asn Leu
                325                 330                 335

Lys Lys Ile Thr Arg Glu Gln Arg Arg His Met Lys Arg Trp Glu Tyr
            340                 345                 350

Phe Ile Ala Ala Glu Glu Val Ile Trp Asp Tyr Ala Pro Val Ile Pro
        355                 360                 365

Ala Asn Met Asp Lys Lys Tyr Arg Ser Gln His Leu Asp Asn Phe Ser
    370                 375                 380

Asn Gln Ile Gly Lys His Tyr Lys Lys Val Met Tyr Thr Gln Tyr Glu
385                 390                 395                 400
```

-continued

```
Asp Glu Ser Phe Thr Lys His Thr Val Asn Pro Asn Met Lys Glu Asp
                405                 410                 415

Gly Ile Leu Gly Pro Ile Ile Arg Ala Gln Val Arg Asp Thr Leu Lys
            420                 425                 430

Ile Val Phe Lys Asn Met Ala Ser Arg Pro Tyr Ser Ile Tyr Pro His
        435                 440                 445

Gly Val Thr Phe Ser Pro Tyr Glu Asp Glu Val Asn Ser Ser Phe Thr
    450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Glu Pro Thr Glu Asn
                485                 490                 495

Asp Ala Gln Cys Leu Thr Arg Pro Tyr Tyr Ser Asp Val Asp Ile Met
            500                 505                 510

Arg Asp Ile Ala Ser Gly Leu Ile Gly Leu Leu Leu Ile Cys Lys Ser
        515                 520                 525

Arg Ser Leu Asp Arg Arg Gly Ile Gln Arg Ala Ala Asp Ile Glu Gln
    530                 535                 540

Gln Ala Val Phe Ala Val Phe Asp Glu Asn Lys Ser Trp Tyr Leu Glu
545                 550                 555                 560

Asp Asn Ile Asn Lys Phe Cys Glu Asn Pro Asp Glu Val Lys Arg Asp
                565                 570                 575

Asp Pro Lys Phe Tyr Glu Ser Asn Ile Met Ser Thr Ile Asn Gly Tyr
            580                 585                 590

Val Pro Glu Ser Ile Thr Thr Leu Gly Phe Cys Phe Asp Asp Thr Val
        595                 600                 605

Gln Trp His Phe Cys Ser Val Gly Thr Gln Asn Glu Ile Leu Thr Ile
    610                 615                 620

His Phe Thr Gly His Ser Phe Ile Tyr Gly Lys Arg His Glu Asp Thr
625                 630                 635                 640

Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Glu Ser Thr Val Met
    690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Glu Phe Asn
            740                 745                 750

Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
    770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815

Asn Ser Val Leu Asn Ser Ser Thr Ala Glu His Ser Ser Pro Tyr Ser
```

-continued

```
            820                 825                 830

Glu Asp Pro Ile Glu Asp Pro Leu Gln Pro Asp Val Thr Gly Ile Arg
        835                 840                 845

Leu Leu Ser Leu Gly Ala Gly Glu Phe Lys Ser Gln Glu His Ala Lys
    850                 855                 860

His Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Lys Asp Pro Pro
        915                 920                 925

Ser Asp Leu Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
            980                 985                 990

Gly Lys Gln Ser Gly His Pro Lys  Phe Pro Arg Val Arg  His Lys Ser
        995                 1000                1005

Leu Gln  Val Arg Gln Asp Gly  Gly Lys Ser Arg Leu  Lys Lys Ser
    1010                1015                1020

Gln Phe  Leu Ile Lys Thr Arg  Lys Lys Lys Lys Glu  Lys His Thr
    1025                1030                1035

His His  Ala Pro Leu Ser Pro  Arg Thr Phe His Pro  Leu Arg Ser
    1040                1045                1050

Glu Ala  Tyr Asn Thr Phe Ser  Glu Arg Arg Leu Lys  His Ser Leu
    1055                1060                1065

Val Leu  His Lys Ser Asn Glu  Thr Ser Leu Pro Thr  Asp Leu Asn
    1070                1075                1080

Gln Thr  Leu Pro Ser Met Asp  Phe Gly Trp Ile Ala  Ser Leu Pro
    1085                1090                1095

Asp His  Asn Gln Asn Ser Ser  Asn Asp Thr Gly Gln  Ala Ser Cys
    1100                1105                1110

Pro Pro  Gly Leu Tyr Gln Thr  Val Pro Pro Glu Glu  His Tyr Gln
    1115                1120                1125

Thr Phe  Pro Ile Gln Asp Pro  Asp Gln Met His Ser  Thr Ser Asp
    1130                1135                1140

Pro Ser  His Arg Ser Ser Ser  Pro Glu Leu Ser Glu  Met Leu Glu
    1145                1150                1155

Tyr Asp  Arg Ser His Lys Ser  Phe Pro Thr Asp Ile  Ser Gln Met
    1160                1165                1170

Ser Pro  Ser Ser Glu His Glu  Val Trp Gln Thr Val  Ile Ser Pro
    1175                1180                1185

Asp Leu  Ser Gln Val Thr Leu  Ser Pro Glu Leu Ser  Gln Thr Asn
    1190                1195                1200

Leu Ser  Pro Asp Leu Ser His  Thr Thr Leu Ser Pro  Glu Leu Ile
    1205                1210                1215

Gln Arg  Asn Leu Ser Pro Ala  Leu Gly Gln Met Pro  Ile Ser Pro
    1220                1225                1230
```

```
Asp Leu  Ser His Thr Thr Leu  Ser Pro Asp Leu Ser  His Thr Thr
    1235                 1240                 1245

Leu Ser  Leu Asp Leu Ser Gln  Thr Asn Leu Ser Pro  Glu Leu Ser
    1250                 1255                 1260

Gln Thr  Asn Leu Ser Pro Ala  Leu Gly Gln Met Pro  Leu Ser Pro
    1265                 1270                 1275

Asp Leu  Ser His Thr Thr Leu  Ser Leu Asp Phe Ser  Gln Thr Asn
    1280                 1285                 1290

Leu Ser  Pro Glu Leu Ser His  Met Thr Leu Ser Pro  Glu Leu Ser
    1295                 1300                 1305

Gln Thr  Asn Leu Ser Pro Ala  Leu Gly Gln Met Pro  Ile Ser Pro
    1310                 1315                 1320

Asp Leu  Ser His Thr Thr Leu  Ser Leu Asp Phe Ser  Gln Thr Asn
    1325                 1330                 1335

Leu Ser  Pro Glu Leu Ser Gln  Thr Asn Leu Ser Pro  Ala Leu Gly
    1340                 1345                 1350

Gln Met  Pro Leu Ser Pro Asp  Pro Ser His Thr Thr  Leu Ser Leu
    1355                 1360                 1365

Asp Leu  Ser Gln Thr Asn Leu  Ser Pro Glu Leu Ser  Gln Thr Asn
    1370                 1375                 1380

Leu Ser  Pro Asp Leu Ser Glu  Met Pro Leu Phe Ala  Asp Leu Ser
    1385                 1390                 1395

Gln Ile  Pro Leu Thr Pro Asp  Leu Asp Gln Met Thr  Leu Ser Pro
    1400                 1405                 1410

Asp Leu  Gly Glu Thr Asp Leu  Ser Pro Asn Phe Gly  Gln Met Ser
    1415                 1420                 1425

Leu Ser  Pro Asp Leu Ser Gln  Val Thr Leu Ser Pro  Asp Ile Ser
    1430                 1435                 1440

Asp Thr  Thr Leu Leu Pro Asp  Leu Ser Gln Ile Ser  Pro Pro Pro
    1445                 1450                 1455

Asp Leu  Asp Gln Ile Phe Tyr  Pro Ser Glu Ser Ser  Gln Ser Leu
    1460                 1465                 1470

Leu Leu  Gln Glu Phe Asn Glu  Ser Phe Pro Tyr Pro  Asp Leu Gly
    1475                 1480                 1485

Gln Met  Pro Ser Pro Ser Ser  Pro Thr Leu Asn Asp  Thr Phe Leu
    1490                 1495                 1500

Ser Lys  Glu Phe Asn Pro Leu  Val Ile Val Gly Leu  Ser Lys Asp
    1505                 1510                 1515

Gly Thr  Asp Tyr Ile Glu Ile  Ile Pro Lys Glu Glu  Val Gln Ser
    1520                 1525                 1530

Ser Glu  Asp Asp Tyr Ala Glu  Ile Asp Tyr Val Pro  Tyr Asp Asp
    1535                 1540                 1545

Pro Tyr  Lys Thr Asp Val Arg  Thr Asn Ile Asn Ser  Ser Arg Asp
    1550                 1555                 1560

Pro Asp  Asn Ile Ala Ala Trp  Tyr Leu Arg Ser Asn  Asn Gly Asn
    1565                 1570                 1575

Arg Arg  Asn Tyr Tyr Ile Ala  Ala Glu Glu Ile Ser  Trp Asp Tyr
    1580                 1585                 1590

Ser Glu  Phe Val Gln Arg Glu  Thr Asp Ile Glu Asp  Ser Asp Asp
    1595                 1600                 1605

Ile Pro  Glu Asp Thr Thr Tyr  Lys Lys Val Val Phe  Arg Lys Tyr
    1610                 1615                 1620
```

-continued

```
Leu Asp  Ser Thr Phe Thr Lys  Arg Asp Pro Arg Gly  Glu Tyr Glu
    1625                 1630                 1635

Glu His  Leu Gly Ile Leu Gly  Pro Ile Ile Arg Ala  Glu Val Asp
    1640                 1645                 1650

Asp Val  Ile Gln Val Arg Phe  Lys Asn Leu Ala Ser  Arg Pro Tyr
    1655                 1660                 1665

Ser Leu  His Ala His Gly Leu  Ser Tyr Glu Lys Ser  Ser Glu Gly
    1670                 1675                 1680

Lys Thr  Tyr Glu Asp Asp Ser  Pro Glu Trp Phe Lys  Glu Asp Asn
    1685                 1690                 1695

Ala Val  Gln Pro Asn Ser Ser  Tyr Thr Tyr Val Trp  His Ala Thr
    1700                 1705                 1710

Glu Arg  Ser Gly Pro Glu Ser  Pro Gly Ser Ala Cys  Arg Ala Trp
    1715                 1720                 1725

Ala Tyr  Tyr Ser Ala Val Asn  Pro Glu Lys Asp Ile  His Ser Gly
    1730                 1735                 1740

Leu Ile  Gly Pro Leu Leu Ile  Cys Gln Lys Gly Ile  Leu His Lys
    1745                 1750                 1755

Asp Ser  Asn Met Pro Val Asp  Met Arg Glu Phe Val  Leu Leu Phe
    1760                 1765                 1770

Met Thr  Phe Asp Glu Lys Lys  Ser Trp Tyr Tyr Glu  Lys Lys Ser
    1775                 1780                 1785

Arg Ser  Ser Trp Arg Leu Thr  Ser Ser Glu Met Lys  Lys Ser His
    1790                 1795                 1800

Glu Phe  His Ala Ile Asn Gly  Met Ile Tyr Ser Leu  Pro Gly Leu
    1805                 1810                 1815

Lys Met  Tyr Glu Gln Glu Trp  Val Arg Leu His Leu  Leu Asn Ile
    1820                 1825                 1830

Gly Gly  Ser Gln Asp Ile His  Val Val His Phe His  Gly Gln Thr
    1835                 1840                 1845

Leu Leu  Glu Asn Gly Asn Lys  Gln His Gln Leu Gly  Val Trp Pro
    1850                 1855                 1860

Leu Leu  Pro Gly Ser Phe Lys  Thr Leu Glu Met Lys  Ala Ser Lys
    1865                 1870                 1875

Pro Gly  Trp Trp Leu Leu Asn  Thr Glu Val Gly Glu  Asn Gln Arg
    1880                 1885                 1890

Ala Gly  Met Gln Thr Pro Phe  Leu Ile Met Asp Arg  Asp Cys Arg
    1895                 1900                 1905

Met Pro  Met Gly Leu Ser Thr  Gly Ile Ile Ser Asp  Ser Gln Ile
    1910                 1915                 1920

Lys Ala  Ser Glu Phe Leu Gly  Tyr Trp Glu Pro Arg  Leu Ala Arg
    1925                 1930                 1935

Leu Asn  Asn Gly Gly Ser Tyr  Asn Ala Trp Ser Val  Glu Lys Leu
    1940                 1945                 1950

Ala Ala  Glu Phe Ala Ser Lys  Pro Trp Ile Gln Val  Asp Met Gln
    1955                 1960                 1965

Lys Glu  Val Ile Ile Thr Gly  Ile Gln Thr Gln Gly  Ala Lys His
    1970                 1975                 1980

Tyr Leu  Lys Ser Cys Tyr Thr  Thr Glu Phe Tyr Val  Ala Tyr Ser
    1985                 1990                 1995

Ser Asn  Gln Ile Asn Trp Gln  Ile Phe Lys Gly Asn  Ser Thr Arg
    2000                 2005                 2010

Asn Val  Met Tyr Phe Asn Gly  Asn Ser Asp Ala Ser  Thr Ile Lys
```

```
    2015                2020                2025

Glu Asn  Gln Phe Asp Pro Pro  Ile Val Ala Arg Tyr  Ile Arg Ile
    2030                2035                2040

Ser Pro  Thr Arg Ala Tyr Asn  Arg Pro Thr Leu Arg  Leu Glu Leu
    2045                2050                2055

Gln Gly  Cys Glu Val Asn Gly  Cys Ser Thr Pro Leu  Gly Met Glu
    2060                2065                2070

Asn Gly  Lys Ile Glu Asn Lys  Gln Ile Thr Ala Ser  Ser Phe Lys
    2075                2080                2085

Lys Ser  Trp Trp Gly Asp Tyr  Trp Glu Pro Phe Arg  Ala Arg Leu
    2090                2095                2100

Asn Ala  Gln Gly Arg Val Asn  Ala Trp Gln Ala Lys  Ala Asn Asn
    2105                2110                2115

Asn Lys  Gln Trp Leu Glu Ile  Asp Leu Leu Lys Ile  Lys Lys Ile
    2120                2125                2130

Thr Ala  Ile Ile Thr Gln Gly  Cys Lys Ser Leu Ser  Ser Glu Met
    2135                2140                2145

Tyr Val  Lys Ser Tyr Thr Ile  His Tyr Ser Glu Gln  Gly Val Glu
    2150                2155                2160

Trp Lys  Pro Tyr Arg Leu Lys  Ser Ser Met Val Asp  Lys Ile Phe
    2165                2170                2175

Glu Gly  Asn Thr Asn Thr Lys  Gly His Val Lys Asn  Phe Phe Asn
    2180                2185                2190

Pro Pro  Ile Ile Ser Arg Phe  Ile Arg Val Ile Pro  Lys Thr Trp
    2195                2200                2205

Asn Gln  Ser Ile Ala Leu Arg  Leu Glu Leu Phe Gly  Cys Asp Ile
    2210                2215                2220

Tyr
```

<210> SEQ ID NO 17
<211> LENGTH: 6910
<212> TYPE: DNA
<213> ORGANISM: Bos Taurus

<400> SEQUENCE: 17

```
agcctctggg agctcactgc agcccggcct gcggacagcc tcgcagaggc agccctaacc     60

cacccccggg gtggtggcgg caggcaagag aaggaaagga accatgttcc tcgcttgccc    120

tggcttctgg gtcctcgtgg tcctaggcag cagctgggca ggctgggga acctaggggc    180

tgaagcagca aagctaaggc agttctacgt agctgctcag agcatcagat ggaactaccg    240

ccccgagtcc acacacctca gttcgaaacc ttttgaaacc tcctttaaga aaattgtcta    300

cagggagtat gaagcatatt ttcagaaaga aaaaccacaa tccagaactt caggacttct    360

tgggcctact ttgtatgctg aagttggaga catcatgaaa gttcacttta agaataaagc    420

acacaagccc ttaagcatcc atgctcaagg aattaagtac agtaaattct cagaaggtgc    480

gtcttactct gaccacacac tccccatgga gaagatggat gatgctgtag ctccgggcca    540

agaatatacc tatgagtgga ttatcagtga gcacagtggg cccacccacg atgaccctcc    600

atgcctcaca cacatctatt actcctatgt aaatctggtg gaggacttca actctggact    660

gattggacct ctgcttattt gtaagaaagg caccctaacc gaggatggaa ctcagaaaat    720

gtttgagaag caacatgtac tgatgtttgc tgtgtttgat gaaagtaaaa gctggaacca    780

gacatcatcc ttaatgtaca cagtcaatgg ctatgtgaat gggacgatgc cagatataac    840
```

-continued

```
agtctgtgcc catgaccaca tcagttggca tctgattgga atgagctctg ggccagaact    900
gttctccatc catttcaatg gtcaggtcct ggagcagaac catcataaga tctcagccat    960
cactctcgtc agcgccacgt ccacaaccgc aaacatgacc gtgagccccg agggaaggtg   1020
gaccatagct tctctcatcc ccagacattt tcaagctggg atgcaggctt acatagacat   1080
taaaaactgt gcaaagaaaa ccagaaatcc taagaaacta actcgagacc agaggcggca   1140
cattaagaga tgggaatact tcattgctgc agaggaagtc atttgggact atgcacctat   1200
aataccagca aacatggaca aaaaatacag atctctgcat ttggataatt tctcaaaccg   1260
aattggaaaa cattataaga aggttgtcta caaacagtac caagatgact ccttcaccaa   1320
acgcctggag gatcccagta gtgaaggaga tgggatcttg ggccctatta tcagagccca   1380
ggtcagagac acactgaaaa tcgtgttcaa aaatatggcc agccgctcct acagcattta   1440
ccctcacggt gtgacattct ctccttatga caatgaagta aactcttcct caacctcagg   1500
cagcaacacc atgatcagag cagttcgacc aggggaaacc tacacttata agtggaacat   1560
cctagaatct gatgaaccca cagaaaatga tgctcagtgc ttaacaagac catactacag   1620
taatgtggac atcacaaggg accttgcttc tggactgata gggcttcttc taatttgtaa   1680
gagcagatcc ttggatagac gaggcataca gagggcagca gacatcgagc agcaggctgt   1740
gtttgccgtg tttgacgaga acaagagctg gtacattgag gacaacatct acaagttttg   1800
tgaaaatcct gagaaagtga aacgtgatga ccccaagttt tatgagtcaa acatcatgag   1860
taatttcact cttccagcta ttaacggcta tgtgcctgag agtataccca tactagggtt   1920
ctgctttgat gacactgtcc agtggcactt ctgcagtgtg ggaacccaga atgacatttt   1980
gaccattcac ttcactgggc actcattcat ctatggaaag aggcacgagg acaccttgac   2040
ccttttcccc atgcaggggg aatccgtgac tgtcacaatg gataatgttg gaacttggat   2100
gttaaccacc atgaattcca atccaagaag caaaaaacta cggctgaggt tcagggatgc   2160
taagtgtatc cggaatgatg atgatgactc ctatgagatt atatatgaac cttcaggatc   2220
tacagccatg actacaaaga aaattcatga ttcttcagaa atcgaagatg aaaatgatgc   2280
tgactctgat taccaggacg aactggcttt aatactaggt cttaggtcat tcagaaattc   2340
atcactgaat caggagaaag atgagctcaa tcttaccgcc ctagctctgg agaaagactc   2400
tgaattcatt cctccgagtg ccaacagatc tcttgattca aattcttctt cccgaagtca   2460
tgttagcagg cttattgcca aaaactttgc agaatctctg aaaactcttc tgcacctgga   2520
agcccctgca gctggttccc ccctggaaca cgctggctta gataagaact cagctctcaa   2580
ccctcccatg gcagagcatt ccagccctta ttctgaagac cctagagaag atcatccact   2640
ctcagatgtc acaggggtaa gcctacttcc atttggcaca ggattcaaaa atcgaaaacc   2700
tgccaaacat caaagattcc aggtaggaag aggccaagca gcaaagcata agttctccca   2760
gacgcgattc ccagcacata aaccaggac acgtttaagc caagacaact cttcttcttc   2820
cagaatgggg ccctgggagg acattcccag tgatctgtta ctcttacaac aaaaggatcc   2880
atataagatt ctgaatggag aatggcattt ggtttctgag aaaggcagtt atgaaataat   2940
ccaagatgct aatgaaaaca agactgttaa taagttgcca aacagccccc agaatgactc   3000
aaggacttgg ggagaaaaca tccctttcaa aaacagtcat ggaaagcaga gtggccaccc   3060
aacatttttg gtaactagac gtaaacctct acaagacaga caggatagaa gaaatagtag   3120
attgaaggaa ggccttccgt taattaggac acgaagaaag aaaaaggaag agaagcctgc   3180
ataccatgtt cctctatctc caaggagttt tcatcctctg agaggagagg tcaatgcctc   3240
```

```
attttcagac agaagacata atcattcatt gttactccat gcgtccaatg aaacatctct   3300
ttccatagac ctcaatcaga cattcccctc tatgaatctt agccttgcag cctcacttcc   3360
tgaccatgac cagacctcac caaatgacac caccagtcag actagctccc ctccagatct   3420
ttatccgaca gtgagcccag aggaacacta tcaaatattc cctattcaag actctgatcc   3480
aacacattct actacagccc ccagtaacag atctcctgat ccaacacatt ctactacagc   3540
ccccagtaac agatctcctc ccacacagcc cagccagata cccaactatg acctaagaaa   3600
cagggccatc cctactgatg tgagtcaaat tttcccttcc ttggaactcg aagtctggca   3660
gacagctacc tctctagacc tcagtcaacc atccatctcc ccagaccttg gccagatggc   3720
actttcccca gaccccggcc aggagtctct ctctccagac cttggccaga cgtccctctc   3780
tccagacctc agccaggagt ctctctcccc agaccttggc cagacagccc tttccccaga   3840
ccccagccag gagtctctct ccccagacct tggccagaca gccctttccc cagaccccag   3900
ccaggagtct ctctccccag accttggcca gacagccctt tccccagacc ccggccagga   3960
gtctctctct ccagaccttg gccagacgtc cctctctcca gacctcagcc aggagtctct   4020
ctccccagac cttggccaga cagccctttc cccagacccc agccaggagt ctctctcccc   4080
agaccttggc cagacagccc tttccccaga ccccagccag gagtctctct ctccagacct   4140
tggccagacg tccctctctc cagaccttgg ccaggagtct ctctccccag accttggcca   4200
gacagccctt tccccagacc ccagccagga gtctctctct ccagaccttg gccagacgtc   4260
cctctctcca gaccttggcc aggagtctct ctccccagac cttggccaga cagccctttc   4320
cccagacctc agccaggagt ctctctctcc agatcttggc cagacacccc tctctccaga   4380
cctcagcctg gagtctcttt ctccagacct cagccagctt gatctcaagc agacatcacc   4440
tcctctagat cttaatcaga catcccacac ttctgaatca agtcagtcat tgcctcttcc   4500
agaatttggt cagactttcc ctaatgcaga tattggtcag atgccatctc ctccaccaga   4560
ctctacacta aataacactt ttataccaga agaatttaat ccgctggttg tagtaggcct   4620
cagtagagat gatggagatt atattgaaat tattccaagg cagaaggaag agagcagtga   4680
agaagactat ggtgaatttg agtttgtagc ctataatgac ccttaccaaa ctgatcttag   4740
gacagatatc aactcctcca gaaatcctga caacattgca gcatggtacc tccgcagcaa   4800
cactggaaac agaaaatatt attacattgc agctgaagaa atatcctggg attattcaaa   4860
atttgtgcaa agtgatgacg ttgactatgt tccagaggac accgtataca agaaagtagt   4920
tttccgaaag taccttgata gcacttttac caaacttgat cctcaggggg agtatgaaga   4980
gcatcttggc atacttggtc cagtcattag agctgaagtg gatgatgtta tccaagttcg   5040
ttttaaaaat ttagcatcca gaccatattc tcttcatgcc catgggcttt cctatgaaaa   5100
atcatcagaa ggaaagactt atgaagatga ctctcctgaa tggtttaagg aggacaatgc   5160
tattcagccc aataaaactt acacctatgt atggcacgcc actacgcgat ccgggccaga   5220
aaaccctgga tctgcctgtc gggcttgggc ctactactca gcagtgaacc cagaaaaaga   5280
catccattca ggcttgatag ggcctcttct gatctgccga aaagggacac ttgataagga   5340
gaccaacatg cctgtggaca tgagagaatt tgtcctgctt tttatggtct ttgatgaaaa   5400
gaagagctgg tattatgaca agaagcccac aaggtcttgg agacgtgcat cctcagaagt   5460
aaaaaactcc catgagtttc atgccatcaa tgggatgatc tacaacttgc ctggcttgag   5520
aatgtacgag caagagtggg tgaggttgca cctgctgaac ttaggcggct cccgagacat   5580
```

-continued

```
tcacgtggtt cactttcatg gccagacctt gctagaaaac ggcactcaac agcaccagtt   5640

aggggtctgg ccccttctgc ctggttcatt taaaactctt gaaatgaagg catcaaaacc   5700

tggctggtgg ctcctagaca cggaagttgg agaaattcag agagcaggga tgcagacacc   5760

atttctcatt gtagacagag aatgtaagat gccaatggga ctaagcactg gcctgatagc   5820

tgactcacag atccaggctt ctgagttttg gggttattgg gaacccaaat tagcaaggtt   5880

aaacaatggt ggatcataca atgcttggat tgcagaaaaa ctttcaacgg aatttaaccc   5940

tgaaccttgg atccaggtag acatgcaaaa ggaagtcctg ctcacgggga tccagaccca   6000

gggcgccaaa cactacctga agccctacta caccaccgag ttctgtgtgg cttacagctt   6060

ggatcggaaa aactggcgta tcttcaaagg gaacagcaca aggaatgtga tgtattttgg   6120

tggcaattca gatgcttcta caataaaaga gaatcagatt gacccacctg ttgtggctag   6180

atacattagg atctctccaa ctggatccta taacaaacct gcccttcgat tggagctgca   6240

aggttgtgag gttaatggat gctccacacc gctgggtatg gaaagtggaa agatagaaaa   6300

caagcaaatc accgcttcct cgtttaaaaa gtcttggtgg ggaaattact gggaaccctt   6360

ccttgcacgt cttaatgccc agggccgtgt aaatgcctgg caagctaagg caaacaacaa   6420

caatcagtgg ttacaaattg atctgctcaa aatcaagaag ataactgcga ttgtaacaca   6480

aggatgcaag tctctgtcct ctgaaatgta tgtgaagagc tacaccatcc actacagtga   6540

ccagggaacg gactggaaac cttacaggga gaaatcctca atggtggaca agattttcga   6600

aggaaataat aatgtcagag gacatgtgaa gaactttttc aacccaccaa tcatctccag   6660

gtttatacgc atcattccta aaacatggaa tcagagtatt gcacttcgct tggaactctt   6720

tggctgtgat atgtactaga attgaatatt ttaaaagata ggagggactc aaagatatca   6780

aaccacttag agtgggcaat gcattttgta gctattttaa gtataaaaaa atttccatta   6840

tttctctttt ttctattaga gaataaaatt ttatatgcaa aacctttatg atataactcc   6900

tgataaccac                                                          6910
```

```
<210> SEQ ID NO 18
<211> LENGTH: 2211
<212> TYPE: PRT
<213> ORGANISM: Bos Taurus

<400> SEQUENCE: 18

Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Arg
            20                  25                  30

Gln Phe Tyr Val Ala Ala Gln Ser Ile Arg Trp Asn Tyr Arg Pro Glu
        35                  40                  45

Ser Thr His Leu Ser Ser Lys Pro Phe Glu Thr Ser Phe Lys Lys Ile
    50                  55                  60

Val Tyr Arg Glu Tyr Glu Ala Tyr Phe Gln Lys Glu Lys Pro Gln Ser
65                  70                  75                  80

Arg Thr Ser Gly Leu Leu Gly Pro Thr Leu Tyr Ala Glu Val Gly Asp
                85                  90                  95

Ile Met Lys Val His Phe Lys Asn Lys Ala His Lys Pro Leu Ser Ile
            100                 105                 110

His Ala Gln Gly Ile Lys Tyr Ser Lys Phe Ser Glu Gly Ala Ser Tyr
        115                 120                 125

Ser Asp His Thr Leu Pro Met Glu Lys Met Asp Asp Ala Val Ala Pro
```

```
    130                 135                 140

Gly Gln Glu Tyr Thr Tyr Glu Trp Ile Ile Ser Glu His Ser Gly Pro
145                 150                 155                 160

Thr His Asp Asp Pro Pro Cys Leu Thr His Ile Tyr Tyr Ser Tyr Val
                165                 170                 175

Asn Leu Val Glu Asp Phe Asn Ser Gly Leu Ile Gly Pro Leu Leu Ile
            180                 185                 190

Cys Lys Lys Gly Thr Leu Thr Glu Asp Gly Thr Gln Lys Met Phe Glu
        195                 200                 205

Lys Gln His Val Leu Met Phe Ala Val Phe Asp Glu Ser Lys Ser Trp
    210                 215                 220

Asn Gln Thr Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
                245                 250                 255

Leu Ile Gly Met Ser Ser Gly Pro Glu Leu Phe Ser Ile His Phe Asn
            260                 265                 270

Gly Gln Val Leu Glu Gln Asn His His Lys Ile Ser Ala Ile Thr Leu
        275                 280                 285

Val Ser Ala Thr Ser Thr Thr Ala Asn Met Thr Val Ser Pro Glu Gly
    290                 295                 300

Arg Trp Thr Ile Ala Ser Leu Ile Pro Arg His Phe Gln Ala Gly Met
305                 310                 315                 320

Gln Ala Tyr Ile Asp Ile Lys Asn Cys Ala Lys Lys Thr Arg Asn Pro
                325                 330                 335

Lys Lys Leu Thr Arg Asp Gln Arg Arg His Ile Lys Arg Trp Glu Tyr
            340                 345                 350

Phe Ile Ala Ala Glu Glu Val Ile Trp Asp Tyr Ala Pro Ile Ile Pro
        355                 360                 365

Ala Asn Met Asp Lys Lys Tyr Arg Ser Leu His Leu Asp Asn Phe Ser
    370                 375                 380

Asn Arg Ile Gly Lys His Tyr Lys Lys Val Val Tyr Lys Gln Tyr Gln
385                 390                 395                 400

Asp Asp Ser Phe Thr Lys Arg Leu Glu Asp Pro Ser Ser Glu Gly Asp
                405                 410                 415

Gly Ile Leu Gly Pro Ile Ile Arg Ala Gln Val Arg Asp Thr Leu Lys
            420                 425                 430

Ile Val Phe Lys Asn Met Ala Ser Arg Ser Tyr Ser Ile Tyr Pro His
        435                 440                 445

Gly Val Thr Phe Ser Pro Tyr Asp Asn Glu Val Asn Ser Ser Ser Thr
    450                 455                 460

Ser Gly Ser Asn Thr Met Ile Arg Ala Val Arg Pro Gly Glu Thr Tyr
465                 470                 475                 480

Thr Tyr Lys Trp Asn Ile Leu Glu Ser Asp Glu Pro Thr Glu Asn Asp
                485                 490                 495

Ala Gln Cys Leu Thr Arg Pro Tyr Tyr Ser Asn Val Asp Ile Thr Arg
            500                 505                 510

Asp Leu Ala Ser Gly Leu Ile Gly Leu Leu Leu Ile Cys Lys Ser Arg
        515                 520                 525

Ser Leu Asp Arg Arg Gly Ile Gln Arg Ala Ala Asp Ile Glu Gln Gln
    530                 535                 540

Ala Val Phe Ala Val Phe Asp Glu Asn Lys Ser Trp Tyr Ile Glu Asp
545                 550                 555                 560
```

```
Asn Ile Tyr Lys Phe Cys Glu Asn Pro Glu Lys Val Lys Arg Asp Asp
                565                 570                 575

Pro Lys Phe Tyr Glu Ser Asn Ile Met Ser Asn Phe Thr Leu Pro Ala
            580                 585                 590

Ile Asn Gly Tyr Val Pro Glu Ser Ile Pro Ile Leu Gly Phe Cys Phe
        595                 600                 605

Asp Asp Thr Val Gln Trp His Phe Cys Ser Val Gly Thr Gln Asn Asp
    610                 615                 620

Ile Leu Thr Ile His Phe Thr Gly His Ser Phe Ile Tyr Gly Lys Arg
625                 630                 635                 640

His Glu Asp Thr Leu Thr Leu Phe Pro Met Gln Gly Glu Ser Val Thr
                645                 650                 655

Val Thr Met Asp Asn Val Gly Thr Trp Met Leu Thr Thr Met Asn Ser
            660                 665                 670

Asn Pro Arg Ser Lys Lys Leu Arg Leu Arg Phe Arg Asp Ala Lys Cys
        675                 680                 685

Ile Arg Asn Asp Asp Asp Asp Ser Tyr Glu Ile Ile Tyr Glu Pro Ser
    690                 695                 700

Gly Ser Thr Ala Met Thr Thr Lys Lys Ile His Asp Ser Ser Glu Ile
705                 710                 715                 720

Glu Asp Glu Asn Asp Ala Asp Ser Asp Tyr Gln Asp Glu Leu Ala Leu
                725                 730                 735

Ile Leu Gly Leu Arg Ser Phe Arg Asn Ser Ser Leu Asn Gln Glu Lys
            740                 745                 750

Asp Glu Leu Asn Leu Thr Ala Leu Ala Leu Glu Lys Asp Ser Glu Phe
        755                 760                 765

Ile Pro Pro Ser Ala Asn Arg Ser Leu Asp Ser Asn Ser Ser Ser Arg
    770                 775                 780

Ser His Val Ser Arg Leu Ile Ala Lys Asn Phe Ala Glu Ser Leu Lys
785                 790                 795                 800

Thr Leu Leu His Leu Glu Ala Pro Ala Ala Gly Ser Pro Leu Glu His
                805                 810                 815

Ala Gly Leu Asp Lys Asn Ser Ala Leu Asn Pro Pro Met Ala Glu His
            820                 825                 830

Ser Ser Pro Tyr Ser Glu Asp Pro Arg Glu Asp His Pro Leu Ser Asp
        835                 840                 845

Val Thr Gly Val Ser Leu Leu Pro Phe Gly Thr Gly Phe Lys Asn Arg
    850                 855                 860

Lys Pro Ala Lys His Gln Arg Phe Gln Val Gly Arg Gly Gln Ala Ala
865                 870                 875                 880

Lys His Lys Phe Ser Gln Thr Arg Phe Pro Ala His Lys Thr Arg Thr
                885                 890                 895

Arg Leu Ser Gln Asp Asn Ser Ser Ser Ser Arg Met Gly Pro Trp Glu
            900                 905                 910

Asp Ile Pro Ser Asp Leu Leu Leu Leu Gln Gln Lys Asp Pro Tyr Lys
        915                 920                 925

Ile Leu Asn Gly Glu Trp His Leu Val Ser Glu Lys Gly Ser Tyr Glu
    930                 935                 940

Ile Ile Gln Asp Ala Asn Glu Asn Lys Thr Val Asn Lys Leu Pro Asn
945                 950                 955                 960

Ser Pro Gln Asn Asp Ser Arg Thr Trp Gly Glu Asn Ile Pro Phe Lys
                965                 970                 975
```

-continued

```
Asn Ser His Gly Lys Gln Ser Gly His Pro Thr Phe Leu Val Thr Arg
            980                 985                 990

Arg Lys Pro Leu Gln Asp Arg Gln  Asp Arg Arg Asn Ser  Arg Leu Lys
        995                 1000                1005

Glu Gly  Leu Pro Leu Ile Arg  Thr Arg Arg Lys Lys  Lys Glu Glu
    1010                 1015                1020

Lys Pro  Ala Tyr His Val Pro  Leu Ser Pro Arg Ser  Phe His Pro
    1025                 1030                1035

Leu Arg  Gly Glu Val Asn Ala  Ser Phe Ser Asp Arg  Arg His Asn
    1040                 1045                1050

His Ser  Leu Leu Leu His Ala  Ser Asn Glu Thr Ser  Leu Ser Ile
    1055                 1060                1065

Asp Leu  Asn Gln Thr Phe Pro  Ser Met Asn Leu Ser  Leu Ala Ala
    1070                 1075                1080

Ser Leu  Pro Asp His Asp Gln  Thr Ser Pro Asn Asp  Thr Thr Ser
    1085                 1090                1095

Gln Thr  Ser Ser Pro Pro Asp  Leu Tyr Pro Thr Val  Ser Pro Glu
    1100                 1105                1110

Glu His  Tyr Gln Ile Phe Pro  Ile Gln Asp Ser Asp  Pro Thr His
    1115                 1120                1125

Ser Thr  Thr Ala Pro Ser Asn  Arg Ser Pro Asp Pro  Thr His Ser
    1130                 1135                1140

Thr Thr  Ala Pro Ser Asn Arg  Ser Pro Pro Thr Gln  Pro Ser Gln
    1145                 1150                1155

Ile Pro  Asn Tyr Asp Leu Arg  Asn Arg Ala Ile Pro  Thr Asp Val
    1160                 1165                1170

Ser Gln  Ile Phe Pro Ser Leu  Glu Leu Glu Val Trp  Gln Thr Ala
    1175                 1180                1185

Thr Ser  Leu Asp Leu Ser Gln  Pro Ser Ile Ser Pro  Asp Leu Gly
    1190                 1195                1200

Gln Met  Ala Leu Ser Pro Asp  Pro Gly Gln Glu Ser  Leu Ser Pro
    1205                 1210                1215

Asp Leu  Gly Gln Thr Ser Leu  Ser Pro Asp Leu Ser  Gln Glu Ser
    1220                 1225                1230

Leu Ser  Pro Asp Leu Gly Gln  Thr Ala Leu Ser Pro  Asp Pro Ser
    1235                 1240                1245

Gln Glu  Ser Leu Ser Pro Asp  Leu Gly Gln Thr Ala  Leu Ser Pro
    1250                 1255                1260

Asp Pro  Ser Gln Glu Ser Leu  Ser Pro Asp Leu Gly  Gln Thr Ala
    1265                 1270                1275

Leu Ser  Pro Asp Pro Gly Gln  Glu Ser Leu Ser Pro  Asp Leu Gly
    1280                 1285                1290

Gln Thr  Ser Leu Ser Pro Asp  Leu Ser Gln Glu Ser  Leu Ser Pro
    1295                 1300                1305

Asp Leu  Gly Gln Thr Ala Leu  Ser Pro Asp Pro Ser  Gln Glu Ser
    1310                 1315                1320

Leu Ser  Pro Asp Leu Gly Gln  Thr Ala Leu Ser Pro  Asp Pro Ser
    1325                 1330                1335

Gln Glu  Ser Leu Ser Pro Asp  Leu Gly Gln Thr Ser  Leu Ser Pro
    1340                 1345                1350

Asp Leu  Gly Gln Glu Ser Leu  Ser Pro Asp Leu Gly  Gln Thr Ala
    1355                 1360                1365

Leu Ser  Pro Asp Pro Ser Gln  Glu Ser Leu Ser Pro  Asp Leu Gly
```

```
    1370                1375                1380

Gln Thr  Ser Leu Ser Pro Asp  Leu Gly Gln Glu Ser  Leu Ser Pro
    1385                1390                1395

Asp Leu  Gly Gln Thr Ala Leu  Ser Pro Asp Leu Ser  Gln Glu Ser
    1400                1405                1410

Leu Ser  Pro Asp Leu Gly Gln  Thr Pro Leu Ser Pro  Asp Leu Ser
    1415                1420                1425

Leu Glu  Ser Leu Ser Pro Asp  Leu Ser Gln Leu Asp  Leu Lys Gln
    1430                1435                1440

Thr Ser  Pro Pro Leu Asp Leu  Asn Gln Thr Ser His  Thr Ser Glu
    1445                1450                1455

Ser Ser  Gln Ser Leu Pro Leu  Pro Glu Phe Gly Gln  Thr Phe Pro
    1460                1465                1470

Asn Ala  Asp Ile Gly Gln Met  Pro Ser Pro Pro Pro  Asp Ser Thr
    1475                1480                1485

Leu Asn  Asn Thr Phe Ile Pro  Glu Glu Phe Asn Pro  Leu Val Val
    1490                1495                1500

Val Gly  Leu Ser Arg Asp Asp  Gly Asp Tyr Ile Glu  Ile Ile Pro
    1505                1510                1515

Arg Gln  Lys Glu Glu Ser Ser  Glu Glu Asp Tyr Gly  Glu Phe Glu
    1520                1525                1530

Phe Val  Ala Tyr Asn Asp Pro  Tyr Gln Thr Asp Leu  Arg Thr Asp
    1535                1540                1545

Ile Asn  Ser Ser Arg Asn Pro  Asp Asn Ile Ala Ala  Trp Tyr Leu
    1550                1555                1560

Arg Ser  Asn Thr Gly Asn Arg  Lys Tyr Tyr Tyr Ile  Ala Ala Glu
    1565                1570                1575

Glu Ile  Ser Trp Asp Tyr Ser  Lys Phe Val Gln Ser  Asp Asp Val
    1580                1585                1590

Asp Tyr  Val Pro Glu Asp Thr  Val Tyr Lys Lys Val  Val Phe Arg
    1595                1600                1605

Lys Tyr  Leu Asp Ser Thr Phe  Thr Lys Leu Asp Pro  Gln Gly Glu
    1610                1615                1620

Tyr Glu  Glu His Leu Gly Ile  Leu Gly Pro Val Ile  Arg Ala Glu
    1625                1630                1635

Val Asp  Asp Val Ile Gln Val  Arg Phe Lys Asn Leu  Ala Ser Arg
    1640                1645                1650

Pro Tyr  Ser Leu His Ala His  Gly Leu Ser Tyr Glu  Lys Ser Ser
    1655                1660                1665

Glu Gly  Lys Thr Tyr Glu Asp  Asp Ser Pro Glu Trp  Phe Lys Glu
    1670                1675                1680

Asp Asn  Ala Ile Gln Pro Asn  Lys Thr Tyr Thr Tyr  Val Trp His
    1685                1690                1695

Ala Thr  Thr Arg Ser Gly Pro  Glu Asn Pro Gly Ser  Ala Cys Arg
    1700                1705                1710

Ala Trp  Ala Tyr Tyr Ser Ala  Val Asn Pro Glu Lys  Asp Ile His
    1715                1720                1725

Ser Gly  Leu Ile Gly Pro Leu  Leu Ile Cys Arg Lys  Gly Thr Leu
    1730                1735                1740

Asp Lys  Glu Thr Asn Met Pro  Val Asp Met Arg Glu  Phe Val Leu
    1745                1750                1755

Leu Phe  Met Val Phe Asp Glu  Lys Lys Ser Trp Tyr  Tyr Asp Lys
    1760                1765                1770
```

Lys Pro Thr Arg Ser Trp Arg Arg Ala Ser Ser Glu Val Lys Asn
1775 1780 1785

Ser His Glu Phe His Ala Ile Asn Gly Met Ile Tyr Asn Leu Pro
1790 1795 1800

Gly Leu Arg Met Tyr Glu Gln Glu Trp Val Arg Leu His Leu Leu
1805 1810 1815

Asn Leu Gly Gly Ser Arg Asp Ile His Val Val His Phe His Gly
1820 1825 1830

Gln Thr Leu Leu Glu Asn Gly Thr Gln Gln His Gln Leu Gly Val
1835 1840 1845

Trp Pro Leu Leu Pro Gly Ser Phe Lys Thr Leu Glu Met Lys Ala
1850 1855 1860

Ser Lys Pro Gly Trp Trp Leu Leu Asp Thr Glu Val Gly Glu Ile
1865 1870 1875

Gln Arg Ala Gly Met Gln Thr Pro Phe Leu Ile Val Asp Arg Glu
1880 1885 1890

Cys Lys Met Pro Met Gly Leu Ser Thr Gly Leu Ile Ala Asp Ser
1895 1900 1905

Gln Ile Gln Ala Ser Glu Phe Trp Gly Tyr Trp Glu Pro Lys Leu
1910 1915 1920

Ala Arg Leu Asn Asn Gly Gly Ser Tyr Asn Ala Trp Ile Ala Glu
1925 1930 1935

Lys Leu Ser Thr Glu Phe Asn Pro Glu Pro Trp Ile Gln Val Asp
1940 1945 1950

Met Gln Lys Glu Val Leu Leu Thr Gly Ile Gln Thr Gln Gly Ala
1955 1960 1965

Lys His Tyr Leu Lys Pro Tyr Tyr Thr Thr Glu Phe Cys Val Ala
1970 1975 1980

Tyr Ser Leu Asp Arg Lys Asn Trp Arg Ile Phe Lys Gly Asn Ser
1985 1990 1995

Thr Arg Asn Val Met Tyr Phe Gly Gly Asn Ser Asp Ala Ser Thr
2000 2005 2010

Ile Lys Glu Asn Gln Ile Asp Pro Pro Val Val Ala Arg Tyr Ile
2015 2020 2025

Arg Ile Ser Pro Thr Gly Ser Tyr Asn Lys Pro Ala Leu Arg Leu
2030 2035 2040

Glu Leu Gln Gly Cys Glu Val Asn Gly Cys Ser Thr Pro Leu Gly
2045 2050 2055

Met Glu Ser Gly Lys Ile Glu Asn Lys Gln Ile Thr Ala Ser Ser
2060 2065 2070

Phe Lys Lys Ser Trp Trp Gly Asn Tyr Trp Glu Pro Phe Leu Ala
2075 2080 2085

Arg Leu Asn Ala Gln Gly Arg Val Asn Ala Trp Gln Ala Lys Ala
2090 2095 2100

Asn Asn Asn Asn Gln Trp Leu Gln Ile Asp Leu Leu Lys Ile Lys
2105 2110 2115

Lys Ile Thr Ala Ile Val Thr Gln Gly Cys Lys Ser Leu Ser Ser
2120 2125 2130

Glu Met Tyr Val Lys Ser Tyr Thr Ile His Tyr Ser Asp Gln Gly
2135 2140 2145

Thr Asp Trp Lys Pro Tyr Arg Glu Lys Ser Ser Met Val Asp Lys
2150 2155 2160

-continued

Ile Phe Glu Gly Asn Asn Asn Val Arg Gly His Val Lys Asn Phe
    2165                2170                2175

Phe Asn Pro Pro Ile Ile Ser Arg Phe Ile Arg Ile Ile Pro Lys
    2180                2185                2190

Thr Trp Asn Gln Ser Ile Ala Leu Arg Leu Glu Leu Phe Gly Cys
    2195                2200                2205

Asp Met Tyr
    2210

<210> SEQ ID NO 19
<211> LENGTH: 1031
<212> TYPE: DNA
<213> ORGANISM: Pseudonaja textilis

<400> SEQUENCE: 19
cgacggcccg ggctggtctg ccaggaagat ttcatgggac tccttatttg cggagacttt 60
gcccctgtgg atccagagag tagaaactct cactcatctc ctcatagggt gtcctttcta 120
tgatgctcca agatgtgttt taatcacacc aatcatttcc aaataaggct gcagagataa 180
atgttatgtt tattatattt caaaggtaac ctcacactca catatcagat ggccaaatat 240
cttcgagttc tacaactacc caaaactttt aattaaatat attgttttat tgccccgttc 300
tttcctattc tcaataacaa atgttgtgtt aaactatttc tctcttcact gtactgtaaa 360
agtactgtac tatactttta ttgtgaaggc tgatcaaaga ttgtaatcaa gatattttag 420
ttgaaaaaaa tatgttttac tgtgctctac tttctgctgc tttttgagat gtgtgagaga 480
gagatgcaaa atgcaattct ctctcatgtt caaatattgc agaaatatac ttacgatagg 540
tagtagcatt agcatttgct aggtcttcct taggaacaag ttgctctgga tgtaggatgt 600
ttctttaagg tttctttatg aaaaactcag agaggaggca gtgaagctct tcccctaagt 660
acaatctgtt ttcaacttct gggtgagctt cctttcaagg tcactatctg tgcttagcag 720
tgaggggcag ctctcctttg aggtatccat cccacacccc atactattaa tcttgtactg 780
actcaaatga ccttacttgg taaagacccg cattttgaat tagtcagcac aatgatctga 840
agcatccata gtcaaacaca aacaggcttt ggaggacatg ataagggctg gagcagaaca 900
acaggaagct tgattgcttg aaccttgttc atagccagcc ctgaaagaga acaaactgtt 960
cttttccatc gataggcacc atggcccctc agctactcct ctgtctgatc ctcacttttc 1020
tagggagtct c 1031

<210> SEQ ID NO 20
<211> LENGTH: 1010
<212> TYPE: DNA
<213> ORGANISM: Pseudonaja textilis

<400> SEQUENCE: 20
cgacggcccg ggctggtctg ccaggaagat ttcatgggac tccttatttg cggagacttt 60
gcccctgtgg atccagagag tagaaactct cactcatctc ctcatagggt gtcctttcta 120
tgatgctcca agatgtgttt taatcacacc aatcatttcc aaataaggct gcagagataa 180
atgttatgtt tattatattt caaaggtaac ctcacactca catatcagat ggccaaatat 240
cttcgagttc tacaactacc caaaactttt aattaaatat attgttttat tgccccgttc 300
tttcctattc tcaataacaa atgttgtgtt aaactatttc tctcttcact gtactgtaaa 360
agtactgtac tatactttta ttgtgaaggc tgatcaaaga ttgtaatcaa gatattttag 420
ttgaaaaaaa tatgttttac tgtgctctac tttctgctgc tttttgagat gtgtgagaga 480

```
gagatgcaaa atgcaattct ctctcatgtt caaatattgc agaaatatac ttacgatagg    540

tagtagcatt agcatttgct aggtcttcct taggaacaag ttgctctgga tgtaggatgt    600

ttctttatga aaactcagag aggaggcagt gaagctcttc ccctaagtac aatctgtttt    660

caacttctgg gtgagcttcc tttcaaggtc actatctgtg cttagcagtg aggggcagct    720

ctcctttgag gtatccatcc cacaccccat actattaatc ttgtactgac tcaaatgacc    780

ttacttggta aagacccgca ttttgaatta gtcagcacaa tgatctgaag catccatagt    840

caaacacaaa caggctttgg aggacatgat aagggctgga gcagaacaac aggaagcttg    900

attgcttgaa ccttgttcat agccagccct gaaagagaac aaactgttct tttccatcga    960

taggcaccat ggcccctcag ctactcctct gtctgatcct cacttttcta              1010
```

<210> SEQ ID NO 21
<211> LENGTH: 1299
<212> TYPE: DNA
<213> ORGANISM: Pseudonaja textilis

<400> SEQUENCE: 21

```
cgacggcccg ggctggtctg ccaggaagat ttcatgggac tccttatttg cggagacttt     60

gcccctgtgg atccagagag tagaaactct cactcatctc ctcatagggt gtcctttcta    120

tgatgctcca agatgtgttt taatcacacc aatcatttcc aaataaggct gcagagataa    180

atgttatgtt tattatattt caaaggtaac ctcacactca catatcagat ggccaaatat    240

cttcgagttc tacaactacc caaaactttt aattaaatat attgttttat tgccccgttc    300

tttcctattc tcaataacaa atgttgtgtt aaactatttc tctcttcact gtactgtaaa    360

agtactgtac tatactttta ttgtgaaggc tgatcaaaga ttgtaatcaa gatattttag    420

ttgaaaaaaa tatgttttac tgtgctctac tttctgctgc tttttgggat gtgtgagaga    480

gagatgcaaa atgcaattct ctctcatgtt caaatattgc agaaatatac ttacgatagg    540

tagtagcatt agcatttgct aggtcttcct taggaaccag gtgctctgga tgtagggtgt    600

ttctttaagg tttctttatg aagaactcag agaggaggca gggaagctct tccccctaag    660

taatctgttt tcaacttctg ggtgagcttc ctttcaaggt cactatctgt gcttagcagt    720

gaggggcagc tctcctttga ggtatccatc ccacgcccca tactattaat cttgtactga    780

ctcaaatgac cttacttggt aaagacccgc attttgaatt agtcagcaca atgatctgaa    840

gcatccatag ccaaactcaa acaggctttg gaggacatga taagggctgg agcagaacaa    900

caggaagctt gattgcttga accttgttca tagccagccc tgtagtgtac ttgtttgcat    960

actcataata ctgcattcct attggacaga tactatcgct taacgattgg tagataacaa   1020

cagttctaat tggacgccta agcagtggga gttttaaata aatgccattg gttgcgagcc   1080

gcgagcagcc gctataaaag ggactgccgc ggctcgactt tagttgaagt tactgacagt   1140

taataaagag ctgaattcaa ctccggtctc gagtctgctt tgttctggcg atagaacaag   1200

aacaagaact gaaagagaac aaaccgttct tttccatcga taggcaccat ggctcctcaa   1260

ctactcctct gtctgatcct cacttttcta tggagtctc                          1299
```

<210> SEQ ID NO 22
<211> LENGTH: 2231
<212> TYPE: DNA
<213> ORGANISM: Pseudonaja textilis textilis

<400> SEQUENCE: 22

-continued

```
acgcggggga agttactgac agttaataaa gagctgaatt aactccggtc tcgagtctgc     60
tttgttctgg cgatagaaca agaacaagaa ctgaaagaga acaaactgtt cttttccatc    120
gataggcacc atggctcctc aactactcct ctgtctgatc ctcacttttc tgtggagtct    180
cccagaggct gaaagtaatg tattcttaaa aagcaaagtg gcaaatagat tttgcaaag    240
aacaaaacga gctaattcac tggttgagga atttaaatct ggaaacattg aaagggaatg    300
cattgaggag agatgttcaa aagaagaagc cagggaggta tttgaagatg acgagaaaac    360
tgagaccttc tggaatgttt atgtagatgg ggatcagtgt tcatcaaacc cctgtcatta    420
tcgcgggata tgcaaagatg gcattggtag ctatacctgt acctgcttgt ctggctatga    480
agggaaaaac tgtgaacgtg tcttatataa gtcctgcaga gtggacaatg gtaactgttg    540
gcacttctgc aaatctgttc aaaacgatat tcaatgttca tgcgctgaag gttacctttt    600
gggagaggat gggcactctt gtgttgctgg aggtaacttt tcatgtggta gaaatatcaa    660
aacaaggaac aagagggaag caagtctgcc tgactttgtg cagtcccata atgcaacttt    720
gctgaaaaaa tctgataatc caagccctga tatcagaatt gttaacggaa tggactgcaa    780
actgggtgaa tgtccgtggc aggcagctct ggtagatgac aagaaaggtg tgttttgtgg    840
aggaacaatt ttgagtccca tctatgtgct tactgcagcc cactgcatta atgagaccga    900
gacgatttca gttgttgtag gagaaataga cagatcaaga gcagaaaccg gacctcttct    960
ttctgtggat aaagtatatg tgcataaaaa atttgttcct cccaaaaaaa gccaggaatt   1020
ctatgaaaag tttgatcttg tcagctatga ctatgatata gccatcatcc aaatgaagac   1080
ccctatccag ttctctgaaa atgtggttcc tgcctgcctt cccacagctg attttgccaa   1140
ccaagtcctc atgaaacaag atttggcat cgttagtgga tttgggggta ttttcgaaag   1200
aggaccgaac tctaaaacac ttaaagtcct taaggttcct tatgtggaca ggcacacctg   1260
catgctttcc agcaattttc caattactcc aactatgttc tgtgctggct atgatactct   1320
gcctcaagat gcatgccaag gagacagcgg ggggccccac atcactgcat acagagatac   1380
ccactttatt actgggattg tcagctgggg ggaaggatgt gcacggaaag gcagatatgg   1440
tatttacaca aaattgtcca aattcatccc ttggataaaa agaataatgc gtcaaaagct   1500
acccagtaca gagtcaagca ctggtcggct ctaaaaatca tccagtgaca tatttcatgc   1560
agctataatg cattgggtta gaacattcat gatatccact ttggttcaga actcttcaga   1620
tgtagggcca tttttaaata taacattcaa gtcatgtagc tttcctattt atcgagacct   1680
tttttcttct ggtattaatc ccttctggaa catagaatga gtaggcgatt tcatttcagc   1740
tcttgtctct cgtgtcctat cttttatgac cttttctaaa gatttataaa ggtttataat   1800
ttataatcct tcaaatagaa gctcagcagg aatatttggt ccctttgtaa tgcaacctcc   1860
agttcccttg agaccatcag ttgggttaat caaggtagtg cccaattcag ctgaattgtt   1920
gtccaattta atttacctca aaccaagcct tcagtactgt tgccttctac ttctatggag   1980
ggggagttag ggacgtcata aaaccttgct ctccgaatcc aacacttcat gtcaaaaatt   2040
tcttgaagaa agtgtacaga attctgtatt tcccaaatgg ttattccact cgcgtgctca   2100
cattttgggt tattttgtgt gatcaaaatt tccagtgaca ggatctgatt gagatgatca   2160
ctaactgggt tataggaccc gaataaaagt gatatattct aaaaaaaaaa aaaaaaaaaa   2220
aaaaaaaaaa a                                                        2231
```

<210> SEQ ID NO 23
<211> LENGTH: 2219

<212> TYPE: DNA
<213> ORGANISM: Pseudonaja textilis textilis

<400> SEQUENCE: 23
acgcggggga agttactgac agttaataaa gagctgaatt aactccggtc tcgagtctgc 60
tttgttctgg cgatagaaca agaacaagaa ctgaaagaga acaaactgtt cttttccatc 120
gataggcacc atggctcctc aactactcct ctgtctgatc ctcacttttc tgtggagtct 180
cccagaggct gaaagtaatg tattcttaaa aagcaaagtg gcaaatagat tttgcaaag 240 aacagaacga gctaattcac tggttgagga atttaaatct ggaaacattg aaagggaatg 300
cattgaggag agatgttcaa aagaagaagc cagggaggta tttgaagatg acgagaaaac 360
tgagaccttc tggaatgttt atgtagatgg ggatcagtgt tcatcaaacc cctgtcatta 420
tcgcgggata tgcaaagatg gcattggtag ctatacctgt acctgcttgt ctggctatga 480
agggaaaaac tgtgaacgtg tcttatataa gtcctgcaga gtggacaatg gtaactgttg 540
gcacttctgc aaacatgttc aaaatgatat tcagtgttca tgtgctgaag gttacctttt 600
gggagaggat gggcactctt gtgttgctgg aggtaacttt tcatgtggta gaaatatcaa 660
aacaaggaac aagagggaag caaatctgcc tgactttgtg cagtcccaga atgcaacttt 720
gctgaaaaaa tctgataatc caagccctga tatcagaatt gttaatggaa tggattgcaa 780
actgggtgaa tgtccgtggc aggcagctct ggtagatgaa aaggaaggtg tgttttgtgg 840
aggaacaatt ttgagtccca tctatgtgct tactgcagcc cactgcatta atgagaccga 900
gacgatttca gttgttgtag gggaaataga caaatcaaga atagaaaccg gacctcttct 960
ttctgtggat aaaatatatg tgcataaaaa atttgttcct cctcaaaaag cctataagtt 1020
tgatcttgcc gcctatgact atgacatagc catcatccaa atgaagaccc ctatccagtt 1080
ctctgaaaat gtggttcctg cctgccttcc cacagctgat tttgccaacc aagtcctcat 1140
gaaacaagat tttggcatcg ttagtggatt tgggcgtatt gtcgaaaaag gaccaaaatc 1200
taaaacactt aaagtcctta aggttcctta tgtggacagg cacacctgca tggtttccag 1260
cgaaactcca attactccaa atatgttctg tgctggctat gatactctgc ctcgagatgc 1320
atgccaggga gacagtgggg ggccccacac cactgtatac agagataccc actttattac 1380
tgggattgtc agctcggggg aaggatgtgc aaggaatggc aaatatggta attacacaaa 1440
actgtccaaa ttcatccctt ggataaaaag aataatgcgt caaaagctac ccagtacaga 1500
gtcaagcact ggtcggctct aaaaatcatc cagtgacata tttcatgcag ctataatgca 1560
ttgggttaga acattcatga tatccacttt ggttcagaac tcttcagatg tagggccatt 1620
tttaaatata acattcaagt catgtagctt tcctatttat cgagaccttt tttcttctgg 1680
tattaatccc ttctggaaca tagaatgagt aggcgatttc atttcagctc ttgtctctcg 1740
tgtcctatct tttatgacct tttctaaaga tttataaagg tttataattt ataatccttc 1800
aaatagaagc tcagcaggaa tatttggtcc ctttgtaatg caacctccag ttcccttgag 1860
accatcagtt gggttaatca aggtagtgcc caattcagct gaattgttgt ccaatttaat 1920
ttacctcaaa ccaagccttc agtactgttg ccttctactt ctatggaggg ggagttaggg 1980
acgtcataaa accttgctct ccgaatccaa cacttcatgt caaaaatttc ttgaagaaag 2040
tgtacagaat tctgtatttc ccaaatggtt attccactcg cgtgctcaca ttttgggtta 2100
ttttgtgtga tcaaaatttc cagtgacagg atctgattga gatgatcact aactgggtta 2160
taggacccga ataaaagtga tatattctaa aaaaaaaaaa aaaaaaaaaa aaaaaaaaa 2219

-continued

<210> SEQ ID NO 24
<211> LENGTH: 1392
<212> TYPE: DNA
<213> ORGANISM: Pseudonaja textilis

<400> SEQUENCE: 24
atggctcctc agctactcct ctgtctgatc ctcacttttc tgtggagtct cccagaggct 60
gaaagtaatg tattcttaaa aagcaaagtg gcaaatagat ttttgcaaag aacaaaacga 120
gctaattcac tggttgagga atttaaatct ggaaacattg aaagggaatg cattgaggag 180
agatgttcaa aagaagaagc cagggaggca tttgaagatg acgagaaaac tgagaccttc 240
tggaatgttt atgtagatgg ggatcagtgt tcatcaaacc cctgtcatta tcgcgggata 300
tgcaaagatg gcattggtag ctatacctgt acctgcttgt ctggctatga agggaaaaac 360
tgtgaacgtg tcttatataa gtcctgcaga gtggacaatg gtaactgttg gcacttctgc 420
aaacatgttc aaaatgatat tcagtgttca tgtgctgaag gttacctttt gggagaggat 480
gggcactctt gtgttgctgg aggtaacttt tcatgtggta gaaatatcaa aacaaggaac 540
aagagggaag caaatctgcc tgactttgtg cagtcccaga atgcaacttt gctgaaaaaa 600
tctgataatc caagccctga tatcagaatt gttaatggaa tggattgcaa actgggtgaa 660
tgtccgtggc aggcagctct ggtagatgaa aaggaaggtg tgttttgtgg aggaacaatt 720
ttgagtccca tctatgtgct tactgcagcc cactgcatta atgagaccga gacgatttca 780
gttgttgtag gggaaataga caaatcaaga atagaaaccg gacctcttct ttctgtggat 840
aaaatatatg tgcataaaaa atttgttcct cctcaaaaag cctataagtt tgatcttgcc 900
gcctatgact atgacatagc catcatccaa atgaagaccc ctatccagtt ctctgaaaat 960
gtggttcctg cctgccttcc cacagctgat tttgccaacc aagtcctcat gaaacaagat 1020
tttggcatcg ttagtggatt tggcgtattt ttcgaaaaag gaccaaaatc taaaacactt 1080
aaagtcctta aggttcctta tgtggacagg cacacctgca tggtttccag cgaaactcca 1140
attactccaa atatgttctg tgctggctat gatactctgc ctcgagatgc atgccaggga 1200
gacagtgggg ggccccacac cactgtatac agagataccc actttattac tgggattgtc 1260
agctcggggg aaggatgtgc aaggaatggc aaatatggta tttacacaaa actgtccaaa 1320
ttcatccctt ggataaaaag aataatgcgt caaaagctac ccagtacaga gtcaagcacc 1380
ggtcggctct aa 1392

<210> SEQ ID NO 25
<211> LENGTH: 1452
<212> TYPE: DNA
<213> ORGANISM: Pseudonaja textilis

<400> SEQUENCE: 25
atggctcctc agctactcct ctgtctgatc ctcacttttc tgtggagtct cccagaggct 60
gaaagtaatg tattcttaaa aagcaaagtg gcaaatagat ttttgcaaag aacaaaacga 120
gccaattcac tgtttgagga atttaaatct ggaaacattg aaagggaatg cattgaggag 180
agatgttcaa aagaagaagc cagggaggca tttgaagatg acgagaaaac tgagaccttc 240
tggaatgttt atgtagatgg ggatcagtgt tcatcaaacc cctgtcatta tggcgggaca 300
tgcaaagatg gcattggtag ctatacctgt acctgcttgt ctggctatga agggaaaaac 360
tgtgaatatg tcttatataa gtcctgcaga gtggacaatg gtgactgttg gcacttctgc 420
aaacctgttc aaaacggaat tcagtgttca tgtgctgaaa gttacctttt gggagaggat 480

```
gggcactctt gtgttgctgg aggtgacttt tcatgtggta gaaatataaa aacaaggaac    540

aagcgggaag caaatctgcc tgactttcaa acagattttt ctgatgacta cgatgagatt    600

gatgaaaata attttgttga aactcctaca aatttctctg gcttagttct cactgtgcag    660

tcccagaatg caactttgct gaaaaaatct gataatccaa gccctgatat cagagttgtt    720

aatggaacag actgcaaact aggtgaatgt ccatggcagg cacttctgct aaatgatgaa    780

ggagatgggt tttgtggagg aacaattttg agtcccatct atgtgcttac tgcagcccac    840

tgcattaacc agaccaagta cattacagtt gttgtagggg aaatagacat atcaagcaaa    900

aaaaccggac gtcttcattc tgtggataaa atatatgtgc atcaaaaatt tgttcctgcc    960

acgtatgact atgacatagc catcatccaa ctgaagaccc ctatccagtt ctctgaaaat   1020

gtggttcctg cctgccttcc cactgctgat tttgccaacc aagtcctcat gaaacaaaat   1080

tttggcatcg ttagtggatt tgggcgtact cgagaaagag gaaagacctc taacacactt   1140

aaagttgtta cgcttcctta tgtggacagg cacacctgca tgctttccag caattttcca   1200

attactcaaa atatgttctg tgctggctat gatactctgc ctcaagatgc atgccaggga   1260

gacagcggag ggccccacat cactgcatac agagataccc actttattac tgggattgtc   1320

agctgggggg aaggatgtgc acagacaggc aaatatggtg tttacacaaa agtgtccaaa   1380

ttcatccttt ggataaaaag aataatacgt caaaagcaac ccagtacaga gtcaagcacc   1440

ggtcggctct aa                                                       1452
```

<210> SEQ ID NO 26
<211> LENGTH: 483
<212> TYPE: PRT
<213> ORGANISM: Pseudonaja textilis

<400> SEQUENCE: 26

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Phe Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Ala Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Gly Gly Thr Cys Lys Asp Gly Ile Gly Ser Tyr Thr Cys Thr Cys
            100                 105                 110

Leu Ser Gly Tyr Glu Gly Lys Asn Cys Glu Tyr Val Leu Tyr Lys Ser
        115                 120                 125

Cys Arg Val Asp Asn Gly Asp Cys Trp His Phe Cys Lys Pro Val Gln
    130                 135                 140

Asn Gly Ile Gln Cys Ser Cys Ala Glu Ser Tyr Leu Leu Gly Glu Asp
145                 150                 155                 160

Gly His Ser Cys Val Ala Gly Gly Asp Phe Ser Cys Gly Arg Asn Ile
                165                 170                 175

Lys Thr Arg Asn Lys Arg Glu Ala Asn Leu Pro Asp Phe Gln Thr Asp
            180                 185                 190
```

```
Phe Ser Asp Asp Tyr Asp Glu Ile Asp Glu Asn Asn Phe Val Glu Thr
        195                 200                 205

Pro Thr Asn Phe Ser Gly Leu Val Leu Thr Val Gln Ser Gln Asn Ala
    210                 215                 220

Thr Leu Leu Lys Lys Ser Asp Asn Pro Ser Pro Asp Ile Arg Val Val
225                 230                 235                 240

Asn Gly Thr Asp Cys Lys Leu Gly Glu Cys Pro Trp Gln Ala Leu Leu
                245                 250                 255

Leu Asn Asp Glu Gly Asp Gly Phe Cys Gly Gly Thr Ile Leu Ser Pro
            260                 265                 270

Ile Tyr Val Leu Thr Ala Ala His Cys Ile Asn Gln Thr Lys Tyr Ile
        275                 280                 285

Thr Val Val Val Gly Glu Ile Asp Ile Ser Ser Lys Lys Thr Gly Arg
    290                 295                 300

Leu His Ser Val Asp Lys Ile Tyr Val His Gln Lys Phe Val Pro Ala
305                 310                 315                 320

Thr Tyr Asp Tyr Asp Ile Ala Ile Ile Gln Leu Lys Thr Pro Ile Gln
                325                 330                 335

Phe Ser Glu Asn Val Val Pro Ala Cys Leu Pro Thr Ala Asp Phe Ala
            340                 345                 350

Asn Gln Val Leu Met Lys Gln Asn Phe Gly Ile Val Ser Gly Phe Gly
        355                 360                 365

Arg Thr Arg Glu Arg Gly Lys Thr Ser Asn Thr Leu Lys Val Val Thr
    370                 375                 380

Leu Pro Tyr Val Asp Arg His Thr Cys Met Leu Ser Ser Asn Phe Pro
385                 390                 395                 400

Ile Thr Gln Asn Met Phe Cys Ala Gly Tyr Asp Thr Leu Pro Gln Asp
                405                 410                 415

Ala Cys Gln Gly Asp Ser Gly Gly Pro His Ile Thr Ala Tyr Arg Asp
            420                 425                 430

Thr His Phe Ile Thr Gly Ile Val Ser Trp Gly Glu Gly Cys Ala Gln
        435                 440                 445

Thr Gly Lys Tyr Gly Val Tyr Thr Lys Val Ser Lys Phe Ile Leu Trp
    450                 455                 460

Ile Lys Arg Ile Ile Arg Gln Lys Gln Pro Ser Thr Glu Ser Ser Thr
465                 470                 475                 480

Gly Arg Leu


<210> SEQ ID NO 27
<211> LENGTH: 463
<212> TYPE: PRT
<213> ORGANISM: Pseudonaja textilis

<400> SEQUENCE: 27

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Val Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Ala Phe Glu Asp Asp Glu Lys Thr Glu Thr Phe
65                  70                  75                  80
```

```
Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys His Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Asn Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Val Gly Glu Ile Asp Lys Ser Arg Ile Glu
            260                 265                 270

Thr Gly Pro Leu Leu Ser Val Asp Lys Ile Tyr Val His Lys Lys Phe
        275                 280                 285

Val Pro Pro Gln Lys Ala Tyr Lys Phe Asp Leu Ala Ala Tyr Asp Tyr
    290                 295                 300

Asp Ile Ala Ile Ile Gln Met Lys Thr Pro Ile Gln Phe Ser Glu Asn
305                 310                 315                 320

Val Val Pro Ala Cys Leu Pro Thr Ala Asp Phe Ala Asn Gln Val Leu
                325                 330                 335

Met Lys Gln Asp Phe Gly Ile Val Ser Gly Phe Gly Arg Ile Phe Glu
            340                 345                 350

Lys Gly Pro Lys Ser Lys Thr Leu Lys Val Leu Lys Val Pro Tyr Val
        355                 360                 365

Asp Arg His Thr Cys Met Val Ser Ser Glu Thr Pro Ile Thr Pro Asn
    370                 375                 380

Met Phe Cys Ala Gly Tyr Asp Thr Leu Pro Arg Asp Ala Cys Gln Gly
385                 390                 395                 400

Asp Ser Gly Gly Pro His Thr Thr Val Tyr Arg Asp Thr His Phe Ile
                405                 410                 415

Thr Gly Ile Val Ser Ser Gly Glu Gly Cys Ala Arg Asn Gly Lys Tyr
            420                 425                 430

Gly Ile Tyr Thr Lys Leu Ser Lys Phe Ile Pro Trp Ile Lys Arg Ile
        435                 440                 445

Met Arg Gln Lys Leu Pro Ser Thr Glu Ser Ser Thr Gly Arg Leu
    450                 455                 460
```

<210> SEQ ID NO 28
<211> LENGTH: 467
<212> TYPE: PRT
<213> ORGANISM: Pseudonaja textilis textilis

<400> SEQUENCE: 28

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Val Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys Ser Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

His Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Asp Lys Lys Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Val Gly Glu Ile Asp Arg Ser Arg Ala Glu
            260                 265                 270

Thr Gly Pro Leu Leu Ser Val Asp Lys Val Tyr Val His Lys Lys Phe
        275                 280                 285

Val Pro Pro Lys Lys Ser Gln Glu Phe Tyr Glu Lys Phe Asp Leu Val
    290                 295                 300

Ser Tyr Asp Tyr Asp Ile Ala Ile Ile Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Val Ser Gly Phe Gly
            340                 345                 350

Gly Ile Phe Glu Arg Gly Pro Asn Ser Lys Thr Leu Lys Val Leu Lys
        355                 360                 365

Val Pro Tyr Val Asp Arg His Thr Cys Met Leu Ser Ser Asn Phe Pro
    370                 375                 380

Ile Thr Pro Thr Met Phe Cys Ala Gly Tyr Asp Thr Leu Pro Gln Asp
385                 390                 395                 400

Ala Cys Gln Gly Asp Ser Gly Gly Pro His Ile Thr Ala Tyr Arg Asp
                405                 410                 415
```

-continued

```
Thr His Phe Ile Thr Gly Ile Val Ser Trp Gly Glu Gly Cys Ala Arg
            420                 425                 430

Lys Gly Arg Tyr Gly Ile Tyr Thr Lys Leu Ser Lys Phe Ile Pro Trp
        435                 440                 445

Ile Lys Arg Ile Met Arg Gln Lys Leu Pro Ser Thr Glu Ser Ser Thr
    450                 455                 460

Gly Arg Leu
465


<210> SEQ ID NO 29
<211> LENGTH: 463
<212> TYPE: PRT
<213> ORGANISM: Pseudonaja textilis textilis

<400> SEQUENCE: 29

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Glu Arg Ala Asn Ser Leu Val Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys His Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Asn Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Val Gly Glu Ile Asp Lys Ser Arg Ile Glu
            260                 265                 270

Thr Gly Pro Leu Leu Ser Val Asp Lys Ile Tyr Val His Lys Lys Phe
        275                 280                 285

Val Pro Pro Gln Lys Ala Tyr Lys Phe Asp Leu Ala Ala Tyr Asp Tyr
    290                 295                 300

Asp Ile Ala Ile Ile Gln Met Lys Thr Pro Ile Gln Phe Ser Glu Asn
305                 310                 315                 320
```

```
Val Val Pro Ala Cys Leu Pro Thr Ala Asp Phe Ala Asn Gln Val Leu
                325                 330                 335

Met Lys Gln Asp Phe Gly Ile Val Ser Gly Phe Gly Arg Ile Val Glu
            340                 345                 350

Lys Gly Pro Lys Ser Lys Thr Leu Lys Val Leu Lys Val Pro Tyr Val
        355                 360                 365

Asp Arg His Thr Cys Met Val Ser Ser Glu Thr Pro Ile Thr Pro Asn
    370                 375                 380

Met Phe Cys Ala Gly Tyr Asp Thr Leu Pro Arg Asp Ala Cys Gln Gly
385                 390                 395                 400

Asp Ser Gly Gly Pro His Thr Thr Val Tyr Arg Asp Thr His Phe Ile
                405                 410                 415

Thr Gly Ile Val Ser Ser Gly Glu Gly Cys Ala Arg Asn Gly Lys Tyr
            420                 425                 430

Gly Asn Tyr Thr Lys Leu Ser Lys Phe Ile Pro Trp Ile Lys Arg Ile
        435                 440                 445

Met Arg Gln Lys Leu Pro Ser Thr Glu Ser Ser Thr Gly Arg Leu
    450                 455                 460


<210> SEQ ID NO 30
<211> LENGTH: 449
<212> TYPE: PRT
<213> ORGANISM: Pseudonaja textilis

<400> SEQUENCE: 30

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Val Glu Glu Phe
        35                  40                  45

Lys Ser Gly Asn Ile Glu Arg Glu Cys Ile Glu Glu Arg Cys Ser Lys
    50                  55                  60

Glu Glu Ala Arg Glu Ala Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys Ser Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

Gln Asn Ala Pro Leu Leu Lys Ile Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Ala Leu Val Asp Asp Lys Lys Gly Val Phe Cys Gly Gly Thr Ile
```

225 230 235 240

Leu Ser Pro Ile Tyr Val Leu Thr Ala Ala His Cys Ile Asn Glu Thr
245 250 255

Glu Thr Ile Ser Val Val Val Gly Glu Ile Asp Arg Ser Arg Ala Glu
260 265 270

Thr Gly Pro Leu Leu Ser Val Asp Lys Val Tyr Val His Lys Lys Phe
275 280 285

Val Pro Pro Lys Lys Ser Gln Glu Phe Tyr Glu Lys Phe Asp Leu Val
290 295 300

Ser Tyr Asp Tyr Asp Ile Ala Ile Ile Gln Met Lys Thr Pro Ile Gln
305 310 315 320

Phe Ser Glu Asn Val Val Pro Ala Cys Leu Pro Thr Ala Asp Phe Ala
325 330 335

Asn Gln Val Leu Met Lys Gln Asp Phe Gly Ile Val Ser Gly Phe Gly
340 345 350

Gly Ile Phe Glu Arg Gly Pro Asn Ser Lys Thr Leu Lys Val Leu Lys
355 360 365

Val Pro Tyr Val Asp Arg His Thr Cys Met Leu Ser Ser Asn Phe Pro
370 375 380

Ile Thr Pro Thr Met Phe Cys Ala Gly Tyr Asp Thr Leu Pro Gln Asp
385 390 395 400

Ala Cys Gln Gly Asp Ser Gly Gly Pro His Ile Thr Ala Tyr Arg Asp
405 410 415

Thr His Phe Ile Thr Gly Ile Val Ser Trp Gly Glu Gly Cys Ala Arg
420 425 430

Lys Gly Arg Tyr Gly Ile Tyr Thr Lys Leu Ser Lys Phe Ile Pro Trp
435 440 445

Ile

<210> SEQ ID NO 31
<211> LENGTH: 1404
<212> TYPE: DNA
<213> ORGANISM: Oxyuranus scutellatus

<400> SEQUENCE: 31
atggctcctc aactactcct ctgtctgatc ctcacttttc tgtggagtct cccagaggcc 60
gaaagtaatg tattcttaaa aagcaaagtg gcaaatagat tttgcaaag aacaaaacga 120 gctaattcac tgtatgagga atttagatct ggaaacattg aaagggaatg cattgaggag 180
agatgttcaa aagaagaagc cagggaggta tttgaagatg acgagaaaac tgagaccttc 240
tggaatgttt atgtagatgg ggatcagtgt tcatcaaacc cctgtcatta tcgcgggaca 300
tgcaaagatg gcattggtag ctatacctgt acctgcttgt ctggctatga agggaaaaac 360
tgtgaacgtg tcttatataa gtcctgcaga gtggacaatg gtaactgttg gcacttctgc 420
aaacctgttc aaaacgatat tcagtgttca tgtgctgaag gttacctttt gggagaggat 480
gggcactctt gtgttgctgg aggtaacttt tcatgtggta gaaatatcaa aacaaggaac 540
aagagggaag caagtctgcc tgactttgtg cagtcccaga atgcaatttt gctgaaaaaa 600
tctgataatc caagccctga tatcagaatt gttaatggaa tggactgcaa actgggtgaa 660
tgtccgtggc aggcagttct ggtagatgaa aaggaagatg cgttttgtgg aggaacaatt 720
ttgagtccca tctatgtgct tactgcagcc cactgcatta accagaccaa gatgatttca 780
gttgttgtag ggaaataaa catatcaaga aaaaaccccg gacgtcttct ttctgtggat 840

-continued

```
aaaatatatg tgcatcaaaa atttgttcct cccaaaaaag gctatgaatt ctatgaaaag    900

tttgatcttg tcagctatga ctatgatata gccatcctcc aaatgaagac ccctatccag    960

ttctctgaaa atgtggttcc tgcctgcctt cccacagctg attttgccaa ccaagtcctc   1020

atgaaacaag attttggcat cgttagtgga tttgggcgta ttttcgaaaa aggacctcaa   1080

tctaaaacac ttaaagtcct taaggttcct tatgtggaca ggcacacctg catgctttcc   1140

agcgaatctc caattactcc aactatgttc tgtgctggct atgatactct gcctcgagat   1200

gcatgccagg gagacagtgg ggggccccac atcactgcat acagagatac ccactttatt   1260

actgggattg tcagctgggg ggaaggatgt gcacagacag gcaaatatgg tgtttacaca   1320

aaagtgtcca aattcatcct ttggataaaa agaataatgc gtcaaaagct acccagtaca   1380

gagtcaagca ctggtcggct ctaa                                          1404
```

<210> SEQ ID NO 32
<211> LENGTH: 467
<212> TYPE: PRT
<213> ORGANISM: Oxyuranus scutellatus

<400> SEQUENCE: 32

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Tyr Glu Glu Phe
        35                  40                  45

Arg Ser Gly Asn Ile Glu Arg Glu Cys Ile Glu Glu Arg Cys Ser Lys
    50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys Pro Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

Gln Asn Ala Ile Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Val Asp Glu Lys Glu Asp Ala Phe Cys Gly Gly Thr Ile
225                 230                 235                 240

Leu Ser Pro Ile Tyr Val Leu Thr Ala Ala His Cys Ile Asn Gln Thr
                245                 250                 255

Lys Met Ile Ser Val Val Val Gly Glu Ile Asn Ile Ser Arg Lys Asn
            260                 265                 270
```

-continued

```
Pro Gly Arg Leu Leu Ser Val Asp Lys Ile Tyr Val His Gln Lys Phe
        275                 280                 285

Val Pro Pro Lys Lys Gly Tyr Glu Phe Tyr Glu Lys Phe Asp Leu Val
    290                 295                 300

Ser Tyr Asp Tyr Asp Ile Ala Ile Leu Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Val Ser Gly Phe Gly
            340                 345                 350

Arg Ile Phe Glu Lys Gly Pro Gln Ser Lys Thr Leu Lys Val Leu Lys
        355                 360                 365

Val Pro Tyr Val Asp Arg His Thr Cys Met Leu Ser Ser Glu Ser Pro
    370                 375                 380

Ile Thr Pro Thr Met Phe Cys Ala Gly Tyr Asp Thr Leu Pro Arg Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Gln
            420                 425                 430

Thr Gly Lys Tyr Gly Val Tyr Thr Lys Val Ser Lys Phe Ile Leu Trp
        435                 440                 445

Ile Lys Arg Ile Met Arg Gln Lys Leu Pro Ser Thr Glu Ser Ser Thr
    450                 455                 460

Gly Arg Leu
465
```

<210> SEQ ID NO 33
<211> LENGTH: 1404
<212> TYPE: DNA
<213> ORGANISM: Oxyuranus microlepidotus

<400> SEQUENCE: 33

```
atggctcctc aactactcct ctgtctgatc ctcacttttc tgtggagtct cccagaggct      60

gaaagtaatg tattcttaaa aagcaaagtg gcaaatagat tttgcaaag aacaaaacga      120

gctaattcac tgtttgagga atttagatct ggaaacattg aaagggaatg cattgaggag     180

agatgttcaa aagaagaagc cagggaggta tttgaagatg acgagaaaac tgagaccttc     240

tggaatgttt atgtagatgg ggatcagtgt tcatcaaacc cctgtcatta tcgcgggaca     300

tgcaaagatg gcattggtag ctatacctgt acctgcttgt ttggctatga agggaaaaac     360

tgtgaacgtg tcttatataa gtcctgcaga gtggacaatg gtaactgttg gcacttctgc     420

aaacctgttc aaaacgatat tcagtgttca tgtgctgaag gttacctttt gggagaggat     480

gggcactctt gtgttgctgg aggtaacttt tcatgtggta gaaatatcaa aacaaggaac     540

aagagggaag caagtctgcc tgactttgtg cagtcccaga atgcaacttt gctgaaaaaa     600

tctgataatc caagccctga tatcagaatt gttaatggaa tggactgcaa actgggtgaa     660

tgtccgtggc aggcagttct ggtagatgaa aaggaaggtg tgttttgtgg aggaacaatt     720

ttgagtccca tctatgtgct tactgcagcc cactgcatta accagaccga gaagatttca     780

gttgttgtag ggaaatagaa caaatcaaga gtagaaaccg gacatcttct ttctgtggat     840

aaaatatatg tgcataaaaa atttgttcct cccaaaaaag gctataaatt ctatgaaaag     900

tttgatcttg tcagctatga ctatgatata gccatcatcc aaatgaagac ccctatccag     960
```

```
ttctctgaaa atgtggttcc tgcctgcctt cccacagctg attttgccaa ccaagtcctc   1020

atgaaacaag attttggcat cattagtgga tttgggcgta ttttcgaaaa aggaccgaaa   1080

tctaacacac ttaaagtcct taaggttcct tatgtggaca ggcacacctg catggtttcc   1140

agcgaatctc caattactcc aactatgttc tgtgctggct atgatactct gcctcgagat   1200

gcatgccagg gagacagtgg ggggccccac atcactgcat acagagatac ccactttatt   1260

actgggattg tcagctgggg ggaaggatgt gctaagaaag gcaaatatgg tatttacaca   1320

aaagtgtcca aattcatcct ttggataaaa agaataatgc gtcaaaagct acccagtaca   1380

gagtcaagca ctggtcggct ctaa                                          1404
```

<210> SEQ ID NO 34
<211> LENGTH: 467
<212> TYPE: PRT
<213> ORGANISM: Oxyuranus microlepidotus

<400> SEQUENCE: 34

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ala Asn Ser Leu Phe Glu Glu Phe
        35                  40                  45

Arg Ser Gly Asn Ile Glu Arg Glu Cys Ile Glu Glu Arg Cys Ser Lys
    50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Phe Gly Tyr Glu Gly Lys Asn Cys Glu Arg Val Leu Tyr Lys Ser
        115                 120                 125

Cys Arg Val Asp Asn Gly Asn Cys Trp His Phe Cys Lys Pro Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Gln Thr
                245                 250                 255

Glu Lys Ile Ser Val Val Val Gly Glu Ile Asp Lys Ser Arg Val Glu
            260                 265                 270

Thr Gly His Leu Leu Ser Val Asp Lys Ile Tyr Val His Lys Lys Phe
        275                 280                 285

Val Pro Pro Lys Lys Gly Tyr Lys Phe Tyr Glu Lys Phe Asp Leu Val
```

```
    290                 295                 300

Ser Tyr Asp Tyr Asp Ile Ala Ile Ile Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Ile Ser Gly Phe Gly
            340                 345                 350

Arg Ile Phe Glu Lys Gly Pro Lys Ser Asn Thr Leu Lys Val Leu Lys
        355                 360                 365

Val Pro Tyr Val Asp Arg His Thr Cys Met Val Ser Ser Glu Ser Pro
    370                 375                 380

Ile Thr Pro Thr Met Phe Cys Ala Gly Tyr Asp Thr Leu Pro Arg Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Lys
            420                 425                 430

Lys Gly Lys Tyr Gly Ile Tyr Thr Lys Val Ser Lys Phe Ile Leu Trp
        435                 440                 445

Ile Lys Arg Ile Met Arg Gln Lys Leu Pro Ser Thr Glu Ser Ser Thr
    450                 455                 460

Gly Arg Leu
465
```

<210> SEQ ID NO 35
<211> LENGTH: 1365
<212> TYPE: DNA
<213> ORGANISM: Pseudechis porphyriacus

<400> SEQUENCE: 35

```
atggctcctc aactactcct ctgtctgatc ctcacttttc tctggagtct cccggaggct      60

gaaagtaatg tattcttaaa aagcaaagag gcaaatagat ttttgcaaag aacaaaacga     120

tctaattcac tgtttgagga atttagacct ggaaacattg aaagggaatg cattgaggag     180

aaatgttcaa aagaagaagc cagggagata tttaaagata acgagaaaac tgaggccttt     240

tggaatgttt atgtagatgg ggatcagtgt tcatcaaacc cctgtcatta tggtgggaca     300

tgcaaagatg gcattggtag ctatacctgt acctgcttgc ctaactatga agggaaaaac     360

tgtgaacatc tcttatttaa gtcctgcaga tttttcaatg gtaactgttg gcacttctgc     420

aaacctgttc aaaacgacac tcagtgttca tgtgctgaaa gttaccgttt gggagatgat     480

gggcactctt gtgttgctga aggtgacttt tcatgtggta gaaatataaa agcaaggaac     540

aagagggaag caagtctgcc tgactttgtg cagtcccaga atgcaacttt gctgaaaaaa     600

tctgataatc caagccctga tatcagaatt attaatggaa tggactgcaa actgggtgaa     660

tgtccatggc aggcagttct gctagataaa gaaggagatg tgttttgtgg aggaacaatt     720

ttgagtccca tctatgtgct tactgcagcc cactgcatta cccagtccaa gcacatttca     780

gttgttgtag gggaaataga tatatcaaga aaagaaacca gacatcttct ttctgtagat     840

aaagcatatg tgcatacaaa atttgttctt gccacctatg actatgatat agccatcatc     900

caattgaaga cccctatcca gttctctgaa aatgtggttc ctgcctgtct tcccactgct     960

gattttgcca accaagtcct catgaaacaa gattttggca tcattagtgg atttgggcat    1020

actcgatctg gaggacagac ctctaacaca cttaaagtcg ttacgattcc ttatgtggac    1080
```

```
aggcacacct gcatgctttc cagcgatttt cgaattactc caaatatgtt ctgtgctggt   1140

tatgatactc tgcctcgaga tgcatgccag ggagacagtg gggggcccca catcactgca   1200

tacagagata cccactttat tactgggatt atcagctggg gggaaggatg tgcaaagaaa   1260

ggcaaatatg gtgtttacac aaaagtgtcc aacttcatcc cttggataaa agcagtaatg   1320

cgtaaacatc aacccagtac agagtcaagc actggtcggc tctaa                    1365


<210> SEQ ID NO 36
<211> LENGTH: 450
<212> TYPE: PRT
<213> ORGANISM: Pseudechis porphyriacus

<400> SEQUENCE: 36

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Glu Ala Asn
            20                  25                  30

Arg Phe Leu Gln Arg Thr Lys Arg Ser Asn Ser Leu Phe Glu Glu Phe
        35                  40                  45

Arg Pro Gly Asn Ile Glu Arg Glu Cys Ile Glu Glu Lys Cys Ser Lys
    50                  55                  60

Glu Glu Ala Arg Glu Ile Phe Lys Asp Asn Glu Lys Thr Glu Ala Phe
65                  70                  75                  80

Trp Asn Val Tyr Val Asp Gly Asp Gln Cys Ser Ser Asn Pro Cys His
                85                  90                  95

Tyr Gly Gly Thr Cys Lys Asp Gly Ile Gly Ser Tyr Thr Cys Thr Cys
            100                 105                 110

Leu Pro Asn Tyr Glu Gly Lys Asn Cys Glu His Leu Leu Phe Lys Ser
        115                 120                 125

Cys Arg Phe Phe Asn Gly Asn Cys Trp His Phe Cys Lys Pro Val Gln
    130                 135                 140

Asn Asp Thr Gln Cys Ser Cys Ala Glu Ser Tyr Arg Leu Gly Asp Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Ile Asn Gly Met Asp Cys Lys Leu Gly Glu Cys Pro Trp Gln
    210                 215                 220

Ala Val Leu Leu Asp Lys Glu Gly Asp Val Phe Cys Gly Gly Thr Ile
225                 230                 235                 240

Leu Ser Pro Ile Tyr Val Leu Thr Ala Ala His Cys Ile Thr Gln Ser
                245                 250                 255

Lys His Ile Ser Val Val Val Gly Glu Ile Asp Ile Ser Arg Lys Glu
            260                 265                 270

Thr Arg His Leu Leu Ser Val Asp Lys Ala Tyr Val His Thr Lys Phe
        275                 280                 285

Val Leu Ala Thr Tyr Asp Tyr Asp Ile Ala Ile Ile Gln Leu Lys Thr
    290                 295                 300

Pro Ile Gln Phe Ser Glu Asn Val Val Pro Ala Cys Leu Pro Thr Ala
305                 310                 315                 320

Asp Phe Ala Asn Gln Val Leu Met Lys Gln Asp Phe Gly Ile Ile Ser
```

-continued

```
            325                 330                 335

Gly Phe Gly His Thr Arg Ser Gly Gly Gln Thr Ser Asn Thr Leu Lys
        340                 345                 350

Val Val Thr Ile Pro Tyr Val Asp Arg His Thr Cys Met Leu Ser Ser
    355                 360                 365

Asp Phe Arg Ile Thr Pro Asn Met Phe Cys Ala Gly Tyr Asp Thr Leu
370                 375                 380

Pro Arg Asp Ala Cys Gln Gly Asp Ser Gly Gly Pro His Ile Thr Ala
385                 390                 395                 400

Tyr Arg Asp Thr His Phe Ile Thr Gly Ile Ile Ser Trp Gly Glu Gly
                405                 410                 415

Cys Ala Lys Lys Gly Lys Tyr Gly Val Tyr Thr Lys Val Ser Asn Phe
            420                 425                 430

Ile Pro Trp Ile Lys Ala Val Met Arg Lys His Gln Pro Ser Thr Glu
        435                 440                 445

Ser Ser
    450


<210> SEQ ID NO 37
<211> LENGTH: 1368
<212> TYPE: DNA
<213> ORGANISM: Hoplocephalus stephensii

<400> SEQUENCE: 37

atggctcctc aactactcct ctgtctgatc ctcacttttc tgtggagtgt cccagaggct     60

gaaagtaatg tattcttaaa aagcaaagtg gcaaatagat tttgcaaag aacaaaacga    120

tctaattcac tgtttgagga aattagacct ggaaacattg aaagggaatg cattgaggag    180

aaatgttcaa aagaagaagc cagggaggta tttgaagata acgagaaaac tgagaccttc    240

tggaatgttt atgtagatgg ggatcagtgt tcatcaaacc cctgtcatta tcacgggaca    300

tgcaaagatg gcattggtag ctatacctgt acctgcttgc ctaactatga agggaaaaac    360

tgtgaaaaag tcttatttaa gtcctgcaga gcgttcaatg gtaactgttg gcacttctgc    420

aaacgtgttc aaagtgaaac tcagtgttca tgtgctgaaa gttaccgttt gggagttgat    480

gggcactctt gtgttgctga aggtgacttt tcatgtggta gaaatataaa agcaaggaac    540

aagagggaag caagtctgcc tgactttgtg cagtcccaga aggcaacttt gctgaaaaaa    600

tctgataatc caagccctga tatcagaatt gttaatggaa tggactccaa actgggtgaa    660

tgtccatggc aggcagttct gataaatgaa aaaggagaag tgttttgtgg aggaacaatt    720

ttgagtccca tccatgtgct tactgcagcc cactgcatta accagaccaa gagcgtttca    780

gttattgtag gggaaataga catatcaaga aaagaaacca gacgtcttct ttctgtggat    840

aaaatatatg tgcatacaaa atttgttcct cccaactatt actatgggca tcaaaacttt    900

gatcgtgtcg cctatgacta tgatatagcc atcatccgaa tgaagacccc tatccagttc    960

tctgaaaatg tggttcctgc ctgccttccc actgctgatt ttgccaacga agtcctcatg   1020

aaacaagatt ctggcatcgt tagtggattt gggcgtattc gatttaaaga accgacctct   1080

aacacactta aagtcattac ggttccttat gtggacaggc acacctgcat gctttccagt   1140

gattttcgaa ttactcaaaa tatgttctgt gctggctatg atactctgcc tcaagatgca   1200

tgcgagggag acagtggggg gccccacatc actgcatacg gagataccca ctttattact   1260

gggattgtca gctgggggga aggatgtgca cggaaaggca aatatggtgt ttacacaaaa   1320

gtgtccagat tcatcccttg gataaaaaaa ataatgagtc taaagtaa                1368
```

<210> SEQ ID NO 38
<211> LENGTH: 455
<212> TYPE: PRT
<213> ORGANISM: Hoplocephalus stephensii

<400> SEQUENCE: 38

Met Ala Pro Gln Leu Leu Leu Cys Leu Ile Leu Thr Phe Leu Trp Ser
1 5 10 15

Val Pro Glu Ala Glu Ser Asn Val Phe Leu Lys Ser Lys Val Ala Asn
20 25 30

Arg Phe Leu Gln Arg Thr Lys Arg Ser Asn Ser Leu Phe Glu Glu Ile
35 40 45

Arg Pro Gly Asn Ile Glu Arg Glu Cys Ile Glu Glu Lys Cys Ser Lys
50 55 60

Glu Glu Ala Arg Glu Val Phe Glu Asp Asn Glu Lys Thr Glu Thr Phe
65 70 75 80

Trp Asn Val Tyr Val Asp Gly Asp Gln Cys Ser Ser Asn Pro Cys His
85 90 95

Tyr His Gly Thr Cys Lys Asp Gly Ile Gly Ser Tyr Thr Cys Thr Cys
100 105 110

Leu Pro Asn Tyr Glu Gly Lys Asn Cys Glu Lys Val Leu Phe Lys Ser
115 120 125

Cys Arg Ala Phe Asn Gly Asn Cys Trp His Phe Cys Lys Arg Val Gln
130 135 140

Ser Glu Thr Gln Cys Ser Cys Ala Glu Ser Tyr Arg Leu Gly Val Asp
145 150 155 160

Gly His Ser Cys Val Ala Glu Gly Asp Phe Ser Cys Gly Arg Asn Ile
165 170 175

Lys Ala Arg Asn Lys Arg Glu Ala Ser Leu Pro Asp Phe Val Gln Ser
180 185 190

Gln Lys Ala Thr Leu Leu Lys Lys Ser Asp Asn Pro Ser Pro Asp Ile
195 200 205

Arg Ile Val Asn Gly Met Asp Ser Lys Leu Gly Glu Cys Pro Trp Gln
210 215 220

Ala Val Leu Ile Asn Glu Lys Gly Glu Val Phe Cys Gly Gly Thr Ile
225 230 235 240

Leu Ser Pro Ile His Val Leu Thr Ala Ala His Cys Ile Asn Gln Thr
245 250 255

Lys Ser Val Ser Val Ile Val Gly Glu Ile Asp Ile Ser Arg Lys Glu
260 265 270

Thr Arg Arg Leu Leu Ser Val Asp Lys Ile Tyr Val His Thr Lys Phe
275 280 285

Val Pro Pro Asn Tyr Tyr Tyr Gly His Gln Asn Phe Asp Arg Val Ala
290 295 300

Tyr Asp Tyr Asp Ile Ala Ile Ile Arg Met Lys Thr Pro Ile Gln Phe
305 310 315 320

Ser Glu Asn Val Val Pro Ala Cys Leu Pro Thr Ala Asp Phe Ala Asn
325 330 335

Glu Val Leu Met Lys Gln Asp Ser Gly Ile Val Ser Gly Phe Gly Arg
340 345 350

Ile Arg Phe Lys Glu Pro Thr Ser Asn Thr Leu Lys Val Ile Thr Val
355 360 365

Pro Tyr Val Asp Arg His Thr Cys Met Leu Ser Ser Asp Phe Arg Ile

```
    370                 375                 380

Thr Gln Asn Met Phe Cys Ala Gly Tyr Asp Thr Leu Pro Gln Asp Ala
385                 390                 395                 400

Cys Glu Gly Asp Ser Gly Gly Pro His Ile Thr Ala Tyr Gly Asp Thr
                405                 410                 415

His Phe Ile Thr Gly Ile Val Ser Trp Gly Glu Gly Cys Ala Arg Lys
            420                 425                 430

Gly Lys Tyr Gly Val Tyr Thr Lys Val Ser Arg Phe Ile Pro Trp Ile
        435                 440                 445

Lys Lys Ile Met Ser Leu Lys
    450                 455


<210> SEQ ID NO 39
<211> LENGTH: 1362
<212> TYPE: DNA
<213> ORGANISM: Notechis scutatus

<400> SEQUENCE: 39

atggctcctc aactactcct ctgtctgatc ctcacttttc tgtggagtct cccagaggct      60

gaaagtaatg tattcttaaa aagcaaagtg gcaaatagat ttttgcaaag aacaaaacga     120

tctaattcac tgtttgagga aattagacct ggaaacattg aaagggaatg cattgaggag     180

aaatgttcaa aagaagaagc cagggaggta tttgaagata acgagaaaac tgagaccttc     240

tggaatgttt atgtagatgg ggatcagtgt tcatcaaacc cctgtcatta tcgcgggaca     300

tgcaaagatg gcattggtag ctatacctgt acctgcttgc ctaactatga agggaaaaac     360

tgtgaaaaag tcttatttaa gtcctgcaga gcattcaatg gtaactgttg gcacttctgc     420

aaacgtgttc aaagtgaaac tcagtgttca tgtgctgaaa gttacctttt gggagttgat     480

gggcactctt gtgttgctga aggtgacttt tcatgtggta gaaatataaa agcaaggaac     540

aagagggaag caagtctgcc tgactttgtg cagtcccaga aggcaactgt gctgaaaaaa     600

tctgataatc caagccctga tatcagaatt gttaatggaa tggactgcaa actgggtgaa     660

tgtccatggc aggcagttct gataaatgaa aaaggagaag tgttttgtgg aggaacaatt     720

ttgagcccca tccatgtgct tactgcagcc cactgcatta accagaccaa gagcgtttca     780

gttattgtag gggaaataga catatcaaga aaagaaacca gacgtcttct ttctgtggat     840

aaaatatatg tgcataaaaa atttgttcct cccaactctt actatcaaaa cattgatcgt     900

ttcgcctatg actatgatat agccatcatc cgaatgaaga cccctatcca gttctctgaa     960

aatgtggttc ctgcctgcct tcccactgct gattttgcca aggaagtcct catgaaacaa    1020

gattctggca tcgttagtgg atttgggcgt actcaatcta taggatatac ctctaacata    1080

cttaaagtca ttacggttcc ttatgtggac aggcacacct gcatgctttc cagtaatttt    1140

cgaattactc aaaatatgtt ctgtgctggc tatgatactc tgcctcaaga tgcatgccag    1200

ggagacagtg gggggcccca catcactgca tacggagata cccactttgt tactgggatt    1260

atcagctggg gggaaggatg tgcacggaaa ggcaaatatg gtgtttacac aaaagtgtcc    1320

aatttcatcc cttggataaa aaaaataatg agtctaaagt aa                       1362


<210> SEQ ID NO 40
<211> LENGTH: 453
<212> TYPE: PRT
<213> ORGANISM: Notechis scutatus

<400> SEQUENCE: 40
```

-continued

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45

Arg Pro Gly Asn Ile Glu Arg Glu Cys Ile Glu Glu Lys Cys Ser Lys
    50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Phe Lys Ser
        115                 120                 125

Cys Arg Ala Phe Asn Gly Asn Cys Trp His Phe Cys Lys Arg Val Gln
    130                 135                 140

Ser Glu Thr Gln Cys Ser Cys Ala Glu Ser Tyr Leu Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Val Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
                245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Lys Lys Phe
        275                 280                 285

Val Pro Pro Asn Ser Tyr Tyr Gln Asn Ile Asp Arg Phe Ala Tyr Asp
    290                 295                 300

Tyr Asp Ile Ala Ile Ile Arg Met Lys Thr Pro Ile Gln Phe Ser Glu
305                 310                 315                 320

Asn Val Val Pro Ala Cys Leu Pro Thr Ala Asp Phe Ala Lys Glu Val
                325                 330                 335

Leu Met Lys Gln Asp Ser Gly Ile Val Ser Gly Phe Gly Arg Thr Gln
            340                 345                 350

Ser Ile Gly Tyr Thr Ser Asn Ile Leu Lys Val Ile Thr Val Pro Tyr
        355                 360                 365

Val Asp Arg His Thr Cys Met Leu Ser Ser Asn Phe Arg Ile Thr Gln
    370                 375                 380

Asn Met Phe Cys Ala Gly Tyr Asp Thr Leu Pro Gln Asp Ala Cys Gln
385                 390                 395                 400

Gly Asp Ser Gly Gly Pro His Ile Thr Ala Tyr Gly Asp Thr His Phe
                405                 410                 415

Val Thr Gly Ile Ile Ser Trp Gly Glu Gly Cys Ala Arg Lys Gly Lys
```

```
            420                 425                 430

Tyr Gly Val Tyr Thr Lys Val Ser Asn Phe Ile Pro Trp Ile Lys Lys
        435                 440                 445

Ile Met Ser Leu Lys
    450


<210> SEQ ID NO 41
<211> LENGTH: 1368
<212> TYPE: DNA
<213> ORGANISM: Tropidechis carinatus

<400> SEQUENCE: 41

atggctcctc aactactcct ctgtctgatc ctcacttttc tgtggagtct cccagaggct     60

gaaagtaatg tattcttaaa aagcaaagtg gcaaatagat tttgcaaag aacaaaacga    120

tctaattcac tgtttgagga aattagacct ggaaacattg aaagggaatg cattgaggag    180

aaatgttcaa aagaagaagc cagggaggta tttgaagata acgagaaaac tgagaccttc    240

tggaatgttt atgtagatgg ggatcagtgt tcatcaaacc cctgtcatta tcgcgggaca    300

tgcaaagatg gcattggtag ctatacctgt acctgcttgc ctaactatga agggaaaaac    360

tgtgaaaaag tcttatatca gtcctgcaga gtggacaatg gtaactgttg gcacttctgc    420

aaacgtgttc aaagtgaaac tcagtgttca tgtgctgaaa gttaccgttt gggagttgat    480

gggcactctt gtgttgctga aggtgacttt tcatgtggta gaaatataaa agcaaggaac    540

aagagggaag caagtctgcc tgactttgtg cagtcccaaa aggcaacttt gctgaaaaaa    600

tctgataatc caagccctga tatcagaatt gttaatggaa tggactgcaa actgggtgaa    660

tgtccatggc aggcagttct gataaatgaa aaaggagaag tgttttgtgg aggaacaatt    720

ttgagtccca tccatgtgct tactgcagcc cactgcatta accagaccaa gagcgtttca    780

gttattgtag gggaaataga catatcaaga aaagaaacca gacgtcttct ttctgtggat    840

aaaatatatg tgcatacaaa atttgttcct cccaactatt actatgtgca tcaaaacttt    900

gatcgtgtcg cctatgacta tgatatagcc atcatccgaa tgaagacccc tatccagttc    960

tctgaaaatg tggttcctgc ctgccttccc actgctgatt ttgccaacga agtcctcatg   1020

aaacaagatt ctggcatcgt tagtggattt gggcgtattc aatttaaaca accgacctct   1080

aacacactta aagtcattac ggttccttat gtggacaggc acacctgcat gctttccagt   1140

gattttcgaa ttactcaaaa tatgttctgt gctggctatg atactctgcc tcaagatgca   1200

tgccagggag acagtggggg gccccacatc actgcataca gagataccca ctttattact   1260

gggattatca gctgggggga aggatgtgca cggaaaggca aatatggtgt ttacacaaaa   1320

gtgtccaaat tcatcccttg gataaaaaaa ataatgagtc taaagtaa               1368


<210> SEQ ID NO 42
<211> LENGTH: 455
<212> TYPE: PRT
<213> ORGANISM: Tropidechis carinatus

<400> SEQUENCE: 42

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45
```

-continued

```
Arg Pro Gly Asn Ile Glu Arg Glu Cys Ile Glu Glu Lys Cys Ser Lys
    50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Tyr Gln Ser
        115                 120                 125

Cys Arg Val Asp Asn Gly Asn Cys Trp His Phe Cys Lys Arg Val Gln
    130                 135                 140

Ser Glu Thr Gln Cys Ser Cys Ala Glu Ser Tyr Arg Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
                245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Thr Lys Phe
        275                 280                 285

Val Pro Pro Asn Tyr Tyr Tyr Val His Gln Asn Phe Asp Arg Val Ala
    290                 295                 300

Tyr Asp Tyr Asp Ile Ala Ile Ile Arg Met Lys Thr Pro Ile Gln Phe
305                 310                 315                 320

Ser Glu Asn Val Val Pro Ala Cys Leu Pro Thr Ala Asp Phe Ala Asn
                325                 330                 335

Glu Val Leu Met Lys Gln Asp Ser Gly Ile Val Ser Gly Phe Gly Arg
            340                 345                 350

Ile Gln Phe Lys Gln Pro Thr Ser Asn Thr Leu Lys Val Ile Thr Val
        355                 360                 365

Pro Tyr Val Asp Arg His Thr Cys Met Leu Ser Ser Asp Phe Arg Ile
    370                 375                 380

Thr Gln Asn Met Phe Cys Ala Gly Tyr Asp Thr Leu Pro Gln Asp Ala
385                 390                 395                 400

Cys Gln Gly Asp Ser Gly Gly Pro His Ile Thr Ala Tyr Arg Asp Thr
                405                 410                 415

His Phe Ile Thr Gly Ile Ile Ser Trp Gly Glu Gly Cys Ala Arg Lys
            420                 425                 430

Gly Lys Tyr Gly Val Tyr Thr Lys Val Ser Lys Phe Ile Pro Trp Ile
        435                 440                 445

Lys Lys Ile Met Ser Leu Lys
    450                 455
```

<210> SEQ ID NO 43
<211> LENGTH: 671
<212> TYPE: DNA
<213> ORGANISM: Demansia vestigiata

<400> SEQUENCE: 43
atggctcctc aactactcct ctgtctgatc cagacttttc tgtggagtct cccagaggct 60
gaaagtaatg tattcttaaa aagcaatgtg gcaaatagat tttgcaaag aacaaaacga 120 gctaattcag ggtttgagga aatttaccct gcaaactttg aaagggaatg cgttgaggag 180
agatgttcaa aagaagaagc cagggaggta tttgaagatg acgagaaaac tgaggccttc 240
tggactgttt atgtagatgg ggatcagtgt ttatcaaacc cctgtcatta tggcgggaca 300
tgcaaagatg gcattggtag ctatacctgt acctgcttgg ctggctatga agggaaaaac 360
tgtgaacatg acttacttaa gtcctgcaga gtggacaatg gtaactgttg gcacttctgc 420
aaacctgttc aaaacgacac tcagtgttca tgtgctgaag gttaccgttt gggagataat 480
gggttctctt gtattgctga aggtgagttt tcatgtggca gaaatataaa atcaaggaac 540
aagagggaag caagtctgcc tgactttcaa acagattttt ctgatgacta tgatgcgatt 600
gatgaaaata atttgattga aactgtgcag tcccagagtg caactttgct gaaaaaatct 660
gataatccaa a 671

<210> SEQ ID NO 44
<211> LENGTH: 473
<212> TYPE: PRT
<213> ORGANISM: Demansia vestigiata

<400> SEQUENCE: 44

Met Ala Pro Gln Leu Leu Leu Cys Leu Ile Gln Thr Phe Leu Trp Ser
1               5                   10                  15

Leu Pro Glu Ala Glu Ser Asn Val Phe Leu Lys Ser Asn Val Ala Asn
            20                  25                  30

Arg Phe Leu Gln Arg Thr Lys Arg Ala Asn Ser Gly Phe Glu Glu Ile
        35                  40                  45

Tyr Pro Ala Asn Phe Glu Arg Glu Cys Val Glu Glu Arg Cys Ser Lys
    50                  55                  60

Glu Glu Ala Arg Glu Val Phe Glu Asp Asp Glu Lys Thr Glu Ala Phe
65                  70                  75                  80

Trp Thr Val Tyr Val Asp Gly Asp Gln Cys Leu Ser Asn Pro Cys His
                85                  90                  95

Tyr Gly Gly Thr Cys Lys Asp Gly Ile Gly Ser Tyr Thr Cys Thr Cys
            100                 105                 110

Leu Ala Gly Tyr Glu Gly Lys Asn Cys Glu His Asp Leu Leu Lys Ser
        115                 120                 125

Cys Arg Val Asp Asn Gly Asn Cys Trp His Phe Cys Lys Pro Val Gln
    130                 135                 140

Asn Asp Thr Gln Cys Ser Cys Ala Glu Gly Tyr Arg Leu Gly Asp Asn
145                 150                 155                 160

Gly Phe Ser Cys Ile Ala Glu Gly Glu Phe Ser Cys Gly Arg Asn Ile
                165                 170                 175

Lys Ser Arg Asn Lys Arg Glu Ala Ser Leu Pro Asp Phe Gln Thr Asp
            180                 185                 190

Phe Ser Asp Asp Tyr Asp Ala Ile Asp Glu Asn Asn Leu Ile Glu Thr
        195                 200                 205

Val Gln Ser Gln Ser Ala Thr Leu Leu Lys Lys Ser Asp Asn Pro Asn

-continued

```
    210                 215                 220

Pro Asp Ile Arg Ile Val Asn Gly Leu Asp Cys Lys Leu Gly Glu Cys
225                 230                 235                 240

Pro Trp Gln Ala Val Leu Ile Asp Glu Lys Gly Thr Ala Phe Gly Gly
                245                 250                 255

Gly Thr Ile Leu Ser Pro Tyr Phe Val Leu Thr Ala Ala His Cys Ile
            260                 265                 270

Asn Lys Thr Lys Ser Ile Ala Val Val Val Gly Gln Val Asp Ile Ser
        275                 280                 285

Arg Lys Glu Thr Arg Arg Leu Leu Ser Val Asp Lys Val Tyr Thr His
    290                 295                 300

Pro Lys Tyr Val His Val Thr Asn Asp Tyr Asp Ile Ala Ile Ile Gln
305                 310                 315                 320

Leu Lys Thr Pro Ile Gln Phe Ser Glu Asn Val Val Pro Ala Cys Leu
                325                 330                 335

Pro Thr Ala Asp Phe Ala Asn His Val Leu Met Lys Gln Asp Phe Gly
            340                 345                 350

Ile Val Ser Gly Phe Gly Arg Ile Glu Glu Lys Gly Pro Thr Ser Asn
        355                 360                 365

Ile Leu Lys Val Val Met Val Pro Tyr Val Asp Arg His Thr Cys Ile
    370                 375                 380

Leu Ser Thr Lys Ile Pro Ile Thr Arg Asn Met Phe Cys Ala Gly Tyr
385                 390                 395                 400

Gly Asn Gln Pro Glu Asp Ala Cys Glu Gly Asp Ser Gly Gly Pro His
                405                 410                 415

Ile Thr Ala Tyr Lys Asp Thr His Phe Leu Thr Gly Ile Val Ser Trp
            420                 425                 430

Gly Glu Gly Cys Gly Arg Asp Gly Lys Tyr Gly Ile Tyr Thr Lys Val
        435                 440                 445

Ser Asn Phe Leu Pro Trp Ile Lys Thr Ile Met Arg Arg Lys Gln Pro
    450                 455                 460

Ser Thr Glu Ser Ser Thr Gly Arg Leu
465                 470
```

<210> SEQ ID NO 45
<211> LENGTH: 1416
<212> TYPE: DNA
<213> ORGANISM: Demansia vestigiata

<400> SEQUENCE: 45

```
atggctcctc aactactcct ctgtctgatc ctcacttttc tgtggagtct cccagaggct     60

gaaagtaatg tattcttaaa aagcaatgtg gcaaatagat ttttgcaaag aacaaaacga    120

gctaattcaa tatttgaaga aattagacct ggaaacattg aaagggaatg cgttgaggaa    180

aaatgttcaa aagaagaagc cagggaggta tttcaagata atgagaaaac tgaggccttc    240

tggactgttt atgtagatgg ggatcagtgt ttatcaaacc cctgtcatta tcgtgggaca    300

tgcaaagatg gcattggtag ctatacctgt acctgcttgc ctggctatga agggaaaaac    360

tgtgaacatg tcgtagttaa gtcctgcaga ctgttcaatg gtaactgttg gcacttctgc    420

aaaactgttc aaaacgacac tcagtgttca tgtgctgaag gttaccgttt gggagttgat    480

gggttctcct gtattgctga aggtgacttt tcatgtggca gaattataaa atcaaggaac    540

aagagggaag caagtctgcc tgactttcat ttttctgatg actatgatgc gattgatgaa    600

aataatttgg ttgaaactgt gcagtcccag agtgcaactt tgctgaaaaa atctgataat    660
```

```
ccaagccctg atatcagaat tgttagtgga ttggactgca aactgggtga atgtccatgg     720

caggcagttc tgatagatga acatggaaaa gcgtttggtg gaggaacaat tttgagtccc     780

tactttgtgc ttactgcagc ccactgcctt aaccagacca aaagcattgc agttgttgta     840

gggcaagtag acatatcaag aaaagaaacc agacatcttc tccatgtgga taaagcatat     900

atgcattcaa aatatgttcg tgccacctat gaccatgata tagccatcct cagactgagg     960

acccctatcc agttctctga aaatgtggtt cctgcctgcc ttcccactgc tgattttgcc    1020

gacgaagtcc tcatgaaaca agattttggc atcgttagtg gatttgggcg tttgcatgaa    1080

agaggatcga cctctgacat acttaaagtc attagggttc cttatgtgga caggtacacc    1140

tgcatgcttt ccagcaacta tcgaattact ccaagtatgt tctgtgctgg ctatggtaat    1200

cagcctcaag atgcatgcca gggagacagt ggggggcccc acatcactgc atacggagat    1260

acccacttta ttactgggat tatcagctgg ggggaaggtt gtggaaggaa aggcaaatat    1320

ggtatttaca caaaagtgtc caatttcatc ccttggataa aaacaataat gcgtcgaaat    1380

caacccagta cagagtcaag cactggtcgg ctctaa                              1416
```

<210> SEQ ID NO 46
<211> LENGTH: 471
<212> TYPE: PRT
<213> ORGANISM: Demansia vestigiata

<400> SEQUENCE: 46

```
Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Asn Val Ala Asn
            20                  25                  30

Arg Phe Leu Gln Arg Thr Lys Arg Ala Asn Ser Ile Phe Glu Glu Ile
        35                  40                  45

Arg Pro Gly Asn Ile Glu Arg Glu Cys Val Glu Glu Lys Cys Ser Lys
    50                  55                  60

Glu Glu Ala Arg Glu Val Phe Gln Asp Asn Glu Lys Thr Glu Ala Phe
65                  70                  75                  80

Trp Thr Val Tyr Val Asp Gly Asp Gln Cys Leu Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Gly Tyr Glu Gly Lys Asn Cys Glu His Val Val Val Lys Ser
        115                 120                 125

Cys Arg Leu Phe Asn Gly Asn Cys Trp His Phe Cys Lys Thr Val Gln
    130                 135                 140

Asn Asp Thr Gln Cys Ser Cys Ala Glu Gly Tyr Arg Leu Gly Val Asp
145                 150                 155                 160

Gly Phe Ser Cys Ile Ala Glu Gly Asp Phe Ser Cys Gly Arg Ile Ile
                165                 170                 175

Lys Ser Arg Asn Lys Arg Glu Ala Ser Leu Pro Asp Phe His Phe Ser
            180                 185                 190

Asp Asp Tyr Asp Ala Ile Asp Glu Asn Asn Leu Val Glu Thr Val Gln
        195                 200                 205

Ser Gln Ser Ala Thr Leu Leu Lys Lys Ser Asp Asn Pro Ser Pro Asp
    210                 215                 220

Ile Arg Ile Val Ser Gly Leu Asp Cys Lys Leu Gly Glu Cys Pro Trp
225                 230                 235                 240
```

```
Gln Ala Val Leu Ile Asp Glu His Gly Lys Ala Phe Gly Gly Gly Thr
                245                 250                 255

Ile Leu Ser Pro Tyr Phe Val Leu Thr Ala Ala His Cys Leu Asn Gln
            260                 265                 270

Thr Lys Ser Ile Ala Val Val Val Gly Gln Val Asp Ile Ser Arg Lys
        275                 280                 285

Glu Thr Arg His Leu Leu His Val Asp Lys Ala Tyr Met His Ser Lys
    290                 295                 300

Tyr Val Arg Ala Thr Tyr Asp His Asp Ile Ala Ile Leu Arg Leu Arg
305                 310                 315                 320

Thr Pro Ile Gln Phe Ser Glu Asn Val Val Pro Ala Cys Leu Pro Thr
                325                 330                 335

Ala Asp Phe Ala Asp Glu Val Leu Met Lys Gln Asp Phe Gly Ile Val
            340                 345                 350

Ser Gly Phe Gly Arg Leu His Glu Arg Gly Ser Thr Ser Asp Ile Leu
        355                 360                 365

Lys Val Ile Arg Val Pro Tyr Val Asp Arg Tyr Thr Cys Met Leu Ser
    370                 375                 380

Ser Asn Tyr Arg Ile Thr Pro Ser Met Phe Cys Ala Gly Tyr Gly Asn
385                 390                 395                 400

Gln Pro Gln Asp Ala Cys Gln Gly Asp Ser Gly Gly Pro His Ile Thr
                405                 410                 415

Ala Tyr Gly Asp Thr His Phe Ile Thr Gly Ile Ile Ser Trp Gly Glu
            420                 425                 430

Gly Cys Gly Arg Lys Gly Lys Tyr Gly Ile Tyr Thr Lys Val Ser Asn
        435                 440                 445

Phe Ile Pro Trp Ile Lys Thr Ile Met Arg Arg Asn Gln Pro Ser Thr
    450                 455                 460

Glu Ser Ser Thr Gly Arg Leu
465                 470
```

<210> SEQ ID NO 47
<211> LENGTH: 33731
<212> TYPE: DNA
<213> ORGANISM: Homo sapiens

<400> SEQUENCE: 47

```
ctgtctgacc gcagctctca agtgtctcag gggctgtggc tctgggcttc gtgctgtcac      60

ttccacagac agacagacat ccccaaaagg ggagcaacca tgctgggcac gactgctgtg     120

gccaccgtgc tctcagccac tttcccatgc ccaaataaaa cgataaaaga ctgggggctt     180

ctgcccatcc tgcctcactt gaccaagagc ccagaagagg atgcgacacc cagggcctca     240

tgggaccacc ggctggcagg ggttctgctc actgggttta tgggtgagac gagcactccc     300

aggagggcca ctgggccggg aagaactgtg gagaatcggg gcacgccctg tcctcccagc     360

tgccagggca cagcatccct tccccacctc aacacccaga ccccagattc accccagttc     420

acttgtcccc acacgagcca caggctgcca cctggggcag gctggcccca ccttggggtt     480

agatgcaggt ccccttgccc cagaaggaga ctgcagcccc tgcagaccta gaaatggcca     540

cagcccatcc ccatgcacca gggggtgagg tggcaggtgg tggaaagggc ctgagggggg     600

cttcttcctt ccaggcgagc acgacctcag cgagcacgac ggggatgagc agagccggcg     660

ggtggcgcag gtcatcatcc ccagcacgta cgtcccgggc accaccaacc acgacatcgc     720

gctgctccgc ctgcaccagc ccgtggtcct cactgaccat gtggtgcccc tctgcctgcc     780
```

-continued

```
cgaacggacg ttctctgaga ggacgctggc cttcgtgcgc ttctcattgg tcagcggctg    840
gggccagctg ctggaccgtg gcgccacggc cctggagctc atggtcctca acgtgccccg    900
gctgatgacc caggactgcc tgcagcagtc acggaaggtg ggagactccc caaatatcac    960
ggagtacatg ttctgtgccg gctactcgga tggcagcaag gactcctgca agggggacag   1020
tggaggccca catgccaccc actaccgggg cacgtggtac ctgacgggca tcgtcagctg   1080
gggccagggc tgcgcaaccg tgggccactt tggggtgtac accagggtct cccagtacat   1140
cgagtggctg caaaagctca tgcgctcaga gccacgccca ggagtcctcc tgcgagcccc   1200
atttccctag cccagcagcc ctggcctgtg gagagaaagc caaggctgcg tcgaactgtc   1260
ctggcaccaa atcccatata ttcttctgca gttaatgggg tagaggaggg catgggaggg   1320
agggagaggt ggggagggag acagagacag aaacagagag agacagagac agagagagac   1380
tgagggagag actctgagga catggagaga gactcaaaga gactccaaga ttcaaagaga   1440
ctaatagaga cacagagatg gaatagaaaa gatgagaggc agaggcagac aggcgctgga   1500
cagaggggca ggggagtgcc aaggttgtcc tggaggcaga cagcccagct gagcctcctt   1560
acctcccttc agccaagccc acctgcacgt gatctgctgg cctcaggctg ctgctctgcc   1620
ttcattgctg gagacagtag aggcatgaac acacatggat gcacacacac acacgccaat   1680
gcacacacac agagatatgc acacacacgg atgcacacac agatggtcac acagagatac   1740
gcaaacacac cgatgcacac gcacatagag atatgcacac acagatgcac acacagatat   1800
acacatggat gcacgcacat gccaatgcac gcacacatca gtgcacacgg atgcacagag   1860
atatgcacac accgatgtgc gcacacacag atatgcacac acatggatga gcacacacac   1920
accaatgcgc acacacaccg atgtacacac acagatgcac acacagatgc acacacaccg   1980
atgctgactc catgtgtgct gtcctctgaa ggcggttgtt tagctctcac ttttctggtt   2040
cttatccatt atcatcttca cttcagacaa ttcagaagca tcaccatgca tggtggcgaa   2100
tgcccccaaa ctctccccca aatgtatttc tcccttcgct gggtgccggg ctgcacagac   2160
tattccccac ctgcttccca gcttcacaat aaacggctgc gtctcctccg cacacctgtg   2220
gtgcctgcca cccactgggt tgcccatgat tcatttttgg agcccccggt gctcatcctc   2280
tgagatgctc ttttctttca caattttcaa catcactgaa atgaaccctc acatggaagc   2340
tattttttaa aaacaaaagc tgtttgatag atgtttgagg ctgtagctcc caggatcctg   2400
tggaattgga tgttctctcc ctgccacagc ccttgtcaat gatatttcac agagaccctg   2460
ggagcacctg ctcaagagtc agggacacac gcatcactaa atgcaagttc ccaggccctg   2520
gctgcagtgg gaggacctgg caagctgcac tcttgctgag tccccagggt ggtggaagaa   2580
gaatgagaaa cacatgaaca gagaaatggg gaggtgacaa acagtgcccc cactcagact   2640
ccggcaagca cggctcagag agtggactcg atgccatccc tgcagggccg tcctgggcac   2700
cactggcact cacagcagca aggtgggcac cattggcact cacagcagca aggcaggcac   2760
cagcaaccca cctcgggggc actcaggcat catctacttc agagcagaca gggtctatga   2820
actacagccg tgggctgctt ccaaggcacc ctgctcttgt aaataaagtt ttatgggaac   2880
acacccatat tagtgtccat ggagtggccg tggcagagac gtccagccgg acagaccagc   2940
tgacccgcca agcccagcat ggttagtgtc aggacctctg ctgaagatgc ttgctgaccc   3000
tggccagacc ccggttccta atgcccccta aacgggacgg gagccagtgg cgggccctga   3060
tccaggtcag agctggctct gctttctctt ttgtccgagt gaccatgcct cagtttcctc   3120
```

-continued

```
atgtgtaaaa caggagccca ccgtgatgct tatggtggga tgagatcagc atggatggaa   3180
caaggccctg gaagggccca tgccatggtc atcgacagca aagccactct gcagacagat   3240
gcttcagtga attggtagaa aattctgcaa ccagaatgcc cggggctcct gagggcctaa   3300
gcccagccca gggttctgga agccactctg acttcttggg agtggaagtt ggcaggactc   3360
ttcctgggaa gaagcggagg gtggggatga gaggacagtt caggagccca cccagaccca   3420
caggaggaaa ctaggggagt catgcggggt cctggtggag cgccagcctc ccttcctgcc   3480
aatgggaaat gcaggcgccc acctcatggt gctgccggag gagggggccc gggactcccc   3540
agaggcttcg ctgaagggcc tgggcgcccc caaaggctac atgtttcata tgggacgtgc   3600
cacctgccac ggctcagctc cagctttctg tgagtggcga gatagaatac ggggaggcca   3660
ctggccatgg gcctgggaca gggtgggatg aggcggcagg cttgggccac caaagccagc   3720
atcgccaccc agcattgatg acaaagactg cgtgtctgcc atgagcatcc tgctgttggt   3780
gcacacaccg cattggtctc tccatacaaa catgcctaga ggcgatgtca gagggtggag   3840
accaggagag gcaggagtca gacatctggt gccaccagga aggcccttct cagaggacca   3900
ggctgtgcgt ggtgcccgcc gtgggaggcc agcctggcgt tggcatccag catcatcagt   3960
ttgtgcagtc gggtggggct cagtgagtgc ctcctgtgtg ccaggcacaa tgacgcacaa   4020
tgtgtgcaca ccaggctcat gtgcaggtgg ctgcgagaca gggcgaccca tcaaggcaga   4080
tgcaccatga ggcagtggcc agtgctgtgg gtgttagggg cattgctccc cggccactac   4140
ggcatagcag gcagtgatcg ccacactggc caagctttag accatttatt ccagagaccc   4200
cagaggcaaa aagcccggct gcacctccca gtgactccca cagccattga gcagagacac   4260
tcaggacctt gtgatgggag gtttctgcac tggagaacga gcccagaagc cctctcagcc   4320
tcggaacagt gtggccagtg gtgggcaggt caggaggggc ttcagacaca gcctgtccct   4380
ccagatggtc acgggaaggt cactccccac agaagtacgt tttggggcca tgcgggcaca   4440
gaaggtttgg gggtgggtgg ggcaggtgcc agcctggcct gtgggaggcc atggtgcaga   4500
tgccaagccc cccccgtgac atgagaccac ctgataccac ccagagagtg gctgtgagcg   4560
gaagggcccg cccagaaaca agcagggcct tggggcagaa gtcctgggct cagatcccac   4620
gctcactgcc agcggcctcg gctcaggctt ctgcgctctc taaacttagt tttctcttct   4680
ggaaaaatga tggggaaaat gatatttgta tgtgaggact gagagttaaa tgtaaacatc   4740
tggaaactac aaaatgagca cgaaatgatg tttttattct tagaacagaa agtccccaca   4800
cccgcggccc tggtgactga tgaggatgag gttctgcggg gcctctctgg ccgcccagct   4860
ctgcctgggg aaggtggggc cagagtggat gtgttcccag cgtggtcact cccctgcctc   4920
gccagcaggt ctcggctcca atcaggaggc ctaagccaag tgataagcag ccagacaaca   4980
gccatcccag ctggggcgtg gactttgctc cagcagcctg tcccagtgag gacagggaca   5040
cagtactcgg ccacaccatg gggcgcccac tgcacctcgt cctgctcagt gcctccctgg   5100
ctggcctcct gctgctcggg gaaagtcgta agtgcccctc gcccttcaga cccaaaagca   5160
gcgccaggga gcagggaggg gcggcagttg gggaaaccct ctcatctctg cagcctggac   5220
ggtgggtgcc ttgagtgctg ccagaggctg ggctcggatg gctgggcttg gcctttccag   5280
ccaacggcat cctcaaggcc agctgtggct ccctggggct gagagtcaga cgggcggatc   5340
agaggtcaca gagacaaaaa cacaaggaca gagtcagaga gagaaaggga gagggaagga   5400
gaaacggaga cacagtgaga tgggaggcca agaggcagag acagaggtag aaagacggag   5460
acagagagag agggaggggt tggggcaggc agagacagga cagttagcca tctgccacca   5520
```

-continued

```
cagggaggca caggacgagg ggcacagcag aggagctccc agggaggagg aggctgagcc   5580
gagccagtgc caccactctc ggactggctc cgtcggggaa ggagctgcct aatgcacagc   5640
tggacaggtg ggggcagcag ggctgtccag gacccccggg tctgtccaaa agcagaggcc   5700
cagacaggac agaagccagg caagcctggg gacagcggag gaagaggagg cccctctggt   5760
ggggacacga gagacaggga ccctagactt gtttgcatcc tggacaaagt ggacaggcag   5820
gggcaccaag gggacccagg cctgggaagg gaatgtgtga gggagagacg gagcaggggg   5880
agaccctcgt ggggtggaaa ggggagaccc ctgggaaggc tgagtggatc ctcagtgcat   5940
cactgaccta aacggcccct ccgcctggtg acttggagct ccagtcacat cacacggggg   6000
tcttctccat cccaccctca accccctgcc ctccccagcc tctgtcccct gagccacatc   6060
ttcctgtctc ccacgcggaa cgggactccc gtcttcatgg ggtactgtgt ggctccaact   6120
cgcccagcct tcttcctccc cctcaggcca cactgccccc tgcaggagcc cactgtgatg   6180
cttgtggtgg gatgagatca gcgtgggtgg aacaaggccc tggaaggacc catgccatca   6240
tcatcgacag caaagctact ctgcaaacag acagatgctt ccgcgaattg gtagaaaatt   6300
ctgcagccgg aatgctctag gatcctgagg ccctaagccc ggcccggggc tcccgaggcc   6360
ctaagcccgg cccgggactc tggaagctgc tctggcttat tgggaatgga agttggcagg   6420
actcctcttc ctgggaagaa gcagagggtg gggatgagaa gacaggccag gagcccaccc   6480
agacccacag gaggaaacta ggggagttat gcagagtcct ggtggagcgc cagcttccct   6540
tcctgccaat gggaaatgca ggcgcccacc tcgcggacct ctgggtccac agggtattgg   6600
caccccttagc tgtgtgatgc gggcctggct cataaccatg gcctgtggtg tccccggggg   6660
ccggcctgga ccctgggtgg acatggccag ccccggagag ccagggccag gccatctctc   6720
tcccctactc tgcctcagag gcctcggcag ctgcactgtg gggtgggtgg ggctgaacac   6780
aggtcccaga aggtcccact caggaccctg ctgtgcacac ttttgatttt aataaaatca   6840
gaatgcgcac agcatctgca gtctagcctt taaacgagca cagctgtcct ggcagtcacg   6900
gaagttcttc tggggcggtg ggacctcagc attcctttgc tggtactgct acaagaaagg   6960
acaatggacc aagtagctta aagcaacaga aacatttctc ccacagctct ggaggctgga   7020
agttcaaaat caaggcgtca gcggggctgg ttcctccaga ggctgggaga gagtctgctc   7080
taggcctgtt tcctggcctc ggggtgccag cggcctcaca gcccatggct tgtgggagca   7140
ttgctcccat cgctgcctcc atcatcgcat ggggttctca ccatggctgt ttttctgtct   7200
tcttttctct cagaaggaca ccagtcattg gatttagggc tcactctact cccataaaat   7260
gtcttcctaa ctaaatacat cacaaaagtt ctatttccaa ttaaggtcag gttctgaggt   7320
tctgggaaag acatgaattt ggagggacat tattcagccc tgtcctgcca cctgtgagtg   7380
ttttctgcaa tccaactttt tattttaata aaatcagaat acgcagagca cctgcagtgc   7440
cagcctttaa actactgctg ttgtactggc aatcattaaa gctacgtggc ttcagtttca   7500
atctttacat tcaacaagtt taaacccatt cttcatgagt ttggacctta ctgactgaaa   7560
attttgcttg ctggtaaaac ttgctcaaat gcagttgctg actgtggaat tcactgatgt   7620
tgccaaaaca acaaacacaa ctgtgtgctc gaggattgca atgctcccaa cagcttctga   7680
agaaacaaac cacacgacaa atgtctacca atctggatgc tccatatcag agttctagag   7740
tgttccatta atttcttgag acaagtgcct aaaaaccttg ttttaatttc gttttgccaa   7800
aatcccattt tactcacatc agaaagtgtg gccacgtggc ccagacccgg cctgctcagt   7860
```

-continued

```
ctgactgaag cgttgatgcg actcagccat aacagatagc agaagcgccc agattcagtc   7920
cagagggctg agccaggcac gccatctttc cttcattccc tcaacacata ttggttaagt   7980
tccggccgtg ctaggcacgg gcatacagct gtgaccaaac acgtcaagtc tttttccagc   8040
ggagggaagg ataagcctgt cagcatgtaa tgtcagagag gggttgggtg ctagaagaca   8100
aatagcacag tgtaagggga tgaaagagac acgagtgggg gcaacgtcag agggcgtggt   8160
cagggagggt gtctcggagg gcgctgggcc tgagccactt gggtatctgt ggaaagaatg   8220
ttccagacag ggaggtgact ggtgcaaaag tcctggggtg tgagtgttgg gctcagccag   8280
ggtcagcgca gagcccagtg tggcagagag aggtgaatga gggcagagtt gaaggtggtg   8340
aggcctggga ggcctggcca tgggaagacc ctgggctctg ttctaagacc actagaggca   8400
gattctgggt agtccttgac ttccttgcat caccctttcc accccgtgcc tgccacctgt   8460
accctcttcc tcacacagtc cagctcaacc ttataggccg tgtcctaccc ccatgagctg   8520
gggagagctg agcaggcttc agggagatgg gaaaaggcgg gaactggaca ggggctgcaa   8580
aggaaaggtg acttcttact ggtcaatcag cctggggatg ctcgggggtg gatgccaagg   8640
ggaacagagc tgtggccgct atcacagaac agcgagttcc tctaagaggt cagaggaggc   8700
gcaagggatc gaccagagac agtgagggcg tcaggctcca gttgagtggg gaccaatcct   8760
tgtggcaagt ctgtgaacca tcactgtggc tctagggtag cagagaaaaa agcaggcata   8820
tgtccatctg gccacaagga aggagaccaa ggggaagaga gaaggtacca agagaggtgt   8880
tcacatggag gtgcgtcaga acaccgaggg caaggcagaa cgcggtcttc agaccccaac   8940
tggagcccag gaggcccgcg agtcccagtt tgggaaacac taagccaggc ttggataact   9000
tgtctgaggc tgtggtcatc ccaacatgag agccagaggc cccaagggag atgggcattc   9060
cccacccctc agcttcctca gtgccttttg tggagtggag gtgacatgag gctgcaggtt   9120
gcagggagcc acgtgtgggc tgcatttcag agcaagtgtg tgggagtgga gcagacacgc   9180
agagtaatgg ggcagggtca agaaataata aatctaagtc tagcgttggt gggataatgt   9240
cggtgtcact aaaagaaatg gggaatttgg aaggtaaagt aactggaggt aggaatgaac   9300
ccaagattta ctaagcacct tctgtatacc aaactcaaca ctaggagttt atacaatctt   9360
taaaacagct ctaagagtag atattataat tcccttctgc caataataaa taataagtga   9420
ctaaggtgtt tttgaagctc aagattgctt gattctgcag tcttgtttta aattttggac   9480
atggagagtt tggagttctg agatgaggga aggcatctgt catagtgaga gagctgaaaa   9540
catggagctc aggacaaaag tcagtgctag agagatcagt tggaagagtt atctttattg   9600
tagtgagaca ttgaattttt cagtggaaaa aaagcacaga aaaagactac agagggccaa   9660
gaaaagaaac tgaggctgtc aaaatgaaaa gaggaggagg agtgggtgag agacaaagga   9720
gacacaggca gagagatgtg gacagcacag cccacagaca cacactctac aagggacaca   9780
gactctcgga tccagggcat tttaaccagc agatcaagac tcatttgcca gtcatgaaat   9840
caactcagta ttttttttta aaagagtaga atcaaataga aaactttgta ctaagtactg   9900
tattttagga aatactaata aatactattt cttgaaagtt ggcatgtatg tgtgtcctgg   9960
cacttcataa attgtactat tatagtttgt aattgaaaca gcatcaccaa tccccacata  10020
acaaagagca gagaccttaa agacgagtgg ggccaggctg aaggggcaca gcttgagcca  10080
aagcacagaa cagtgggctg aaagcaccct agggagggag aattcaagga agggggcttg  10140
ggtggccagg ctgagccagc gtgagcatgt gaggaggctg gtgagctgat tgggtgggat  10200
gtgtctactt ctccagagaa gggtgcatgg gtctagagca ggtgcctcat gctgtacctc  10260
```

```
atagagaact ggggggaggg gggaaatggg catttccctc cacagccccc aaagtgcctg  10320
aggaaagtgt tgataaagaa gccaaactct gtaaaatatt tgaagagatt tattctgagc  10380
caaatgtgag gaccacgacc catgacacag ccttggaagg tcctgagaac atgtgtccaa  10440
ggtagttggg tcacagcttg attttatgta ttttaggggg acagaagtta catacagaca  10500
ccaatcaata agcataagtt gtacactggt tcgttccaga aaaggggaag gtgggggctt  10560
ccaggtcata ggtggcttca aagatattct gattggcaat cagttgaaag agttattatc  10620
taaagacctg gaataaatgg aaaggagtat ctgggttaag ataagaggtt gtggagacca  10680
aggttcttgt tatgtagatg aagactcata ggtggccacc cttagaggga atagatggca  10740
actgtttcct cttcagacct ttaaaaggtg ctacacacat ggccaggcgc cttggctcat  10800
cctgtaatcc cagcactttg ggaggctgag gcaggtggat cacttaaggt caggagttca  10860
agaccagcct ggccaacatg gtgaaactcc atctctacta aaaatacaaa aattagccgg  10920
gtgtggtggt gcttgcctgt agtttcagct actcgggagg ctgagacagt agaatctcct  10980
cctgaggcag gacaatggct tgaacctggg aggcagatgt tgcagtgagc tgagattgtg  11040
ccattgcact ccagcctgga tgacagagca aaacaccatc ttaaagagaa aaaaaaaaaa  11100
aaaaaaaaaa aaaggtgcta gactctcagc tcagaaaaag acctggaatg gtaagggggt  11160
tctctacaga atgtggattt ccctgagata gctttgcagg gccatttcaa aatatgtcaa  11220
acaaatacaa tttggagtaa aatcatttat tttagggcct gctatatgtc atgtgatcct  11280
atactagaga agtcaggttg gaaactggta tcttattgct acaaagactc tgtttggtca  11340
gcctcaaggt ctcttaacgt gaatgctggt cagctgtgcc cgaattccaa aggaagaaat  11400
aatgaggcgt gtgggacctg cttcccctca tggcctcaac tagtctttca ggttcctatg  11460
gaattccctt ggcagagagg acgggtccac tcagtgagtt gggggcttag aattttattt  11520
ttggtttaca agagagtgat ccgccttttg tgatctggat atggcaaggg acatggcagt  11580
cagggagcat aggtgagggg gagcctgggt gagggtgacc agagctttta accctgtcct  11640
ccctgccttc cagtgttcat ccgcagggag caggccaaca acatcctggc gagggtcacg  11700
agggccaatt cctttcttga agagatgaag aaaggacacc tcgaaagaga gtgcatggaa  11760
gagacctgct catacgaaga ggcccgcgag gtctttgagg acagcgacaa gacggtaagg  11820
gctggggata gcctggctgt tggtaaggag ctcaggccac agcgccctcg ctggccccgc  11880
tgctccgtcc atccaggggg gcggcctgga ggaaggggca gcgtgcgcga aggctttcag  11940
gggcggggcc cagcaaatcg aggcctcggc ggagtcctgc ccacagggac atcagtgccg  12000
cccccgcgct gactccttcc cggcgaggac tcagcgggga gggatgcgcc caagtccctt  12060
gagggtcaca gggcttctgc cagagttaag ttctatttaa aaataaaatg ttaacctaaa  12120
aaccaatagt catggtctcg gccagcgcct cgccgagttg cagtgagctg agatcgtgcc  12180
ctcccacgcc cgcagcccgc gtcctgcctt ggcctccgta gtcgctgaga gccacagcct  12240
agagcgccag cgcgcaggcg cacaactgac gccaggccac gaacccagta ctgctcctgc  12300
acagcagaag cactagcact gaggccgggc ggcgaacccg gcactgcgcc tgcgcagcaa  12360
aaggacacgc actgaggcca ggccgcgaac ccagcacggt gcctgcgcag caggaagacc  12420
ggcatccaca ccggacgacg aacccagcat cgcgcctgcg cagtaggagg agagcaatgc  12480
caccaggccg cgattgcgca gccgcagcag ccccgcgcgg aagacgctac cctcctctcc  12540
cccgaagagg cggggcttcg aacgaacctg gaaatggccg aggggtctcg acttcctcac  12600
```

-continued

```
cccaggcatc aggaaaggtg cctgcaggac agggctctga agtggaagtg ggcggtggtg  12660
atgccgaact gacaagaatg agctgaagag aagaaagtag ccgagaaggg ggccaagccg  12720
gagctcagtg agcaacagct aggccagccg cggctggtgc catcagccac accactaact  12780
gtggacccaa atggaaactt tgaggcccct tacaggtccc ccagcgcagg ccaccgccga  12840
aggttactgg ggaagacccc tgcagcttcc atgtggacat tactcgcttg cttcatcccg  12900
gagtgcagtc acctgcagcc tgggaccacc tgactgatgt caccctggag atccatgcca  12960
aaagagctgg ggaaagttca ccttctaatg acccctgcgg accagggtga agttacaagt  13020
tatggccagg tcaaggaatt ataagtcaat aaataaactg cctcagggag acgtactcag  13080
agtccaggaa aatctaggaa acaccaagaa gggcgagcgc agcatcagcc cctgcaaaat  13140
tgcactgctg cctcctggct cacatgttgc cccatcctta ctttagcctc aaaggcaagg  13200
agacccaata ttatttgagt acttggattt gatcctgagt gactttctga gaaagcagtg  13260
tatcatctgc cctaagatca ccacatatat gacaaggttt ttggatgagt tgagatttct  13320
agacattgaa accctcatga tgaacgtcat cccgggtagc aggggctaag cctttcatca  13380
cctgctacaa caagctggac attaacttgt atttgagaat tgctccagga ctctaccttc  13440
agatgctggt tagtagcatt gactggattt atgaaattgg atgccagtta aggaataaga  13500
gaatgtattt gatttgccac cctatatggt ctgtgcagac tgtcatgatc tcattgaaat  13560
ccaagaaaag attatgtcag ggatgaagca catcacaggt ggttacaagg tcacccacca  13620
tccagatggc tcagaaagcc aaacctatgg gttgacttct cctcaccctt ctggagaatc  13680
agtgtggtag aagagcttga aaaagtgctg ggtgtgacgc tgccagaaac taacctcttt  13740
ggaactgaag aaactcaaaa aattattggt gatatctatg taacaaaagc ttttgaaagt  13800
cttctacctc agaacatatt caggcgcctt gataaacttg tcaaggagtt cctgaaagtg  13860
acttacatca gtcccacatt tatctgttat cacctgcaga taatgagctc tttgaccaaa  13920
tgatctctct aagagggtct cactgagcac tttgagctat ttgtcatgaa gatagctgaa  13980
tgtttccatg cagcaacagc agcagctgtt gacaaacaag acaaggccag caaagatgat  14040
gaggccacat tcatagatga aagcttccat gcaaccctgg aatatgggct tccgcccaca  14100
gctggttgga gcgtgacaat caaatgtgtt accatgtttc tcacagactc ccacaacatc  14160
aaggaaatat ttctgactcc tggcatgaaa cttgaagaaa gagaatgtag cagccactaa  14220
tacaatggaa agcgcaacat tgacacgtct atctagaaaa ttttaattgt ctaagttgtg  14280
tgactcagat atctttgcat ttctgcaaaa gatcaaggtc tactctaatt cttaattaaa  14340
ttaagaattc ctttttatta cttgttagca aataaatggc ttgtctctaa cagaaaaaat  14400
ttagaatttt cggaaatatt ttcaaatact tcttatatat acatatattt ttttccactg  14460
gtagaatttt tctttagtaa aagtaaataa tgctgatcca agtttatgtt tcactcagca  14520
tcgtttctca aacactcttc tttacttata tatagctacc ctatagctaa gctatatttt  14580
attgtatgat gcatttactc ttttcagagt ttggccatat aagttatttc taaatattgc  14640
tattaggaaa acacatatgc atgcatttct tctagattat catctaagag tggcttctcc  14700
agagagagac gactgaatta aaggttatca acaagttcca attccagata agatgaagaa  14760
atcacattcc acactgcctc tcccactgag tgtagctcca aaacatggat agaatgcatg  14820
tagcagctat ttgacgaccc taaaaagtaa atcgcagtgt attgcagaat aagactacaa  14880
ttagatgtat gatatgatac aactggctgt gagtttatca ttttttcctc cagtcttcca  14940
gacatcactt gacctgaatc taatggacat ttataggatt ctcaacaata gcaaagtaca  15000
```

```
ctttccttcc acatatggaa aattcctcaa ggtagactat atcctgtgtc ttaaagcata  15060
cctcaataaa aagattgaac tcacataaag tatgttttct gaccataatg gaattaaagt  15120
aaaaattact aacagaaaaa taactggaaa cttccctaag tactcggaaa ttaagtcaca  15180
catgtataaa taatctgtga gtcaaagaga aaattttaag gggagtaaga aagtattttg  15240
agctgaacaa aaatgaatat gtaacataaa atctgtggga tgcagctaaa aaagcagtgt  15300
ttcaagggaa atttatagca ttaaatgctc acatgggaaa agaaagacgg tctcaaattg  15360
tttatgtaag cttccacttt aataaactag aaaaaaagaa aaaaataaac caaaaggaaa  15420
ttgaaaaagc agaaatcaaa gaaatttaaa acaaaaataa tagacaaaat taataagctg  15480
atgaaactca aacaagactg acaggaataa aaacaaacaa acaaaaacaa gaaaaaggac  15540
ctatgttgga aatggaagag aggggacatc actacagaaa ctgtagatgt taaatgtata  15600
ataagaaaat actttgaaca actctgcata tataaatttg catgagattt gaacttggat  15660
gaaatgagcc tattcttcaa taccacaagc caccaaaaca tacacaaggt gaaagagata  15720
cctgccaatt caattcttaa tttaaaacct tctgaaaaag taatgttcag gtacagatgg  15780
tttcactggt agaattttac caaacatttc aaaaagaaca ccaattctat acaactcttc  15840
cagaacatag aagagggaac acttcttagt ttgtcttagg ccagcattac cctgatgtca  15900
aaaccagaca aatactgaaa acaaaaacca ccctacgtaa caatatctct catgaatcta  15960
gacataaaaa tcctcaacaa aatattagca aacggtgcag caatatattt ttaaaagagt  16020
aataatacac catgaccaag tgagtttttc tggggcacac atgactggct caatatttaa  16080
aaataattat gtaatccacc atataaacaa aagagaacat ccacataatc atgtcaattg  16140
atgcaacaaa caaatctggc aaaatttaac atccatttat gattttataa aaaacctatc  16200
agcagaatat gaataggagg gaattttatg aacataataa agttcatcta caaagagtct  16260
acagttgata ttatacttaa aggtgaaaac tgaaggtttt ctccctgaga ctggaacaac  16320
acaagaatgt ccattcccaa cactcctaat tcaacattat actggaagtc ctagctctaa  16380
ggaaggcctt cagtaagtca agaaaaagaa ataaagttat cactatttga agatgacatg  16440
atcatgcata tagaaaatcc taaagaatgt gaaggggaaa aaagcttgtt ttagtccctt  16500
ctcacgctgc tgtgaagaac tacccgagac tgggtaattt ataaaggaaa aaaggtttaa  16560
ttgactcagt tctacatgtc taaggagacc tcagtaaact tacaatcatg gcagaaaagg  16620
aagcaaacgt gctcttcttc acatggctgt aggagggaga agaatgagag ccgagcaaaa  16680
ggggaatcct cttaaaaaaa atcagatctc atgagaacat actcccacga gaacagcatg  16740
gaggaaccac cctcacgatt cagttacctc ccacttggtc cctctcacta cacatgggga  16800
ttatgggaac tacaattcaa gatgagattt gggtggggac agagccaaac catatcaatg  16860
ctcctaaaat ttgcaaatga gtgtaacaag gtcacagaat acaaggtcag cacatgtgtt  16920
aatcacattt ttatgtaata gcaatgcaca gttatttgta agccaaaaat ttttaaatgc  16980
catttacaat tgcttcaaag aaaattatat acttatatgt aaagctaata aaacatatac  17040
aggatcttta tcccaaaatc tacaaaattc caatgaaagt atttaaacag acctaaataa  17100
atagagacac atacagtgtt catggattga aagactcaac atattaagat atcaattttc  17160
ggccgggcgc ggtggctcat gcctgtaatc ccagcacttt gggagaccga ggtgggtgga  17220
tcacctaagg tcgggagttc gagaccagcc tggccaacat ggtgaaaccc cgtctctact  17280
aaaaaaatac aaaaattagc tgggcgtggt ggtgtgcgcc tgtaatccca gctactcggg  17340
```

-continued

```
aggctgaggc aggagaatca cttgaacctg ggaggtgaag gttgcagtga gccaagatca  17400
agccattgca ctccagcctg ggcaacaaga gcgaaactct gtctccaaaa aaaaaaaaac  17460
aaaagaaaag aaagaattgt ctttttcaac aaattatatt agtctcagtc tgtttgtgct  17520
tctataacaa aatagatcag actgggtaaa ttataaacag aataaggtta ttgctcacag  17580
ttatggaggc tgggaagtcc tccaagatca agaaaccagc agatatgggg cctgatgagg  17640
gcctggtctc tgcttccaag acggtgcctc atggctgtat cctcacctga cagaaggcag  17700
aagcacagaa gggacaaaca ctgtgtgaag cctcttttat aaggacatta atcctattca  17760
caagggcaga gccttcatgg cctaatcacc tcctaaagat ctcaccctta atactattac  17820
attgtcgatt aaattttaac atatgtatgg ggggcatgtt gagaccatag cagtgttgga  17880
acaattatat atttatatgc aaaaaaatga acctgaccta aacttcacaa ttatacaaaa  17940
attaacacaa tatagataat agatccaaac ataaaataca aaactataaa acttttagga  18000
gaaaatacaa caaaatttat gacatggagc taggcaaaaa ttcttagaca ttgacaccaa  18060
aagaatgatt aataaaagaa aaaagtcata aattggactt tatcaaaatt aaaacctttt  18120
gcacttcaga aataaacact gttaagagga tgaaaataca agctacaaac taagagaaaa  18180
tatttgcaaa tcacatatcc aacaaaggaa tcatattcgg aatatataaa gaaatcttaa  18240
cagatcagaa gaagaaaata aacactcagt taaacaaaag accttaacag ccaactcgcc  18300
aaagaggata tatggataga aaataaacat gtgagaagat actcaacatt attagctctt  18360
acagaaatgc agataaaaac cacaataaga acgactatat actcatagag taaaaaacac  18420
tgacacagaa cagcgctggt taagacacgg agaaagcaga actttgatac actgctcgtg  18480
ggaatgcaaa atggcacggc cactttgaaa aggaatttga cagtttctta taaagttata  18540
taaggttacc acaggactcg gcaatcccat ttctgggcat ttaccctaga gaaatgaaaa  18600
cttatttcca cataaaatcc tgtacataaa tgtctatagc aactctagtc tttttttttt  18660
tttttaattt ttattttttg agacagagtc ttcccgttgc ccaggctggg gtgcaatggc  18720
acaatctcgg ctcactacaa cctcctcctc tcaggttcaa gtgattctcc tgcctcagcc  18780
tcccaagtag ctgggattac aggtgtgtgc caccatggca ggctaattct tgtacttttt  18840
tttttttttt tttttttttt tttttttttt gagacggagt ctcgctctgt cgcccaggct  18900
ggagtgcagt ggcgggatct cggctcactg caagctccgc ctcccgggtt cacgccattc  18960
tcctgcctca gcctcccaag tagctgggac tacaggcgcc cgccactacg cccggctaat  19020
tttttgtatt tttagtagag acggggtttc accgttttag ctgggatggt ctcgatctcc  19080
tgacctcgtg atccgcccgc ctcggcctcc caaagtgctg ggattacagg cgtgagccac  19140
cgcgcccggc caattcttgt acttttagta gagatggggt ttcaccatgt tggccaggct  19200
ggtctcgaac tcctgacctc aagtgatcca cccgcctcag cctcccaaag tgctgggatt  19260
ataggcgtga ggcaccacgc ctggccagca actctattct taattgccaa aagctggaag  19320
taagataaat gtcttttgct gggtgtaccc atacaatata acagttgtca gcaacaacaa  19380
gtaagaaagt attgatacaa cttgcatgaa tttcaaaggc tttgtattga atgaaaagct  19440
agtttcacaa ggtcctataa taaacacttt catttacatg acatgctcaa taggttgtta  19500
tcattgtgat aaagaataga ttagtggtgg gacagggttt gccaagggtt ggcaggtggg  19560
ggagatggca tggggtattt ggggggggaag gatggacctg tactgcatcc tgatgatgct  19620
ggtggctaca gaagtctctc catgtgttga aattcataga agtgtacacc aaaacattgg  19680
ttttgctgtg tgagaatttt aaaagtaaaa aagtaagaag atagtgtatt tgcttcctag  19740
```

```
ggcaaccata acaaagcact acaaacgcct taaaataaca gggatttatt gtcgcagctt  19800
tggagacaag tctgaaatta gggtgtcagc agtgttggtt ccttctggag gctctgggag  19860
agtctctgtc ccaggctctc tgctcgcttc caggagcacc cggcaatcat gggcatcctt  19920
gggctgcgga cgcgtcgctc ctgtctctgc tttcatcttc gcatggcctt ctctctctgt  19980
gcctctgtgt gacttttttct gtctcttata aggactttct cctttattta gggcccacac  20040
tgacccagca tgatctcttc tacagccttg gcttagttaa catctgcaaa gacccgattt  20100
ccaattaagg ttctattctg aggctgcagg tggacctgaa ttagcaggga gggcactatt  20160
caaccaactg tagagagtta aaaaacaata agcctgtgga catttttag cgtaatctag  20220
gctcttgatg acctgtttta aactaatcag caatgaatat ttttcagcta acgtaatgac  20280
tattgacaag cacgtgaccc ttgtctgaat gttaactcag gcatagcaac taaaaaccat  20340
ccattgacca gctcgggagt agcaaacaga gcaagccatt cttggtgcaa cctgtttcta  20400
ggtaattaac ttgaaaatat tttcaatatt caacaaagat ggttcattta agatgactga  20460
agccacatct tcacagatgc agaagatctg aatagctttc ctctttagat tgaatagttc  20520
tagaacaatt cattcctaaa agtgacttcc attggggaaa atatcctatt cagcttgagt  20580
cacttaatta tggttgttat tggtataaaa tgtctctgtt ttccctaata tatttttaaa  20640
tttctttttt ccttttagaa tgaattctgg aataaataca aaggtcagta tttttctgt  20700
tttaaccttc agtgagaggg gttcatcagg atatttgaat tttgaaaata gttcctgaat  20760
ttcctttctg cttttgttct cattttactc atttaagact ttttccctca gggtgtttcc  20820
ataatagtta ttgtaaaaga gtttttagag taattttata ctaatcctag ttttgttatt  20880
gagttagaga tatatattta aatcagttca ttctcatttg aggataccaa attccatgat  20940
aacttttctt aaataaaagt gtattcggta aaagcaaaaa acagagtctg aaagattaga  21000
ttcccgacta aggtaaccac cttgatttaa tgcttaatag catctgaagt ggcctcagtc  21060
atgactacct ggtaacagta ttcacatttc tcaaaatgac aactgggcct atctctaaat  21120
gagattgtgt aaatcctcca agaaatggga agccccgtgt tagtgtttgc cttctccttt  21180
tgccccagga tgatttggaa agaggaaccc taacctcctc tcccgtcaag gcccagccca  21240
gaaatgagca tcaggctctc acctttcctc catccttcca gttggtccct gtggtcacct  21300
ctgactgtaa acacactgca aaacaccggc aaaaatcaaa aagctgggcc ggtgatccac  21360
ctagataaag gcatcacgta cacatggcca caaaaggggg tggatcaaat aaagtccaaa  21420
gagggggagt tgtttacaga gaaaccggaa gactcttcca gttatctgaa cggcagggcc  21480
aaggttagca cagcaaaact gtttccatga tgccggaaac agcttgcaga ctccagtttc  21540
gaaatcctct ctttgcagat ggcgaccagt gtgagaccag tccttgccag aaccagggca  21600
aatgtaaaga cggcctcggg gaatacacct gcacctgttt agaaggattc gaaggcaaaa  21660
actgtgaatt atgtaggttc ctctgcttgg tataccttca gatcagatgc ccctgaagag  21720
tggcaggtgg gcgggggaag aagtgaaaac gcctaatgaa acaatcttaa gtcatttctg  21780
atttacaaag tctgggctct attataccta ttatactgtg ccactatagc aatagaaaaa  21840
aaagccccaa tatgtccccc aaacgattcg gtttgggggc atgatgagag agacacagtc  21900
acttctctgc tcctccgaga gagactgtag aacattgatg aagcgtgtga tccattcatg  21960
tgtaaacagg agtggactct ctgttttcct tggggccaag tgcattgccc tgttattcct  22020
gctccttgtg accctgtgca gtgattctaa atcacctctt atttatgtgt atggatgcag  22080
```

gtgtcaatat ttgtgaatat ttgtgattgg ccaattataa aaatttgata catttaatta 22140
gttctacgtg gaaaaatcac taagtgcttt ctctaatgtg gtgattaagt tttaaataaa 22200
aagttaggct actgttagat caatttccct aaggaaaaag atttgcattt cttttaaagt 22260
acttaattga tcatcttttt tttttttttt tttgagatgg agtctcgctc tgtggcccag 22320
gctagagtgc agtggcacga tctcagctca ccgcaagctc cgcctgccag gttcacgcca 22380
ttctcctgcc tcagcctccc aagtagctgg gactataggc cccggccacc agtcccggct 22440
aatttttttt ttttttaatt ttttagtgga gacggggttt caccgtgtta gccaggatgg 22500
tctcgatctc ctgacctggt gatccgcccg cttcgacctc ccaaagtgct gggattacag 22560
gcgtgaggca cagcgccggc ctaattgatc atctttagac tgtgttctta gattggatta 22620
cttttgagtt ttccctgatg agaatatcaa ttacgcatca ttccattcca agtccgcagt 22680
cgcctccctg gaacaccatt tggtaactta tgaggcataa ccctgttcag gctcccaggg 22740
ctattatgca cattttctaa aatttcaggc atgttgatct ttgcactgtg attacttttt 22800
catcaaaagc cacacagagg gatgtggagt gaccgtaatg tgagtgctgc tggggcaggg 22860
ggtaccggcc atcccggagg tgtgaggggc aggtacctgg agcctggctt ctggctacac 22920
cgggcactgc accatgagct ccccgtgacc cgtgaggttg cccttcaagg caagtgtacc 22980
tgtcgcctgg ctctggccct ttgctcaacc caatggccgc tttgtggctg acaggcaagt 23040
ggatgtagct ggcacccttg ggccagccca gcctccattt ctccagctgt ccccagagcc 23100
aacgtgcctc tcctttgcag tcacacggaa gctctgcagc ctggacaacg gggactgtga 23160
ccagttctgc cacgaggaac agaactctgt ggtgtgctcc tgcgcccgcg ggtacaccct 23220
ggctgacaac ggcaaggcct gcattcccac aggtaggagg cacgttgggc cacagccacc 23280
cgctgccgct gggccgggcc agggaggaca agcccgtgcc agggggtggg gacacaggca 23340
tgttctgggc gggcctggca ggtaacagtg acaccaagag gacaggactg agccctgggc 23400
tccgggccca ggtggttcaa acatgaagac catgaggttt ggaaacagac ccattatttc 23460
tgtaagccag atctgctgtt taacctcagc ttccccatct gacaaatggg accaacacta 23520
ttgcctgact gcttgggtga tccctggagc actttgcatg atgcctggcc caccgcaggc 23580
cctcagtctg cattgggact gtggggggat ccagtgcaag ggctcaaagc accagggcag 23640
gcaaagggca gagctggccc gaggaactgg agctaaggtg cggggctggg ataggagtca 23700
ggggacgctc aggctctgag ctccttttac caggaccagt gttcattgaa cgtagttttt 23760
cttttccttg atgaatgtgg acaacaggcg gccagagggc agtgagcaca ggacaggcag 23820
gggactgggc agggtgggga cgagcctccc tgtcctgacc ccgtgggcat tgcctacgct 23880
gggcttgcct ggctgccggc acttccacac ggccagcaca catgaggccc tcgaaggcgg 23940
ggcctaggcg tcacagctgc accttgcaca gcaaccccac tcccactcat agctggcccg 24000
acccgcagcg ttggcctcac ccgggggcat attcgaaggg cagagttcca ggcccgcctt 24060
ttcaagagcc tggtgaccca gctcaccttc cggcttcagg tgcggctcag cccccagacc 24120
gtgttctgcc cccggctacc atgactgtcc cctccagaca caggttactc ccgagtgttc 24180
tgtcactctt cctttcatat ccttcttacc gaaaacaatt tacttccaaa gatgagtgat 24240
cacgaaaaga ccgggttcca tatgcatcct tcaagcgctg cttcaattat gtgcctgaaa 24300
catctcagca agtgaaagac actgtggctg accttgctac tggcaatgac attcaagctt 24360
aagctggtta aaaaatattt taactgaagt catttcttga catacacacg aatatttttt 24420
aattctagaa acaatcacaa atccatttaa aaccaagtgt gggccgggtg cagtagctca 24480
tgcctgtaat cccagcattt tgggaggcca aggcgggcgg atcatgaggt caggagatcg 24540
agaccatcct ggccaacaca gtgaaacccc gtctctagta aaaatacaaa aaaaaaaaaa 24600
aattagctgg gcatggtggt gcacgcctgt agtcccagct gctcaggagg ctgaggcaag 24660
agaatggcgt gaacctggaa ggcggagctt gcactgagca ctgagccgag attgcgccac 24720
tgcgctccag cctgggcaac agaatgagac tctgtctcaa aaaaaaaaaa aaaaaaaaaa 24780
tcaaaaggca aatgtgatgt gtgaaaataa aattacataa tctactttgt agtgcaaaaa 24840
gttcaggctg ggcaaggtgg ctcacgcctg taatcccagc actttgggaa gccaaggtgg 24900
gtggatcacc tgaggtcagg agttcaagac cagcctggcc aacatggtga aaccctgtct 24960
ctataaaaaa aaaaatacaa aaacttagct gggcgtggtg gcgcacgcct gtaatcccag 25020
ctactcggga ggctgaggca ggagaatcgc ctgaacccag gaggtggagg ttgcaatgag 25080
ccaagatcat gccattgcac tccagcctgg gagacaagag agaaactcca tctcaaaaaa 25140
aaaaaaaagt tcagttccaa ataatggatg aactcagaac ttggaagggt ggtgactgca 25200
cacatggaca gagctgaggc acggcggggt ggaggcccct gcggctggca gattcaccgg 25260
agcctcctca gactgcgcag gagcacagca agtaaacagc taagctgtgc ccatctgacc 25320
ccagacacgt gtggccacag agaagcccct tgccatccat tccccccctcc tctcctctcc 25380
tgctccccca cacccctgcc ttcctccaac atgtttcagc cattctcttg gccttggtgc 25440
cctaattggc cgttatacaa aaggaagctt cctaacatct cggcgtggcc tctctgggag 25500
ctgtgctatt ccagacgctc tcctgtgcct ccagttgttt gcgtgcgcca ttccttctgc 25560
ctgaaaactt tttttcttc aatgtttcat taggaaaagt tttccaacac acagcacact 25620
ggaaagaatt ttgcagggag tcgcacacgc ccagcacttg ggttctcctg ttggcatcct 25680
ccggccagat gcattcatcc catttcgccc ggcccgtttg tctctgtcca tccgtcaagc 25740
tttcttgact tcttggtgca ttttcaggca aaccgcagac gccaacactc ccctcgctgc 25800
ctgggttgct gcctggcgtc cattgttcac aggcggtcac ctgaggggag gccaacgctc 25860
ggacagctgc gctcacctgc agatccgacc cctgccgacg acgtggggcc tcgccctgca 25920
agcccgctgc ccctccgggt gcccctgcgc tctgcctccc ggctctctga ctcttctccc 25980
tcagggtgag ctgtgcaggc tatggggagc ctctctctgt gctgaaggcc ccggccgtcc 26040
tctttctttc agggccctac ccctgtggga aacagaccct ggaacgcagg aagaggtcag 26100
tggcccaggc caccagcagc agcggggagg cccctgacag catcacatgg aagccatatg 26160
atgcagccga cctggacccc accgagaacc ccttcgacct gcttgacttc aaccagacgc 26220
agcctgagag gggcgacaac aacctcacca ggatcgtggg aggccaggaa tgcaaggacg 26280
gggagtgtcc ctggcaggta acagtaggat gtcccctcgg gcctgctgga gagaccacct 26340
gtcccgctgt gcacctcggg gaggccagcc tgacacttgg aatagcaatc cgggaaggaa 26400
ctgttccgaa ctaggacaga ggggctccgc cacccaagcc tgcctgcctg tcccctccct 26460
ccgggcagcc aaggaggctg tgagctccac agggaagtgg ccggggctga gggagaggct 26520
gggcccaggc aacgcccccc tcagcccctt cccactgggc atttccatgg ctgcccgtgg 26580
catgcccagg acgatgctgt cctgtgaaac agaagagagg gagaaggcgc agccacacgc 26640
tcaagtgtcc tcaaacctcc cctacaccag gagacaaggc taaagccagg gagccaccca 26700
cactgcaggg gcatcagcgg gcaggaggac ggtgccgggt gggcaaggcc tccatctgct 26760
cttctgtttg acgggaggca gaaagagttg gtgtcctcgc ttcatttcta attttggaat 26820

-continued

```
tttttaccc aaacacctaa atcctatgga ggtagatagt accttagaga aaaacacatc  26880
tacttatttt caaaggtaaa aaagaaaatc actctttgag gctttttgt taagagacag  26940
taccttgctc tgttgcccag gctggagtgc agtgtcgcga tctcggctca ctgcaacctc  27000
cacctcctgg gttcaagcga ttctcatgcc tcagactccc aagtagctgg aattacgggc  27060
gcccgctact tacgcctggc taattttttt ttttttttga gacggagtct cactctgtcg  27120
cccaggctgg agtgcagtgg cgcgatctcg gctcactgca acctccacct cccaggttca  27180
tgtcattctc ctgcttcagc ctcccgagta gctgggacta caggcgcctg ccaccacgcc  27240
cagctaattt tttttgtatt tttagtagag acggggtttc accgtgttag ccaggatggt  27300
ctccatctcc tgacctggtg atctgcccac ctcagcctcc caaagtgctg ggattacagg  27360
cgtgagacaa tgtgcccggc catgcctggc taattttttt atttttaata gagacaggaa  27420
tttcaccatg ttggccaggc tggtctcaaa ctccaggcct catgtgatcc accctcctca  27480
gccacccaaa gtgctggagt tacaggtgtg agccactata ccaggtccta atctttgatt  27540
gttgatttgg actaatgctg ccagattaaa caaataaaag cacaatactt tcaattaaat  27600
ttcaatttca cataaactag aaatacatta aacaaaagca caatactttc aattaaattt  27660
caatttcaca taaactagaa atactttcag tgtaagtatg ttccaagtat cgcatgaagc  27720
atacatatgc gaaaaattat ttgctgttta tctgattcaa gtcaaactag gtgtattagt  27780
cagttttcac actgctgaca catacatacc cgagactggg taatttataa agaaaaagag  27840
gttgaatgaa ctcacagttc cacgtggctg gggaggcctc accgtcacgg tggaaggcgc  27900
aaggcacgtc ttacatggcg gcagcaagac agagaatgag agaacaagca aaaggggttt  27960
ccccttagaa aaccatcagc tcttgtgaga cttattcact tccaccagaa cagcatgggg  28020
aaaccgccct cacgattcag ttacctccca ccaggtccct cccacaacac acgggaaata  28080
tgggagctac agtttgagat gagatttggg tggggacaca gccaaacctt gttgctgggc  28140
atcctgtatt ttctctggca atcctcactt ggacttgaat tttcagcgcc caaaaccaga  28200
atgtcctctc ctacaagcaa gaatctcaga gctgccagcg cccccatgaa ttcccccagg  28260
tcttccccca ccccagaccg tgtggcgggt gagcctctgt ctaactataa agagccaagc  28320
gagagaggga tgcactgagg tggctctgca atgcatgttt gttgagggcc ttctgtgtgt  28380
caggcactga gccgggtgct gtgtaggtgg gatatgaaac catgaagcct ctctgtgacc  28440
aatacacaga aatctcaacc tagttaggga gctgagaccg aaatcctccc agtcccaggc  28500
actgtgtggt tggggcaaga acctcgatgc aggagacccc accgaggatg agcaggaaaa  28560
gcctcttgtg gggctgagga gctggacttg gagctgcagg cggggttttg gaggggttcc  28620
tgggctgggg gaccagggtg gggcgccctg gagggctcac tggaggggcc ctcgcccagc  28680
ctgttgaggt ttgcgattct tgtttcctgg ttcgagtctt ggcaagtggg cctcatctgc  28740
atctttagga agaatggttg gtgttcgtgt cttagaaagc ctgactttcc ctcatgtaag  28800
ctggatgatg agttgacaaa ttatgcaaaa aagaggcaaa aacatgaccc cttttctagc  28860
catgaatgtt ttaagaaatg ttttaagact cggtattgtc agtagtttca ttggtctgta  28920
catgtgccca gccactatca caggacggga aactccccag agaaaagaaa accaaaatat  28980
gcccgggctc caaacttgca agtccagctc cctagggaca gcatgtggca cccctgtcag  29040
tgcttgctcc cctgggaccg tgttccaagt cctggcaggt aggagaccct tcacaggagc  29100
tgccacaggg acccccagga agtcacctgg gatggaggtg tccgtgcacc atgggggaca  29160
ggctcacact gctgaaccgt cgggacacca ggcaggcaca ccggttgagg cagatgatgt  29220
```

```
ttctgcacag actggcgtct cctggtccca ggtagaaatc ctgccacaga gacgggaaag  29280
gctgctccca cagggagcat cttttccaaa gcatggacag atgtgtcgtg tgcatgagac  29340
tttagagagc tctgtgatgg agttggtaga aagaagagat gactccctat atcagtgagt  29400
gtgtggcaca ggcagagaaa agagacagac aaggaactgt ccttgggtgg atggcaggag  29460
accgaagagg acagcttggc atggggaggg ccgggcagtg ccacctgaag agctggcttc  29520
tcagtcaggc aacacctgtc cacctggcca gccacactga gcctgtcacg tctgtcacag  29580
gccctgctca tcaatgagga aaacgagggt ttctgtggtg gaaccattct gagcgagttc  29640
tacatcctaa cggcagccca ctgtctctac caagccaaga gattcaaggt gagggtaggt  29700
aagtgaccaa cagcccccag ggccgtggtg aggggcaccg tcactgtctg cttttcagaa  29760
accactaaag ctgatggaat ttgttgggaa cactggttga aatcctgaaa tcctatttgt  29820
aggggttagg ggcatttcac agaggaagaa gatgaggaag cagaggaagg ggaagagtgg  29880
ggaggaggac ggggagggga ggcgaaccag cccagccctt ctcccactgg gtgtccaggt  29940
ctcgggtctc cgagtctctg ggtcccgggt ctctgggtct gcatgtccag ctaatgttct  30000
gtgtctcagt gtcttttatt gggagccttc cagacctccc tttctcttta acatactctg  30060
aacaccaagc acctctgtct cttctatttt tatttgtggg attgtttcat taacatctgt  30120
ctttgtccac tagaccctag agctgctcag tacaaaccca acacaagcta caaatgcaag  30180
caatatatgt aaactgatat ttttctaaca ttaaatgttc tattatacat tttaaaatat  30240
aaaaaaacag gctgggtgtg gtggctcatg cctgtaatcc cagcactttg ggaggctgag  30300
gcgggcagat cacctgaggt caggagtttg agatcagcct ggccagcatg gcgaaacccc  30360
atctctacta aaaaatacaa aaattagccg ggcatggtgg cacgggcctg taatcccagc  30420
tacttgggaa gctgaggcag gagaaccact tgaacccggg aggtggaggt tgcagtgagc  30480
tgagattgtg ccattgcact ccagcccggg caacagagca aaactctgtc tcaaaaaaaa  30540
aaaaaaaata tatatatata tatatgtata tatatatgtg tatatatata tacatatata  30600
tacacacaca cacacaattt ccataatata tcttatttaa ctcaacatat tgaaaatatt  30660
actttttcca tgtgtaatca tgttaaaggt gtaataacac attccgcaca ttttctttca  30720
tgctaagtct ctattttacg ttcatggcac aactatttta cactctcagc cagcggccac  30780
accgcacaac ctgggtctgg gatgccaaaa gccttcggtc ctgggacgcc tcgttggtgc  30840
ccacgactgg cacagacgat gcacccgcca aaggacacag gagtggcggc cgtctaaaga  30900
accaaacgtg tgagacagga ccagtggttc cctgggcagc aaggctgaca ggcactttta  30960
tttgctgctt tgcacttccc tctatttttc aaattttcaa aagtgatcac gtgccatttt  31020
taatttaaaa aaatatatat aacttcctta aaaagcaacg gatgtgcgag agcatgtccc  31080
tggctgagct gagcacagtc ccactcgtct gtcccagggg accggaacac ggagcaggag  31140
gagggcggtg aggcggtgca cgaggtggag gtggtcatca agcacaaccg gttcacaaag  31200
gagacctatg acttcgacat cgccgtgctc cggctcaaga cccccatcac cttccgcatg  31260
aacgtggcgc ctgcctgcct ccccgagcgt gactgggccg agtccacgct gatgacgcag  31320
aagacgggga ttgtgagcgg cttcgggcgc acccacgaga agggccggca gtccaccagg  31380
ctcaagatgc tggaggtgcc ctacgtggac cgcaacagct gcaagctgtc cagcagcttc  31440
atcatcaccc agaacatgtt ctgtgccggc tacgacacca agcaggagga tgcctgccag  31500
ggggacagcg ggggcccgca cgtcacccgc ttcaaggaca cctacttcgt gacaggcatc  31560
```

-continued

```
gtcagctggg gagagggctg tgcccgtaag gggaagtacg ggatctacac caaggtcacc  31620
gccttcctca agtggatcga caggtccatg aaaaccaggg gcttgcccaa ggccaagagc  31680
catgccccgg aggtcataac gtcctctcca ttaaagtgag atcccactca aggcctggtt  31740
tgtctctcga ttgccgcctt gccctggctt ctcccgccct gttgaggtgg gaaggtgaag  31800
tgtctgtctg gaacaccagc ttccgccctt cccagctagg ctggggattc ctccagggaa  31860
tattctagtc tgtgggggca ggatggaggc tccagggatg atactgtgcc atgactgcca  31920
tgggcattcc tttccccaga taccttcctg catctgggtc acgcccagag gcagatggga  31980
gcctgtgcag gccccgtggc gtcgggaggg gcccacacgt tggcgcagcc tccccaagac  32040
cccccacttg gcctggtctc tcttgttcct cttgggaatt ggacacctcc ccggtgactg  32100
cctatgaccc gcagactccc tgggagggaa acgtccagaa agcttctcat tggggcggac  32160
attttacatt aacttaaaca accaggtgct cttcaactgc acggtgccag gccccacccc  32220
agctcaggct tgtgtggtgg gggccacagg catcccccgg gcaggtgacc tgctcaccag  32280
gcagcgacct gacctggcac agttggcccc caccgtggcc acccttagaa ccccctgtgg  32340
gctttagcat gcctgcatcc aggccacagc ctggccactg aaatcagtct ctggagtgaa  32400
gctggccagg agcttctgga agcttctgga gctcctcagg tgctgagtgg tggtggcgtg  32460
gcaggcgggg cttcgggggg ctcctcctct cctagggtcc agatgtttag tccttgccct  32520
gctgcaatcc ggcactgtcc ctaggcctca agttaactgg ccatgaaaat caaatgaact  32580
ttcggtaaac agaaaagatt ccggacaagg cctgccgtgt gtctcccaaa cgtctcctgc  32640
agtttgcgtc ttgtgtaatg tccctaagca aagttcaaca gttctagtac aaaaactccc  32700
caaaaaagtc atgagctggg caaaaccgtt cgtaaacaga tgttgcgaag tcagggaaaa  32760
tcaaagtgga caggtgttcg acctcccaga aacggtctga ggaggggccg gtctcccagg  32820
gtgggcggga gggcattcct ggcctgcccg ctctgaggcc ttctccgtgg agctggctgt  32880
cgggctcctc gccggccctt cctggagaaa aggcttctgc ctcggagcta gcctgctgtt  32940
gggctgcgtt tcctaggcag ccacgtggtc cccagggccc cagaggtaaa ccctggactt  33000
ggattcccgt ttctggaaat caaaggttga gtggggtcca gagagaactc tgggaaaata  33060
attacaattg aaaccccccca tcgccatcac tgtctgcacc ctggttcctg ccgcactggg  33120
tgtctggtgc ccgtgcccgt ctcaggatag aaaggaaact ggaggctgca gagagaagga  33180
cctgatgggt cgtagctcag catctgccga agccccatct agaaataggt tctcgtcctg  33240
ggaggtgtgg gagggagcct cgggagggag acagcaggag gagaggcccc agtcctggac  33300
acgcgctggg ggttgaagtc tcggctctgc aggctcctgt gctgcgtggc agggattttc  33360
tctctgccta aatatcgtct tcataagtaa aggcaagtgg gctaaaccta tgtcatctcc  33420
gtgttaactc agaatagtct aggcctgggc caggggacac tttgtgatct gagaccccca  33480
gaattccctg agggaggccc agctctgttt cgggaaataa ctgaagcggc tgtttgtgcg  33540
aggtgagacc ctgaggaccg agagcagcag gaggtcatgg tggggagcaa aaacgggaaa  33600
agtgattccg cctgagactg agggagagag aacccaggtg agaccctgag gactgtgagc  33660
agcaggaggt cacggtgggg agtaaagatg ggaaaagtga ttccgcctga gagtgaggga  33720
gagagaacag a                                                       33731
```

<210> SEQ ID NO 48
<211> LENGTH: 467
<212> TYPE: PRT
<213> ORGANISM: Homo sapiens

<400> SEQUENCE: 48

Leu Leu Gly Glu Ser Leu Phe Ile Arg Arg Glu Gln Ala Asn Asn Ile
1 5 10 15

Leu Ala Arg Val Thr Arg Ala Asn Ser Phe Leu Glu Glu Met Lys Lys
20 25 30

Gly His Leu Glu Arg Glu Cys Met Glu Glu Thr Cys Ser Tyr Glu Glu
35 40 45

Ala Arg Glu Val Phe Glu Asp Ser Asp Lys Thr Asn Glu Phe Trp Asn
50 55 60

Lys Tyr Lys Asp Gly Asp Gln Cys Glu Thr Ser Pro Cys Gln Asn Gln
65 70 75 80

Gly Lys Cys Lys Asp Gly Leu Gly Glu Tyr Thr Cys Thr Cys Leu Glu
85 90 95

Gly Phe Glu Gly Lys Asn Cys Glu Leu Phe Thr Arg Lys Leu Cys Ser
100 105 110

Leu Asp Asn Gly Asp Cys Asp Gln Phe Cys His Glu Glu Gln Asn Ser
115 120 125

Val Val Cys Ser Cys Ala Arg Gly Tyr Thr Leu Ala Asp Asn Gly Lys
130 135 140

Ala Cys Ile Pro Thr Gly Pro Tyr Pro Cys Gly Lys Gln Thr Leu Glu
145 150 155 160

Arg Arg Lys Arg Ser Val Ala Gln Ala Thr Ser Ser Ser Gly Glu Ala
165 170 175

Pro Asp Ser Ile Thr Trp Lys Pro Tyr Asp Ala Ala Asp Leu Asp Pro
180 185 190

Thr Glu Asn Pro Phe Asp Leu Leu Asp Phe Asn Gln Thr Gln Pro Glu
195 200 205

Arg Gly Asp Asn Asn Leu Thr Arg Ile Val Gly Gly Gln Glu Cys Lys
210 215 220

Asp Gly Glu Cys Pro Trp Gln Ala Leu Leu Ile Asn Glu Glu Asn Glu
225 230 235 240

Gly Phe Cys Gly Gly Thr Ile Leu Ser Glu Phe Tyr Ile Leu Thr Ala
245 250 255

Ala His Cys Leu Tyr Gln Ala Lys Arg Phe Glu Gly Asp Arg Asn Thr
260 265 270

Glu Gln Glu Glu Gly Gly Glu Ala Val His Glu Val Glu Val Val Ile
275 280 285

Lys His Asn Arg Phe Thr Lys Glu Thr Tyr Asp Phe Asp Ile Ala Val
290 295 300

Leu Arg Leu Lys Thr Pro Ile Thr Phe Arg Met Asn Val Ala Pro Ala
305 310 315 320

Cys Leu Pro Glu Arg Asp Trp Ala Glu Ser Thr Leu Met Thr Gln Lys
325 330 335

Thr Gly Ile Val Ser Gly Phe Gly Arg Thr His Glu Lys Gly Arg Gln
340 345 350

Ser Thr Arg Leu Lys Met Leu Glu Val Pro Tyr Val Asp Arg Asn Ser
355 360 365

Cys Lys Leu Ser Ser Ser Phe Ile Ile Thr Gln Asn Met Phe Cys Ala
370 375 380

Gly Tyr Asp Thr Lys Gln Glu Asp Ala Cys Gln Gly Asp Ser Gly Gly
385 390 395 400

Pro His Val Thr Arg Phe Lys Asp Thr Tyr Phe Val Thr Gly Ile Val

```
                405                 410                 415

Ser Trp Gly Glu Gly Cys Ala Arg Lys Gly Lys Tyr Gly Ile Tyr Thr
            420                 425                 430

Lys Val Thr Ala Phe Leu Lys Trp Ile Asp Arg Ser Met Lys Thr Arg
        435                 440                 445

Gly Leu Pro Lys Ala Lys Ser His Ala Pro Glu Val Ile Thr Ser Ser
    450                 455                 460

Pro Leu Lys
465
```

<210> SEQ ID NO 49
<211> LENGTH: 1529
<212> TYPE: DNA
<213> ORGANISM: Bos Taurus

<400> SEQUENCE: 49

```
ctcagcaccg ccctgggcgg cctcctgcgg ccggcgggga gcgtgttcct gccccgggac     60

caggcccacc gtgtcctgca gagagcccgc agggccaact cattcttgga ggaggtgaag    120

cagggaaacc tggagcgaga gtgcctggag gaggcctgct cactagagga ggcccgcgag    180

gtcttcgagg acgcagagca gacggatgaa ttctggagta aatacaaaga tggagaccag    240

tgtgaaggcc acccgtgcct gaatcagggc cactgtaaag acggcatcgg agactacacc    300

tgcacctgtg cggaagggtt tgaaggcaaa aactgcgagt tctccacgcg tgagatctgc    360

agcctggaca atgggggctg cgaccagttc tgcagggagg agcgcagcga ggtgcggtgc    420

tcctgcgcgc acggctacgt gctgggcgac gacagcaagt cctgcgtgtc cacagagcgc    480

ttcccctgtg ggaagttcac gcagggacgc agccggcggt gggccatcca caccagcgag    540

gacgcgcttg acgccagcga gctggagcac tacgaccctg cagacctgag ccccacagag    600

agctccttgg acctgctggg cctcaacagg accgagccca gcgccgggga ggacggcagc    660

caggtggtcc ggatagtggg cggcagggac tgcgcggagg gcgagtgccc atggcaggct    720

ctgctggtca acgaagagaa cgagggattc tgcgggggca ccatcctgaa cgagttctac    780

gtcctcacgg ctgcccactg cctgcaccag gccaagaggt tcacggtgag ggtcggcgac    840

cggaacacag agcaggagga gggcaacgag atggcacacg aggtggagat gactgtgaag    900

cacagccgct ttgtcaagga gacctacgac ttcgacatcg cggtgctgag gctcaagacg    960

cccatccggt tccgccggaa cgtggcgccc gcctgcctgc ccgagaagga ctgggcggag   1020

gccacgctga tgacccagaa gacgggcatc gtcagcggct tcgggcgcac gcacgagaag   1080

ggccgcctgt cgtccacgct caagatgctg gaggtgccct acgtggaccg cagcacctgt   1140

aagctgtcca gcagcttcac catcacgccc aacatgttct gcgccggcta cgacacccag   1200

cccgaggacg cctgccaggg cgacagtggc ggcccccacg tcacccgctt caaggacacc   1260

tacttcgtca caggcatcgt cagctgggga gaagggtgcg cgcgcaaggg caagttcggc   1320

gtctacacca aggtctccaa cttcctcaag tggatcgaca agatcatgaa ggccagggca   1380

ggggccgcgg gcagccgcgg ccacagtgaa gcccctgcca cctggacggt cccgcccccc   1440

cttccgctct gagcgggctc cctccctgcc tgattagagc tgtgtcctct ccttaaaaaa   1500

aaaaaaaaaa aaaaaaaaaa aaaaaaaaa                                     1529
```

<210> SEQ ID NO 50
<211> LENGTH: 492
<212> TYPE: PRT
<213> ORGANISM: Bos Taurus

<400> SEQUENCE: 50

Met Ala Gly Leu Leu His Leu Val Leu Leu Ser Thr Ala Leu Gly Gly
1               5                   10                  15

Leu Leu Arg Pro Ala Gly Ser Val Phe Leu Pro Arg Asp Gln Ala His
            20                  25                  30

Arg Val Leu Gln Arg Ala Arg Arg Ala Asn Ser Phe Leu Glu Glu Val
        35                  40                  45

Lys Gln Gly Asn Leu Glu Arg Glu Cys Leu Glu Glu Ala Cys Ser Leu
    50                  55                  60

Glu Glu Ala Arg Glu Val Phe Glu Asp Ala Glu Gln Thr Asp Glu Phe
65                  70                  75                  80

Trp Ser Lys Tyr Lys Asp Gly Asp Gln Cys Glu Gly His Pro Cys Leu
                85                  90                  95

Asn Gln Gly His Cys Lys Asp Gly Ile Gly Asp Tyr Thr Cys Thr Cys
            100                 105                 110

Ala Glu Gly Phe Glu Gly Lys Asn Cys Glu Phe Ser Thr Arg Glu Ile
        115                 120                 125

Cys Ser Leu Asp Asn Gly Gly Cys Asp Gln Phe Cys Arg Glu Glu Arg
    130                 135                 140

Ser Glu Val Arg Cys Ser Cys Ala His Gly Tyr Val Leu Gly Asp Asp
145                 150                 155                 160

Ser Lys Ser Cys Val Ser Thr Glu Arg Phe Pro Cys Gly Lys Phe Thr
                165                 170                 175

Gln Gly Arg Ser Arg Arg Trp Ala Ile His Thr Ser Glu Asp Ala Leu
            180                 185                 190

Asp Ala Ser Glu Leu Glu His Tyr Asp Pro Ala Asp Leu Ser Pro Thr
        195                 200                 205

Glu Ser Ser Leu Asp Leu Leu Gly Leu Asn Arg Thr Glu Pro Ser Ala
    210                 215                 220

Gly Glu Asp Gly Ser Gln Val Val Arg Ile Val Gly Gly Arg Asp Cys
225                 230                 235                 240

Ala Glu Gly Glu Cys Pro Trp Gln Ala Leu Leu Val Asn Glu Glu Asn
                245                 250                 255

Glu Gly Phe Cys Gly Gly Thr Ile Leu Asn Glu Phe Tyr Val Leu Thr
            260                 265                 270

Ala Ala His Cys Leu His Gln Ala Lys Arg Phe Thr Val Arg Val Gly
        275                 280                 285

Asp Arg Asn Thr Glu Gln Glu Glu Gly Asn Glu Met Ala His Glu Val
    290                 295                 300

Glu Met Thr Val Lys His Ser Arg Phe Val Lys Glu Thr Tyr Asp Phe
305                 310                 315                 320

Asp Ile Ala Val Leu Arg Leu Lys Thr Pro Ile Arg Phe Arg Arg Asn
                325                 330                 335

Val Ala Pro Ala Cys Leu Pro Glu Lys Asp Trp Ala Glu Ala Thr Leu
            340                 345                 350

Met Thr Gln Lys Thr Gly Ile Val Ser Gly Phe Gly Arg Thr His Glu
        355                 360                 365

Lys Gly Arg Leu Ser Ser Thr Leu Lys Met Leu Glu Val Pro Tyr Val
    370                 375                 380

Asp Arg Ser Thr Cys Lys Leu Ser Ser Ser Phe Thr Ile Thr Pro Asn
385                 390                 395                 400

Met Phe Cys Ala Gly Tyr Asp Thr Gln Pro Glu Asp Ala Cys Gln Gly

-continued

```
                405                 410                 415

Asp Ser Gly Gly Pro His Val Thr Arg Phe Lys Asp Thr Tyr Phe Val
            420                 425                 430

Thr Gly Ile Val Ser Trp Gly Glu Gly Cys Ala Arg Lys Gly Lys Phe
        435                 440                 445

Gly Val Tyr Thr Lys Val Ser Asn Phe Leu Lys Trp Ile Asp Lys Ile
    450                 455                 460

Met Lys Ala Arg Ala Gly Ala Ala Gly Ser Arg Gly His Ser Glu Ala
465                 470                 475                 480

Pro Ala Thr Trp Thr Val Pro Pro Pro Leu Pro Leu
                485                 490


<210> SEQ ID NO 51
<211> LENGTH: 30
<212> TYPE: PRT
<213> ORGANISM: Echis carinatus

<400> SEQUENCE: 51

Asp Cys Leu Pro Gly Trp Ser Ser His Glu Gly His Cys Tyr Lys Val
1               5                   10                  15

Phe Asn Gln Glu Met Tyr Trp Ala Asp Ala Glu Lys Phe Cys
            20                  25                  30


<210> SEQ ID NO 52
<211> LENGTH: 30
<212> TYPE: PRT
<213> ORGANISM: Echis carinatus

<400> SEQUENCE: 52

Asp Cys Leu Pro Asp Trp Phe His Tyr Glu Gly His Cys Tyr Arg Val
1               5                   10                  15

Phe Asp Glu Pro Lys Lys Trp Ala Asp Ala Glu Lys Phe Cys
            20                  25                  30


<210> SEQ ID NO 53
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 53

His Glu Xaa Xaa His Xaa Xaa Gly Xaa Xaa His
1               5                   10
```